US012525343B2

(12) United States Patent
Bell et al.

(10) Patent No.: US 12,525,343 B2
(45) Date of Patent: Jan. 13, 2026

(54) ARTIFICIALLY INTELLIGENT ROUTING AGENT FOR ROUTING PORTIONS OF A TASK THROUGH MULTIPLE CUSTOMIZED AGENTS, AND SYSTEMS, DEVICES, AND METHODS OF USE THEREOF

(71) Applicant: Tempus AI, Inc., Chicago, IL (US)

(72) Inventors: Joshua Michael Bell, Chicago, IL (US); Alberto Coroleu Bonet, Barcelona (ES); Christopher Shane Colley, Naperville, IL (US); Guillem Garcia i Gomez, Girona (ES); Jacob Erwin Lee, Chicago, IL (US); Anthony Jennings Massery, Chicago, IL (US); Manuel Jesús Morillo Jiménez, Seville (ES); Jonathan H. Ozeran, Deerfield, IL (US)

(73) Assignee: Tempus AI, Inc., Chicago, IL (US)

( * ) Notice: Subject to any disclaimer, the term of this patent is extended or adjusted under 35 U.S.C. 154(b) by 57 days.

(21) Appl. No.: 18/741,503

(22) Filed: Jun. 12, 2024

(65) Prior Publication Data

US 2024/0404687 A1 Dec. 5, 2024

Related U.S. Application Data

(63) Continuation of application No. PCT/US2024/031728, filed on May 30, 2024.

(Continued)

(51) Int. Cl.

*G16H 40/20* (2018.01)
*G06Q 10/0631* (2023.01)
*G06Q 10/0633* (2023.01)

(52) U.S. Cl.

CPC ....... *G16H 40/20* (2018.01); *G06Q 10/06316* (2013.01); *G06Q 10/0633* (2013.01)

(58) Field of Classification Search

None

See application file for complete search history.

(56) References Cited

U.S. PATENT DOCUMENTS

2012/0124022 A1* 5/2012 Goping .................. G16H 40/67 707/705
2018/0260239 A1 9/2018 Vadapandeshwara (Continued)

OTHER PUBLICATIONS

Sycara et al., Distributed Intelligent Agents, 0885-9000/96/$4,00 0 Dec. 1996 IEEE Expert.*

(Continued)

*Primary Examiner* — David J Stoltenberg

(74) *Attorney, Agent, or Firm* — MORGAN, LEWIS & BOCKIUS LLP

(57) ABSTRACT

This application describes, amongst other things, methods and systems for building and deploying agents. An example method includes obtaining orchestration data about a set of task-specific components selected to provide a response to the prompt, where each respective task-specific components in the set of task-specific components is configured to assist with a respective clinical task of the one or more clinical tasks. The method further includes, determining an order in which each respective task-specific components of the set of task-specific components should be utilized to prepare a complete response to the prompt that address the one or more clinical tasks based on the obtained orchestration data about the set of task-specific components. The method also includes, in accordance with the determined order, providing first data related to the prompt to a first task-specific component and receiving a first response from the first task-specific component.

20 Claims, 51 Drawing Sheets

Related U.S. Application Data

(60) Provisional application No. 63/515,532, filed on Jul. 25, 2023, provisional application No. 63/505,018, filed on May 30, 2023.

(56) References Cited

U.S. PATENT DOCUMENTS

| | | | | |
|---|---|---|---|---|
| 2019/0019106 | A1 | 1/2019 | Driscoll et al. | |
| 2020/0321084 | A1 | 10/2020 | Bucur | |
| 2021/0035680 | A1* | 2/2021 | Chen | G06Q 10/06316 |
| 2021/0174941 | A1* | 6/2021 | Mathur | G06F 11/3698 |
| 2022/0199254 | A1 | 6/2022 | Tuysuzoglu | |
| 2022/0261288 | A1* | 8/2022 | Viswanathan | G06F 9/50 |
| 2022/0374558 | A1* | 11/2022 | Patel | G06F 30/12 |
| 2022/0391729 | A1* | 12/2022 | Duford | G06Q 10/0633 |

OTHER PUBLICATIONS

Clarke et al., One Agent To Rule Them All: Towards Multi-agent Conversational AI, arXiv:2203.07665v1 [cs.CL] Mar. 15, 2022.*

Teemu Leppanen; Distributed Artificial Intelligence with Multi-Agent Systems for MEC; 978-1-7281-1856-7/19/$31.00 © 2019 IEEE.*

Liu et al. An Intelligent Human Agent Interaction Support System in Medicine; 2023 26th International Conference on Computer Supported Cooperative Work in Design (CSCWD) 979-8-3503-3168-4/23/$31.00 © 2023 IEEE | DOI: 10.1109/CSCWD57460.2023.10152686.*

Krizhevsky; Alex et al. "ImageNet Classification with Deep Convolutional Neural Networks", Advances in Neural Information Processing Systems 25, University of Toronto, 2012, pp. 1-9.

Larochelle; Hugo et al. "Exploring Strategies for Training Deep Neural Networks", Journal of Machine Learning Research 1, 2009, pp. 1-40.

Li, D., et al. "How Long Can Context Length of Open-Source LLMs truly Promise?," Workshop on Instruction Tuning and Instruction Following at NeurIPS 2023, pp. 1-7.

McLachlan; G. J. et al. "A mixture model-based approach to the clustering of microarray expression data", BioInformatics, vol. 18, No. 3, 2002, pp. 413-422.

Menéndez, M.L. "The Jensen-Shannon Divergence," J. Franklini Inst., vol. 334B, No. 2, 1997, pp. 307-318.

Vincent; Pascal et al. "Stacked Denoising Autoencoders: Learning Useful Representations in a Deep Network with a Local Denoising Criterion", Journal of Machine Learning Research 11 (2010), pp. 3371-3408.

Xiong, W., et al. "Answering Complex Open-Domain Questions With Multi-Hop Dense Retrieval," Published as a conference paper at ICLR, Feb. 19, 2021, XP081882576, pp. 1-19.

Zakka, C. et al. "Almanac: Knowledge-Grounded Language Models for Clinical Medicine," arxiv.org, Cornell University Library, XP091450420, Mar. 1, 2023, pp. 1-14.

Zamani, H. et al. "Retrieval-Enhanced Machine Learning," Perspective Paper, SIGIR '22, Jul. 11-15, 2022, pp. 2875-2886.

Zeiler; Matthew D. "Adadelta: an Adaptive Learning Rate Method", Computer Science, CoRR, vol. abs/1212.5701, 2012, pp. 1-6.

Wang; Zekun, et al. "Interactive Natural Language Processing," arXiv, May 22, 2023, pp. 1-110.

* cited by examiner

500

To join patient and molecular master file tables in R, you should use the `patient_id` column as the primary key while joining. First, filter the molecular master file (MMF) based on the specific data you need.
Here's an example of how you can achieve this in R:

```R
# Assuming you have data in two data frames:
patient_data and molecular_data

# Filter molecular_data for the specific gene and column
of interest (e.g., KRAS copy number)
filtered_molecular_data <- molecular_data %>%
filter(gene == "KRAS") %>% select(patient_id,
copy_number)

# Join the patient_data and filtered_molecular_data
using the 'patient_id' column
Combined_data <- merge(patient_data,
filtered_molecular_data, by="patient_id")
```

Please ensure you have the necessary data frames (`patient_data` and `molecular_data`) loaded into your R environment before executing the code. You can find example manipulations of the MMF in the Molecular_Data_Training folder, as mentioned in document xxx.

How many copies of a gene are needed for it to be considered amplified?

FIG. 12C

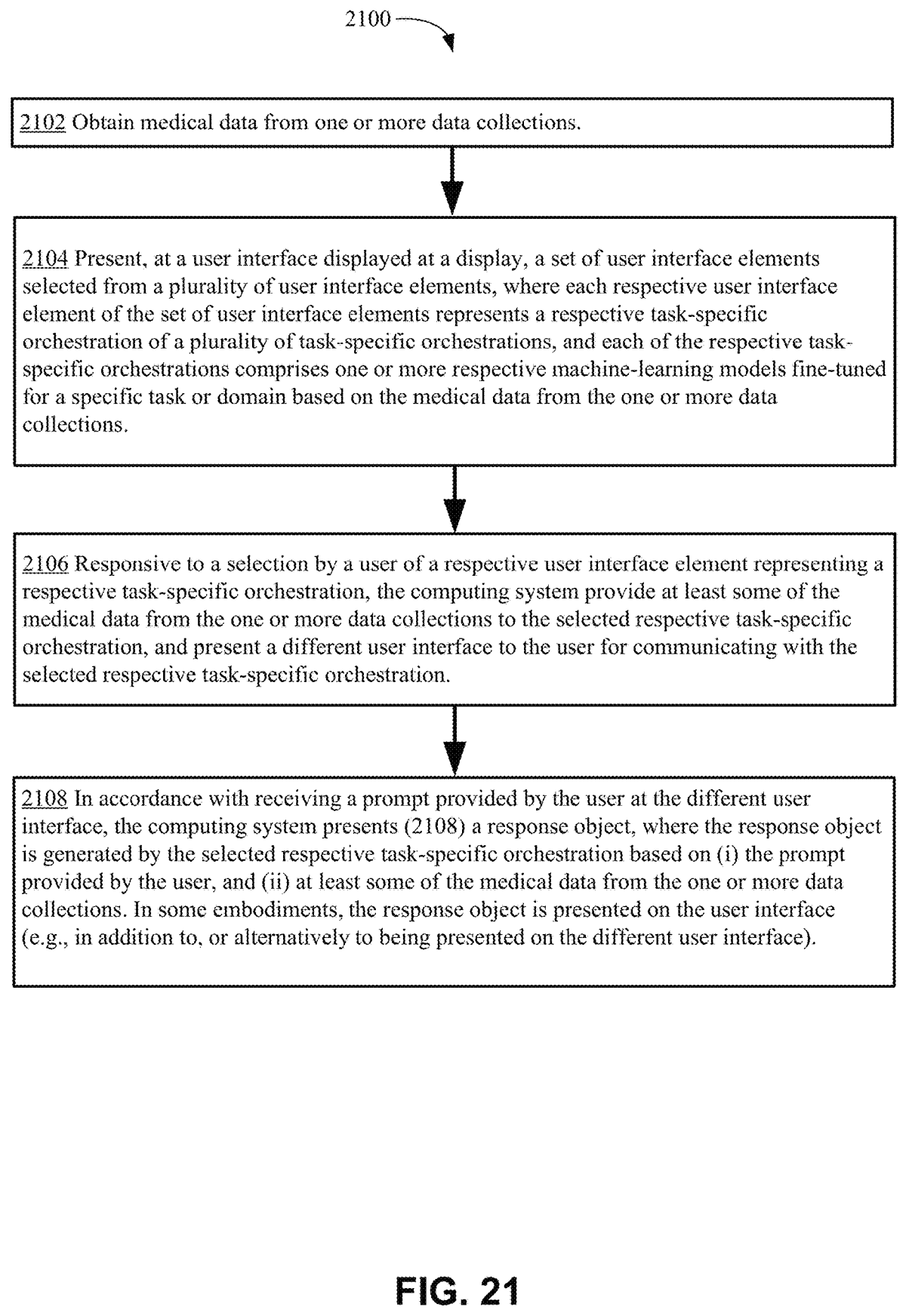

2100

2102 Obtain medical data from one or more data collections.

2104 Present, at a user interface displayed at a display, a set of user interface elements selected from a plurality of user interface elements, where each respective user interface element of the set of user interface elements represents a respective task-specific orchestration of a plurality of task-specific orchestrations, and each of the respective task-specific orchestrations comprises one or more respective machine-learning models fine-tuned for a specific task or domain based on the medical data from the one or more data collections.

2106 Responsive to a selection by a user of a respective user interface element representing a respective task-specific orchestration, the computing system provide at least some of the medical data from the one or more data collections to the selected respective task-specific orchestration, and present a different user interface to the user for communicating with the selected respective task-specific orchestration.

2108 In accordance with receiving a prompt provided by the user at the different user interface, the computing system presents (2108) a response object, where the response object is generated by the selected respective task-specific orchestration based on (i) the prompt provided by the user, and (ii) at least some of the medical data from the one or more data collections. In some embodiments, the response object is presented on the user interface (e.g., in addition to, or alternatively to being presented on the different user interface).

FIG. 21

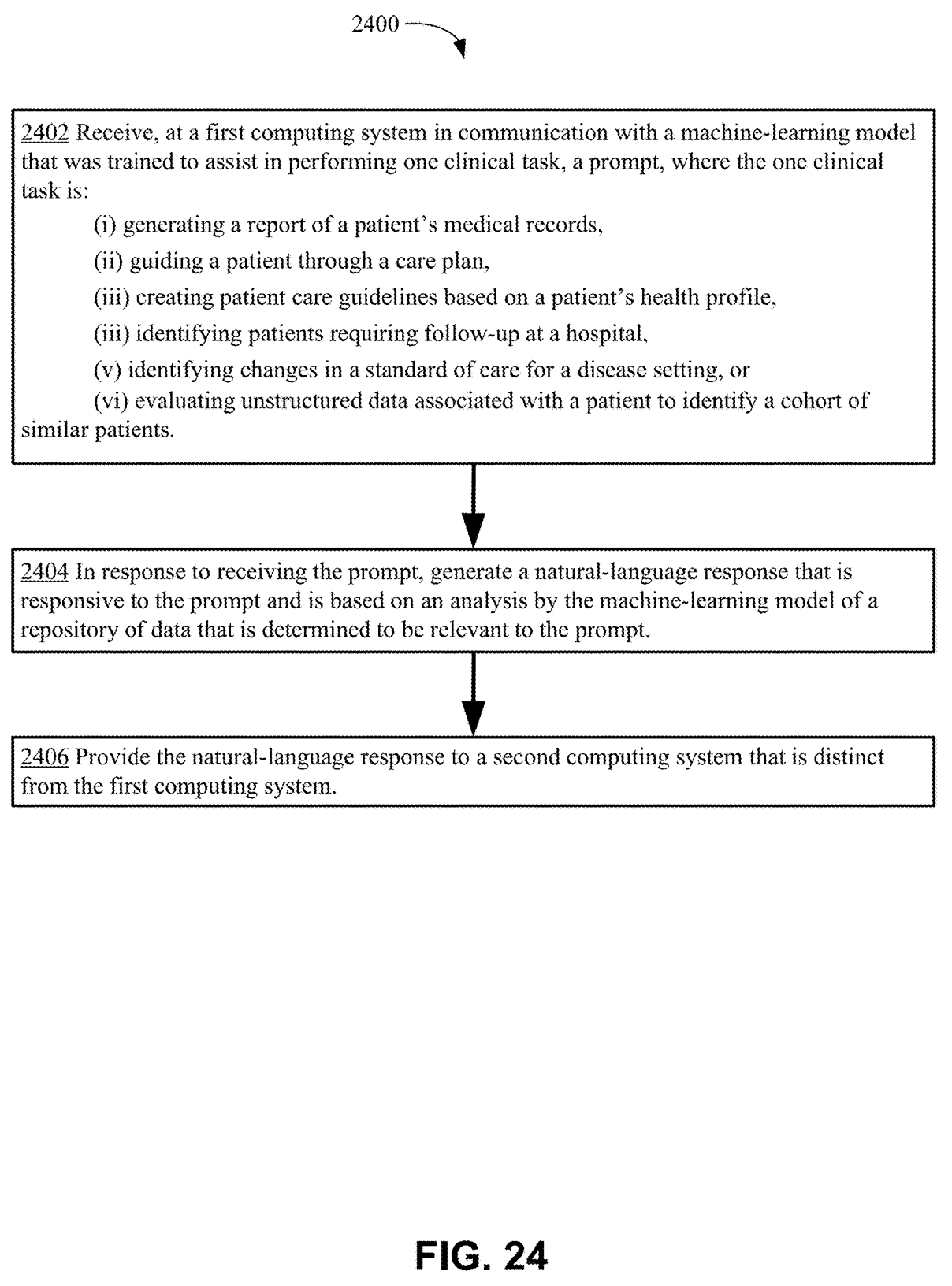

2400

2402 Receive, at a first computing system in communication with a machine-learning model that was trained to assist in performing one clinical task, a prompt, where the one clinical task is:

(i) generating a report of a patient's medical records, (ii) guiding a patient through a care plan, (iii) creating patient care guidelines based on a patient's health profile, (iii) identifying patients requiring follow-up at a hospital, (v) identifying changes in a standard of care for a disease setting, or (vi) evaluating unstructured data associated with a patient to identify a cohort of similar patients.

2404 In response to receiving the prompt, generate a natural-language response that is responsive to the prompt and is based on an analysis by the machine-learning model of a repository of data that is determined to be relevant to the prompt.

2406 Provide the natural-language response to a second computing system that is distinct from the first computing system.

FIG. 24

ARTIFICIALLY INTELLIGENT ROUTING AGENT FOR ROUTING PORTIONS OF A TASK THROUGH MULTIPLE CUSTOMIZED AGENTS, AND SYSTEMS, DEVICES, AND METHODS OF USE THEREOF

RELATED APPLICATIONS

This application is a continuation application of PCT Patent Application No. PCT/US24/31728, entitled "An Artificially Intelligent Routing Agent for Routing Portions of a Task Through Multiple Customized Agents, and Systems, Devices, and Methods of Use Thereof" filed on May 30, 2024, which claims priority to U.S. Prov. App. No. 63/505,018, filed on May 30, 2023, and entitled "AI-Enabled Clinical Assistant," and to U.S. Prov. App. No. 63/515,532, filed on Jul. 25, 2023, and entitled "Systems and Methods for Generating and Deploying Task-Specific Agents," each of which is hereby incorporated by reference in its entirety.

TECHNICAL FIELD

The disclosed embodiments relate generally to using task-specific orchestrations, including but not limited to generating, coupling, and deploying task-specific machine learning agents.

BACKGROUND

Many professions require complex thought where people need to consider many factors when selecting solutions to encountered situations, hypothesize new factors and solutions, and test new factors and solutions to ensure that they are effective. For instance, oncologists considering specific patient cancer states, optimally should consider many different factors when assessing the patient's cancer state as well as many other factors when crafting and administering an optimized treatment plan. For example, these factors include the patient's family history, past medical conditions, current diagnosis, genomic/molecular profile of the patient's hereditary DNA and of the patient's tumor's DNA, current nationally recognized guidelines for standards of care within that cancer subtype, recently published research relating to that patient's condition, available clinical trials pertaining to that patient, available medications and other therapeutic interventions that may be a good option for the patient and data from similar patients. In addition, cancer and cancer treatment research are evolving rapidly so that researchers need to continually utilize data, new research and new treatment guidelines to think critically about new factors and treatments when diagnosing cancer states and optimized treatment plans.

In particular, it is no longer reasonable for an oncologist to be familiar with all new research in the field of cancer care. Similarly, it is extremely challenging for an oncologist to be able to manually analyze the medical records and outcomes of thousands or millions of cancer patients each time they want to make a specific treatment recommendation regarding a particular patient they are treating. As an initial matter, oncologists often do not even have access to health information from institutions other than their own. In the United States, implementation of the federal law known as the Health Insurance Portability and Accountability Act of 1996 ("HIPAA") places significant restrictions on the ability of one health care provider to access health records of another health care provider. In addition, health care systems face administrative, technical, and financial challenges in making their data available to a third party for aggregation with similar data from other health care systems. Where multiple institutions are responsible for the development of a single, aggregated repository, there can be significant disagreement over the structure of the data dictionary or data dictionaries, the methods of accessing the data, the individuals or other providers permitted to access the data, the quantity of data available for access, and so forth. Moreover, the scope of the data available to be searched is overwhelming for any oncologist wishing to conduct a manual review. Every patient has health information that includes hundreds or even thousands of data elements. When including sequencing information in the health information to be accessed and analyzed, such as from next-generation sequencing, the volume of health information that could be analyzed grows intensely. A single FASTQ or BAM file produced in the course of whole-exome sequencing, for instance, takes up gigabytes of storage, even though it includes sequencing for only the patient's exome, which is just a small fraction of the whole human genome.

Tools have been and continue to be developed to help oncologists diagnose cancer states, select and administer optimized treatments and explore and consider new cancer state factors, new cancer states (e.g., diagnosis), new treatment factors, new treatments and new efficacy factors. For instance, large cancer databases have been developed and are maintained for access and manipulation by oncologists to explore diagnosis and treatment options as well as new insights and treatment hypotheses. Computers enable access to and manipulation of cancer data and derivatives thereof.

While conventional computers and workstations operate well as data access and manipulation interfaces, they have several shortcomings. First, using a computer interface often requires an oncologist to click many times, on different interfaces, to find a specific piece of information. This is a cumbersome and time-consuming process that often does not result in the oncologist achieving the desired result of receiving the answer to the question they are trying to ask. Additionally, in many cases oncological and research data activities include a sequence of consecutive questions or requests (hereinafter "requests") that home in on increasingly detailed data responses where the oncologist/researcher has to repeatedly enter additional input to define next level requests as intermediate results are not particularly interesting.

Recently, large language models (LLMs), such as ChatGPT by OpenAI, have become increasingly popular for answering a variety of questions using human language. However, LLMs suffer from a lack of performance robustness when utilized to evaluate niche information or respond to specific, niche questions, particularly in the medical context. For instance, conventional LLMs are trained on a large universe of data that does not well-represent niche subject matters, leading to inaccuracies or gaps in evaluations and outputs provided by LLMs. Moreover, LLMs are prone to over tuning when trained on niche data sets, causing the LLM to perform poorly on unseen data excluded from the training data.

Additionally, LLMs are resource intensive, requiring a significant amount of computational and financial resources to train and employ. For instance, conventional LLMs may have context windows with a capacity between 8,000 tokens and 100,000 tokens, but fail to maintain output accuracy and precision when processing large numbers of tokens. See Li, Dacheng, et al., 2023, "How Long Can Context Length of Open-Source LLMs truly Promise?," NeurIPS, Workshop on Instruction Tuning and Instruction.

SUMMARY

Thus, the inventors of the present application recognized a need for systems and methods that allow a user to query medical information (and other types of information) using natural language, intuitive interfaces, and follow-up questions.

The present disclosure describes, amongst other things, generating, deploying, and interacting with machine-learning agents (e.g., machine-learning orchestrations). For example, agents may be generated and deployed using an agent builder component (e.g., in a control plane) and/or an agent builder user interface. The deployed agents may be stored in an agent host (and optionally updated via the agent builder component). The agents may be task-specific, and generation of the agents may include identifying an appropriate machine-learning model and configuration of the model for the specific task. The agents may be configured via a configuration file and communicatively coupled to one or more datasets, one or more tools (e.g., formatting, data access, and/or analysis tools), and/or one or more output components. In this way, the systems and methods described herein allow users without programming expertise to generate, deploy, and interact with agents to obtain and analyze medical (and other types) of data. Identifying the correct agent type for a given task can improve performance and reduce computer and storage costs. Moreover, the systems and methods described herein restrict what data the agents can access and edit, which improves security and prevents data corruption and unauthorized access.

In accordance with some embodiments, the present disclosure provides systems and methods for guiding a user through generating, modifying, and/or deploying a task-specific machine-learning model, such as within a user interface of a client device. In some embodiments, the user interface is accessible through a display device, such as through an internet address access, which, in turn, presents a library of agents and/or an agent module for building customized agents and/or predetermined agents, deploying customized and/or predetermined agents, and/or executing the customized and/or predetermined agents. The user interface further allows for customization of data which may be provided to the agent via a collection of documents.

In accordance with some embodiments, the present disclosure provides systems and methods for generating, configuring, and/or maintaining an architecture of an agent (also sometimes referred to as an agent module or an agent component). In some embodiments, the architecture includes the framework of a plurality of interconnected nodes that enables the agent to be executed, such as via a communication network at a remote client device. In some embodiments, the systems and methods maintain the architecture of the agent, such as a plurality of interconnected nodes including an input node (e.g., initial terminal node) and an output node (e.g., final terminal node) that is deployed and/or executable within the cloud architecture. In some embodiments, the systems and methods retain a conditional logical associated with the agent, which allows the agent to perform a specific function, such as how API calls are handled to accommodate execution and embedding agents within other cloud-based software systems.

In accordance with some embodiments, the present disclosure provides systems and methods for a framework for configuring an agent using one or more coarse-grain logics, such as an arrangement of nodes within a node architecture of interconnected nodes, and/or one or more fine-grain logics, such as a modifiable weight of a respective node within the node architecture, to structure how the agent responds to a variety of prompts received from different users. In some embodiments, the agent receives a prompt that includes structured data and/or text files as an input, which is then applied to the node architecture in accordance with the coarse- and fine-grain logics. For example, information from a prompt may be provided to a node associated with a first model trained on tumor screening in the plurality of interconnected blocks and a ground truth associated with the structured data is transformed into an acceptable form for intake by the first model.

In accordance with some embodiments, the present disclosure provides systems and methods for a user interface framework, which allows for provisioning access to secure data based on user credentials, allowing access to different user interface elements to users based on tools and/or external services, and allowing creation and/or storage of personalized agent modules, such as for collaboration within third party users.

In accordance with some embodiments, a method of configuring a task-specific agent includes (i) receiving a request from a user for an agent configured to perform a specific task; (ii) in response to the request, identifying a first agent type from a set of agent types based on one or more requirements for performing the specific task, where each agent type of the set of agent types corresponds to a respective language model; (iii) generating a model component having the first agent type, where generating the model component includes generating a set of operating instructions for the model component; (iv) generating an implementation component for the agent, the implementation component configured to communicatively couple the model component to a set of components based on the one or more requirements for performing the specific task, where the set of components comprise one or more of: a set of data sources, a set of tools, and a set of output components; and (v) deploying the agent to a working environment, where the agent comprises the model component and the implementation component.

In accordance with some embodiments, a method of identifying subjects includes: (i) receiving a request from a user to identify subjects meeting a set of criteria; (ii) obtaining, via a language model component, a set of protocols from the request; (iii) generating, via the language model component, one or more structured queries based on the set of protocols; (iv) transmitting, via the language model component, the one or more structured queries to one or more databases; and (v) in response to transmitting the one or more structured queries, receiving, from the one or more databases, a set of subjects meeting the set of criteria.

In accordance with some embodiments, a computing system is provided, such as a cloud computing system, a server system, a personal computer system, and/or other type of electronic device. The computing system includes control circuitry and memory storing one or more sets of instructions. The one or more sets of instructions include instructions for performing any of the methods described herein.

In accordance with some embodiments, a non-transitory computer-readable storage medium is provided. The non-transitory computer-readable storage medium stores one or more sets of instructions for execution by a computing system. The one or more sets of instructions include instructions for performing any of the methods described herein.

Thus, devices and systems are disclosed with methods for providing clinical assistance by generating, deploying, and using agents. Such methods, devices, and systems may complement or replace conventional methods, devices, and systems for providing clinical assistance.

The features and advantages described in the specification are not necessarily all inclusive and, in particular, some additional features and advantages will be apparent to one of ordinary skill in the art in view of the drawings, specification, and claims provided in this disclosure. Moreover, it should be noted that the language used in the specification has been principally selected for readability and instructional purposes and has not necessarily been selected to delineate or circumscribe the subject matter described herein.

BRIEF DESCRIPTION OF THE DRAWINGS

So that the present disclosure can be understood in greater detail, a more particular description can be had by reference to the features of various embodiments, some of which are illustrated in the appended drawings. The appended drawings, however, merely illustrate pertinent features of the present disclosure and are therefore not necessarily to be considered limiting, for the description can admit to other effective features as the person of skill in this art will appreciate upon reading this disclosure.

FIGS. 12A-12D illustrate example user interfaces for interacting with a digital assistant in accordance with some embodiments.

FIG. 21 is a flow diagram illustrating an example method of interacting with a task-specific orchestration in accordance with some embodiments.

FIG. 24 is a flow diagram illustrating an example method of performing a clinical task in accordance with some embodiments.

In accordance with common practice, the various features illustrated in the drawings are not necessarily drawn to scale, and like reference numerals can be used to denote like features throughout the specification and figures.

DETAILED DESCRIPTION

Figure 1:
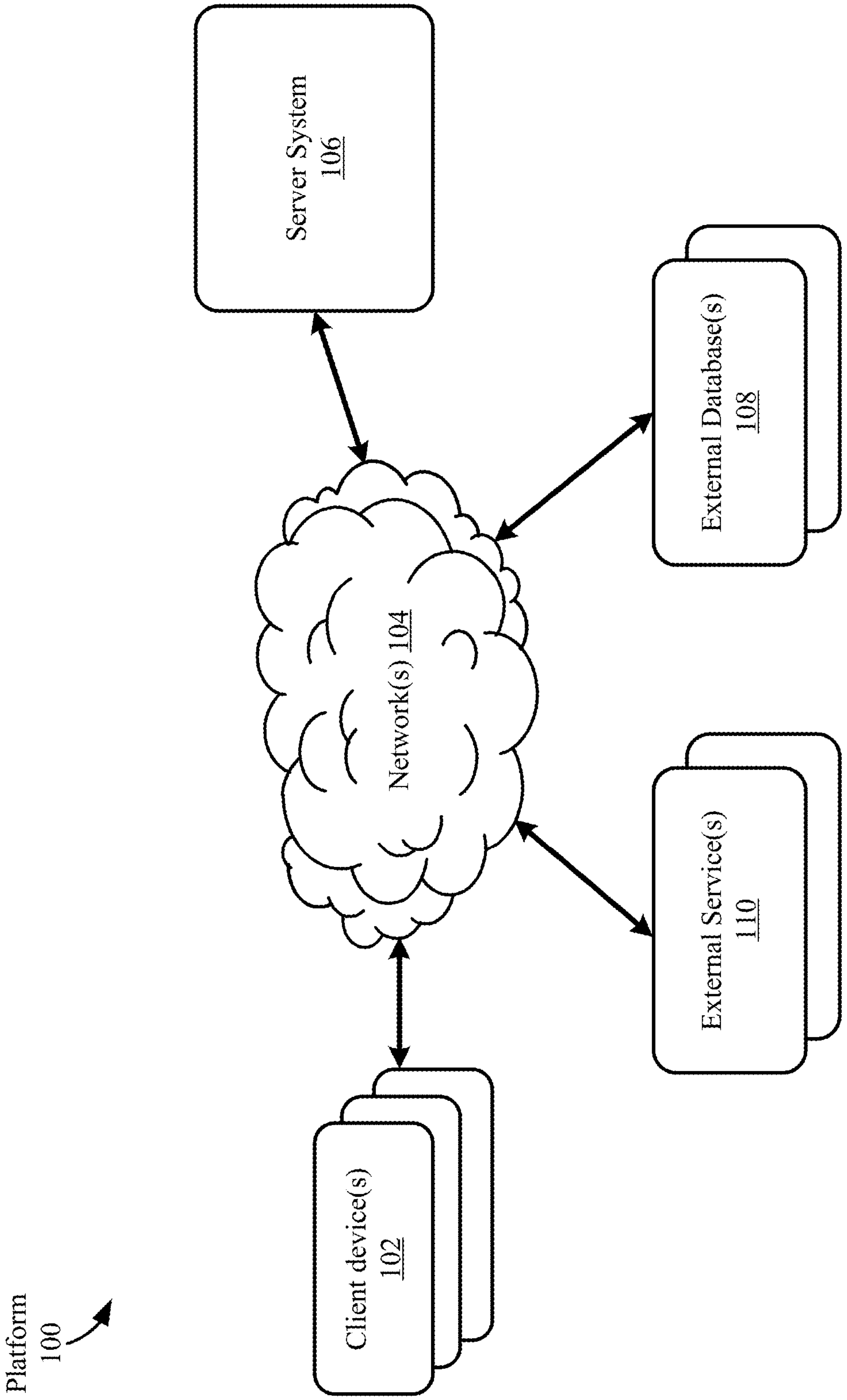
FIG. 1 is a block diagram illustrating an example platform in accordance with some embodiments.

The present disclosure describes, among other things, a platform for generating, deploying, and using task-specific orchestrations (e.g., task-specific agents) that include task-specific machine-learning models (e.g., language models, transformer models, and other types of models) for specific tasks and/or within specific domains. The platform may include a plurality of individual task-specific orchestrations that may operation independently or in combination to return accurate and relevant information (e.g., identifying target cohorts, clinical trial information, and/or members of target populations). In some embodiments, each task-specific orchestration (or agent) may include one or more machine-learning models, such as a language model trained and/or fine-tuned on a particular domain. The platform may also include one or more composite orchestrations (e.g., composite agents) that give instructions to, and combine results from, a plurality of task-specific orchestrations configured for different tasks.

In some embodiments, the platform acts as an operating system for implementing task-specific orchestrations for performing clinical tasks. The platform may include one or more of the following example components. For example, a genetic sequencing component with downstream molecular bioinformatics may operate to call out relevant biomarkers in DNA, RNA, or their derivatives for a specimen (e.g., a tumor biopsy) that is sequenced and reported back to an ordering physician. As another example, a pathology imaging component may operate on cellular and/or slide level images to identify relevant biomarkers from cells within imaged specimen. As another example, a radiological imaging component may operate on larger images of the body through various radiology imaging technologies to identify the presence or longitudinal progression of tumors. Each of these components may include, or communicate with, a corresponding agent to identify and/or report information relevant to a user query or request.

As an example, an agent may be configured by a user using a user interface (e.g., a console of a web or desktop application) and deployed to various environments (e.g., an alpha environment, a beta environment, a client environment, and/or a production environment). Each environment may be linked to different sources, have different permissions, and/or have different authorized users. In some embodiments, precision medicine principles are employed in customizing the user interfaces, such as modifications based on a set of subjects (e.g., patients) associated with the user of the application. An environment may be defined by access to data sources and/or users. The agent configuration may be stored in a control plane. The agents themselves may execute in the appropriate workload planes (e.g., data planes), and the workload planes may not have access to the control plane. In this example, the agent builder in the control plane is configured to push configurations into the various environments. For example, this synchronization may be fast enough that a user can configure an agent and immediately test out the configuration in the interactive console in a working environment. An example architecture includes two components: an agent builder in a control plane that hosts the user interface (UI) for configuring agents, and an agent host in a workload plane that hosts the UI and API for interacting with deployed agents. When an agent configuration is changed or an agent version is deployed, the agent builder may inform the agent host in each environment so that the updated agent can be deployed. For example, this may be via a pubsub message to the agent-config topic or via a simple HTTP request. In some embodiments, the agent builder utilizes a cognitive architecture that includes memory modules and action spaces. For example, the cognitive architecture organizes agents along three dimensions: their information storage (e.g., divided into working and long-term memories); their action space (e.g., divided into internal and external actions); and their decision-making procedure (e.g., structured as an interactive loop with planning and execution).

As another example, after deployment, an agent may receive a user query (e.g., requesting information about clinical trials), generate a structured application programming interface (API) call, use the generated API call to query a remote server to retrieve a relevant result, and reformat the relevant information to return to the user. In some embodiments, each action is performed by a different agent builder block component (also sometimes referred to as a builder block, block, or node). In some embodiments, the agent is configured for multiple types of tasks. In these embodiments, the agent may identify the intent of a user's query (e.g., to search for clinical trials or identify adverse events) and respond accordingly. In some embodiments, the agent is configured for only one type of task (e.g., is a task-specific agent). In some of these embodiments, the agent does not identify an intent of the user (e.g., the agent may assume the intent). In some embodiments, the agent receives the intent from a different component or system. The agent may also interface with other agents to obtain additional information for the user query (such as patient records or relevant guidelines). In some embodiments, the agent includes a pretrained language model (e.g., trained on a particular domain and/or using particular databases). In some embodiments, the agent queries an unstructured database (e.g., in addition, or alternatively, to generating the API call).

The platform, or components thereof, may be used in conjunction with any medical field (e.g., to assist physicians in the treatment of any associated disease state therein), such as on oncology, endocrinology (e.g., diabetes), mental health (e.g., depression and related pharmacogenetics), and cardiovascular disease. For example, the platform may also include a cardiology-based component (e.g., comprising one or more agents) that operates on electrocardiogram (ECG) data to identify patients having an elevated risk for cardiovascular disease. As another example, the platform may include a data curation component (e.g., comprising one or more agents) that obtains raw (e.g., unstructured) data and structures it into a common and useful format as a repository (e.g., a multimodal database) of clinical data from which other agents, models, and/or components may operate. As another example, the platform may be configured to search within the clinical data to identify cohorts of related patients and/or generate insights and/or analytics. As another example, the platform may be configured to monitor an electronic health record (EHR) to identify care gaps and/or reminders to physicians to take action with a respective patient. In this way, the platform may serve as a docket manager for physicians that identifies issues/events the physicians didn't manually docket to ensure patients and other subjects get timely care. The platform may also be configured to track and/or catalog relevant therapies (e.g., on label and/or off label use) for a set of disease states. The platform may also track and/or catalog relevant clinical trials (e.g., in multiple countries and/or from multiple authorities) for a set of disease states.

As discussed below, the platform may include an AI-enabled assistive user interface (which may sometimes be described herein as a clinical assistant or digital assistant) that provides access to patient insights. The AI-enabled assistive user interface may use one or more task-specific orchestrations that each include language models and/or other types of machine learning.

In some embodiments, the platform includes a hub component that allows physicians to order, track, and view test results, and export patient data. In some embodiments the hub component provides insights into genomic alterations, treatment implications, as well as clinical trial matching. The hub component may be used in conjunction with the AI-enabled clinical assistant to allow physicians to interact using conversational language including natural language inputs, follow-up questions, and remarks. The platform may also include a peer-to-peer messaging component for physicians and other medical experts to share knowledge, insight, and/or perspective on medical fields such as molecular oncology (e.g., as it pertains to patient care). The messaging component may be used in conjunction with the AI-enabled clinical assistant to engage in, and optionally learn from, the conversations on the messaging component. For example, the AI-enabled clinical assistant may be invoked in conversation to provide insights and/or data for a particular topic or conversation. The platform may also include an electronic health record (EHR) interface component (e.g., comprising one or more agents) configured to allow physicians, and optionally other users, to view, edit, and/search an EHR. The EHR interface component may be communicatively coupled with one or more services and/or databases to obtain updated information and reports (e.g., via push notifications). The EHR interface component may be used in conjunction with the AI-enabled clinical assistant to search, edit, summarize, and/or reform an EHR. The platform may also include a research analytical component (e.g., comprising one or more agents) that provides de-identified patient/clinical data and insights.

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

FIG. 1 is a block diagram illustrating a platform 100 in accordance with some embodiments. In some embodiments, the platform 100 is an AI platform (e.g., the AI platform discussed previously). The platform 100 includes one or more client devices 102 communicatively coupled to a server system 106 via one or more networks 104. In accordance with some embodiments, the platform 100 further includes, or communicates with, one or more external services 110 and one or more external databases 108. In some embodiments, the one or more networks 104 include public communication networks, private communication networks, or a combination of both public and private communication networks. For example, the one or more networks 104 can be any network (or combination of networks) such as the Internet, other wide area networks (WAN), local area networks (LAN), virtual private networks (VPN), metropolitan area networks (MAN), peer-to-peer networks, and/or ad-hoc connections. In some embodiments, the platform 100 includes only a subset of the components shown in FIG. 1. For example, the platform 100 may include only one of: of a client device 102 or a server system 106.

In some embodiments, a client device 102 is associated with one or more users. In some embodiments, each user is separately authenticated (e.g., assigned distinct/unique authentication tokens). In some embodiments, a client device 102 is a personal computer, mobile electronic device, wearable computing device, laptop computer, tablet computer, mobile phone, feature phone, smart phone, a speaker, television (TV), and/or any other electronic device capable of interacting with a user (e.g., an electronic device having an I/O interface). The client device(s) 102 may communicatively couple to other components of the platform 100 wirelessly and/or through a wired connection (e.g., directly through an interface, such as an HDMI interface).

In some embodiments, the client device(s) 102 send and receive information, such as queries and results, through network(s) 104. For example, the client device(s) 102 may send a query or request to the server system 106, the external service(s) 110, and/or the external database(s) 108 through network(s) 104. As another example, the client device(s) 102 may receive results and other responses from the server system 106, the external service(s) 110, and/or the external database(s) 108 through network(s) 104. In some embodiments, two or more client devices 102 communicate with one another (e.g., resending and responding to queries and requests). The two or more client devices 102 may communicate via the network(s) 104 or directly (e.g., via a wired connection or through a peer-to-peer wireless connection).

In some embodiments, the server system 106 includes multiple electronic devices communicatively coupled to one another. In some embodiments, the multiple electronic devices are collocated (e.g., in a datacenter), while in other embodiments, the multiple electronic devices are geographically separated from one another. In some embodiments, the server system 106 stores and provides clinical and/or patient data. In some embodiments, the server system 106 trains, publishes, and/or utilities one or more agents and/or language models. In some embodiments, the server system 106 receives and responds to queries and requests from the client device(s) 102 using the one or more agents and/or language models. In some embodiments, the server system 106 includes multiple nodes and/or clusters configured to handle different types of tasks and/or handle requests and queries from different geographical locations.

In some embodiments, the client device(s) 102 and/or the server system 106 communicate with the external service(s) 110 and/or the external database(s) 108 via an application programming interface (API). In some embodiments, the external service(s) 110 and/or the external database(s) 108 are maintained/operated by a third party to the platform 100. In some embodiments, the external service(s) 110 include agents, location services, time services, web-enabled services, and/or services that access information stored external to the platform 100. In some embodiments, the external database(s) 108 include one or more medical databases, clinical databases, subject databases, research databases, and/or general knowledge databases. In some embodiments, the external database(s) 108 comprise one or more of the databases shown in FIG. 4.

Figure 2A:
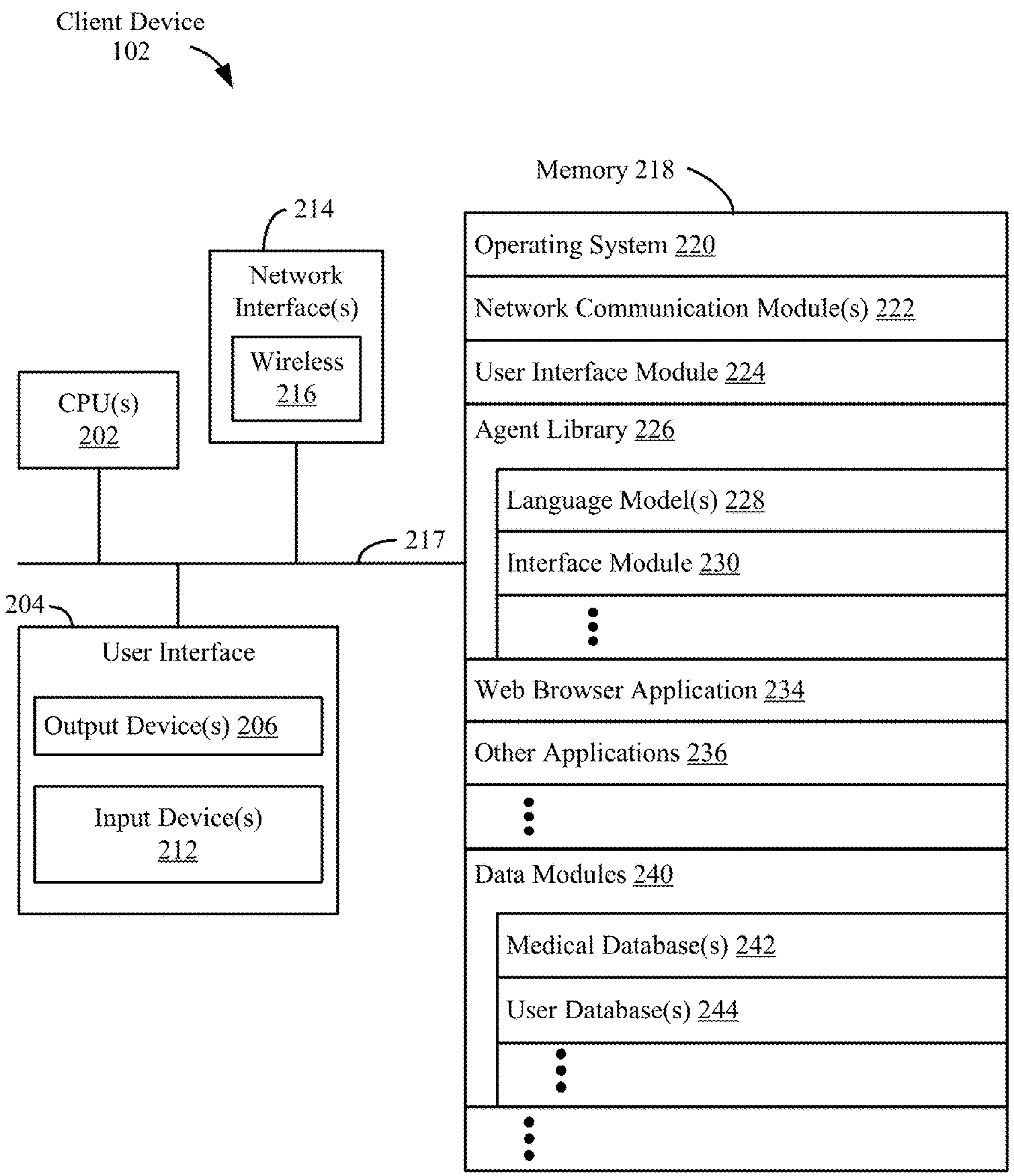
FIGS. 2A and 2B are block diagrams illustrating an example client device in accordance with some embodiments.

FIG. 2A is a block diagram illustrating a client device 102 in accordance with some embodiments. The client device 102 includes one or more central processing units (CPUs) 202, a user interface 204, one or more network (or other communications) interfaces 214, memory 218, and one or more communication buses 217 for interconnecting these components. In some embodiments, the client device 102 includes a processor or other control circuitry (e.g., in addition, or alternatively, to the CPUs 202). For example, the client device 102 may include one or more GPUs and/or DPUs (e.g., for performing machine learning tasks). The communication buses 217 optionally include circuitry (sometimes called a chipset) that interconnects and controls communications between system components. Optionally, the client device 102 includes a location-detection component, such as a global navigation satellite system (GNSS) (e.g., GPS (global positioning system), GLONASS, Galileo, BeiDou) or other geo-location receiver, and/or location-detection software for determining the location of the client device 102.

In some embodiments, client device 102 includes one or more sensors including, but not limited to, accelerometers, gyroscopes, compasses, magnetometer, light sensors, near field communication transceivers, barometers, humidity sensors, temperature sensors, proximity sensors, range finders, and/or other sensors/devices for sensing and measuring various environmental conditions.

The user interface 204 includes output device(s) 206 and input device(s) 212. In some embodiments, the input device(s) 212 include a keyboard, mouse, a track pad, and/or a touchscreen. In some embodiments, the user interface 204 includes a display device that includes a touch-sensitive surface, in which case the display device is a touch-sensitive display. In client devices that have a touch-sensitive display, a physical keyboard is optional (e.g., a soft keyboard may be displayed when keyboard entry is needed). In some embodiments, the output device(s) 206 include a speaker and/or a connection port for connecting to speakers, earphones, headphones, or other external listening devices. In some embodiments, the input device(s) 212 include a microphone and/or voice recognition device to capture audio (e.g., speech from a user).

In some embodiments, the one or more network interfaces 214 include wireless and/or wired interfaces for receiving data from and/or transmitting data to other client devices 102, the server system 106, and/or other devices or systems. The data communications may be carried out using any of a variety of custom or standard wireless protocols (e.g., NFC, RFID, IEEE 802.15.4, Wi-Fi, ZigBee, 6LoWPAN, Thread, Z-Wave, Bluetooth, ISA100.11a, WirelessHART, MiWi, etc.). Furthermore, the data communications may be carried out using any of a variety of custom or standard wired protocols (e.g., USB, Firewire, Ethernet, etc.). For example, the one or more network interfaces 214 may include a wireless interface 216 for enabling wireless data communications with other client devices 102, systems, and/or or other wireless (e.g., Bluetooth-compatible) devices. Furthermore, in some embodiments, the wireless interface 216 (or a different communications interface of the one or more network interfaces 214) enables data communications with other WLAN-compatible devices and/or the server system 106 (via the one or more network(s) 104).

The memory 218 includes high-speed random-access memory, such as DRAM, SRAM, DDR RAM, or other random-access solid-state memory devices; and may include non-volatile memory, such as one or more magnetic disk storage devices, optical disk storage devices, flash memory devices, or other non-volatile solid-state storage devices. The memory 218 optionally includes one or more storage devices remotely located from the CPU(s) 202. The memory 218, or alternately, the non-volatile memory solid-state storage devices within the memory 218, includes a non-transitory computer-readable storage medium. In some embodiments, the memory 218 or the non-transitory computer-readable storage medium of the memory 218 stores the following programs, modules, and data structures, or a subset or superset thereof:

- an operating system 220 that includes procedures for handling various basic system services and for performing hardware-dependent tasks;
- network communication module(s) 222 for connecting the client device 102 to other computing devices connected to one or more network(s) 104 via the one or more network interface(s) 214 (wired or wireless);
- a user interface module 224 that receives commands and/or inputs from a user via the user interface 204 (e.g., from the input device(s) 212) and provides outputs via the user interface 204 (e.g., the output device(s) 206);
- an agent library 226 that includes a plurality of agent modules 6102 (e.g., agent building blocks and/or generated agents). In some embodiments, the agent library 226 works in conjunction with an assistant module at the server system 106 (e.g., the assistant module 316). In some embodiments, the agent library 226 includes the following modules (or sets of instructions), or a subset or superset thereof:
  - one or more models 228 that engage with a user and/or perform specific tasks in furtherance of a user request or query. In some embodiments, the model(s) 228 include one or more large language models, such as GPT-3, GPT-4, BioGPT, and PaLM-2; and
  - an interface module 230 that allows the model(s) 228 communicate with other applications, components, and devices (e.g., via an API or structured query). In some embodiments, the interface module 230 is, or includes, an agent (e.g., a task-specific orchestration), a task-specific orchestration creator application, one or more orchestration libraries (e.g., orchestration marketplaces) for selecting orchestrations for performing tasks as discussed herein;
- a web browser application 234 for accessing, viewing, and interacting with web sites;
- other applications 236, such as applications for word processing, calendaring, mapping, weather, stocks, time keeping, virtual digital assistant, presenting, number crunching (spreadsheets), drawing, instant messaging, e-mail, telephony, video conferencing, photo management, video management, a digital music player, a digital video player, 2D gaming, 3D (e.g., virtual reality) gaming, electronic book reader, and/or workout support; and
- one or more data modules 240 for handling the storage of and/or access to data such as medical data, clinical data, patient data, and user data. In some embodiments, the one or more data modules 240 include:
  - one or more medical databases 242 for storing medical data (e.g., regarding therapies, drugs, treatments, patients, cohorts and/or diseases); and
  - one or more user databases 244 for storing user data such as user preferences, user settings, and other metadata.

In some embodiments, one or more agent modules 6102 are configured to engage with a user in an integrated, conversational manner using natural language dialog, and/or invoke external services when appropriate to obtain information or perform various actions.

Figure 2B:
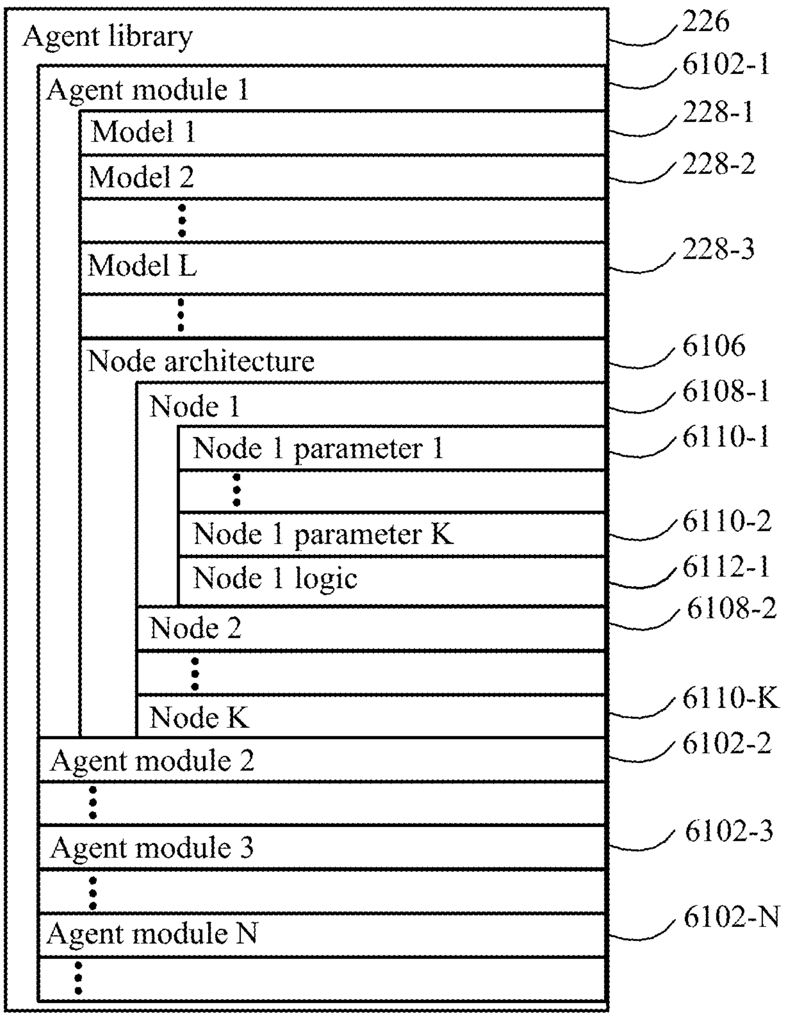

Referring to FIG. 2B, in some embodiments, the platform 100 provides a plurality of agent modules 6102 and a system for managing and deploying these agent modules 6102, such as managing through various blocks (e.g., agent builder blocks) realized in the form of one or more nodes 6108. In some embodiments, each respective agent module 6102 is associated with a defined domain of information and/or a task-specific capability, which allows for retrieving a particular agent module 6102 based on information determined from a prompt provided by a user and/or based on a selection of the agent module 6102 by the user. In some embodiments, an agent module 6102-1 is configured for a first specific task of generating a summary report of a patient's medical records, a second agent module 6102-2 is configured for a second specific-task of guiding a patient through a care plan, a third agent module 6102-3 is configured for a third specific-task of creating patient care guidelines based on a patient's health profile, a fourth agent module 6102-4 is configured for a fourth specific-task of identifying patients requiring follow-up at a hospital, a fifth agent module 6102-5 is configured for a fifth specific-task of identifying changes in a standard of care for a disease setting, a sixth agent module 6102-6 is configured for a sixth specific-task of evaluating unstructured data associated with a patient to identify a cohort of similar patients, a seventh agent module 6102-7 is configured for a seventh specific-task of phenotyping a subject, or a combination thereof. However, the present disclosure is not limited thereto. In some embodiments, the agent library 226 is at one or more client devices 102 and/or server system 106.

In some embodiments, each agent module 6102 provides range of content and functionality that an end-user can engage with and/or configure for such engagement through one or more nodes 6108 associated with the agent module 6102, from a simple static response to sophisticated knowledge systems that facilitate automated conversations and data analysis leading to solutions and integrated transactions with external systems. Collectively, the one or more nodes 6108 form some or all of a node architecture 6106 associated with the agent module 6102, which defines rules for traversing between nodes. In some embodiments, each respective agent 6102 has a corresponding node architecture 6106, which provides a one-to-one relationship between agent modules 6102 and node architectures 6106. In some embodiments, a respective agent module 6102 supports the generation of additional agent modules 6102 that engage with one or more models 228 and/or nodes 6108 of a node architecture 6106 of the respective agent module 6102 or a different agent module 6102. In some embodiments, a respective agent module 6102 supports the selection of agent modules 6102 in a library of agent modules, and defining flexible integrations of these agent module 6102 into various system architectures. However, the present disclosure is not limited thereto.

In some embodiments, each agent module 6102 provides a defined scope for engaging in a workflow. Accordingly, in some embodiments, each agent module 6102 is configured to assist end users to either resolve a question and/or problem or to fulfill a specific request for retrieving information, such as through a conversational communications framework. Some embodiments provide an ability to create, manage, and administer agent modules 6102 to make them available for use in creating, editing, or deleting agent modules 6102 via a user interface, e.g., by using a user-interface-based agent module builder or the like.

Some embodiments provide a user-interface-based agent module designer to assist in the creation and editing of agent modules 6102 and/or a workflow associated with a variety of agent modules 6102 (the workflow is also sometimes also referred to as an assembly or orchestration). In some embodiments, this workflow is manifested as a node architecture that includes a plurality of interconnected nodes. In some embodiments, the agent module designer includes the ability to define the name of an agent module 6102, create an agent module 6102, edit an agent module 6102, delete individual nodes 2210 associated with an agent module 6102, expand and/or collapse node 6108 branches, the ability to see and edit the conditional logic for a node 6108, and the ability to see node traversals (e.g., when one or more nodes 6108 connect to a different node 6108).

In some embodiments, a node 6108 of an agent module 6102 reflects one or more decision points within an agent module 6102, such as one or more predetermined decision points. In some embodiments, an agent module 6102 evaluates data (e.g., a prompt provided by a user at a client device 102, an output from a different agent module 6102, etc.), such as graphical data from a client device 102 by parsing and/or evaluating the incoming data for recognized keywords, phrases, ground truth labels, etc. For example, based on detection of recognized features, an agent module 6102 may process information associated with the data received from the client device 102 in a particular direction within the plurality of interconnected nodes 6108, such as from a node 6108-1 associated with an agent module 6102-1 to a node 6108-2 associated with the agent module 6102-1 and/or from the node 6108-1 associated with the agent module 6102-1 to a node 6108-2 associated with the agent module 6102-1. Thus, in some embodiments, the use of one or more nodes 6108 associated with a respective agent module 6102 in a plurality of interconnected nodes 6108 is similar to walking through a decision tree, with different nodes 6108 associated with different agent modules 6102, where each different agent module 6102 evaluates information based on associated conditional logic to progress information in the plurality of interconnected nodes 6108. However, the present disclosure is not limited thereto. In some embodiments, each node in the plurality of interconnected nodes 6108 comprises conditional logic that can evaluate data, retrieve data, generate data, or a combination thereof, e.g., based on an evaluation of information inputted to the respective node 6108. In some embodiments, each node in the plurality of interconnected nodes 6108 takes some action, such as generating a message and/or sending information to another node 6108 in the same agent module 6102 as the respective node, or a different node 6108 of another agent module 6102, or the like.

Figure 20:
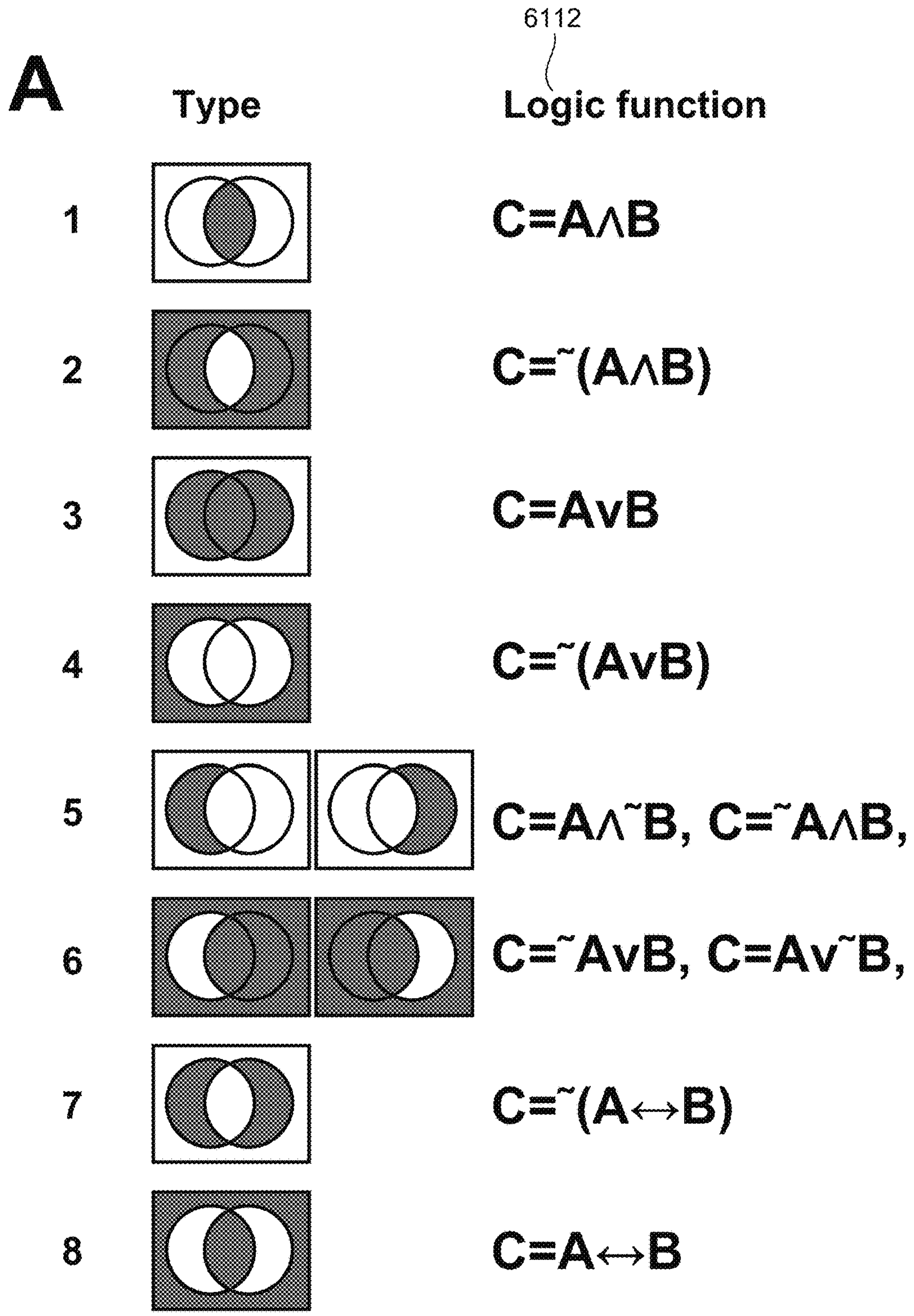
FIG. 20 illustrates examples of various logic functions that are implemented in some embodiments of the present disclosure.

In some embodiments, a corresponding node architecture 6106 associated with one or more respective agent modules 6102 defines conditional logic 6112, at least in part, for performing a specific clinical task. For example, each respective node 6108 may include corresponding logic 6112, which defines a workflow for handling one or more tasks assigned to the respective node 6108. In some embodiments, the conditional logic of the node architecture 6106 is executed in accordance with a first order of a first set of interconnected nodes 6108 from a plurality of nodes 6108 based on the corresponding logic 6112 of each node 6108 in the set of interconnected nodes 6108. Accordingly, the logic 6112 allows for granular configuration of each respective node 6108 that when collectively coupled through interconnected nodes of the node architecture 6106, define a conditional logic of the node architecture. For example, referring briefly to FIG. 20, the logic 6112 may include one or more AND, OR, XOR, and/or NOT operations within the logic 6112. As an example, a corresponding logic 6112 requires presence of a first condition but not a second condition or third condition.

In some embodiments, the plurality of nodes includes one or more data source nodes 6108 associated with a specific task of obtaining data elements from a remote data source (e.g., an external database 108). In some embodiments, the corresponding logic 6112 allows for connecting to a corresponding database, e.g., by using an access token associated with the corresponding agent module 6102, communicating at least a portion of the obtained data to one or more nodes 6108, and/or execute one or more queries to identify/analyze such data. In some embodiments, each node architecture 6106 includes at least one input node, which forms an initial terminal node in an order of nodes 6108. In some embodiments, the node architecture includes a plurality of paths to traverse from an input to an output node, such as paths of branching trees. In some embodiments, each respective node 6108 represents a computational process, such as a function, an input, an output, or the like, that is realized when data is applied to the node 6108. Moreover, since each node is interconnected, such by an edge, to at least one other node 6108, the output from one node 6108 may be supplied as input to a different node 6108 in order to form chains, or orders, or nodes in the node architecture 6106.

In some embodiments, the memory 218 includes one or more modules not shown in FIGS. 2A and 2B. For example, the memory 218 may include one or more agent modules (e.g., a retriever component) that are distinct from the agent library 226. In some embodiments, the client device 102 includes one or more standalone agents (e.g., that execute and operate at the client device 102) and/or one or more dependent agents (e.g., that operate in conjunction with a component at a remote device, such as the server system 106). In some embodiments, one or more agents are generated/trained at the server system 106 and deployed at the client device 102.

Although FIGS. 2A and 2B illustrate the client device 102 in accordance with some embodiments, FIGS. 2A and 2B are intended more as a functional description of the various features that may be present in a client device than as a structural schematic of the embodiments described herein. In practice, and as recognized by those of ordinary skill in the art, items shown separately could be combined and some items could be separated.

Figure 3:
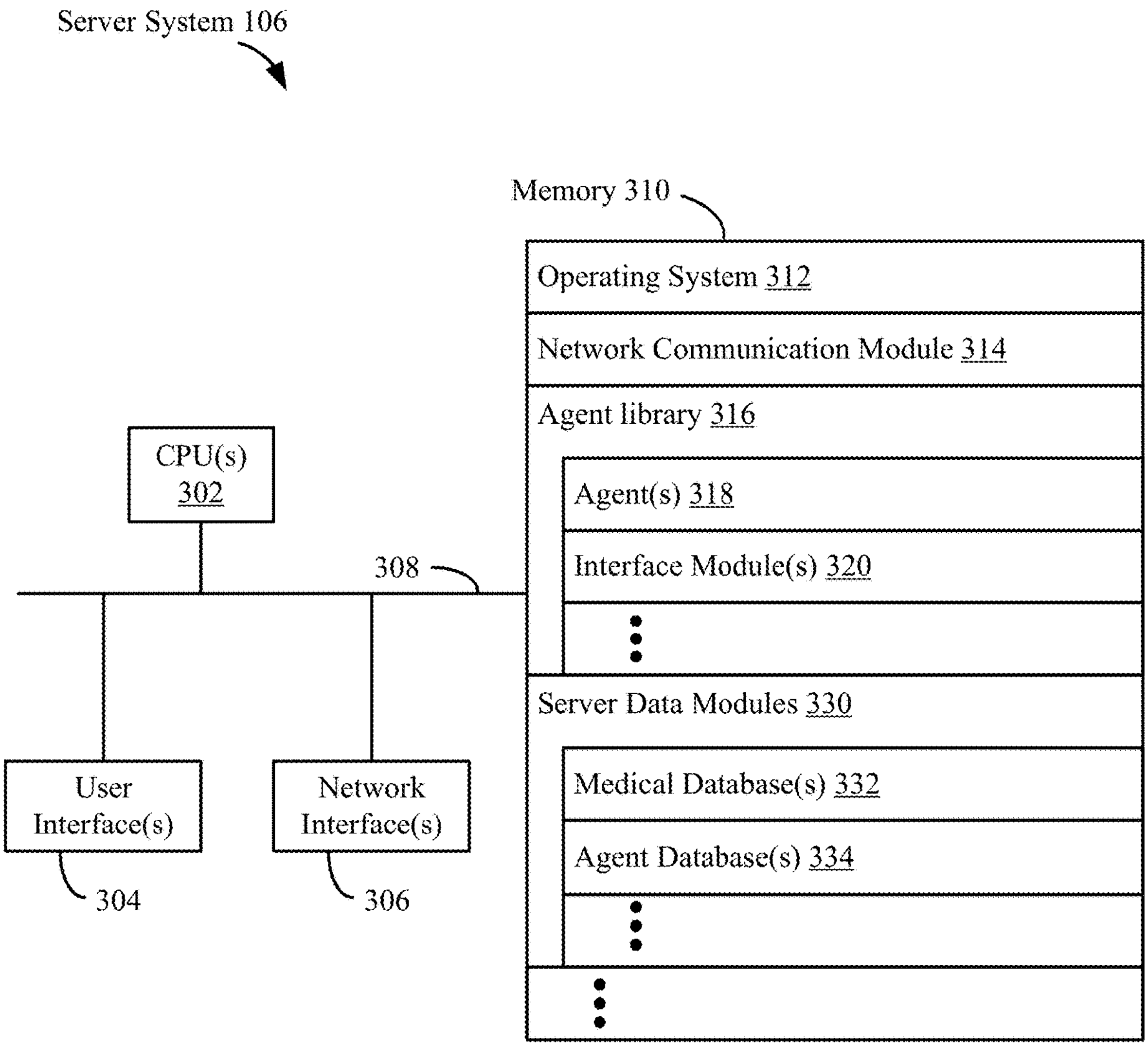
FIG. 3 is a block diagram illustrating an example server system in accordance with some embodiments.

FIG. 3 is a block diagram illustrating a server system 106 in accordance with some embodiments. In accordance with some embodiments, the server system 106 includes one or more CPUs 302, one or more user interfaces 304, one or more network interfaces 306, memory 310, and one or more communication buses 308 for interconnecting these components. In some embodiments, the server system 106 includes other types of control circuitry and/or processors (e.g., in addition to, or alternatively to the CPUs 302). For example, the server system 106 may include one or more GPUs or DPUs for machine learning tasks.

The memory 310 includes high-speed random-access memory, such as DRAM, SRAM, DDR RAM, or other random access solid-state memory devices; and may include non-volatile memory, such as one or more magnetic disk storage devices, optical disk storage devices, flash memory devices, or other non-volatile solid-state storage devices. The memory 310 optionally includes one or more storage devices remotely located from one or more CPUs 302. The memory 310, or, alternatively, the non-volatile solid-state memory device(s) within the memory 310, includes a non-transitory computer-readable storage medium. In some embodiments, the memory 310, or the non-transitory computer-readable storage medium of the memory 310, stores the following programs, modules and data structures, or a subset or superset thereof:

- an operating system 312 that includes procedures for handling various basic system services and for performing hardware-dependent tasks;
- a network communication module 314 that is used for connecting the server system 106 to other computing devices connected to one or more networks 104 via one or more network interfaces 306 (wired or wireless);
- an assistant module 316 that engages with a user (e.g., a remote user) in an integrated, conversational manner using natural language dialog, and invokes external services when appropriate to obtain information or perform various actions. In some embodiments, the assistant module 316 works in conjunction with an agent library at a client device 102 (e.g., the agent library 226). In some embodiments, the assistant module 316 includes the following modules (or sets of instructions), or a subset or superset thereof:
  - one or more agents 318 that are configured to perform specific tasks or perform tasks within specific domains (e.g., any of the agents described herein, such as a retriever agent and a target population membership agent); and
  - one or more interface modules 320 that allows the agent(s) 318 to communicate with other agents, applications, components, and devices (e.g., via an API or structured query); and
- one or more server data modules 330 for handling the storage of and/or access to data (e.g., clinical and user data). In some embodiments, the one or more server data modules 330 include:
  - one or more medical databases 332 for storing medical data (e.g., regarding therapies, drugs, treatments, patients, cohorts, and/or diseases); and
  - one or more agent databases 334 for storing agent data such as settings, training, instructions, and other metadata.

In some embodiments, the server system 106 includes web or Hypertext Transfer Protocol (HTTP) servers, File Transfer Protocol (FTP) servers, as well as web pages and applications implemented using Common Gateway Interface (CGI) script, PHP Hyper-text Preprocessor (PHP), Active Server Pages (ASP), Hyper Text Markup Language (HTML), Extensible Markup Language (XML), Java, JavaScript, Asynchronous Javascript and XML (AJAX), XHP, Javelin, Wireless Universal Resource File (WURFL), and the like.

In some embodiments, the memory 310 includes one or more modules not shown in FIG. 3. For example, the memory 310 may include one or more agent modules (e.g., a retriever component) that are distinct from the assistant module 316. In some embodiments, the server system 106 includes one or more standalone agents (e.g., that execute and operate at the server system 106) and/or one or more dependent agents (e.g., that operate in conjunction with a component at a remote device, such as a client device 102). In some embodiments, the memory 310 includes an agent library (e.g., the agent library 226).

Although FIG. 3 illustrates the server system 106 in accordance with some embodiments, FIG. 3 is intended more as a functional description of the various features that may be present in a server system than as a structural schematic of the embodiments described herein. In practice, and as recognized by those of ordinary skill in the art, items shown separately could be combined and some items could be separated. For example, some items shown separately in FIG. 3 could be implemented on single servers and single items could be implemented by one or more servers. In some embodiments, the clinical database(s) and/or the agent database(s) 334 are stored on devices that are accessed by the server system 106 (e.g., the external database(s) 108). The actual number of servers used to implement the server system 106, and how features are allocated among them, will vary from one implementation to another and, optionally, depends in part on an amount of data traffic that the server system handles during peak usage periods as well as during average usage periods.

Each of the above identified modules stored in the memory 218 and 310 corresponds to a set of instructions for performing a function described herein. The above identified modules or programs (e.g., sets of instructions) need not be implemented as separate software programs, procedures, or modules, and thus various subsets of these modules may be combined or otherwise re-arranged in various embodiments. In some embodiments, the memory 218 and 310 optionally store a subset or superset of the respective modules and data structures identified above. Furthermore, the memory 218 and 310 optionally store additional modules and data structures not described above.

Figure 4:
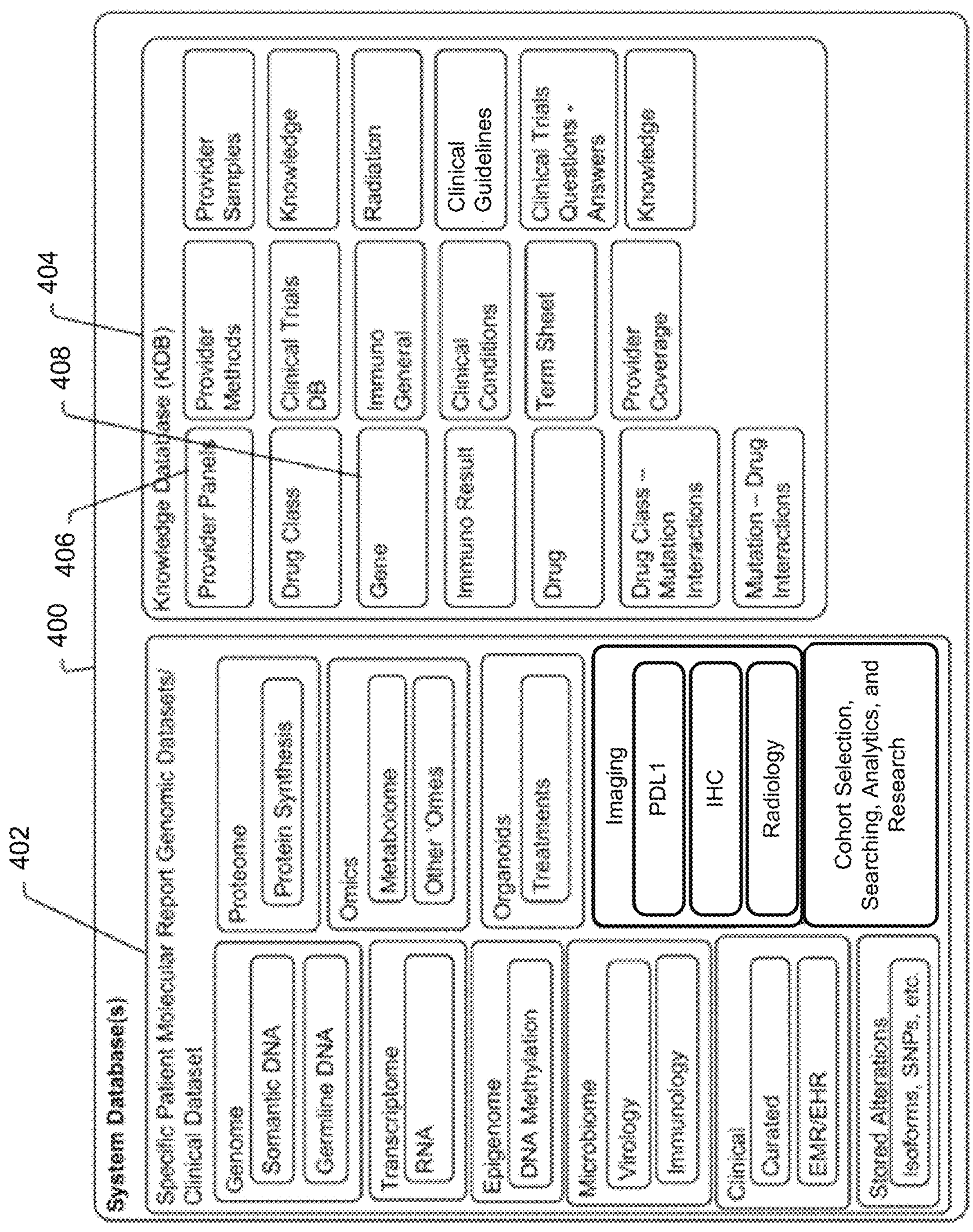
FIG. 4 is a block diagram illustrating example databases in accordance with some embodiments.

FIG. 4 is a block diagram illustrating system database(s) 400 in accordance with some embodiments. In some embodiments, at least a portion of the system database(s) 400 is optionally stored at a client device 102 (e.g., as the medical database(s) 242), the server system 106 (e.g., as the medical database(s) 332), and/or the external database(s) 108, which advantageously allows for an edge at and/or near the client device 102, such as via the communication network. However, the present disclosure is not limited thereto.

Figure 14:
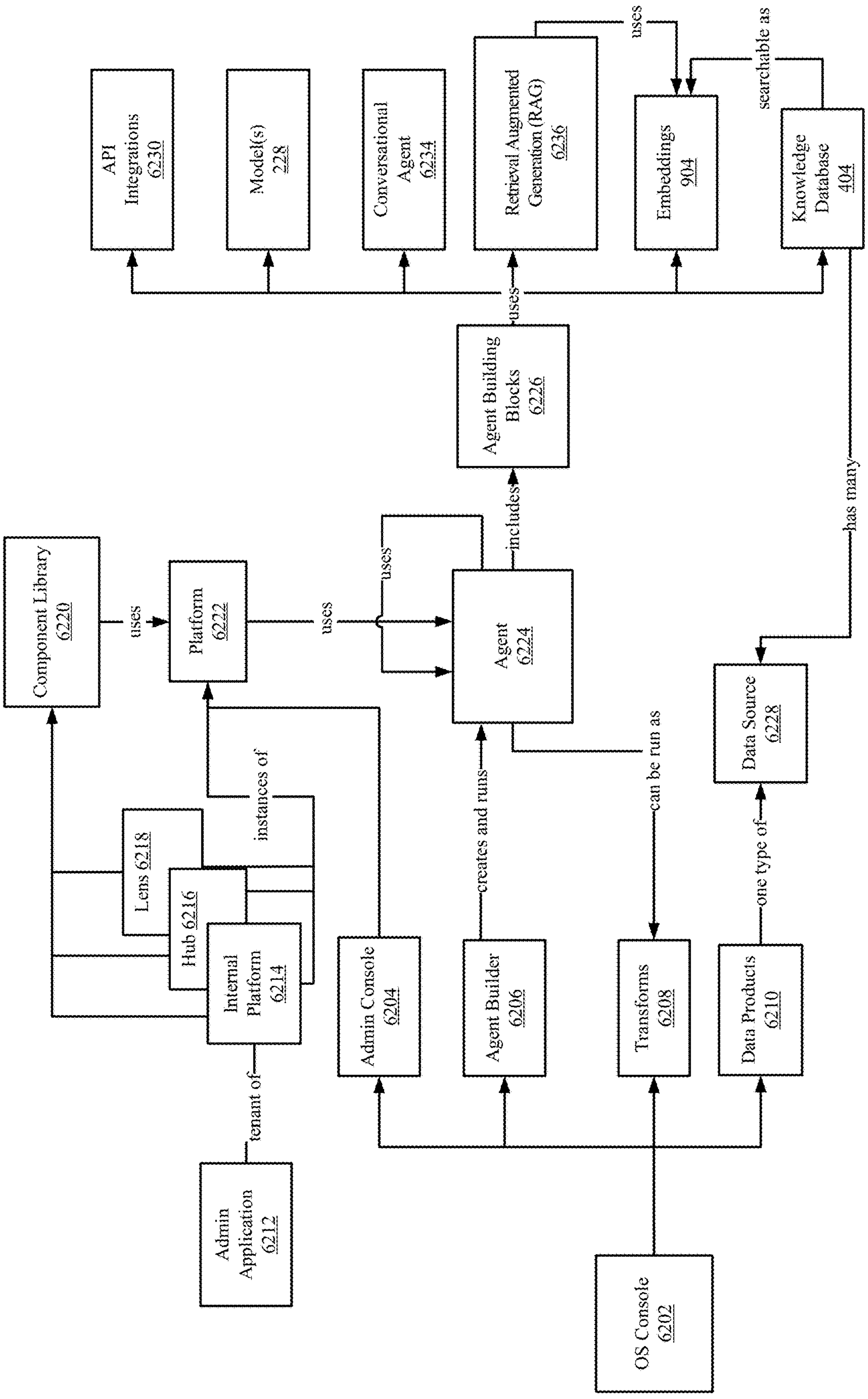
FIG. 14 illustrates an example workflow for implementing and/or interacting with an agent in accordance with some embodiments.

In some embodiments, the system database 400 includes molecular report genomic datasets and clinical datasets 402 and/or a non-patient specific knowledge database (KDB) 404 in accordance with some embodiments, such as knowledge database 404 of FIG. 14. In some embodiments, the datasets 402 include, among other data, genome, transcriptome, epigenome, microbiome, clinical, stored alterations proteome, -omics, organoids, imaging and cohort and propensity data sets. For example, the cohort selection, searching, analytics, and research datasets may include data about tumors of unknown origin (TUO) predictors, metastasis predictors, and survival analytics. As an example, the imaging datasets may include radiology imaging data, immunohistochemistry imaging data, positron emission tomography (PET) data, and/or single-photon emission computed tomography (SPECT) imaging data. The imaging datasets may include data regarding nodule identifiers, tracking, and/or longitudinal analytics. In some embodiments, the KDB 404 includes separate sub-databases related to specific information types including, as shown, provider panels 406 (e.g., information related to genetic panels supported by the service provider that operates the system), drug classes (e.g., drug class specific information (e.g., do drugs of a specific class work on pancreatic cancer, what drugs are considered to be included in a specific drug class, etc.)), specific genes 408, immuno results (e.g., information related to treatments based on specific immuno biomarker results), specific drugs, drug class-mutation interactions, mutation-drug interactions, provider methods (e.g., questions about processes performed by the service provider), clinical trials, immuno general, clinical conditions such as clinical diseases, term sheets (e.g., definitions of industry specific terms), provider coverage (e.g., information about provider tests and results), provider samples (e.g., information about types of samples that can be processed by the provider), knowledge (e.g., scripted questions and answers on various frequently asked questions that do not fall into other sub-databases), radiation (e.g., information related to suitable radiation treatments given specific cancer states), clinical guidelines (e.g., national guidelines related to classification of cancer states, accepted treatments, etc.) and clinical trials questions-answers (e.g., information related to locations and administrators of clinical trials. Organizing the KDB 404 into sub-databases may make it easier to manage those databases as information therein evolves over time and also enables addition of new sub-databases related to other defined information types. In some embodiments, the clinical datasets 402 and/or the KDB 404 is arranged in a different manner than is shown in FIG. 4 (e.g., with different sub-databases and/or with a different organizational scheme). Advantageously, by utilizing multiple datasets associated with different domains of subject matter and/or applying a classification system to the datasets, the knowledge database provides a storage system for data, such as medical records and clinical documentation that one or more agent modules 6102 can retrieve based on a task-specific requirement associated with a respective domain or classification. Moreover, in some embodiments, the knowledge database 404 allows for storing such data with deidentifying controls in order allow for training on and/or analysis of the stored data without risk of leaking confidential and/or privileged information.

Figure 5A:
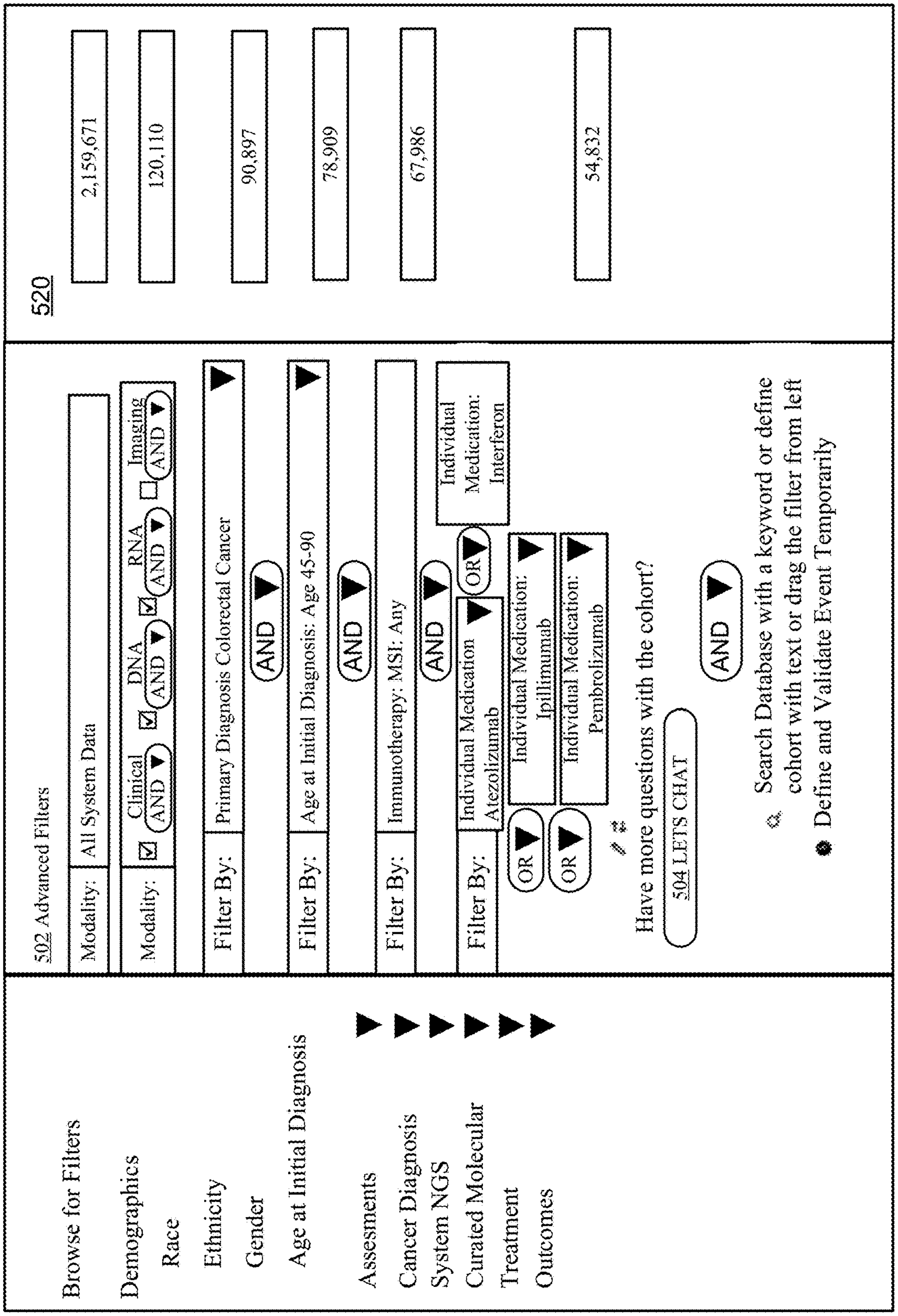
FIGS. 5A and 5B illustrate example user interfaces for searching database(s) in accordance with some embodiments.
Figure 5B:
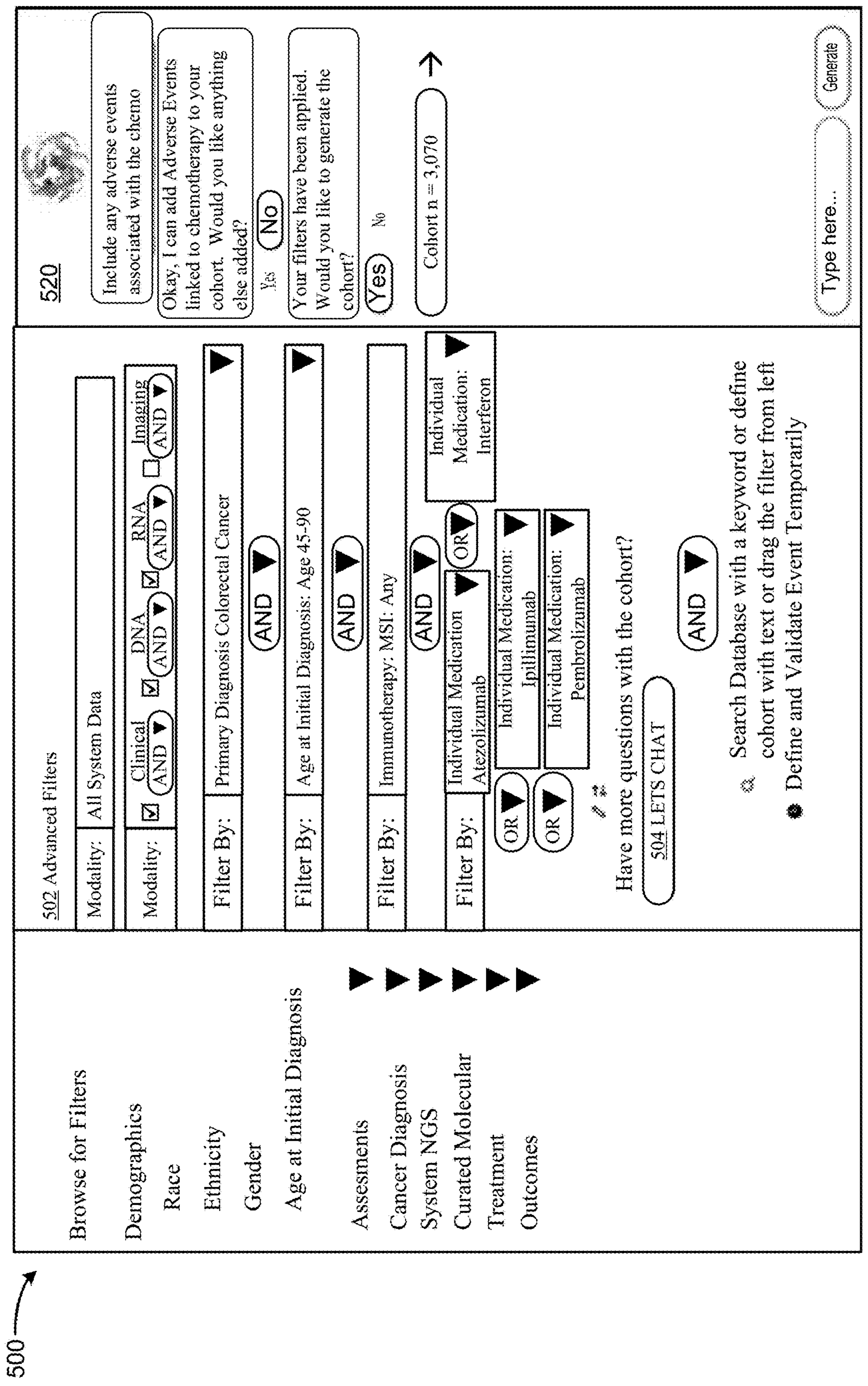

FIGS. 5A-5B illustrate example user interfaces for searching database(s) (e.g., data modules 240 of FIG. 2A, data modules 330 of FIG. 3, and/or database(s) 400 of FIG. 4) in accordance with some embodiments. In some embodiments, the user interface 500 shown in FIG. 5A includes a first set of user interface elements for allowing a user to search multiple types of data and apply specific filters to identify a result set, such as search for a first classification of data from one or more external databases 108 and/or the data modules 240 associated with the agent module 6102. The user interface 500 includes affordances 502 (e.g., advanced filters) for manually applying filters. In some embodiments, the user interface 500 also includes one or more user interface elements, such as the user interface element 504, for interacting with an agent to search (e.g., to identify a cohort with text). In some embodiments, a prompt user interface is presented within the user interface 500, which may be a user interface for interacting with a general-purpose language model and/or one or more task-specific orchestrations. For example, the user may enter a text prompt such as "patients diagnosed with colorectal cancer greater than 45 years old treated with atezolizumab or durvalumab or interferon" and the agent module 6102 provides a response in accordance with a corresponding node architecture 6106 associated with the agent module 6102 (which may be visually represented in other user interfaces of the application (e.g., a workflow representation). In some embodiments, the agent module 6102 generates one or more nodes 6108 of the node architecture responsive to the prompt, such as one or more filters based on the text prompt. As a non-limiting example, if a first prompt includes a plurality of graphical data of chest x-rays from a single human, the agent module 6102 may provide the plurality of graphical data to a first filter of a node 6110-1 associated with screen chest x-ray modalities for a first biomarker. Moreover, in some embodiments, the agent module 6102 generates a second filter to compare one or more features associated with the plurality of graphical data and identify, or generate, a corresponding subject identifier, in a library of subject identifiers, uniquely associated with the subject. However, the present disclosure is not limited thereto. In some embodiments, the user interface 500 updates to show the filters applied by the agent in response to the text prompt.

In some embodiments, the user interface 500 includes an agent window or section in which a user may ask the agent questions regarding filters, data, and/or modality. The user interface 500 shown in FIG. 5B includes an agent portion 520 in which the user may pose prompts to the agent module 6102 and view information returned and/or generated by the agent module 6102 or another (connected) agent module 6102 other than the one that received the prompt. In this way, the amount of time for data analysis may be reduced (e.g., via generative AI-powered and human-in-the-loop assistants) which reduces the computational processing burden for the client device 102 and/or server system 106. The user interfaces described herein allow users to submit requests for feasibility assistance including (i) requests to create a feasibility from scratch, (ii) editing, adjusting, and/or verifying saved query logic, and/or (iii) answering questions from users during a cohort cutting workflow. In some embodiments, solution architects may answer the questions or generating queries based on user input.

For example, an agent module 6102 may be configured to help solve pain points in using an application, an unknown/niche dataset, and/or user interface to reduce the number of user inputs required as well as automatically identify responsive data from extremely large collections of data (e.g., reducing the number of follow-ups and query revisions needed to identify the responsive data). For example, an agent module 6102 can increase user-driven cohort cutting via human-in-the-loop feasibility assistants, simplify documentation navigation and discovery by providing an LLM-driven chatbot (e.g., embedded with knowledge center content). In some embodiments, some or all of the knowledge database 404 is searched, indexed, and/or analyzed to associate user-created free text with corresponding outputs from task-specific agent modules 6102. In some embodiments, data from the knowledge database 404 is used to train machine-learning models with the agent modules 6102.

In some embodiments, a system (e.g., the platform 100 or a component thereof) determines (e.g., using a machine-learning model different than the model receiving the prompt) that a prompt provided by the user includes a natural language description of a cohort (e.g., a patient cohort, including a set of one or more patients) the user wants to build. In some embodiments, the cohort is explicitly identified through the natural language description. In some embodiments, the cohort is derived from the natural language description by parsing the prompt, such as by applying the prompt to a node 6108-1 of a node architecture 6106 that is configured to pre-process (e.g., parse) one or more portions of the description as a request to apply a filtering operation to the cohort. In some embodiments, the node 6108-1 identifies an intent and/or one or more commands from the request. In some embodiments, the request causes a modification to the affordances 502 of the user interface 500 (e.g., causing a filter funnel to be displayed on the user interface 500). In this way, users of the application are able to more effectively and efficiently interact with a data source by using natural language prompts to cause operations that would otherwise require multiple user inputs to a plurality of different user interface elements and/or navigating through different user interfaces (e.g., a first set of user interfaces for determining the filtering operation based on a natural language prompt, and a second set of user interfaces for implementing the filtering operation (e.g., within a different web or desktop application)). In some such embodiments, this parsing advantageously allows users to view, understand, and modify any of the filters in a modular way, which allows for identifying cohorts of patients. Furthermore, since the agent module 6102 is associated with the data module 240, one or more external databases 108, and/or the system databases 400, which are updated with current information through the communication network or local updates, such as up-to-date medical records (e.g., live collections), the agent module 6102 identifies one or more cohorts or subjects based on real-time information associated with the subjects through the filter processing of data stored in these databases (e.g., unseen/protected data). In some embodiments, the agent module 6102 provides processing output to convey the reasoning to the user through a response displayed at the client device 102, which may be presented within an user interface element of the user interface 500.

In some embodiments, an agent module is configured to construct a funnel call (e.g., in JSON) and apply one or more filters to the call, such as a first node associated with a first filter and/or a second node associated with a second filter and a third filter. For example, a single node 6108 may be generated that has a parameter 6110 for every possible filter and a corresponding logic 6112 for applying data to the possible filter and/or combinations of filters associated with the node 6108. In this example, the parameters 6110 are denoted as optional and the function is fed that into a model 228. In another example, a node 6108 is generated for every filter where the parameters 6110 match the inputs of the filter and the response (e.g., a JSON) is appended to a larger funnel object call.

As a simple illustrative example, if a user enters a prompt such as "who is Leo DiCaprio's girlfriend? What is her current age raised to the 0.43 power" an agent module may provide the following processing output:

Example 1 - Example Agent Processing Output

```
> Entering new PlanAndExecute chain...
steps=[Step(value='Search for Leo DiCaprio's girlfriend on the internet."),
Step(value='Find her current age.'), Step(value='Raise her current age to the 0.43 power
using a calculator or programming language.'), Step(value='Output the result.'),
Step(value="Given the above steps taken, respond to the user's original question.")]
> Entering new AgentExecutor chain...
Action:
. . .
{
  "action": "Search",
  "action_input": "Who is Leo DiCaprio's girlfriend?"
}
. . .
Observation: DiCaprio broke up with girlfriend Camila Morrone, 25, in the summer of
2022, after dating for four years. He's since been linked to another famous supermodel -
Gigi Hadid. The power couple were first supposedly an item in September after being
spotted getting cozy during a party at New York Fashion Week.
Thought: Based on the previous observation, I can provide the answer to the current
objective.
Action:
. . .
{
  "action": "Final Answer",
  "action_input": "Leo DiCaprio is currently linked to Gigi Hadid."
}
. . .
```

-continued

| Example 1 - Example Agent Processing Output |
| --- |
| > Finished chain.<br>****<br>Step: Search for Leo DiCaprio's girlfriend on the internet.<br>Response: Leo DiCaprio is currently linked to Gigi Hadid.<br>> Entering new AgentExecutor chain . . .<br>Action:<br>. . . |

Example 1 shows a portion of a processing output (e.g., the first step). The processing output continues until the agent module 6102 obtains a response to each of the questions in the original query. In some embodiments, each step is performed by a different node 6108 and/or agent module 6102. In this way, a user may learn to interact with an agent module 6102, understand the rationale behind the response(s), and understand from where the data is obtained by the agent module 6102 that causes the response(s). This allows the user to modify their prompt and/or instruct the agent to modify its response process to obtain a desired result, or modify the agent module 6102 itself, such as an order of the nodes in the node architecture 6106, one or more parameters 6110 of a respective node of the node architecture 6106, one or more logics of the node 6108, or the like.

Figure 6:
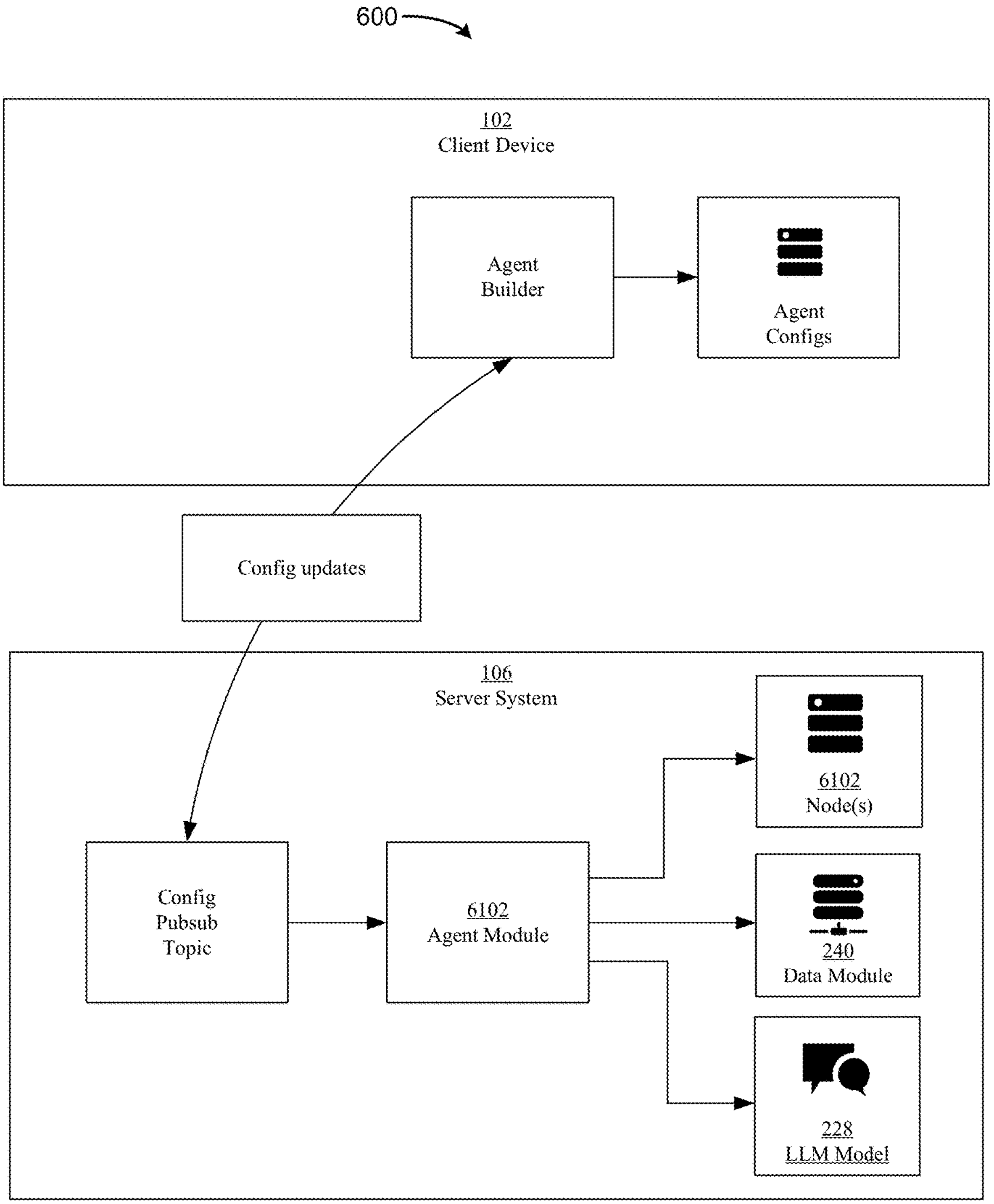
FIG. 6 illustrates an example architecture for deploying agents in accordance with some embodiments.

FIG. 6 illustrates an example system architecture for deploying agents (e.g., agent modules 6102) in accordance with some embodiments. The architecture 600 shown in FIG. 6 includes an agent builder component in a control plane of a client device 102. The control plane may function as a supervisor of data, coordinating communication between different components and collecting data from a data plane (e.g., a working environment presented on a display of the client device 102). In some embodiments, the control plane resides above the data plane (e.g., above the working environments) and enforces rules for the data plane, which allows for partitioning the data plane to prevent unauthorized or unauthenticated control of the data plane from unsecure client devices, such as those unassociated with a portion of the data plane. However, the present disclosure is not limited thereto. In some embodiments, the agent builder hosts a user interface for configuring agent modules, such as by configuring the corresponding node architecture 6106 associated with the agent module 6102. In some embodiments, the agent builder component is communicatively coupled to an agent library 226 in the control plane that stores a plurality of agent modules 6102, such as the agent module 6102, and to an agent host (e.g., via a config pubsub component) in a working environment. The agent module 6102 in the working environment may be communicatively coupled to an agent library 226 in the working environment, a document index (e.g., one or more data sources, such as knowledge database 404 and/or external databases 108), and a large language model (e.g., a model 228). In some embodiments, the agent library 226 includes a user interface and API for interacting with deployed agents. In some embodiments, the large language model in FIG. 6 represents a node 6108 (e.g., a task-specific agent) as described herein.

In some embodiments, the agent builder includes a frontend and a backend. In some embodiments, the agent builder frontend includes an access component (e.g., an administrative console, such as the user interface 1830 in FIG. 18D, which may be a home user interface that a user is presented with upon providing access credentials to the application), an agent list (e.g., an agent library, such as the user interface 1830 in FIG. 18E, which may include a plurality of task-specific orchestrations to which the user has access, e.g., based on the access credentials provided to the application), an agent builder component (e.g., either or both of the user interfaces 1812 and 1822 respectively, which may include a first representation of the node architecture 6106 (e.g., a form-builder representation) and a second representation of the node architecture 6106 (e.g., a workflow representation)), and/or a data source management component. In some embodiments, the agent builder backend includes a database layer, an API service, and/or a configuration publisher component. In some embodiments, the frontend and the backend of the agent builder are executed on separate electronic devices.

In some embodiments, the agent host includes a frontend and a backend. In some embodiments, the agent host frontend includes an access component, an agent list, an interaction console, and/or a document console. In some embodiments, the agent host backend includes a websocket for interactive user, a database layer, an API access to deployed agents, tools and/or custom chain implementation, a document loader, and/or a configuration subscription component. In some embodiments, the frontend and the backend of the agent host are executed on separate electronic devices.

In some embodiments, the agent builder component is configured to generate, deploy, and/or update one or more agent modules 6102 and/or a corresponding node architecture 6106 to one or more working environments (e.g., one or more workload planes). In some embodiments, each agent module 6102 is associated with an agent type. In some embodiments, the agent type includes a type of model 228 and/or conditional logic 6112, such as an implementation configuration. For example, an agent module 6102 may include a language model associated with a first node 6108 and a corresponding, type-specific logic that further associates the agent module 6102, through the first node 6108, with a particular domain, such as a first configuration implementation for applying the prompt to the model 228 if the prompt is associated with a first modality and a second configuration implementation if the prompt is associated with a second modality different from the first modality. In some embodiments, the logic 6112 is specified in a corresponding agent module 6102 configuration file, which advantageously allows for configuring the logic after applying various prompts to the agent module 6102 and/or using multiple client devices (e.g., end users) to configure the logic 6112. However, the present disclosure is not limited thereto.

In some embodiments, agent module types include transform agent modules (e.g., performing functions such as data transformations, regular expressions, and string templating), authorization agent modules, language model agent modules (e.g., applying inputs to a large language model), data collection agent modules (e.g., RAG modules), super agent modules (e.g., aware of other agent types and their capabilities and configured to instantiate and/or delegate to the appropriate agent modules), sequential agent modules (e.g., including multiple models and/or tools coupled together in a sequential fashion), tool-using agent modules, coding agent modules (e.g., configured to generate code in particular programming languages), and categorization agent modules (e.g., configured to determine an intent, domain, or other categorization for user inputs). In some embodiments, the language model agent modules provide/store context information such as conversation history, user preferences, subject details, and the like. In some embodiments, the data collection agent modules are couplable to external data sources (e.g., the external service(s) 110 and/or the external database(s) 108). In some embodiments, a sequential agent module includes a recursive agent module (e.g., repeating and/or refining outputs until predetermined criteria are met). In some embodiments, a super agent module is configured to compare available agent module types and recommend a particular agent module type for a particular situation/purpose. In some embodiments, a coding agent module is configured to generate code for new agent modules based on inputs (e.g., natural language inputs) from a user. In some embodiments, a categorization agent module is a component of a routing agent module. For example, the categorization agent module determines an intent/domain for an input and the routing agent module routes the input to a downstream component in accordance with the determined intent/domain. In some embodiments, a sequential agent module is a component of a routing agent module. For example, the routing agent module coordinates operation (e.g., data transmission and timing) of multiple components and/or modules. In some embodiments, each agent module is generated/provided with guardrails (e.g., enforcing privacy, security, data typing, etc.). In some embodiments, an agent module is configured to recognize whether data is protected health information (PHI) and take appropriate action. For example, an agent module may disable information sharing options when providing PHI.

In some embodiments, different agent module types are associated with (e.g., trained on, instructed on, and/or coupled to) different domains (e.g., different subjects, types of data, and/or classes of data) in a plurality of domains. For instance, in some embodiments, the plurality of domains forms an input space, with defines a universe of data associated with a variety of subject matters. In some embodiments, the input space defines an N-dimensional space of data obtained from a plurality of data sources, in which N is a positive integer, such as two, three, four, ten, etc. In some embodiments, each respective domain in the plurality of domains defines a partition classification or subset of data, such as one or more specific data sets of system databases 400 of FIG. 4. However, the present disclosure is not limited thereto.

As a non-limiting example, consider a first input space associated with a plurality of medical records, in which each medical record in the plurality of medical records includes a plurality of text data and a plurality of graphical data associated with a corresponding patient. Accordingly, a plurality of domains collectively defined by information obtained from the plurality of medical records allows for classify the information and training the agent module 6102 of the information classified domain, such as a first domain associated with a statin drug class of FIG. 4 and a second domain associated with a glucagon-like peptide (GPL) agonist drug class. As a non-limiting example, an agent module 6102-1 is associated with a first domain for generating a summary report of a patient's medical records, an agent module 6102-2 is associated a second domain for guiding a subject, such as a patient or a medical practitioner associated with the patient, through a care plan, an agent module 6102-3 associated with a third domain for creating patient care guidelines based on a patient's health profile, an agent module 6102-4 associated with a fourth domain for identifying patients requiring follow-up at a hospital, an agent module 6102-5 associated with a fifth domain for identifying changes in a standard of care for a disease setting, and/or an agent module 6102-6 associated with a sixth domain for evaluating unstructured data associated with a patient to identify a cohort of similar patients.

An example agent type is a database-interfacing agent module (e.g., an agent module 6102) associated with one or more data source nodes 6108. An example database-interfacing agent may be an adverse effects agent that has access to an FDA label database and is configured to interpret adverse effect information from the database. The configuration of the tool-using agent may include a custom prompt for the model 228 and one or more data sources that the agent database-interfacing module may access and/or use.

Another example agent type is a custom-chain agent module (e.g., a super agent module) that takes an input prompt, analyzes the prompt (e.g., parsing the prompt into one or commands and/or a plurality of tokens), and transmits information from the parsed prompt (e.g., commands and/or tokens) to a model 228 or other component, such as a node 6108 of the custom-chain agent module or a different node 6108 of a different agent module 6102). For example, an agent module 6102 may obtain data from different databases (e.g., external databases 108, knowledge database 404, etc.), in which the data is obtained in a variety of different formats and/or structures, such as unstructured text, structured text, tables, charts, graphical data, and/or the like. In some embodiments, the agent module 6102 reformats and/or restructures the data obtained from the databases for application to the model 228 and/or a different agent module 6102. In some embodiments, the agent module 6102 evaluations and/or obtains an optimal set of parameters for inputting data to the model 228 and/or a different agent module 6102 and/or translates the data obtained from the databases based on the optimal set of parameters. In some embodiments, the obtained data is restructured into a homogenous dataset (e.g., different hospitals may use different codes for the same procedure, such is homogenized by the agent module 6102 into a uniform coding). The configuration of the custom-chain agent module 6102 may include a sequence of nodes 6108 associated with the custom-chain agent module 6102 and/or other nodes 6108 associated with other agent modules 6102 to be used by the custom-chain agent module 6102 and/or definitions of corresponding chain objects. In this way, an agent module 6102 may be considered a configuration of a particular agent type for a particular task through a plurality of interconnected nodes 6108 that form a node architecture 6106 of the agent module 6102 (e.g., represented as a database object). One example of the super agent module is described with respect to a workflow representation in FIGS. 19A-19B. Accordingly, the super-agent module 6102 allows for dissecting complex evaluations and logics into a reasoning path through the plurality of interconnected nodes 6108, which makes arriving at an accurate and precise response computationally less burdensome. In some embodiments, the agent modules 6102 are accessible via an interaction console and/or an application programming interface (API) as illustrated in FIGS. 18A-18F and 19A-19B.

A simplified example agent module configuration is shown below in Example 2.

Example 2 - Example Agent Configuration

```
{
"id": "1234" // primary key
"name": "adverse-effects",
"description": "Looks up drug adverse effects from FDA labels",
"type": "chatbot-agent-with-tools", // this particular type corresponds to a model
prompted to choose from available tools
"data_classification": "INTERNAL",
"owners": [example owner],
"visibility": "INTERNAL",
"required_roles": ["EXAMPLE_READER"],
"data_stores": [ ],
}
```

In some embodiments, one or more parts of the agent configuration are stored in a separate versioning table (e.g., linked by agent ID). In this way, an agent configuration may be edited without affecting a deployed agent version. A simplified example agent version configuration is shown below in Example 3.

Example 3 - Example Agent Version Configuration

```
{
  "id": "1234" // foreign key linking this version to an agent
  "version": 52, // editing the agent config creates a new version
  "console_deployed_environments": {"alp": true, "bet": true, "prd": false},
  "api_deployed_environments": {"alp": true, "bet": true, "prd": false}, // whether to
  enable API access in addition to interactive access
  // agent-type-specific configuration object
  "config": {
    "tools": [ {"name": "fda-label-adverse-effects-highlights"} ],
    "llm": {
      "model": "xxxx"
       "temperature": {
       "value": 0;
       "editable": true, // whether this value is editable in the interaction console
      },
    "max_tokens": {"value": 1024, "editable": false}
    }
  }
}
```

In an example scenario, a user configures an agent in the console and then deploys it to one or more environments (e.g., workload planes and/or control planes). For this scenario, the agent configuration is stored in the control plane (e.g., as shown in FIG. 6). As shown in FIG. 6, the agents themselves execute in the appropriate working environments, and working environments do not have access to the control plane. The agent builder in the control plane is configured to push configurations into the various environments (e.g., via the config pubsub component shown in FIG. 6). In some embodiments, when an agent configuration is changed or an agent version is deployed, the agent builder informs the agent host in each environment so that the updated agent can be deployed. This may be via a pubsub message to the agent-config topic or via a simple HTTP request.

The architecture 600 allows for flexibility in supporting a variety of deployment strategies for each respective agent module 6102. For example, some end-users, e.g., those using agent modules 6102 interactively and without engineering support, expect to operate their agent modules 6102 entirely within a production working environment. In some embodiments, the administrator, such as creator, of an agent module 6102 is able to choose a deployment style suitable for their application, such as by restricting the agent module 6102 to one or more domains, one or more databases 108, one or more services 110, or a combination thereof. For example, a first user may wish to employ a user interface that includes one or more user interface elements described with respect to the application (e.g., the user interface 500) by directly embedding the components within a web page, and a second user may wish to interact with an API that is configured to receive user requests and provide responses in the form of data structures, which the second user may integrate into different user interface elements not associated with the application.

In some embodiments, users of an agent builder user interface in the control plane are provided with a production access token that can also make requests to the production agent host. In some embodiments, an integrated user interface is presented to a user that shows both the agent builder having a plurality of input features visualized through a representation and the interaction console without concerning the users with the differences between the control plane and the working environments. For example, for users who want to test out agent modules 6102 in a lower environment, a link may be provided to open that agent module 6102 in a new tab or frame of an application. In some embodiments, a request to authenticate is presented and an access token is obtained by the agent module 6102 for that environment. In some embodiments, the user interface includes an indication of which environment is currently active.

In some embodiments, the data module 240 (e.g., document index) shown in FIG. 6 includes one or more of: a static corpus, a dynamic corpus, an embedding model (e.g., a model 228), a chunking strategy, a storage back-end, a data classifier (e.g., public, internal, or secret), and/or a visibility setting (e.g., private, public, or restricted by role). In some embodiments, the data module maintains an index of data that may be ephemeral or permanent. In some embodiments, data elements associated with data files (e.g., documents) are evaluated via a chunking process, embeddings are generated for the chunks generated from the chunking process, and the embeddings are inserted into a database (e.g., embeddings 6240 of FIG. 14). In some embodiments, the data module 240 includes a set of retrieval parameters (e.g., for a number of documents to retrieve and/or a similarity measure). In some embodiments, the data module 240 corresponds to a set of databases (e.g., medical databases), such as the database(s) 400 in FIG. 4. In some embodiments, a parameter associated with a node 6108 of a respective agent module 6102 and/or model 228 includes selecting one or more document indices to retrieve from via the data module 240. In some embodiments, embeddings are created and siloed for future use. In some embodiments, each embedding is associated with one or more access control lists (ACLs).

Tools are a mechanism by which agent modules can integrate with other components and with the outside world. In some embodiments, tools are made available to the agent modules as agent builder blocks. Some tools may be general-purpose, and others may be custom for a particular integration. Different agent module types may have different access to tools: for example, a langchain agent may be configured with a set of available tools, and the model may be configured to choose when and how to use them, whereas a langchain chain may follow a fixed sequence of steps. In some embodiments, an agent configuration defines when and how tools are invoked. As an example, a tool may be configured with a fixed base URL so that the agent can't make authentication requests to some other service. In some embodiments, a tool is configured to use an end-user's access token to authenticate, rather than granting an access role to the agent's machine user. In some embodiments, a tool is restricted to certain endpoints and/or methods (e.g., only GET requests) so that the tool is restricted from performing admin tasks on behalf of a user who lacks admin privileges (e.g., write permissions).

In some embodiments, a tool has parameters that are specified when configuring the agent modules and/or parameters (e.g., the parameters 6110) that can be specified at invocation time by the agent module itself. An example tool is an authentication request tool configured to fetch an internal URL using a user's access token. The authentication request tool may include the following parameters: name, description, base URL, and/or input parameters (e.g., specifiable by the agent). For example, an example authentication request tool may have an order identifier as an input parameter. Another example tool is an external request tool that fetches an external URL. The parameters for the external request tool may include: name, description, base URL, and/or input parameters. Another example tool is an email tool that sends an email. The parameters for the email tool may include destination, subject, and/or body.

Example task-specific agents modules include (i) an agent module configured to send emails summarizing which customers are facing issues with orders and/or identifying retraining opportunities, (ii) an agent module configured to generate data tables, JSON schema, and other data translations, (iii) an agent module configured to find orders within a group of clients that have particular flags and/or provide a summary by client, flag, etc. (e.g., with timestamp for order creation timing), (iv) an agent module for identifying behavioral changes in ordering habits and adjust orders accordingly (e.g., increase delays and/or cancel orders) and sending notifications, (v) an agent module for generating inclusion/exclusion criteria from a protocol document, generating structured queries (e.g., SQL queries) from a structured list, and/or generate specifications (e.g., YAML specifications) from structured lists of inclusion/exclusion criteria, and (vi) an agent module for answering questions about particular trials based on information in the protocol and/or other trial materials or documentation.

As an example, an agent module 6102 configured to identify and/or evaluate adverse effects receives a user query regarding adverse effects associated with a particular drug. In this example, the agent module 6102 parses the query in order to identify the drug name from the query and applies the drug name to one or more nodes 6108 in order to obtain a set of adverse effects associated with the drug. In this example, the agent module 6102 provides a response with a description of the set of adverse effects.

Example 4 below shows a simplified example configuration for an adverse effects agent.

Example 4 - Example Adverse Effects Agent Configuration

```
extract_drug_name = LLMChain(
    prompt=extract_drug_name_prompt,
    llm=llm,
    output_key='drug_name",
    verbose=true,
)
highlights_lookup = FdaLabelChain( fda_labels_client, verbose=true)
analyze_document = LLMChain(
    prompt=answer_prompt,
    llm=llm,
    output_key="text",
    verbose=true,
)
combined = SequentialChain(
    chains=[extract_drug_name, highlights_lookup, analyze_document],
    input_variables=["query"]
    output_variables=["text", "fda_label_web_url", "product_name",
"generic_name"],
    verbose=true,
    return_all=true,
)
```

Example 5 below shows an example chain definition for the agent module 6102.

Example 5 - Example Adverse Effects Agent Chain Definition

```
{
"type: "chain",
"chain": {
'type": "SequentialChain",
"chains": [
  {
  "type": "LLMChain",
```

-continued

Example 5 - Example Adverse Effects Agent Chain Definition

```
  "prompt": "Determine if the input query contains the name of a drug.\n\nReturn
the one or two word name of the drug and nothing else.\n\nIf the input does not contain a
drug name, return \"NOT FOUND\".\n\nInput: {query}\nOutput: ",
   "output_key": "drug_name"
   },
   {
   "type": "FdaLabelChain"
   },
   {
   "type": "LLMChain",
   "prompt": "Use the following FDA label excerpt to answer the question at the
end.\n\n{adverse_effects_raw}\n\nQuestion: {query}\nHelpful Answer: ",
   "output_key": "text"
   },
],
"input_variables": ["query"],
"output_variables": ["text", "fda_label_web_url", "product_name", "generic_name"]
 }
}
```

In some embodiments, a type or classification of agent module 6102 is selected for a specific task based on an analysis of a set of different types or classifications. In some embodiments, the analysis includes comparing label-dependent spectra from the output of a pretrained model 228. For example, the comparison may be performed using a Jensen-Shannon (JS) divergence of a principal component analysis (PCA) decomposed output spectra. In some circumstances, models 228 that are better suited for a downstream task have a larger JS divergence. JS divergence is described in Menendez et al., 1997, "The Jensen-Shannon divergence," Journal of the Franklin Institute 334(2), pp. 307-314, which is hereby incorporated by reference in its entirety for all purposes. Additionally, some models 228 have greater information capacity at intermediate layers. The greater information capacity may be determined by measuring the dimensionality of the PCA reduced spectra coming from the output of the layer. In some embodiments, a decomposed spectra selector of pretrained models is configured to perform the above analysis.

One of ordinary skill in the art will appreciate there is a large number of pretrained and fine-tuned deep language models (DLMs) available. However, the performance of each model for a downstream fine-tuning task can vary greatly. Therefore, a process (e.g., a heuristic) for model selection can save time and energy, compared to training several models and choosing the most performant one afterwards.

In some circumstances, models that are better fit for the downstream task are better at separating data according to the label of each respective datapoint. This can be seen by examining the label dependent statistics in the output of the task dependent output head. When downstream training has not occurred, this can still be done by examining the label dependent spectra of the data coming from the output of the pretrained model. A useful metric for determining the label-dependent spectra separation is the JS divergence. Often the spectra is multidimensional, so the JS divergence can be calculated and summed along the dimensions of the spectra. This can be problematic because high dimensional outputs have an innate advantage simply because of the larger number of dimensions contributing to the sum. Not only does naive JS divergence favor higher dimensional outputs, it also does not account for intra-output correlations.

To circumvent this issue, the spectra can be decomposed into its first N principal components necessary to account for 99% cumulative explained variance ratio, where N is a positive integer. In some embodiments, N is 1, 2, 3, 4, 5, 6, 7, 8, 9, 10, between 10 and 20, between 20 and 50, between 10 and 100, or between 1 and 1000. Pretrained DLMs with higher PCA-reduced JS divergence can lead to better downstream classification performance because they have an innate edge in discriminating label dependent data. For example, there is a correlation between the PCA-reduced JS divergence and the macroscopic F1 of the DLM against the test data. Thus, in some scenarios, the choice of pretrained model has a large impact on the final performance.

The macroscopic F1 score for the DLM against the test data may be derived from precision and recall of the DLM. Precision is the accuracy of positive predictions made by the DLM. It can be considered the ratio of true positive (TP) predictions to the total number of positive predictions (true positive+false positive). Recall (also sometimes called sensitivity or true positive rate) measures the ability of the DLM to correctly identify positive instances. It can be considered the ratio of true positive predictions to the total number of actual positive instances (true positive+false negative). The F1 score can then be calculated as the harmonic mean of precision and recall:

$$F1 = \frac{2 \times \text{precision} \times \text{recall}}{\text{precision} + \text{recall}} \quad \text{Equation 1–F1 Score for DLMs}$$

The macroscopic F1 score can be obtained by calculating the F1 score for each class separately and then averaging the F1 scores across all classes. It treats each class equally and is useful when there are imbalanced datasets with varying class distributions. In this way, the macroscopic F1 score provides a more comprehensive evaluation of the DLM's performance by taking into account its ability to classify all classes correctly, not just the majority class.

The correlation between the PCA-reduced JS divergence and the macroscopic F1 of the test data holds for an image modality as well. In the computer vision domain and modality, greater PCA-reduced JS divergence of the model output spectra indicates better downstream performance. Additionally, in some scenarios, the layer that yields the highest PCA dimension leads to the strongest results. For example, a full example model when trained yielded a macroscopic test F1 score of 0.76, and the same model with layers only up to layer 8 (e.g., maximum PCA dimension) yielded a macroscopic test F1 score of 0.86, which is considerably better.

In some embodiments, an analysis of the PCA-reduced JS divergence is used for (i) selecting the appropriate agent module 6102 and/or model 228 for a specific task (e.g., selecting the appropriate agent module), (ii) identifying the appropriate dimensionality of the agent module 6102 and/or model 228 (e.g., reduced dimensionality), (iii) optimizing one or more node parameters of the agent module 6102 and/or model 228 for best use (e.g., layer selection), (iv) optimizing one or more inputs of the agent module 6102 and/or model 228 (e.g., which combination of inputs provide the best early divergence), (v) creating embeddings to identify if combinations of the agent module 6102 and/or model 228 that are beneficial, (vi) pruning the agent modules 6102 and/or models 228 deterministically, or (vii) a combination thereof. For example, optimizing the agent module 6102 and/or model 228 configuration for best use may include selecting the node and/or layer of the model with highest dimension after reduction.

As an example scenario, a user obtains a set of labeled data with which to train a classifier. The user may split the data into train, validation, and test data sets. A set of pretrained agent modules 6102 and/or models 228 are identified by a first agent module 6102 that may fit to the task (e.g., transformers, convolutional neural networks, and/or recurrent neural networks). Each of the agent modules 6102 and/or models 228 may be run over the validation set of data and the spectra from the last layer of the pretrained model and/or agent module may be examined (e.g., before entering the classification head). This yields a tensor of shape (N, D) where N is the number of examples in the validation set, and D is the dimensionality of the output from the last layer of the pretrained model and/or agent. To remove linear dependence, a 99% PCA reduction may be applied on the output that yields a new tensor of shape (N, D_pca). The JS divergence may be calculated between the class labels (e.g., in a one-vs-rest fashion for each component and sum). The pretrained agent modules 6102 and/or models 228 that yield the highest summed JS divergence may then be selected. The selected agent modules 6102 and/or models 228 may correspond to a particular type or classification. In some embodiments, agent modules 6102 and/or models 22 in the set of pretrained models has 2, 3, 4, 5, 6, 7, 8, 9, 10, between, 10 and 20, between 20 and 30, or more than 30 nodes and/or layers.

Figure 7A:
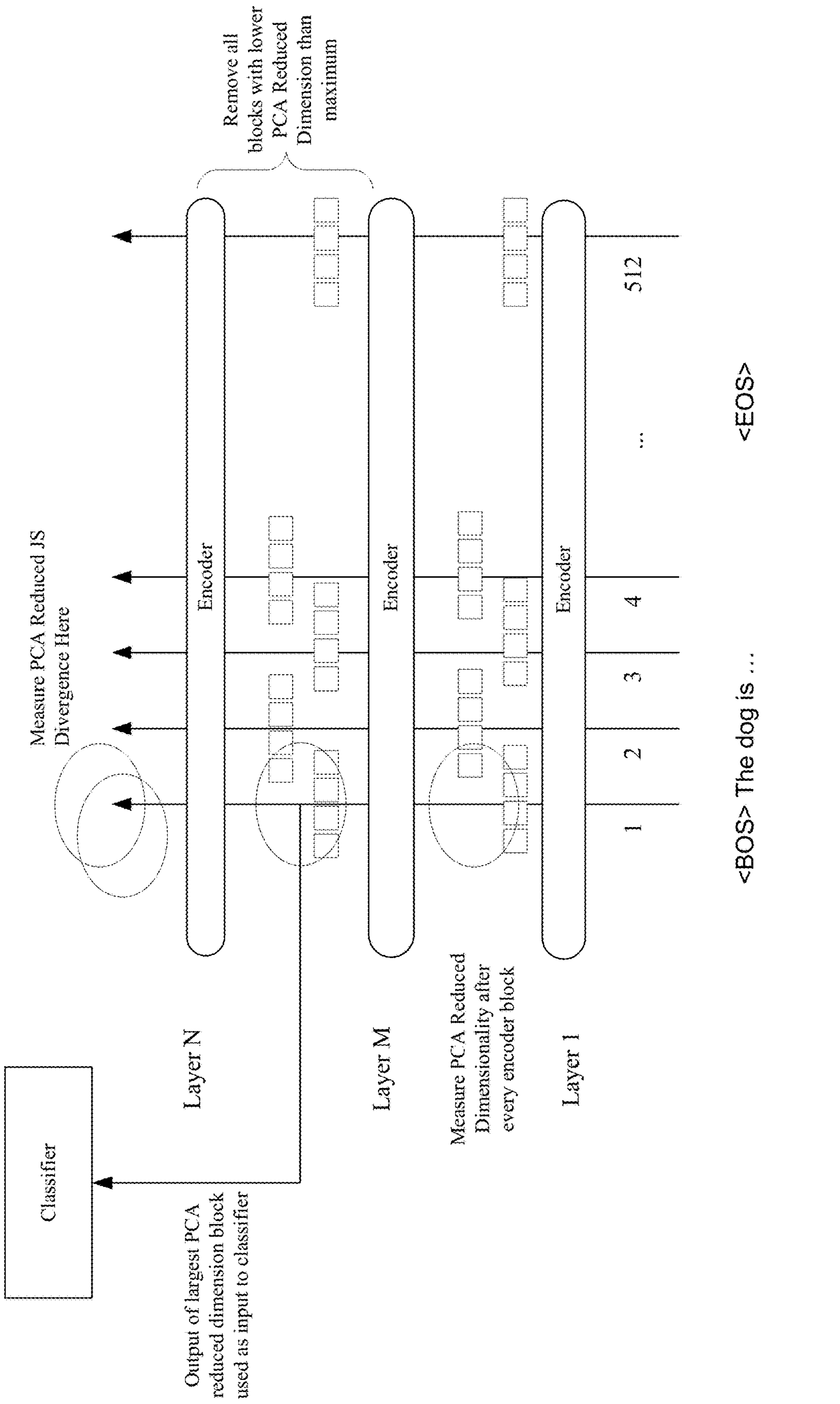
FIGS. 7A-7E illustrate an example process for model selection in accordance with some embodiments.
Figure 7B:
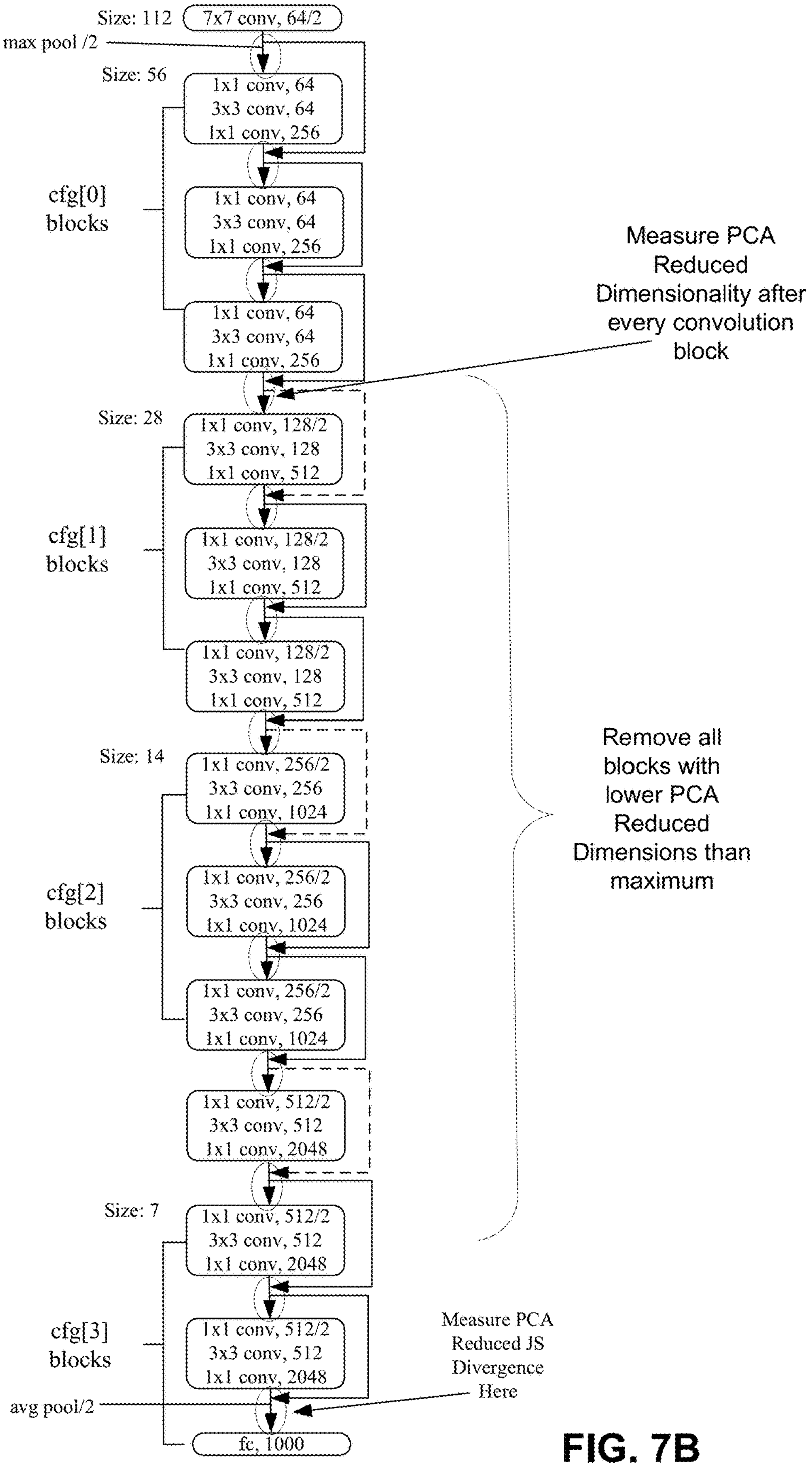
Figure 7C:
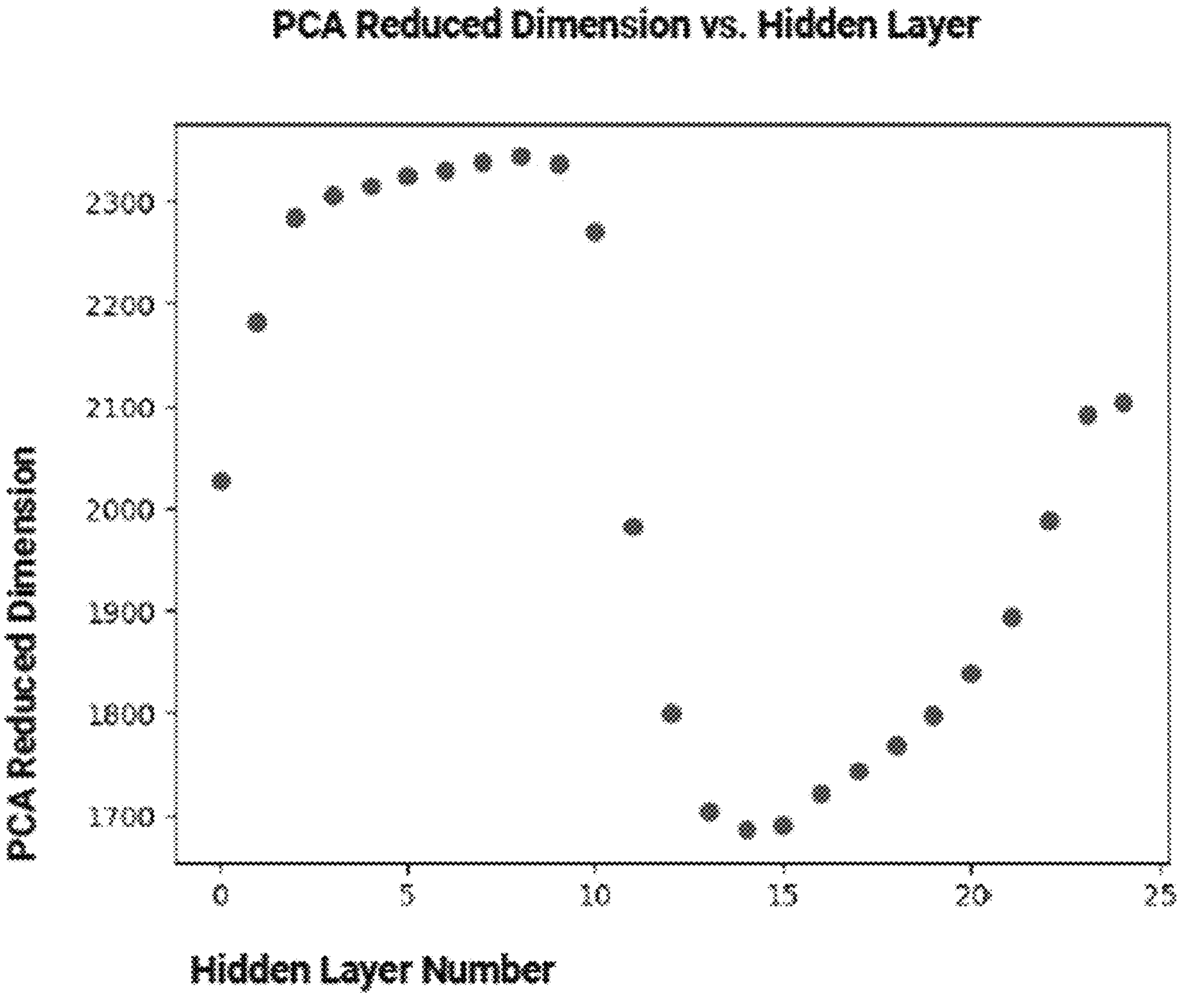

Additionally, a portion of an agent module 6102 and/or model 228 may be identified as useful for a particular dataset and/or domain of information, such as a first agent for use in a genome domain, a second agent module for use in a microbiome domain, a third agent for use in an imaging domain, a fourth agent module for use in a drug domain, and the like. The spectra from the $0^{th}$ element of each hidden layer may be obtained and a 99% PCA reduction performed and then the dimension may be recorded. For example, the node and/or layer of the agent module 6102 and/or model 228 with the largest PCA-reduced dimension may be selected and all nodes and/or layers following the selection may be discarded. The output of the selection may be fed to the classification head (and agent module 6102 and/or model 228 finetuning can then be performed). FIG. 7A shows an example agent module 6102 with multiple hidden interconnected nodes forming layers, and PCA-reduced JS divergence and PCA-reduced dimensionality measure points. FIG. 7B shows another example agent module 6102 and/or model 228 with multiple interconnected nodes forming layers and potential removal of nodes and/or layers after a select node and/or layer is identified. FIG. 7C shows a graph of PCA-reduced dimension versus hidden layer number for an example agent module 6102 and/or model 228.

Figure 7D:
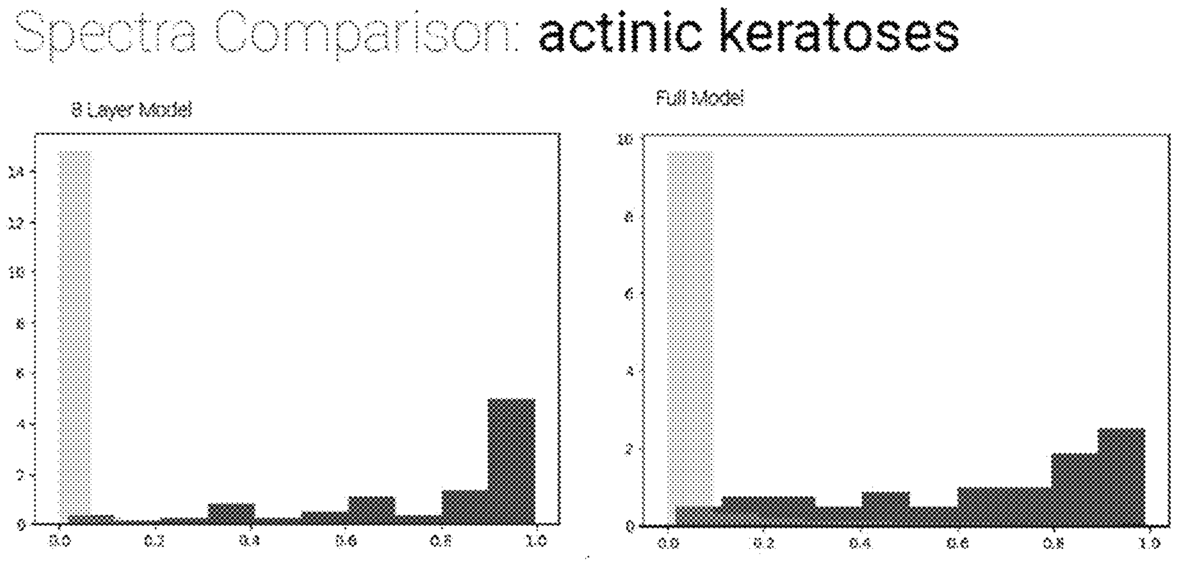
Figure 7E:
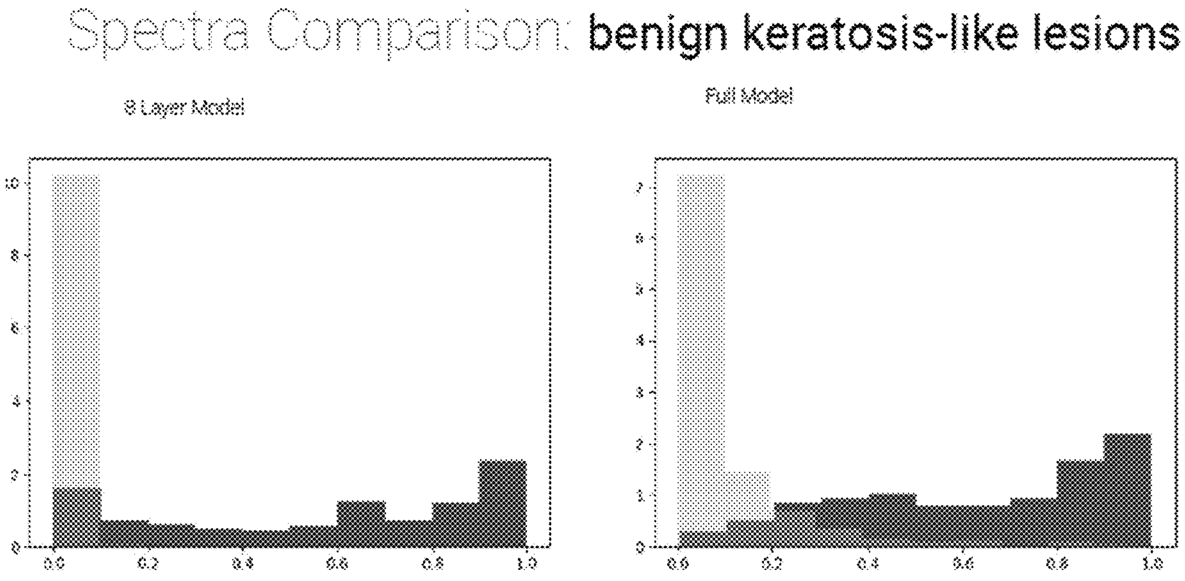

As shown in FIG. 7C, the $8^{th}$ hidden layer of the example model has the highest PCA-reduced dimension. FIGS. 7D and 7E show spectra comparisons between the reduced $8^{th}$ hidden layer model and the full example model for particular datasets. Table 1 below shows a comparison between the reduced $8^{th}$ hidden layer model and the full model in this example after each was trained on the listed datasets.

TABLE 1

Example model comparison

| | dataset | Precision | Recall | F1 | Support |
|---|---|---|---|---|---|
| 8-layer model | actinic_keratoses | 0.68 | 0.92 | 0.78 | 144 |
| | benin_keratosis-like-lesions | 0.94 | 0.81 | 0.87 | 42 |
| | basal_cell_carcinoma | 0.87 | 0.72 | 0.79 | 142 |
| | dermatofibroma | 0.98 | 0.9 | 0.94 | 858 |
| | vascular_lesions | 0.89 | 0.96 | 0.92 | 67 |
| | melanoma | 1 | 0.89 | 0.94 | 18 |
| | melanocytic_Nevi | 0.91 | 0.71 | 0.8 | 14 |
| | micro avg | 0.92 | 0.88 | 0.9 | 1285 |
| | macro avg | 0.9 | 0.84 | 0.86 | 1285 |
| | weighted avg | 0.93 | 0.88 | 0.9 | 1285 |
| | samples avg | 0.88 | 0.88 | 0.88 | 1285 |
| full model | actinic_keratoses | 0.92 | 0.5 | 0.65 | 144 |
| | benin_keratosis-like-lesions | 0.93 | 0.62 | 0.74 | 42 |
| | basal_cell_carcinoma | 0.61 | 0.75 | 0.67 | 142 |
| | dermatofibroma | 0.95 | 0.89 | 0.92 | 858 |
| | vascular_lesions | 0.75 | 0.9 | 0.82 | 67 |
| | melanoma | 1 | 1 | 1 | 18 |
| | melanocytic_Nevi | 0.83 | 0.36 | 0.5 | 14 |
| | micro avg | 0.88 | 0.82 | 0.85 | 1285 |
| | macro avg | 0.86 | 0.72 | 0.76 | 1285 |
| | weighted avg | 0.9 | 0.82 | 0.85 | 1285 |
| | samples avg | 0.82 | 0.82 | 0.82 | 1285 |

As shown in Table 1, the reduced 8-layer model exceeded the performance of the full model on these datasets. Additionally, the reduced model is less computationally expensive than the full model.

Figure 8A:
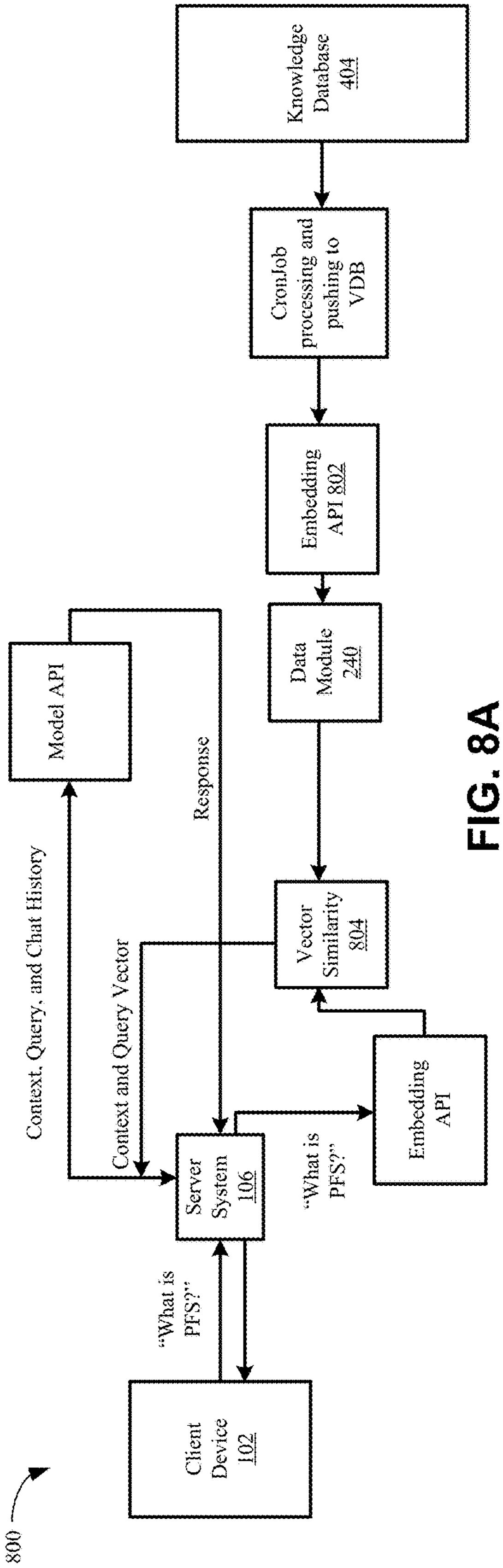
FIGS. 8A and 8B illustrate example model architectures in accordance with some embodiments.
Figure 8B:
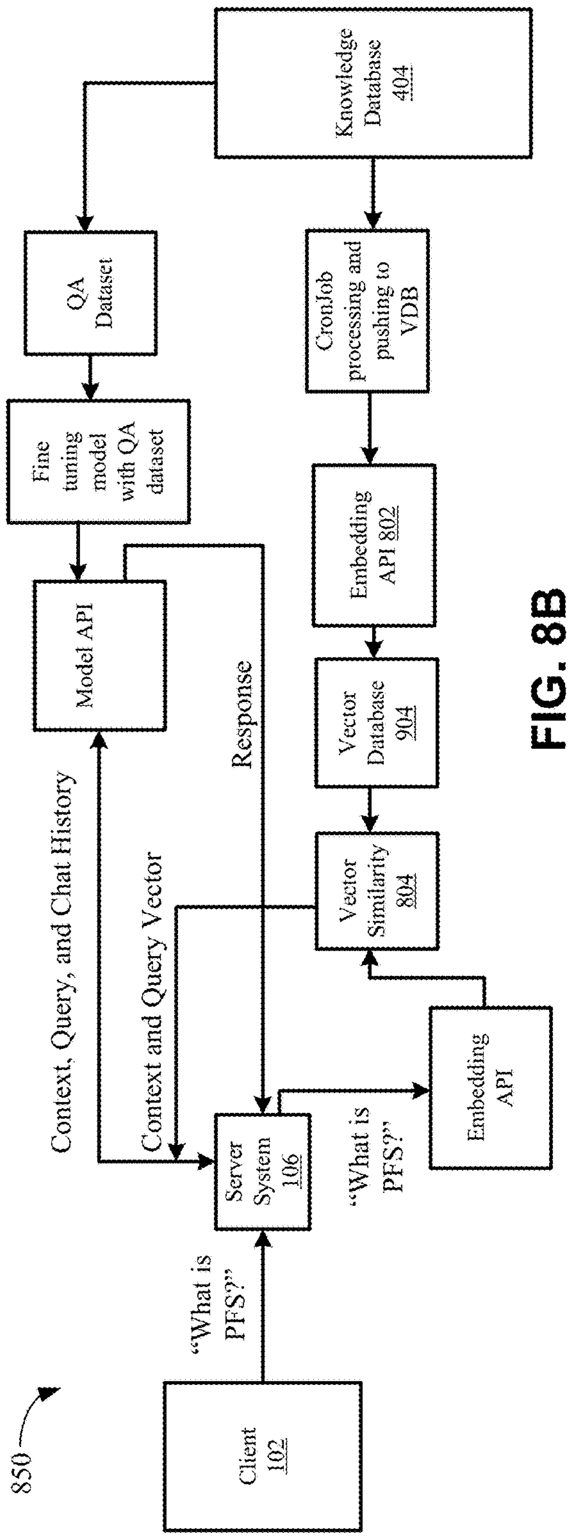

FIGS. 8A and 8B illustrate example agent module 6102 architectures (e.g., an agent module architecture 800 and an agent module architecture 850) in accordance with some embodiments. In some embodiments, the agent module architectures of FIGS. 8A and 8B illustrate a workflow of a corresponding plurality of interconnected nodes. However, the present disclosure is not limited thereto. For ease of description, the example agent module 6102 architectures depicted in FIGS. 8A and 8B are described with respect to devices, systems, and techniques described with respect to FIGS. 1 to 6. However, a skilled artisan will recognize that various alternative and/or additional devices, systems, and techniques may be used to perform the same or similar operations.

FIG. 8A shows the agent module architecture 800 where a client device 102 sends a query (e.g., text of a prompt provided by a user, or other data based on a determined intent of one or more portions of the text of the prompt), stating "what is PFS?", to the server system 106, which includes a backend component (e.g., an implementation component of an agent module 6102). In some embodiments, the backend component includes or sends the query to an embedding component (e.g., an embedding API 802, embeddings 6240 of FIG. 8C, embeddings 6240 of FIG. 14, etc.), which may be configured to generate an embedding based on one or more portions of the query text received from the client device 102 and/or another agent module 6102. In some embodiments, the query embedding is compared to embeddings in a vector database 6240 (e.g., to determine and provide a vector similarity 804) and results are sent to the backend component as context with the query vector and/or a different agent module 6102 in accordance with the logic 6112 of the node architecture. In some embodiments, the agent module 6102 sends the context, query, and optionally chat history to a node 6108 associated model 228 component (e.g., a large language model). The model 228 outputs a response to the agent module 6102, such as a terminal node, which transmits the response to the client device 102, in accordance with some embodiments.

In some embodiments, embeddings are generated from data in a knowledge database 404 and the embeddings are stored in a vector database 6240 (e.g., as illustrated in FIGS. 8A and 14). In some embodiments, documents from the knowledge database 404 are split into snippets and the snippets are tokenized and added to the vector database 6240. In some embodiments, snippets of consecutive text are extracted from each patient file and stored as chunks (snippets, where the term chunk and snippet are used interchangeably). In some embodiments, each chunk includes between 100 and 1000 characters. In some embodiments, the chunking (splitting) algorithm makes the chunks overlapping. In an example chunking algorithm, the chunks each consist of 512 characters and each chunk has 128 characters of overlap with another chunk extracted from the data in the knowledge database.

In some embodiments, the documents are split into chunks and/or snippets based on fixed character length (with optional overlap), fixed token length (with optional overlap), and/or section-based splitting (e.g., identifying section headings and splitting on those). In some embodiments, a prompt for the agent module 6102 includes retrieved patient context, inclusion/exclusion criteria, and a question to determine if the patient satisfies the criteria.

FIG. 8B shows an example similar to the example of FIG. 8A, except that in FIG. 8B data from the knowledge database (e.g., a question-and-answer dataset) is used to finetune the model component (e.g., the model API (e.g., for a model 228), a task-specific machine-learning model, etc.), in accordance with some embodiments. In some embodiments, the query embedding process is replaced, or supplemented, with other types of searching (e.g., Elasticsearch). In some embodiments, the other types of searching are performed on a database 108 that includes document snippets. In some embodiments, one or more conversation histories of a chat history associated with a user of the client device 102 are obtained from the client device 102 or the server system 106. For instance, in some embodiments, a respective agent module 6102 is associated with data module 240 that includes one or more conversation histories of various prompts and/or responses from a plurality of users.

In some embodiments, the vector similarity is based on a cosine distance, Euclidian distance, Manhattan distance, Jaccard distance, correlation distance, Chi-square distance, Mahalanobis distance, and/or a semantic comparison of embeddings. Consider $X^p=[X_1^p, \ldots, X_n^p]$ and $X^q=[X_1^p, \ldots, X_n^q]$ to be two embeddings to be compared. Also consider maxi and min; to be the maximum value and the minimum value of an $i^{th}$ attribute of an embedding in a data set, respectively. The distance between $X^p$ and $X^q$ is defined for each distance metric in Table 2 below:

TABLE 2

| Distance Metrics | |
|---|---|
| Type | Distance Metric |
| Euclidean | $d(X^p, X^q) = \sqrt{\sum_{i=1}^{n} (X_i^p - X_i^q)^2}$ |
| Manhattan | $d(X^p, X^q) = \sum_{i=1}^{n} \lvert X_i^p - X_i^q \rvert$ |
| Maximum Value | $d(X^p,X^q) = \text{argmax}_i \lvert X_i^p - X_i^q \rvert$ |
| Normalized Euclidean | $d(X^p, X^q) = \sqrt{\frac{1}{n}\sum_{i=1}^{n} \left(\frac{X_i^p - X_i^q}{\max_i - \min_i}\right)^2}$ |
| Normalized Manhattan | $d(X^p, X^q) = \frac{1}{n}\sum_{i=1}^{n} \frac{\lvert X_i^p - X_i^q \rvert}{\max_i - \min_i}$ |
| Normalized Maximum Value | $d(X^p, X^q) = \text{argmax}_i \frac{\lvert X_i^p - X_i^q \rvert}{\max_i - \min_i}$ |
| Dice Coefficient | $d(X^p, X^q) = 1 - \frac{2\sum_{i-1}^{n} X_i^p X_i^q}{\sum_{i-1}^{n} X_i^{p^2} + \sum_{i-1}^{n} X_i^{q^2}}$ |
| Cosine coefficient | $d(X^p, X^q) = 1 - \frac{\sum_{i-1}^{n} X_i^p X_i^q}{\sqrt{\sum_{i-1}^{n} X_i^{p^2} \cdot \sum_{i-1}^{n} X_i^{q^2}}}$ |
| Jaccard coefficient | $d(X^p, X^q) = 1 - \frac{\sum_{i-1}^{n} X_i^p X_i^q}{\sum_{i-1}^{n} X_i^{p^2} + \sum_{i-1}^{n} X_i^{q^2} - \sum_{i-1}^{n} X_i^p X_i^q}$ |

In some embodiments, the query, context, and chat history is formatted (e.g., vectorized) and input to the model 228. In some embodiments, the response from the model component is parsed and formatted by the agent module 6102 and the formatted response is transmitted to the client device 102.

Figure 9A:
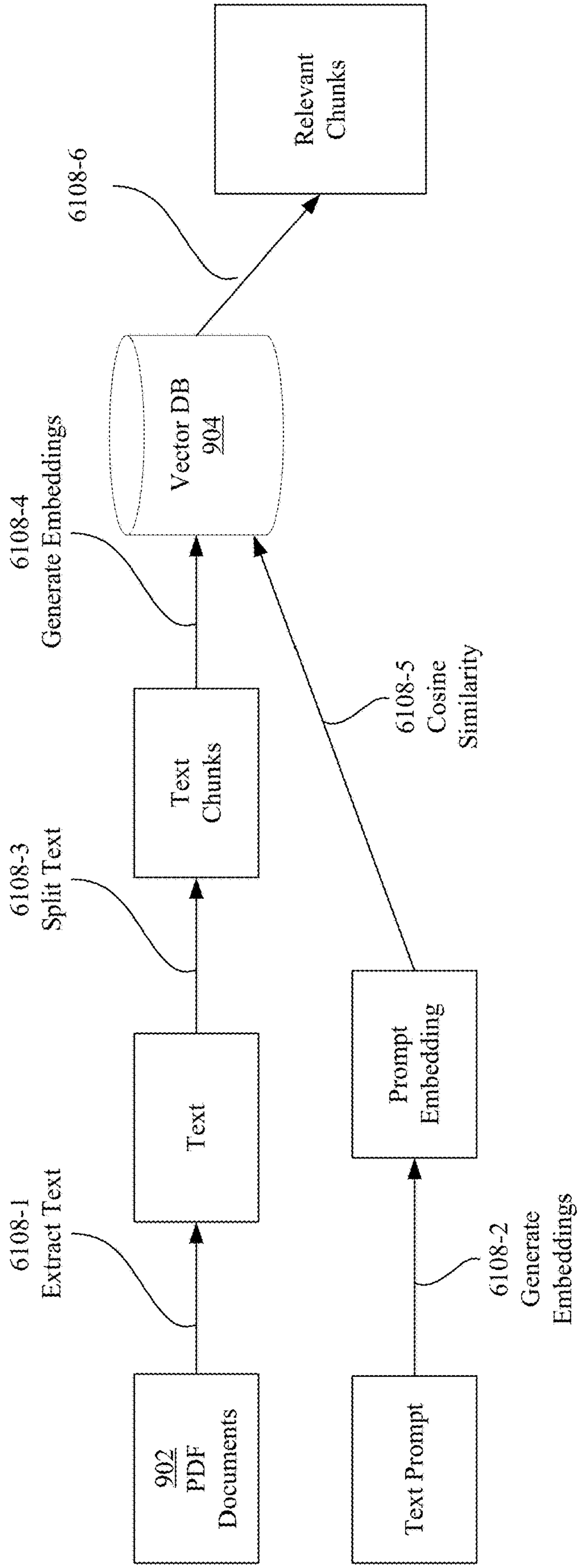
FIGS. 9A-9C illustrate example processes for data vectorization and query processing in accordance with some embodiments.
Figure 9B:
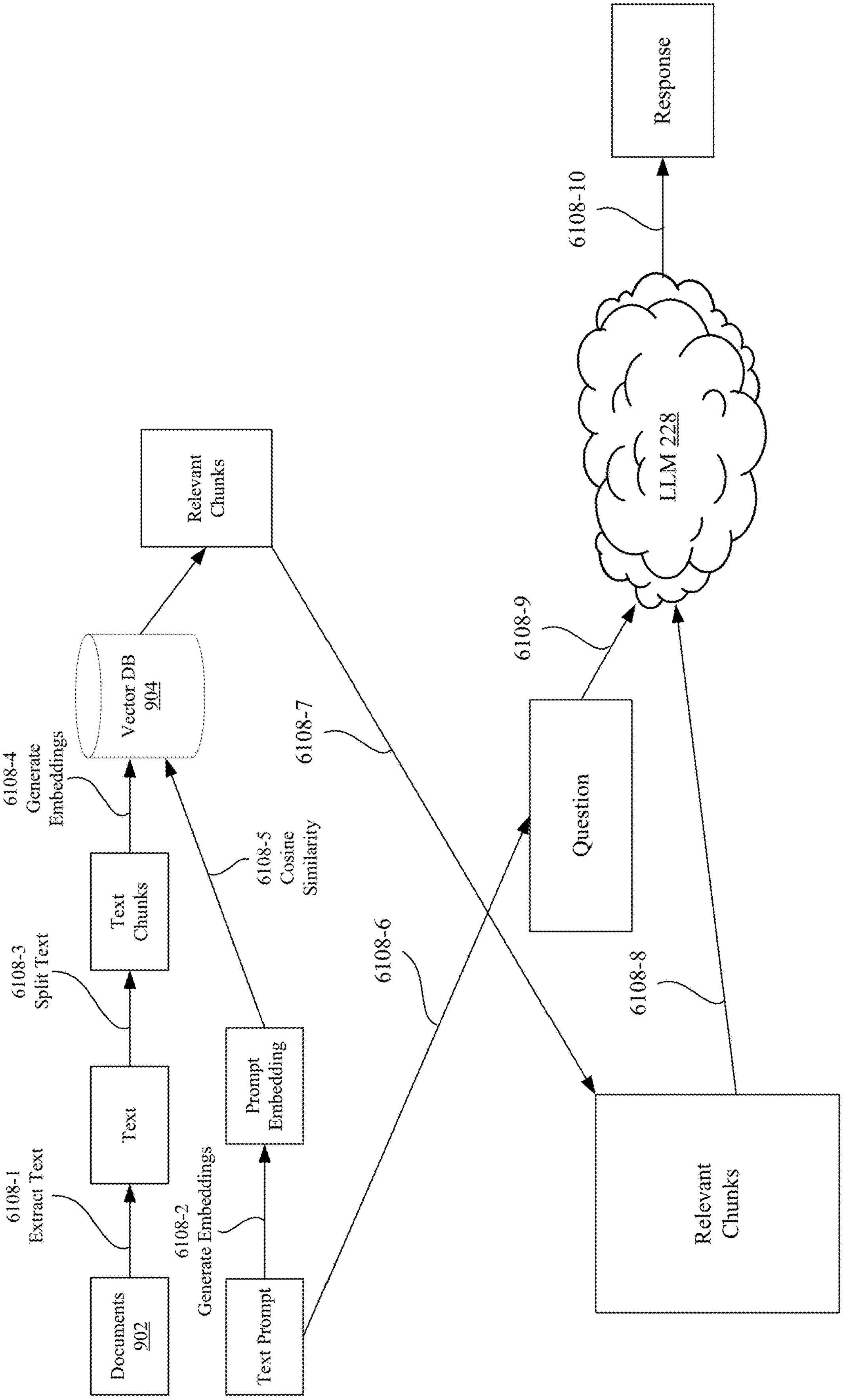
Figure 9C:
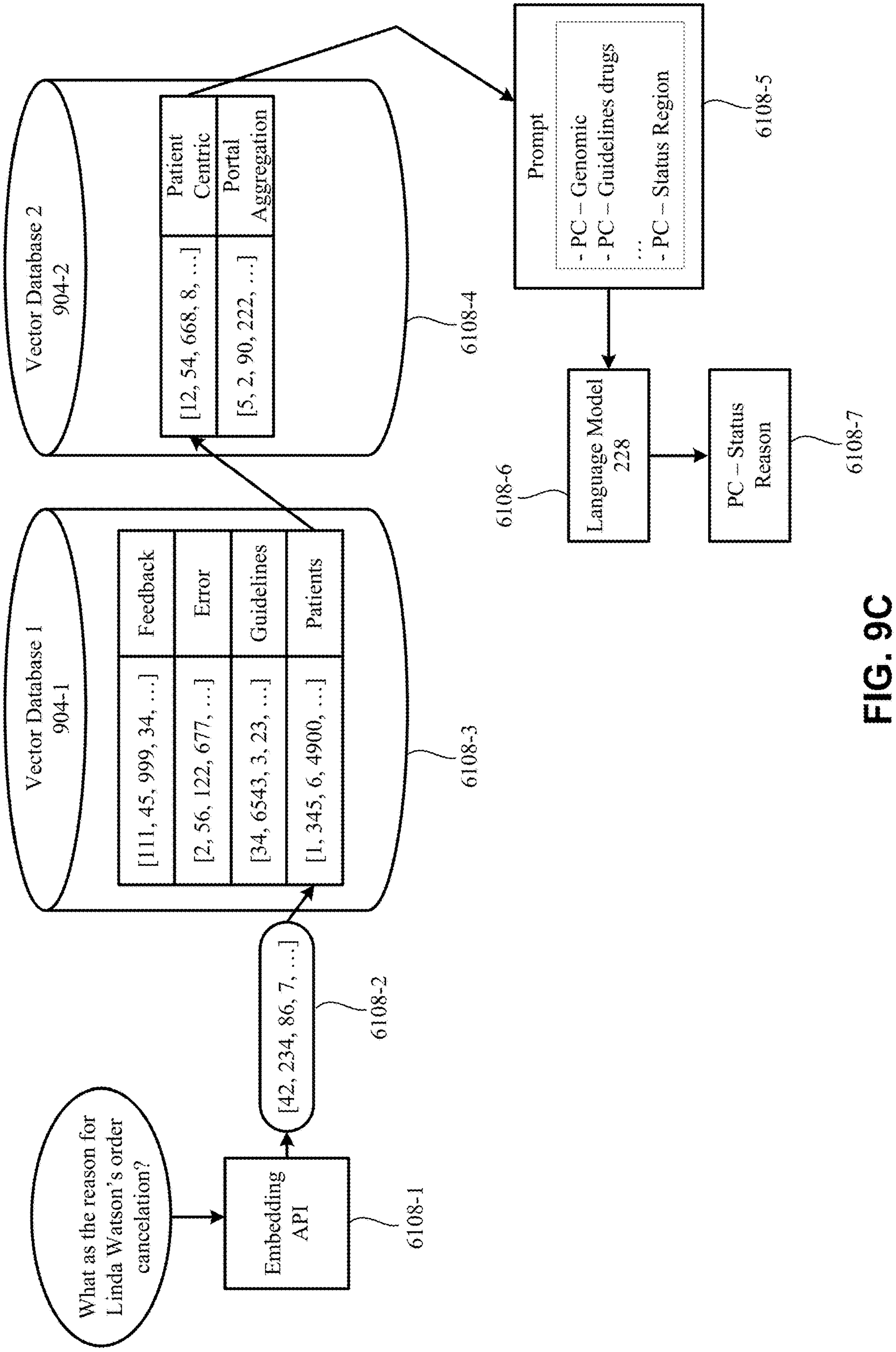

FIGS. 9A-9C illustrate example processes for data vectorization and query processing in accordance with some embodiments. FIG. 9A shows a process of generating embeddings from documents (e.g., PDF documents 902). In some embodiments, the documents are obtained from a medical database (e.g., clinical trial protocol documents from a clinical trial database), which may be a live collection of medical data (e.g., including a means for obtaining real-time updates to the data source). In some embodiments, embeddings are also generated from metadata corresponding to the documents and stored in a vector database 904.

FIG. 9A also shows a process of generating a question embedding and using a cosine similarity with vectors in a vector database 6240 to identify relevant chunks of the documents. It will be appreciated that, rather than using the cosine similarity search, a distance metric, such as the distance metrics discussed above, can be used. FIG. 9B shows the question and relevant chunks being input to a large language model (LLM) and the LLM generating an answer (e.g., the relevant chunks are used as context by the LLM for answering the question).

FIG. 9C shows an example where a query vector is generated from a query via an embedding API. The query vector is used to identify a similar vector, denoted as "Patients" in a first vector database. The similar vector from the first vector database (and/or the query vector) is used to identify a second similar vector in a second vector database. The query vector and the second similar vector (and optionally the first similar vector) are provided to a language model via a prompt. The language model outputs an answer to the query, which is, optionally reformatted, and transmitted to the user. In the example of FIG. 9C the query is "what is the reason for Linda Watson's order cancelation" and the language model outputs a status reason as the answer.

As discussed above, in some embodiments, an agent module (e.g., the backend component) is configured to perform intent matching and/or parameter extraction on the user queries and requests. In some embodiments, the intent is assumed (e.g., the agent module is configured for a specific task). In some embodiments, the agent module extracts domain-specific parameters. For an example query "show patients with MSI high, TMB less than 20, which have been diagnosed with central neurocytoma in the past four months" the extracted parameters may be ["mis": "high", "tmb": "{"lt" "20"}, "diagnosis": "central neurocytoma", "date_range": { . . . }].

In some embodiments, an agent module is configured to automatically populate a structured query (e.g., an SQL query) from a user query and transmit the structured query to a structured database. For example, the agent module may obtain a particular schema, obtain inclusion and exclusion criteria, and generate a structured query for a database based on the criteria identified from the query and the schema of the database to be searched. In some embodiments, the structured query is transmitted to another agent module or component to interact with one or more structured databases. For example, a user query of "how many patients are older than 18?" may be converted to an SQL query "SELECT COUNT (*) FROM demographic WHERE age >18."

An example of configuration parameters 6110 of one or more nodes 6108 of an agent module 6102 for a process for finding patients that meet inclusion/exclusion criteria for a cohort (e.g., using the process shown in FIG. 9B) is shown below in Example 6.

Example 6 - Example Configuration Parameters

```
{
'cache_path':
'cohort_name':
'n_patients':
'embedding_batch_size':
'device':
'doc_chunk_size':
'doc_chunk_overlap':
'text_seperators':
'embedding_model':
'instructor_embed_instruction':
'instructor_query_instruction':
'prompt_template_name':
'generator_queries':
'vector_store_db_name':
'generator_model':
'n_retrieved_docs':
'temperature':
'top_p':
'tok_k':
'max_output_tokens':
'output_parser':
'chunking_config_hash':
'embedding_config_hash':
}
```

Considering the extensive volume of text contained within a real-world data (RWD) warehouse of EHRs, it becomes impractical to process the entirety of a patient's clinical notes within the context window of a model (e.g., an LLM). In some embodiments, this challenge is addressed by implementing a retrieval-augmented generative (RAG) approach to identify relevant portions of EHR text, e.g., relevant portions of unstructured clinical notes. A RAG approach proves to be more efficient and effective than providing the model with larger context windows. In some embodiments, RAG is a two-step process that involves retrieving relevant documents from a corpus (e.g., a large corpus with thousands or millions of documents) and then feeding the retrieved documents into a model to generate an analysis and response.

In some embodiments, clinical notes from an EHR are divided into individual segments, also referred to herein as snippets (e.g., chunk, as illustrated in FIG. 9A). One example method for segmenting unstructured clinical data (e.g., clinical notes) includes tokenizing the unstructured clinical data to obtain a plurality of tokens and segmenting the plurality of tokens to obtain a plurality of segments (snippets), e.g., where each respective segment in the plurality of segments has approximately a same number of tokens.

In some embodiments, the individual snippets are evaluated to determine whether they include information pertinent to determining whether the subject has a target medical condition. In some embodiments, the evaluation is performed by natural language processing. In some embodiments, the evaluation is performed based on pattern recognition of regular expressions (Regex) related to the target medical condition. In some embodiments, the use of Regex avoids introducing bias through additional hyperparameter tuning and narrows the focus to assessing the model's capability in diagnosing diseases. However, other retrieval models can be used instead of, or in addition to, Regex. For example, in some embodiments, the snippets are evaluated using Term Frequency-Inverse Document Frequency. In some embodiments, the snippets are evaluated using Cohere's re-rank. In some embodiments, the snippets are evaluated using Instructor embeddings.

In some embodiments, the snippets are retrieved by using a model (e.g., an LLM) to identify portions of a medical record that include information relating to the target medical condition. In some embodiments, a prompt is given to the model to identify any portion of a medical record that is relevant to an indication of the disease diagnosis. In some embodiments, the identified portion (e.g., snippet) is defined to be within a specific range of characters. For example, in some embodiments, the identified portion must be from X to Y characters in length, where X is a minimum length and Y is a maximum length. In some embodiments, the identified portion (e.g., snippet) is defined to be within a specific range of token length. For example, in some embodiments, the identified portion must be from X to Y tokens in length, where X is a minimum length and Y is a maximum length. In some embodiments, the identified portion (e.g., snippet) must satisfy a relevance threshold. For instance, in some embodiments, a set of candidate portions are identified and ranked in terms of relevance to the medical condition relative to each other and the top X number of candidate portions are selected for retrieval. In some embodiments, the ranking is limited to portions obtained from a single document within a medical record. In some embodiments, the ranking is applied across a plurality of documents within the medical record.

While the RAG approach reduces the amount of text processed by the model, RWD clinical notes often comprise many pages of text. Consequently, the Regex retriever is still likely to return a large number of snippets determined to include information pertinent to determining whether the subject has a target medical condition, which may exceed the model's context window. In some embodiments, a map-reduce approach is employed to address this issue. Map-reduce allows for parallel execution of the model on individual snippets, improving efficiency and reducing processing time. It also facilitates handling of large numbers of identified snippets by distributing the processing load across multiple iterations. By generating individual outputs for each snippet, the chain can extract specific information that contributes to a more comprehensive final result.

Accordingly, in some embodiments, each identified snippet is presented as context to the model, along with a set of instructions to facilitate decision-making. In some embodiments, the model is asked through a prompt to indicate whether the snippet indicates that the subject has PH. In some embodiments, the prompt instructs the model to answer in a yes or no form, or in a yes, no, or uncertain form. In some embodiments, the prompt further instructs the model to support its answer with evidence. In some embodiments, by prompting the model to support its answer with evidence, the model will essentially summarize the relevant portion of the snippet, reducing the context that will be fed into a second model (e.g., in a map-reduce model chain).

In some embodiments, the prompt includes a statement that steers the model. For example, referring again to the example of phenotyping for pulmonary hypertension, in some embodiments, the prompt instructs the model to count a 'possible' case of PH as 'no' answer. In some embodiments, the prompt instructs the model to count a clinical note of a history of PH as a 'yes' answer. In some embodiments, the model is further provided with examples of evidence that indicate the presence of the target medical condition. In some embodiments, the model is further provided with examples of evidence that do not indicate the presence of the target medical condition. In some embodiments, the model is further provided with evidence that indicate the absence of the target medical condition. In some embodiments, the prompt includes a Chain-of-Thought (CoT) phrase. Use of CoT enhances reasoning by models.

Outputs generated for individual snippets by the model are then aggregated to formulate the final decision. In some embodiments, the aggregation is performed using a model. In some embodiments, the model is provided the outputs from the snippet evaluation as context and is provided the same instructional prompts as for the evaluation of the individual snippets. In some embodiments, the model is provided the outputs from the snippet evaluation as context but is provided different instructional prompts as for the evaluation of the individual snippets. For example, in some embodiments, the model is asked whether any of the outputs from the snippet evaluation indicate a positive diagnosis for the target medical condition. In some embodiments, the aggregation is a max aggregation function, which checks if any of the individual snippet queries returned a positive diagnosis and, if so, assigns a positive label to the patient as whole.

In some embodiments, the snippet evaluation and aggregation step are performed using the same model. In some embodiments, the snippet evaluation and aggregation steps are performed by the model after a single prompt asking the model whether the subject has the medical condition based on evidence contained within the snippets. In some embodiments, the snippet evaluation and aggregation step are performed in series, such that the model is provided separate prompts for the two steps. In some embodiments, the snippet evaluation and aggregation step are performed using different models.

In some embodiments, a user prompt is received at an API with instructions to retrieve snippets and then present them to an AI component responsive to a user prompt. In some embodiments, the API receives a prompt relating to a first subject or group of subjects. In some embodiments, medical records for the subject or group of subjects have already been parsed (snippetized) and snippets saved to a curated database. In some embodiments, the snippitized records have also been sorted to identify snippets related to a target medical condition, e.g., in the curated database. In some such cases, the API retrieves the presorted snippets from the database and presents them to an AI component. In other embodiments, where the medical records have not been snippetized, the API retrieves the medical record and directs a module (e.g., a natural language processing module) to parse the medical record into snippets and optionally sort the snippets to identify those snippets related to the target medical condition. Similarly, in some embodiments where the medical records have been snippetized but have not been sorted, the API retrieves the snippets and directs a module (e.g., a natural language processing module) to identify those snippets related to the target medical condition. The API then presents the identified snippets to the AI component (e.g., a model such as an LLM) in parallel (e.g., via separate instances of the AI component) or sequentially and asks the AI component whether each snippet indicates that the subject has the target medical condition, and optionally to provide reasoning for the answer. The AI component generates answers for each of the snippets and optionally the secondary logic (reasoning) for each answer. The API also includes instructions for aggregating the component answers into a final answer as to whether the subject has the target medical condition. In some embodiments, the API asks the model to aggregate the component answers, and optional secondary logic, such that the AI component may not provide component answers externally, but rather returns a single answer for the subject, which is returned as the response to the API prompt containing the query.

Figure 9D:
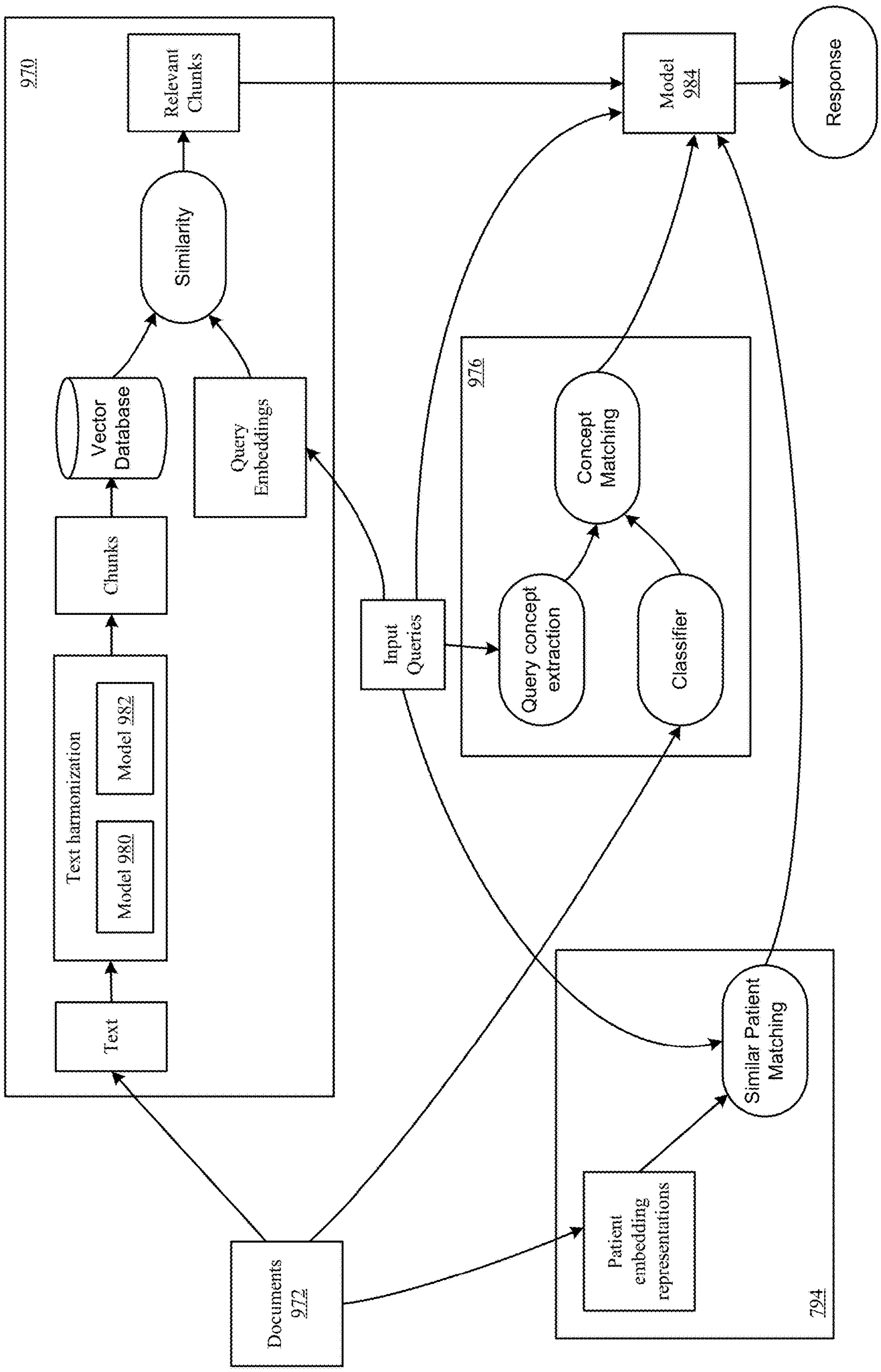
FIG. 9D illustrate an example process for patient querying in accordance with some embodiments.

FIG. 9D illustrate an example process for patient querying in accordance with some embodiments. In the example of FIG. 9D, document information from documents 972 (e.g., patient documents) is provided to systems 970, 974, and 976 (e.g., agent modules or assemblies). In some embodiments, the documents 972 includes one or more types of documents (e.g., PDF documents, image documents, text documents, word processor documents, etc.). In some embodiments, the documents 972 comprise one or more data collections and correspond to one or more databases.

In accordance with some embodiments, the system 970 (e.g., a first agent module) is configured to extract text from the documents 972 (e.g., using various text recognition and extraction techniques). The system 970 may be considered as an example of a concept-specific retrieval assembly. The extract text is harmonized (e.g., using a model 980 and a model 982). In some embodiments, the model 980 is configured to convert image data into textual data (e.g., extract text chunks that may contain lossy OCR content). In some embodiments, the model 982 is a document classification model (e.g., configured to identify chunks with relevant information and discard chunks without relevant information). The extracted text is chunked and stored as embeddings in a vector database (e.g., using processes described above with respect to FIGS. 9A-9C). The system 970 also obtains query embeddings from user queries and identifies similar embeddings in the vector database to output text chunks that are relevant to the user queries. In some embodiments, the user queries are generated based on inclusion/exclusion (IE) criteria. In some embodiments, the system 970 is configured to return text chunks corresponding to a particular patient. For example, the system 970 obtains a patient identifier from the user queries and outputs only text chunks mapped to the patient identifier.

In accordance with some embodiments, the system 974 (e.g., a second agent module) is configured to obtain patient embedding representations from the documents 972 and identify patients that are similar to a patient identified or characterized in the input queries. In some embodiments, the system 974 is configured to identify patients that meet a set of IE criteria (e.g., a set of criteria provided in the input queries or by another agent module). In some embodiments, the system 974 is configured to identify patient cluster(s) associated with the set of IE criteria (or similar to the IE criteria).

In accordance with some embodiments, the system 976 (e.g., a third agent module) is configured to classify the documents 972 and identify a subset of the documents that have a classification that matches (or is similar to) a classification extracted from the input queries. In some embodiments, for the identified subset of documents, the system 976 is configured to provide document identifiers, document links, and/or the documents themselves.

In the example of FIG. 9D, the outputs of the systems 970, 974, and 976 are provided to a model 984 (e.g., a large language model configured to understand user queries) along with information from the user queries. In some embodiments, the model 984 is configured to provide an output that incorporates information from each of the systems 970, 974, and 976 (e.g., a summary of the information from the other systems). In some embodiments, the model 984 is configured to provide a natural language output for a user.

Figure 10A:
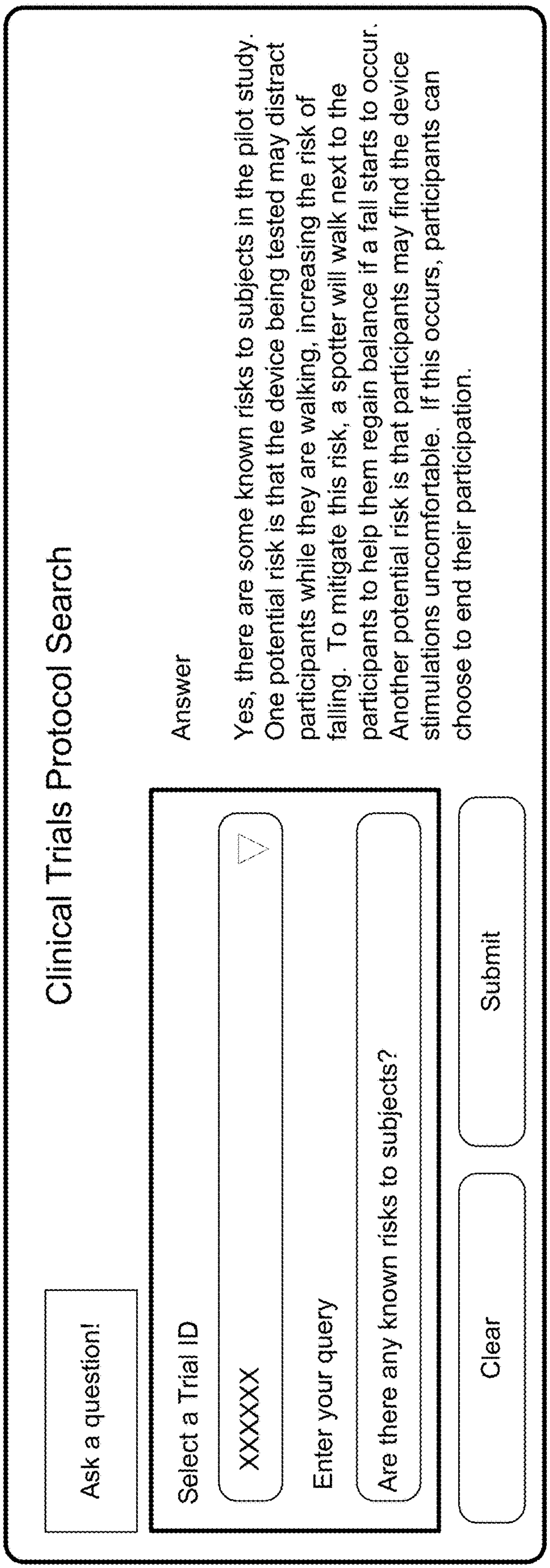
FIGS. 10A-10C illustrate example user interfaces for agent-based searching in accordance with some embodiments.
Figure 10B:
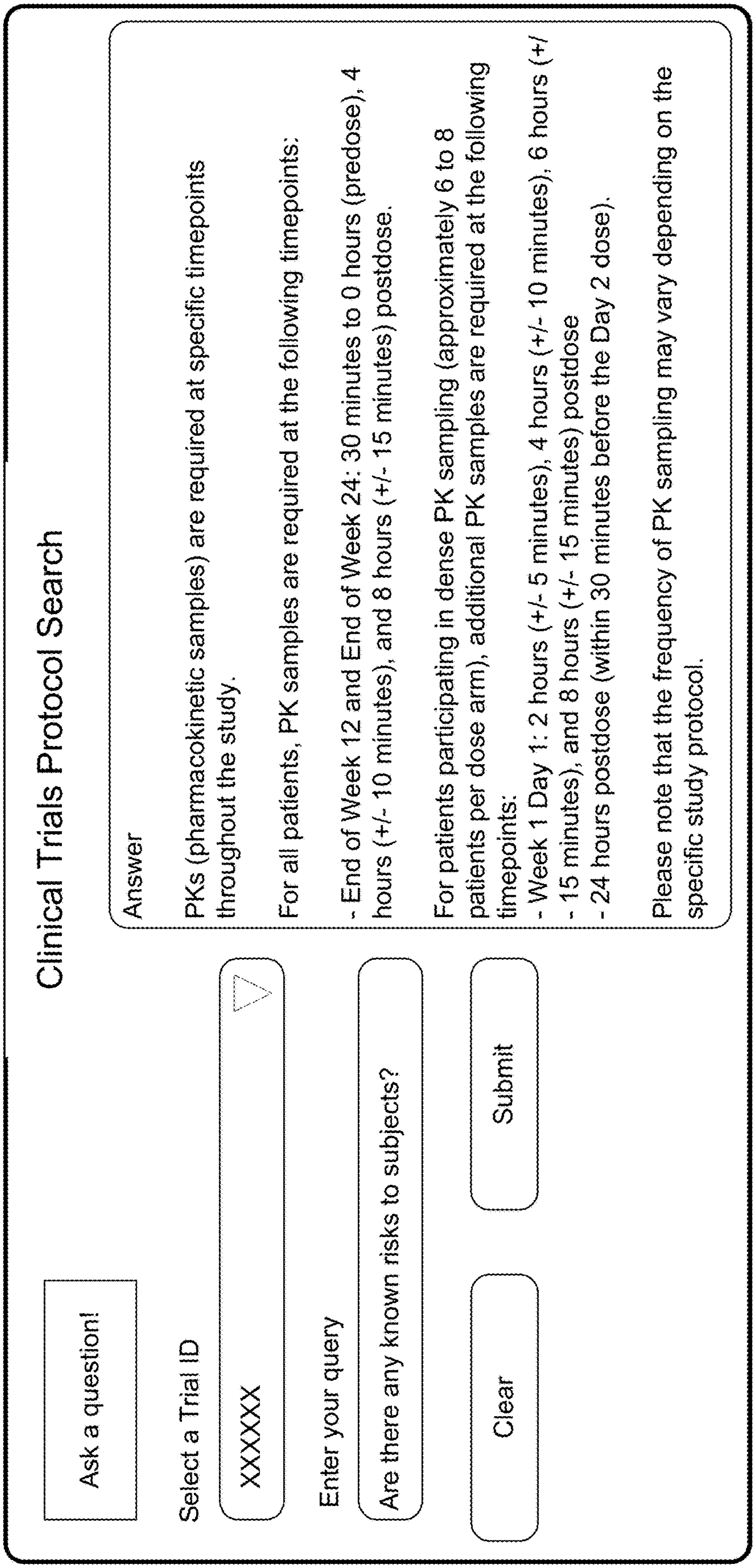
Figure 10C:
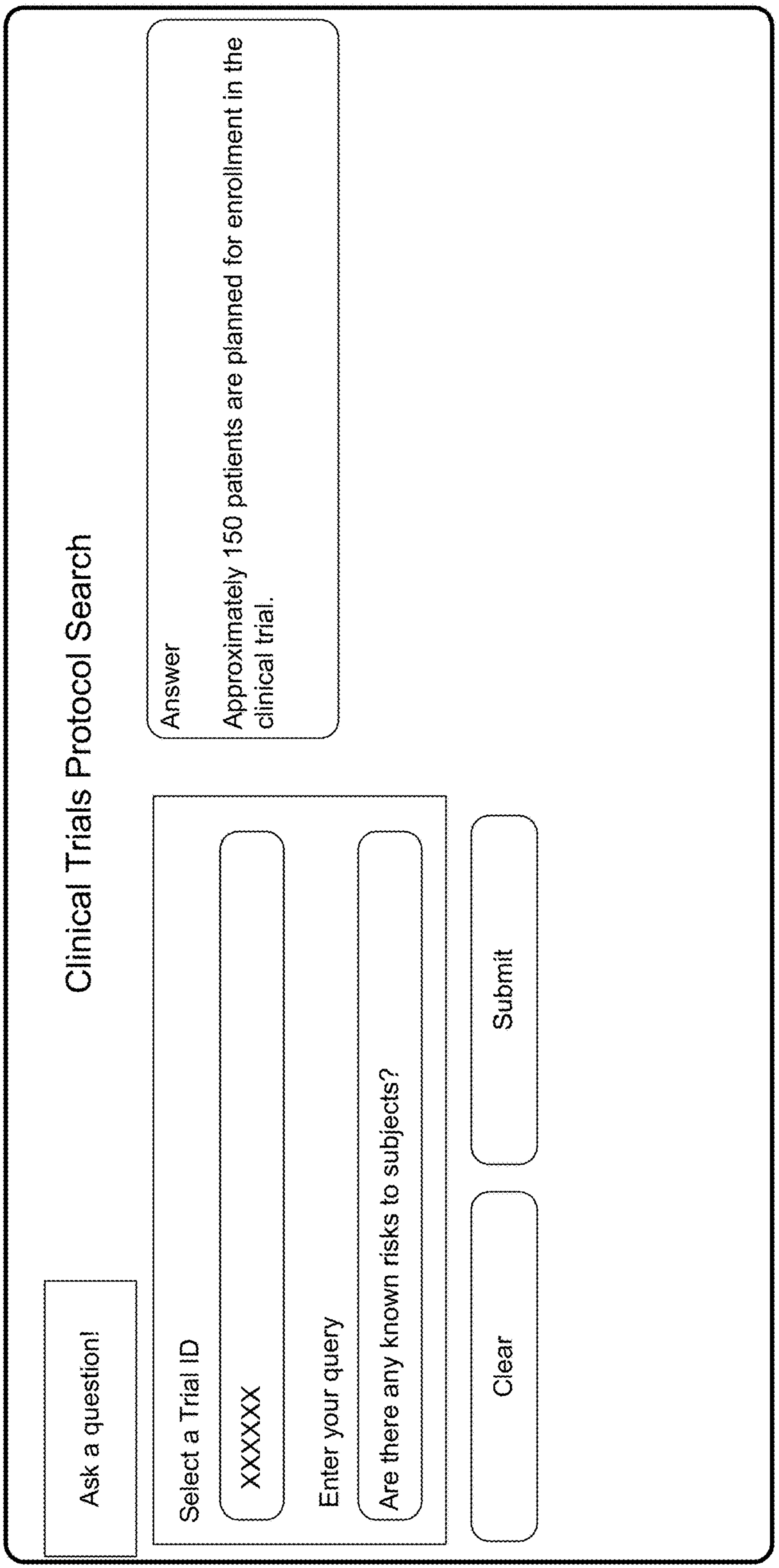

FIGS. 10A-10C illustrate example user interfaces for agent-based searching in accordance with some embodiments. In the examples of FIGS. 10A-10C, a trial identifier is selected and a query for the trial is input by a user. The trial identifier and the query are received by an agent module (e.g., a clinical-trials agent module) and the agent module provides a natural language response. In some embodiments, the trial query is received without a trial identifier (e.g., the query is received with a subject identifier and/or other information about the trial). In some embodiments, an agent module identifies the corresponding trial based on information in the query. For example, a first agent module identifies the trial, and a second agent module applies the query to the trial (and optionally formats the response for the user).

In some embodiments a digital assistant (e.g., including a super-agent module and a cohort-building agent module) is configured to allow users to efficiently and accurately narrow down a set of subjects (e.g., patients) within a subject dataset and/or verify that the set of subjects is the desired cohort. For example, the digital assistant is configured to assist users with determining (i) whether an existing cohort is accurate (e.g., is the set of subjects responsive to the user's research question), (ii) whether the existing cohort is missing some subjects from the patient dataset, and/or (iii) whether the user has identified the full and accurate patient records for the set of subjects. In some embodiments, users interact with the digital assistant via a search user interface. In some embodiments, the digital assistant is configured to convert natural language inputs from the users into structured queries (e.g., by identifying intent and/or query parameters).

Figure 11A:
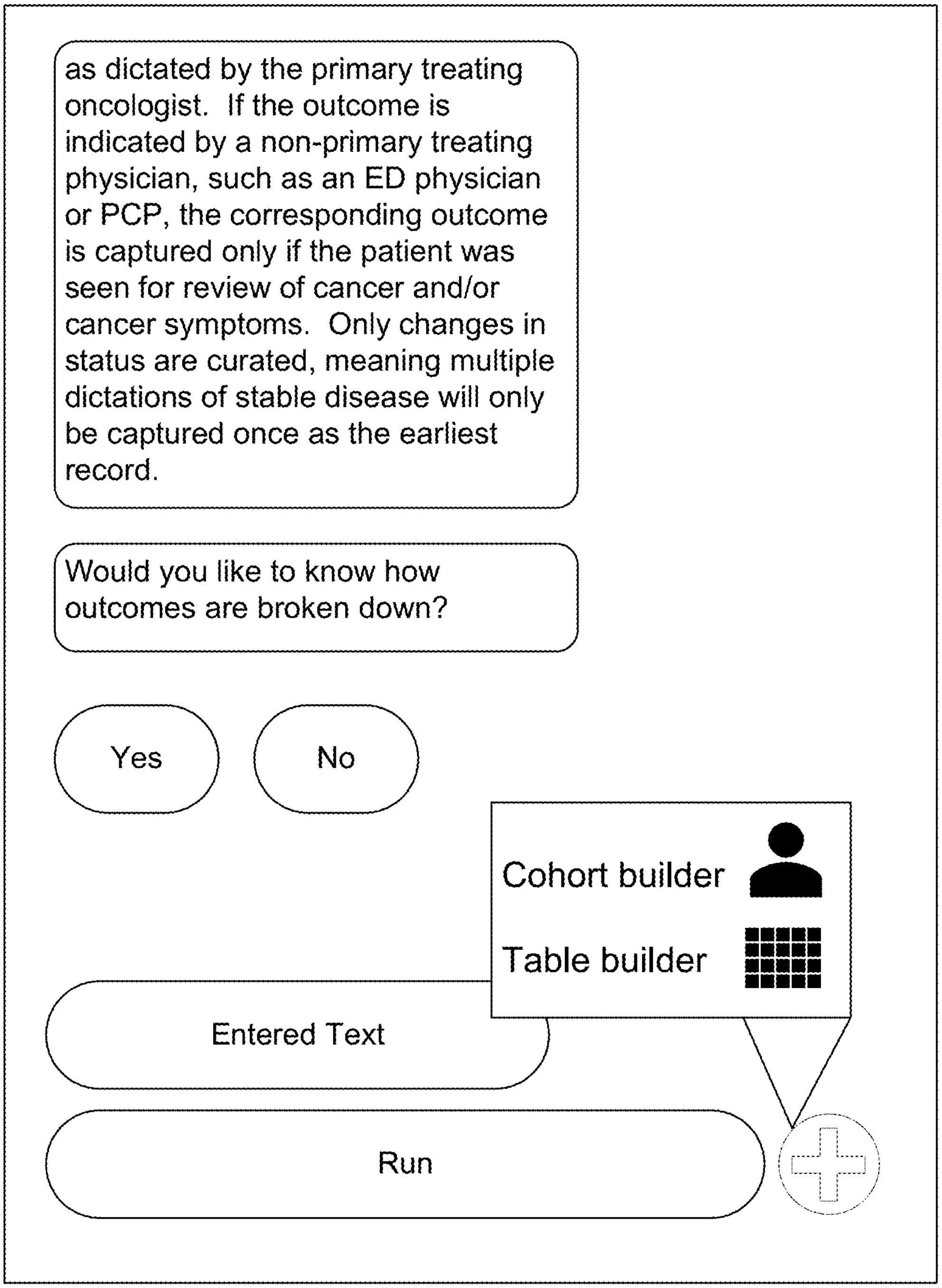
FIGS. 11A-11C illustrate example user interfaces for interacting with a digital assistant in accordance with some embodiments.
Figure 11B:
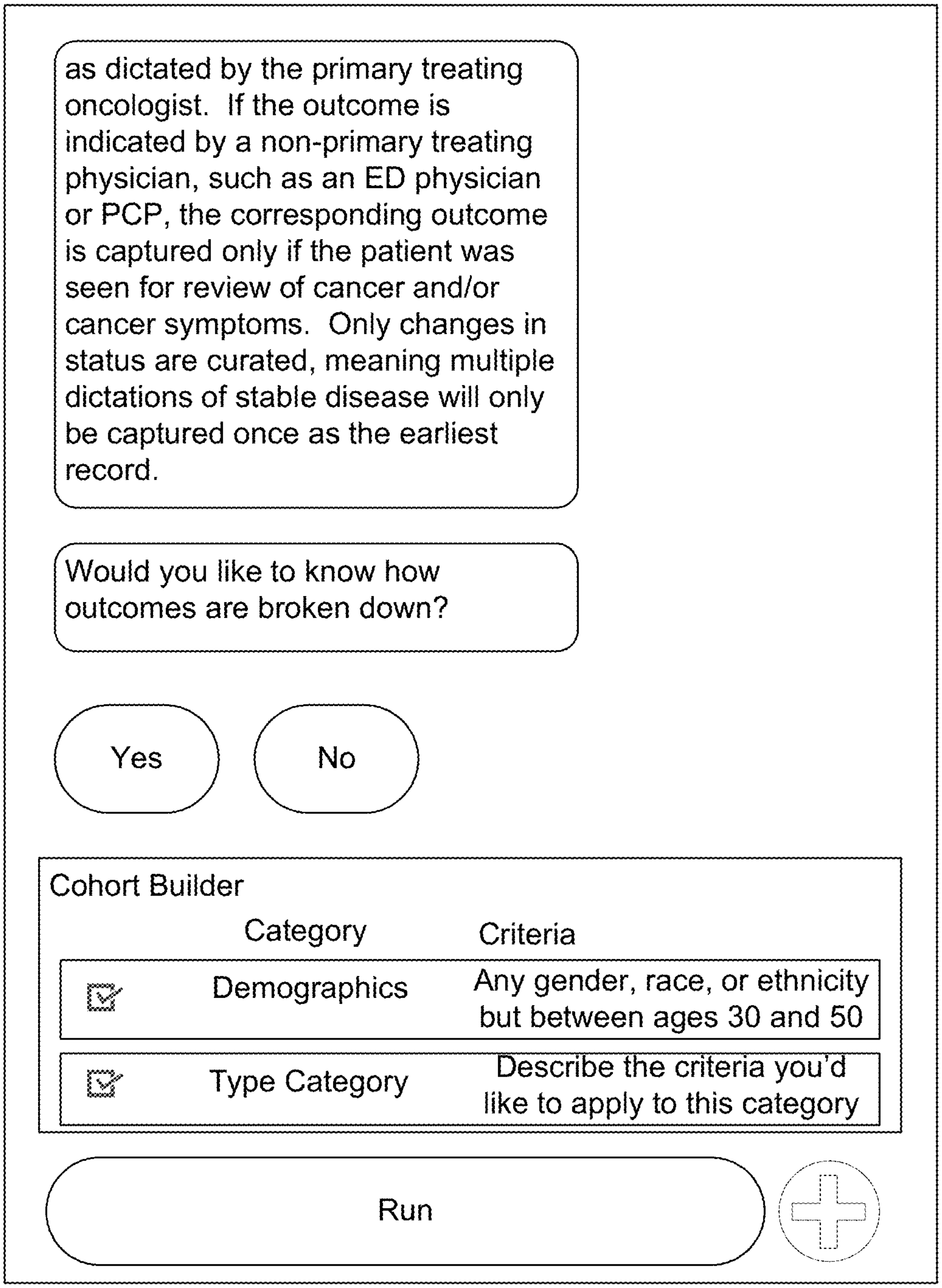
Figure 11C:
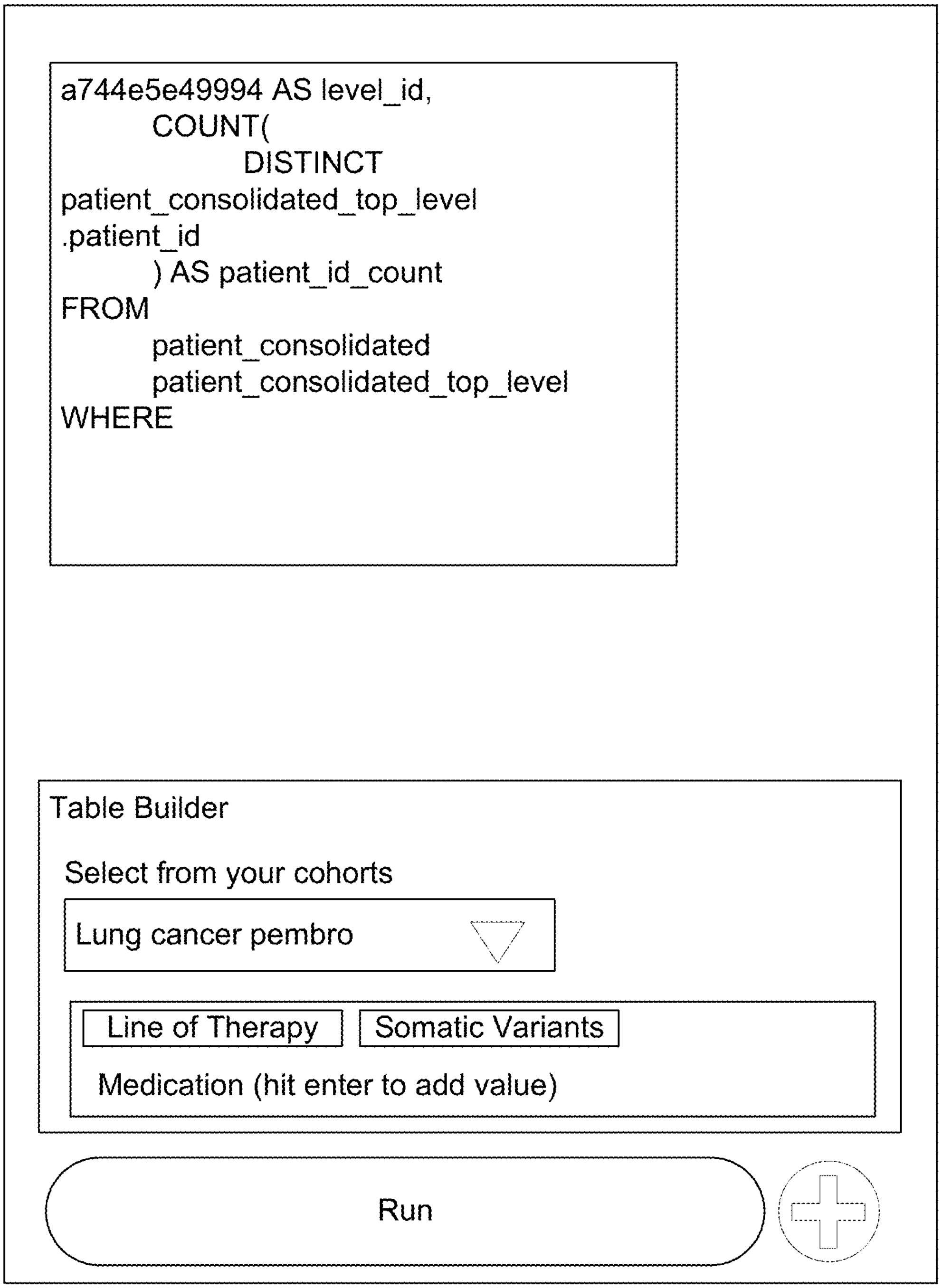

In some embodiments, the digital assistant (or a cohort-building agent module of the digital assistant) includes one or more templates and/or tools to assist users. For example, a cohort builder template and/or a table builder template may be provided (e.g., as illustrated in FIGS. 11A-11C). These templates can provide information used by a user for asking a digital assistant to assist with their task. For example, with the table builder template, a user could select from their deliveries and then type in various data concepts that they'd like to pull across numerous tables in their delivery into a primary table that they can use for their analysis. With the template, the digital assistant is configured to determine which delivery the user is working with and therefore which columns are available, giving it a higher chance of successfully completing the task of creating a new table for the user. As mentioned above, in some embodiments, the digital assistant is, or includes, a super-agent module configured to intake user queries and identify appropriate agent modules for addressing the queries (e.g., identifying a cohort-building agent module to answer cohort-related queries).

In some embodiments, the digital assistant comprises an ensemble of agent modules. In some embodiments, the digital assistant includes a frontend agent module (e.g., including a language model) configured to identify commands and/or tokens in user queries. In some embodiments, the digital assistant includes a routing agent module configured to route subsets of the commands and/or tokens to appropriate agent modules (e.g., based on the query intent, previous interactions, and/or information about the particular user or subject). In some embodiments, the digital assistant (and/or one or more of the agent modules of the digital assistant) has access to information about the patient or subject associated with a query or command and the digital assistant tailors the response (e.g., personalizes the response) to the patient or subject. In some embodiments, the digital assistant maintains information about previous interactions (e.g., previous commands, queries, and responses) and uses the maintained information to inform subsequent interactions. In some embodiments, the digital assistant uses information about previous interactions as context information for a query. In some embodiments, the digital assistant uses information about the patient or subject (e.g., age, gender, medical history, current medications, etc.) as context information for the query. n some embodiments, the digital assistant uses information about the user (e.g., a medical professional) as context information for the query (e.g., the user's field of research, current patients, medical specialties, medical network, access to medical equipment, etc.).

FIGS. 11A-11C illustrate example user interfaces for interacting with a digital assistant in accordance with some embodiments. FIG. 11A shows an interface for interacting with a digital assistant. The interface in FIG. 11A includes an affordance for opening a cohort builder tool or a table builder tool. FIG. 11B shows the digital assistant interface including a section with the cohort builder tool. FIG. 11C shows the digital assistant interface including a section with the table builder tool. As illustrated by FIGS. 11A-11C, the digital assistant may be provided with various tools that are selected by the user (e.g., the cohort builder in FIG. 11B and the table builder in FIG. 11C). In some embodiments, the digital provides different tools to the user based on the user's requests and/or queries. In some embodiments, each tool corresponds to a different agent module of the digital assistant. In some embodiments, a single agent module includes multiple tools. In some embodiments, the digital assistant (or a super-agent module of the digital assistant) identifies tools from a set of pre-generated tools based on user intent and provides the user with access to the tools. In some embodiments, the digital assistant provides a selected tool with information about the query, the user, a patient, a subject, and/or other context information (e.g., to pre-populate one or more fields of the tool and/or otherwise configure the tool). In some embodiments, the digital assistant uses a routing agent module to communicate select information with the tool.

FIGS. 12A-12D illustrate example user interfaces for interacting with a digital assistant in accordance with some embodiments. In some embodiments, the digital assistant is composed of one or more agent modules (e.g., task-specific agent modules). In some embodiments, the digital assistant is communicatively coupled with one or more agent modules (e.g., task-specific agent modules). For example, the digital assistant may include an API agent module (e.g., a frontend module) to receive/parse user queries and commands, a super-agent module to identify the appropriate agent modules and/or tools for responding to respective queries and/or commands, and a routing agent module to transmit information to and from the identified modules and tools. In some embodiments, the super-agent module is configured to compile information from the identified modules and tools to generate a complete response to a respective query or command. In some embodiments, the API agent module is configured to transform the complete response to a natural language response and to provide the natural language response to the user. In some embodiments the digital assistant includes one or more transform agent modules to transform data into a format and/or structure required for a particular tool. In some embodiments, a transform agent module is configured to validate the data to ensure it is appropriate for the corresponding tool (e.g., and provide error information when the data is not appropriate). In some embodiments, the digital assistant is communicatively coupled to two or more databases (e.g., the external database(s) 108 and/or the database(s) 400 in FIG. 4). In some embodiments, the digital assistant includes one or more interfacing agent modules configured to interface with corresponding databases.

Figure 13:
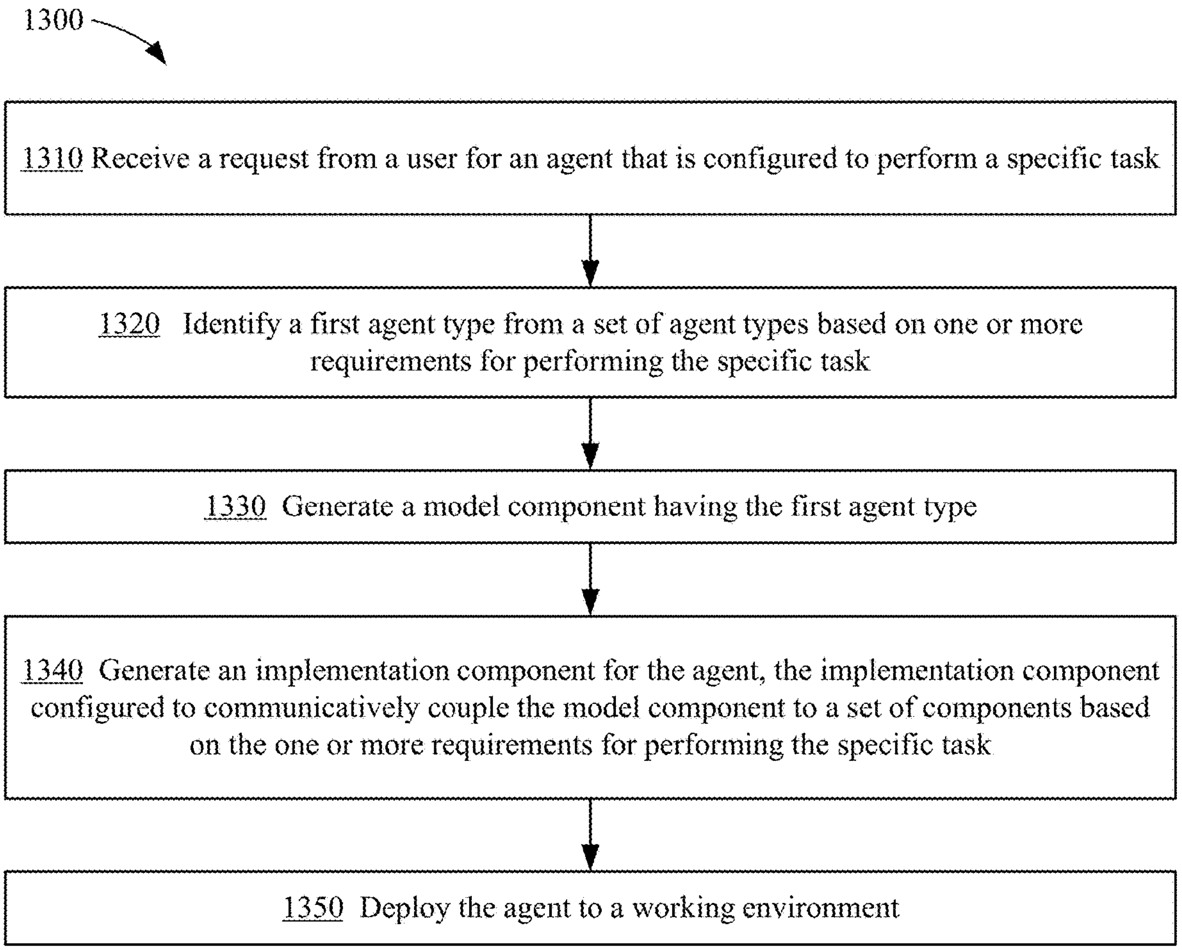
FIG. 13 is a flow diagram illustrating an example method of deploying an agent in accordance with some embodiments.

FIG. 13 is a flow diagram illustrating an example method 1300 of deploying an agent module in accordance with some embodiments. The method 1300 is performed at a computing system (e.g., a client device, server system, and/or service platform) having one or more processors (e.g., the CPUs 202 and/or 302) and memory (e.g., the memory 218 and/or 310). In some embodiments, the memory stores one or more programs configured for execution by the one or more processors. At least some of the operations shown in FIG. 13 correspond to instructions stored in a computer memory or a computer-readable storage medium. In some embodiments, the computing system is the platform 100, the client device(s) 102, and/or the server system 106.

The computing system receives (1310) a request from a user for an agent module that is configured to perform a specific task. For example, the specific task may be customer support assistance, cohort building, or writing code. In some embodiments, the request includes one or more requirements for performing the specific task. In some embodiments, the request identifies a desired agent type for the agent. An example task includes identifying inclusion and exclusion criteria from a protocol document and generating a structured query based on the identified inclusion and exclusion criteria. Another example task includes generating an inclusion and exclusion criteria table (or sheet) and/or generating a set of inclusion and exclusion criteria (e.g., as YAML annotation) for storage in a database. Other example tasks include identifying inclusion and/or exclusion for trials, patient discovery and feasibility, and medical document generation.

As mentioned above, example agent types for the agent modules include, amongst others, (i) an API broker agent configured to interact with an API in response to natural language inputs, (ii) a document search agent configured to interact with a database and/or index in response to natural language inputs, (iii) a model broker agent that has access and knowledge to interact with machine learning models, (iv) a template document generator agent configured to generate content in the format of a template, (v) a copilot assistant agent configured to be embedded in an application and use a knowledge base and/or question and answer pairs to assist a user of the application, (vi) a data product producer agent configured to interpret schema-specific data products and answer questions, find specific data products, and/or create new data products, (vii) a composite agent configured to act as an orchestrator of multiple subordinate agents, (viii) a natural language search agent that allows for open-ended questions answering and summarization with multi-step conversation support, (ix) an SQL database agent configured to query one or more SQL databases, tables, and views in response to a natural language input, (x) a vertex database agent configured to query one or more vector databases in response to natural language input, and (xi) a feasibility agent configured to search a multimodal library of patient data for a specific set of attributes provided in natural language.

The computing system identifies (1320) a first agent type from a set of agent types based on one or more requirements for performing the specific task. For example, the first type of agent may be a tool-using agent, a chain agent (e.g., a super agent), a routing agent, and/or a transform-enabled agent. In some embodiments, each agent type of the set of agent types corresponds to a respective language model. In some embodiments, each agent type corresponds to a different model (e.g., a different type of model, a different size of model, and/or a differently fine-tuned model).

The computing system generates (1330) a model component having the first agent type. In some embodiments, generating the model component includes generating a set of operating instructions for the model component. In some embodiments, generating the model component includes fine tuning and/or otherwise training a model of the model component.

The computing system generates (1340) an implementation component for the agent, the implementation component configured to communicatively couple the model component to a set of components based on the one or more requirements for performing the specific task. In some embodiments, the set of components include one or more of: a set of data sources, a set of tools, and a set of output components.

The computing system deploys (1350) the agent to a working environment (e.g., a test environment or a production environment). In some embodiments, the agent consists of the model component and the implementation component. An example agent receives as input (i) a prompt for a clinical trial, (ii) historical feasibility studies, (iii) clinical data, and/or (iv) therapies data and is configured to output a set of identified subjects for the clinical trial. Another example agent is configured to assist a clinical development researcher. The agent (e.g., the implementation component) is configured to identity a user intent from a user query/request and provide (i) potential query expansion, (ii) identify corresponding concepts, interfaces, and/or datasets, (iii) provide query validation, (iv) identify data sources to be searched, (v) suggest and/or apply filters, and/or (vi) provide other user guidance. Example user intents include identifying particular cohorts (e.g., a breast cancer cohort or a colorectal cancer cohort) and, given a particular drug target and an indication, identify expressions and/or perform specific analysis.

An example task may be coding, and the agent may be configured to generate code in a particular coding language based on natural language inputs from a user. For example, the user specifies the particular coding language, the inputs and the desired output for the code. Another example task may be workspace manipulation, and the agent may be configured to manipulate data within the workspace and/or provide explanations, suggestions, and/or recommendations for manipulating the data. Another example task may be interpreting claims data, and the agent may be configured to interpret (unstructured) claims data, such as notes and descriptions, and identify trends and/or make predictions based on the claims data. The agent may also be configured to understand therapy and/or treatment trends, markets, and/or landscape (e.g., based on historical claims data). For example, the agent may be configured to identity gaps in commercialization based on the historical claims data. In some embodiments, the historical claims data is obtained from a set of databases. In some embodiments, the set of databases are controlled/maintained by separate entities and/or have different formatting and/or structure. As discussed in detail below, FIGS. 14-18 illustrate various workflows for implementing and/or interacting with agent modules in accordance with some embodiments.

Although FIG. 13 illustrates a number of logical stages in a particular order, stages which are not order dependent may be reordered and other stages may be combined or broken out. Some reordering or other groupings not specifically mentioned will be apparent to those of ordinary skill in the art, so the ordering and groupings presented herein are not exhaustive. Moreover, it should be recognized that various stages could be implemented in hardware, firmware, software, or any combination thereof.

FIG. 14 illustrates an example workflow for implementing and/or interacting with an agent in accordance with some embodiments. The example workflow includes an admin flow from admin application 6212 (e.g., an admin page, portal, or user interface) to various components such as internal platform 6214, secure platform 6216, and search analysis component 6218. In accordance with some embodiments, the components interact with a component library 6220. The components 6214, 6216, and 6218 may be instances of the platform 6222. The example workflow also includes a flow from OS console 6202 (e.g., a user page, portal, or user interface) to an admin console 6204, an agent builder component 6206, a transform component 6208, and/or a data product component 6210. For example, the flow may be based on an intent of the user (e.g., to build an agent, use an agent, perform admin operations, and/or access data products). The data source 6228 may be any of the data sources described herein. In some embodiments, the data source 6228 comprises information from the knowledge database(s) 404 (or any of the other databases described herein). In some embodiments, an agent 6224 (e.g., composed of one or more agent modules) is used to interact with the user. The agent 6224 is composed of agent building blocks 6226 and may use API integrations 6230, models 6232, conversational agent components 6234, RAG component 6236, embeddings 6240 (e.g., vectors of data from knowledge database(s) 404).

Figure 15:
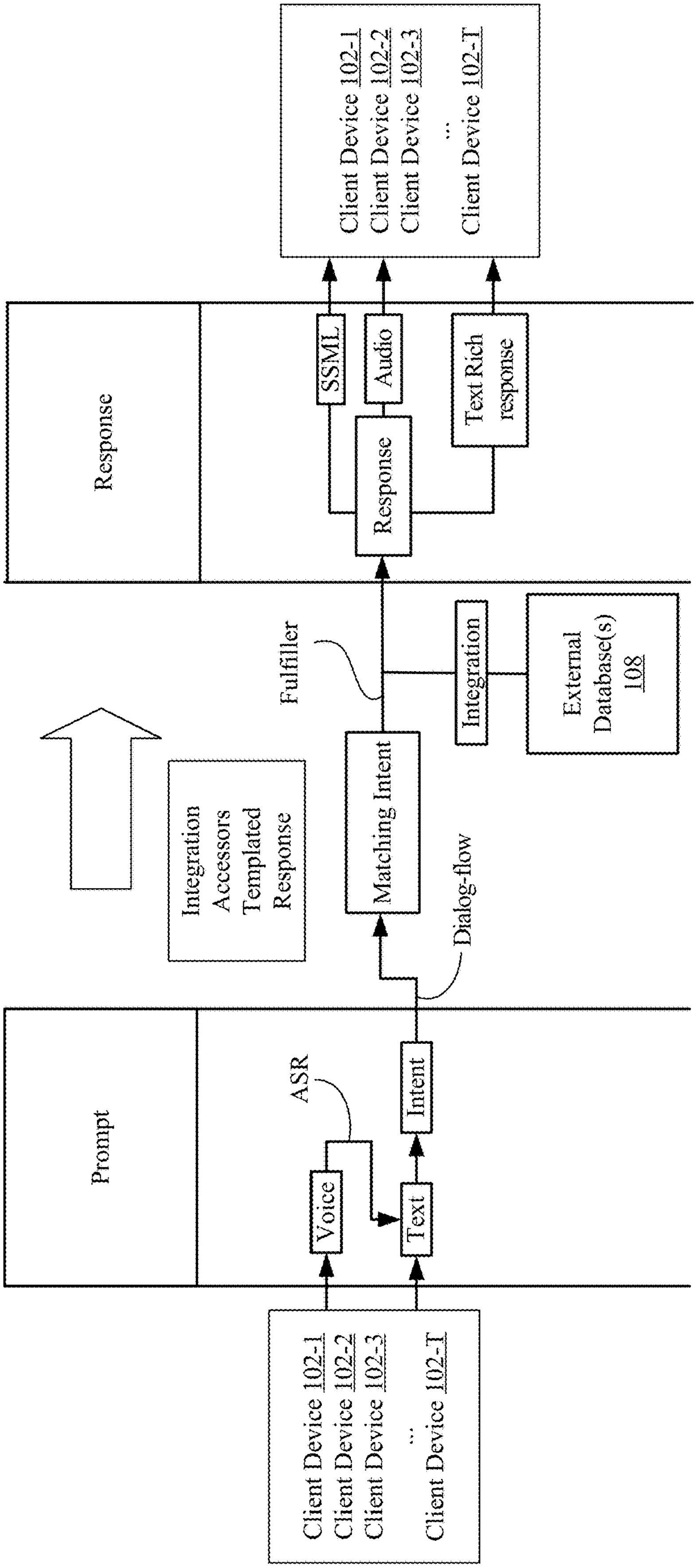
FIG. 15 illustrates another example workflow for implementing and/or interacting with an agent in accordance with some embodiments.
Figure 16:
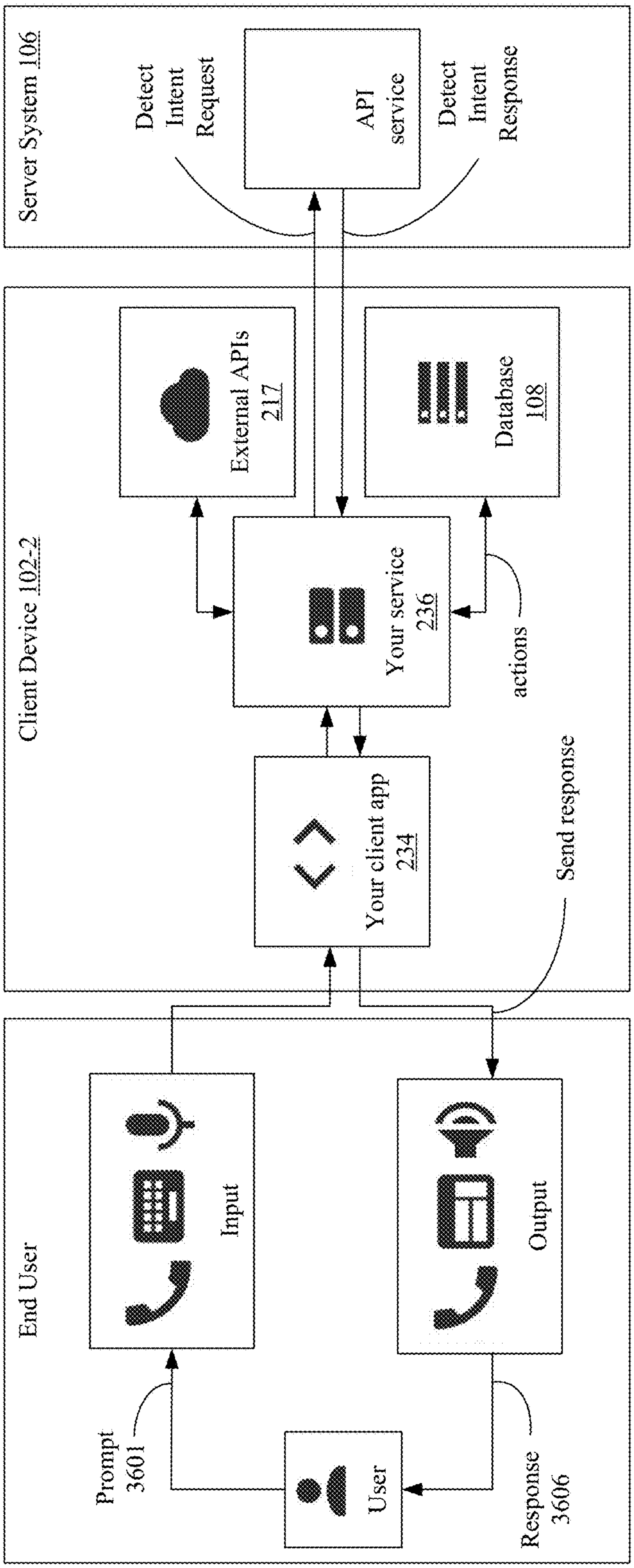
FIG. 16 illustrates another example workflow for implementing and/or interacting with an agent in accordance with some embodiments.

FIGS. 15 and 16 illustrate example workflows for implementing and/or interacting with an agent in accordance with some embodiments. As shown in FIG. 15, users may submit prompts (e.g., via voice and/or text inputs). Automatic speech recognition (ASR) may be performed on the prompts (e.g., using an agent module) to identify an intent of the prompt. After the intent is identified, an appropriate fulfiller (e.g., agent module, tool, or ensemble thereof) is selected and passed the intent and one or more parameters (and/or other context information). The fulfiller may be communicatively coupled to one or more external databases 108 (e.g., the knowledge database(s) 404). In this way, the fulfiller may retrieve and analyze response information from the external database(s) 108. After the fulfiller determines a response, the response may be transformed (e.g., to audio and/or text data) and then provided to the user. FIG. 16 illustrates a similar example of receiving a prompt 3601 and generating a response 3606. In the example of FIG. 16, the service may include one or more agent modules and/or one or more tools (e.g., selected by a super agent module). In some embodiments, the client application comprises a user interface (e.g., a web interface). In some embodiments, the client application comprises a digital assistant (e.g., as described previously with respect to FIGS. 11 and 12).

Figure 17:
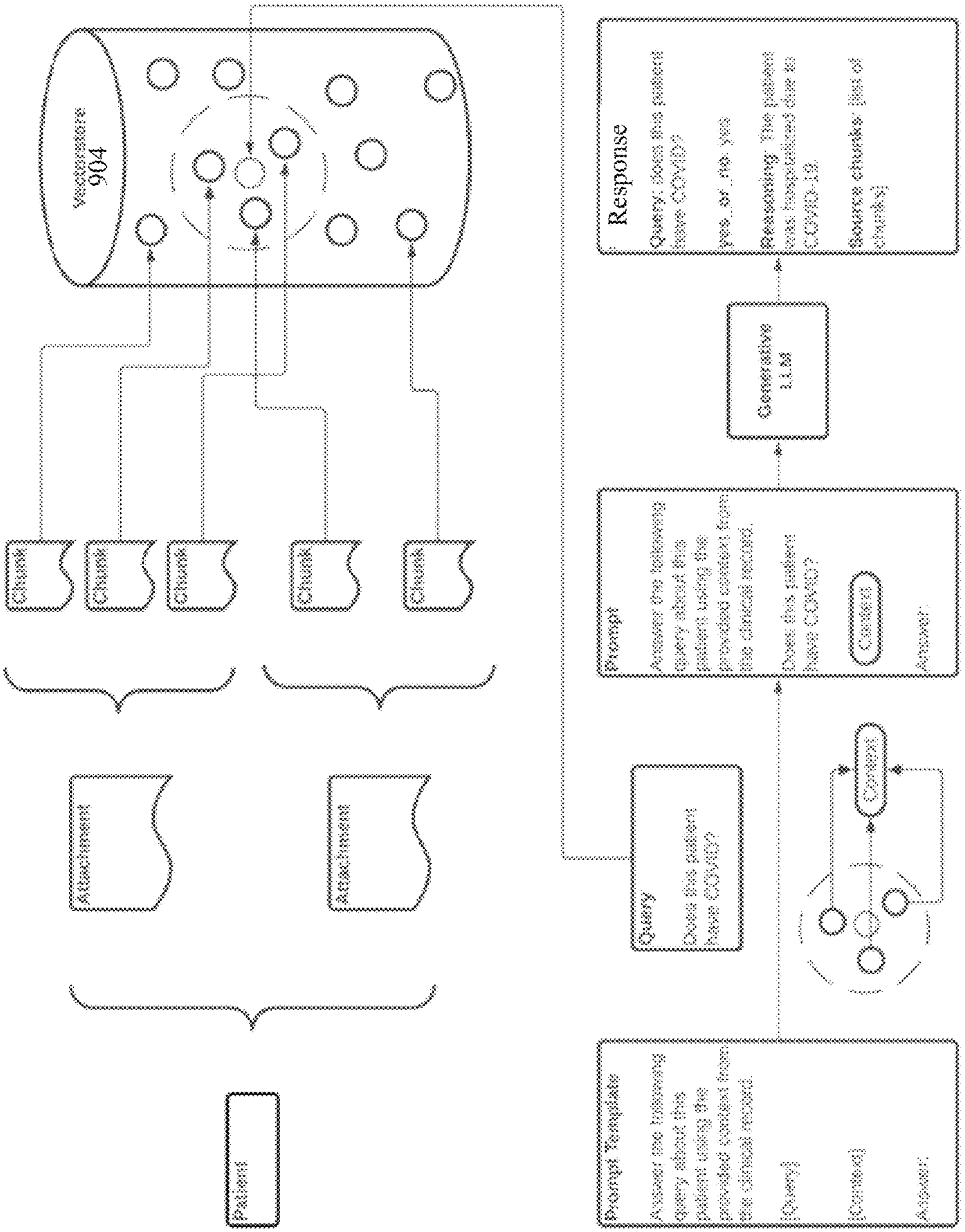
FIG. 17 illustrates an example agent module in accordance with some embodiments.

FIG. 17 illustrates an example retrieval-augmented generative (RAG) agent module in accordance with some embodiments. As shown in FIG. 17, a RAG agent module may include an embedding model (e.g., configured to generate embeddings from patient documents), a prompt interface, a generative model, and one or more transform (e.g., parser) components.

FIGS. 18A to 18F illustrate an example sequence of a user's interaction with an example agent-builder application 1800 (e.g., an application for creating task-specific orchestrations, including composite orchestrations (e.g., chains of agents)), in accordance with some embodiments. As discussed herein, the agent-builder application 1800 may include various user inputs for causing operations to modify respective orchestrations (e.g., the agent module 6102) associated with the user of the agent-builder application 1800. In accordance with some embodiments, the user may access the agent-builder application 1800 by providing user credentials from the client device 102 to the server system 106.

In some embodiments, aspects of the agent-builder application 1800 are modified based on information about the user accessing the agent-builder application. For example, the data collections (e.g., accessible via a user input directed to a data collections user interface element 1806) available to the user are based on the specific credentials provided by the user to access the agent-builder application 1800. In this way, the system allows the user to apply precision medicine principles by providing interactions that are specific to the user (e.g., patient data about a patient cohort). In some embodiments, different users may have different levels of access to the tools and data available within the platform and/or agent framework. For example, a first set of users (e.g., consumers) may have access to a respective user interface associated with the home user interface element 1802, while a second set of users (e.g., builders) may also have access to a user interface associated with the user interface element 1804 (e.g., an agents' tab). In this way, users are able to interact with the agent-builder application 1800 without explicitly making a determination whether they are authorized to use a particular aspect of the agent-builder application 1800.

As will become apparent to one of skill in the art after reading the descriptions of the sequence of interactions illustrated by the FIGS. 18A to 18F, the embodiments described herein provide technical improvements to users by providing efficient and effective solutions for a user to generate a solution to a complex clinical task or set of clinical tasks that would otherwise require a user to provide a plurality of different inputs to a plurality of components and/or applications.

Figure 18A:
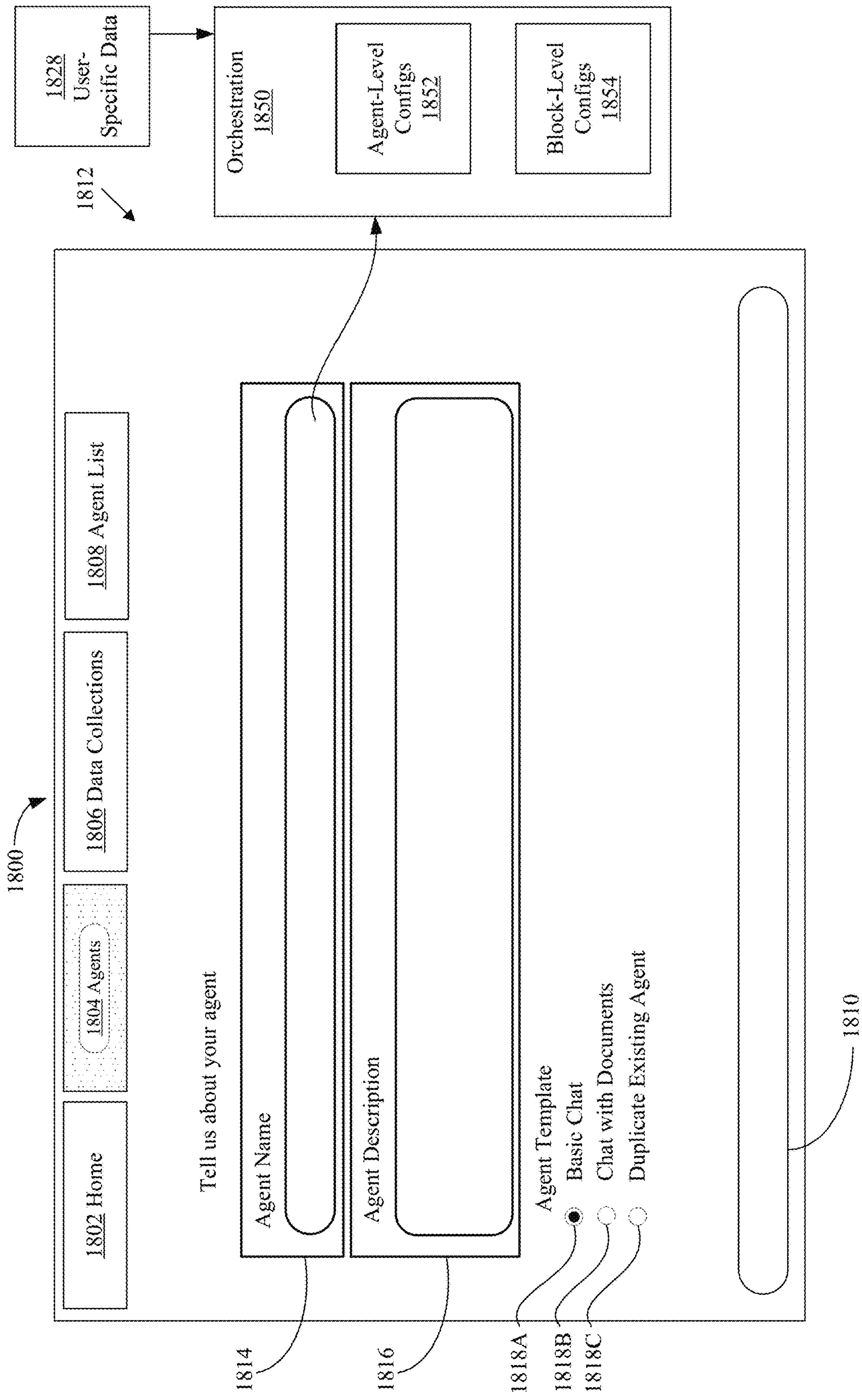
FIGS. 18A-18F illustrate example user interactions with an example orchestration creator application in accordance with some embodiments.

FIG. 18A shows a user interface 1812 of the agent-builder application 1800 in accordance with some embodiments. The user interface 1812 includes a form-builder user interface element 1814 for interacting with (e.g., instantiating and/or configuring) an agent module 6102 in accordance with some embodiments. In some embodiments, the user interface 1812 includes global user interface elements that are present within different respective user interfaces of the agent-builder application, as described herein. For example, the user interface 1812 includes respective user interface elements for accessing different user interfaces of the agent-builder application 1800 (e.g., a user interface element 1802 for accessing a home user interface, which may include one or more components of the user interface described with respect to FIGS. 10A to 10C, a user interface element 1804 for accessing an agent-builder user interface, a user interface element 1806 for accessing a data viewing user interface, such as the user interface 500 described with respect to FIGS. 5A and 5B, and a user interface element 1808 for viewing a list of task-specific orchestrations (e.g., task-specific agents) that are available to the user accessing the agent-builder application 1800. For example, the global user interface elements may include a prompt user interface element 1810 for initiating a chat session with a respective agent module of the agent-builder application 1800.

The user interface 1812 includes a plurality of user interface elements for modifying an orchestration 1850 (e.g., a task-specific orchestration, which may comprise an agent module 6102 and/or an agent architecture 6106) in accordance with some embodiments. For example, the user interface 1812 includes a user interface element 1814 for naming the orchestration 1850, and a user interface element 1816 for providing a description of the orchestration. In some embodiments, other users having access to the data associated with the orchestration 1850 may access and/or implement the orchestration by selecting it from an agent library (e.g., the agent library 226). In accordance with some embodiments, the user interface 1812 also includes a template-selector section for interacting with a plurality of user interface elements corresponding to different default orchestrations that the user can select to provide an initial node architecture 6106 to the orchestration 1850 (e.g., a user interface element 1818A for creating a task-specific orchestration for interacting with a general-purpose machine-learning model, a user interface element 1818B for interacting with a task-specific orchestration that includes a machine-learning model (e.g., a general-purpose machine-learning model and/or a task-specific machine learning model) that has been trained with specific data (e.g., from a data collection that is continuously updated in real-time), and a user interface element 1818C for interacting with a task-specific orchestration that was previously created within the task-specific orchestration creator application.

As illustrated in a symbolic block diagram in FIG. 18A, the orchestration 1850 (e.g., task-specific agent) is instantiated in accordance with the user providing an input directed to the respective user interface element 1818B for interacting with a task-specific orchestration that uses data provided by the user (e.g., a medical document, live collection data). In some embodiments, the orchestration 1850 includes one or more agent-level configurations 1852 (e.g., orchestration-level attributes, agent settings) and one or more block-level 1854 configurations (e.g., node-level attributes, model settings).

As shown in FIG. 18A, when the orchestration is instantiated based on the user's input, user-specific data 1828 is provided to the orchestration 1850. In some embodiments, based on the orchestration 1850 being instantiated by the user input directed to the user interface element 1818B, a respective machine-learning model of the task-specific agent is trained (e.g., automatically, without further input provided by the user) on clinician-specific patient data (e.g., precision medicine) based on data associated with the respective user accessing the task-specific orchestration creator application 1800.

Figure 18B:
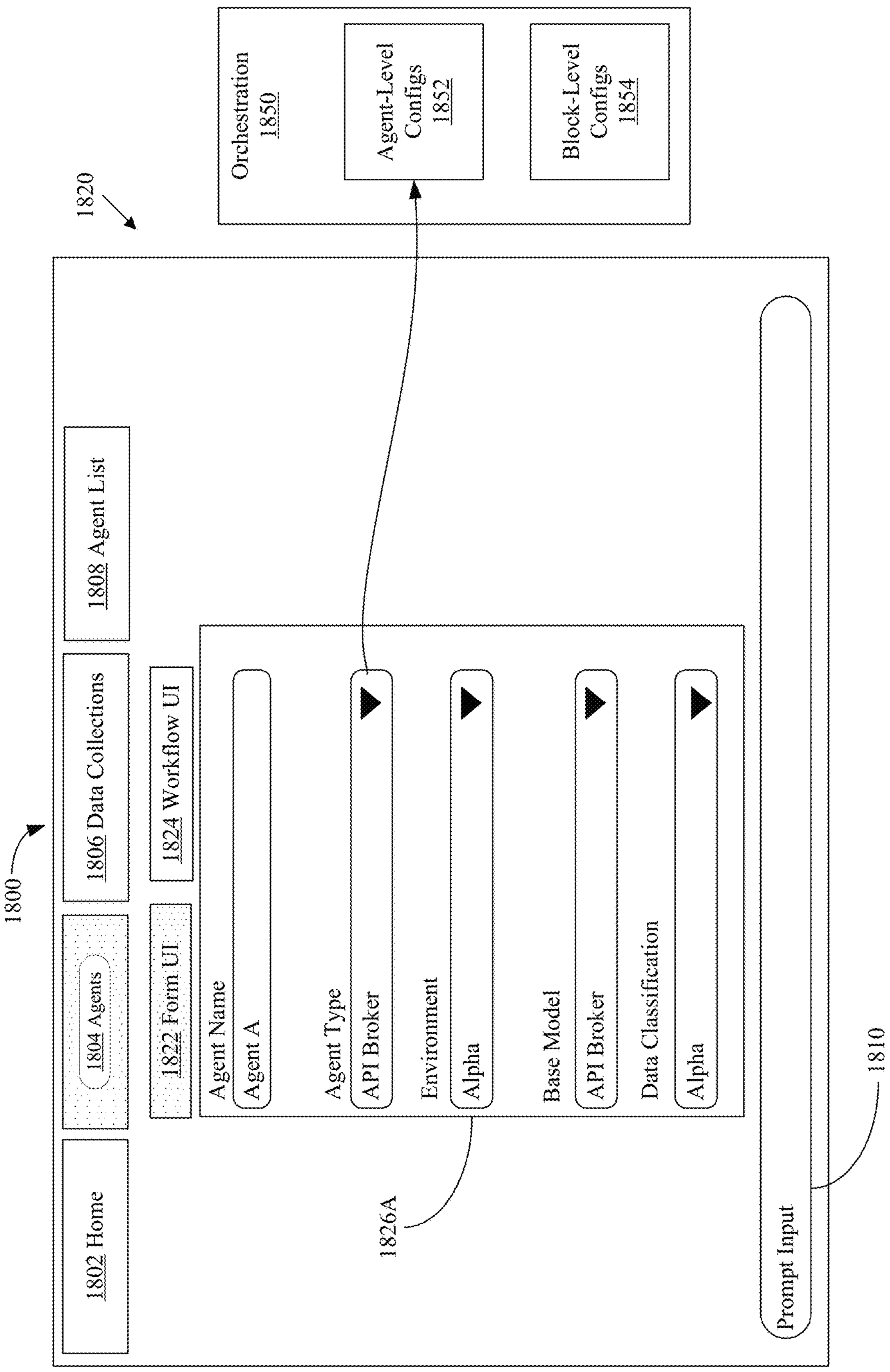

FIG. 18B illustrates a user interface 1820 (a task-builder form user interface element) of the agent-builder application 1800 that includes a plurality of user interface elements for modifying the orchestration 1850 that was instantiated in FIG. 18A. In accordance with some embodiments, the user interface 1820 of the task-specific orchestration creator application 1800 includes a set of user interface elements (e.g., a form user interface view 1822, a workflow user interface view 1824) for toggling a respective representation of the task-specific orchestration 1850. The user interface 1820 includes a set of user interface elements 1826A for modifying aspects of the orchestration 1850. In accordance with some embodiments, some respective interactions with the set of user interface elements 1826A cause the agent-level configurations 1852 to be modified, while other interactions with the set of user interface elements 1826A cause the block-level configurations 1854 to be modified. For example, a user selection of an agent type (e.g., an API broker agent) may cause one or more agent-level configurations 1852 to be modified without causing any modifications to any block-level configurations 1854.

Figure 18C:
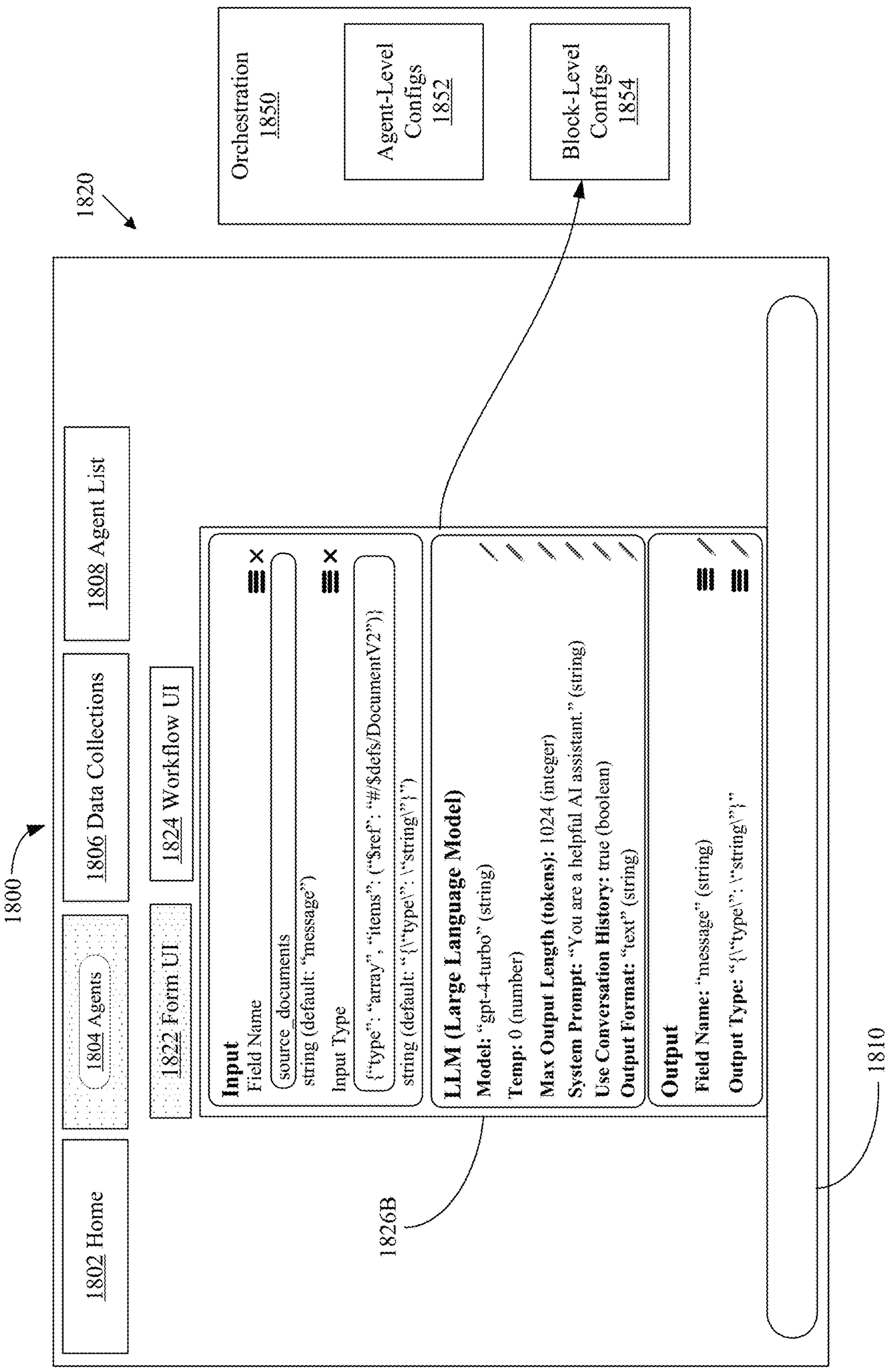

FIG. 18C illustrates another example of the user interface 1820 of the agent-builder application 1800 that includes a set of user interface elements 1826B for modifying the orchestration 1850. For example, the set of user interface elements 1826B includes a user interface element for configuring a machine-learning model (e.g., a large-language model) of the orchestration 1850, which may cause modifications to the block-level configuration 1854 of the orchestration 1850. In accordance with some embodiments, the task-specific machine-learning model is an agent module 6102 of the orchestration 1850.

Figure 18D:
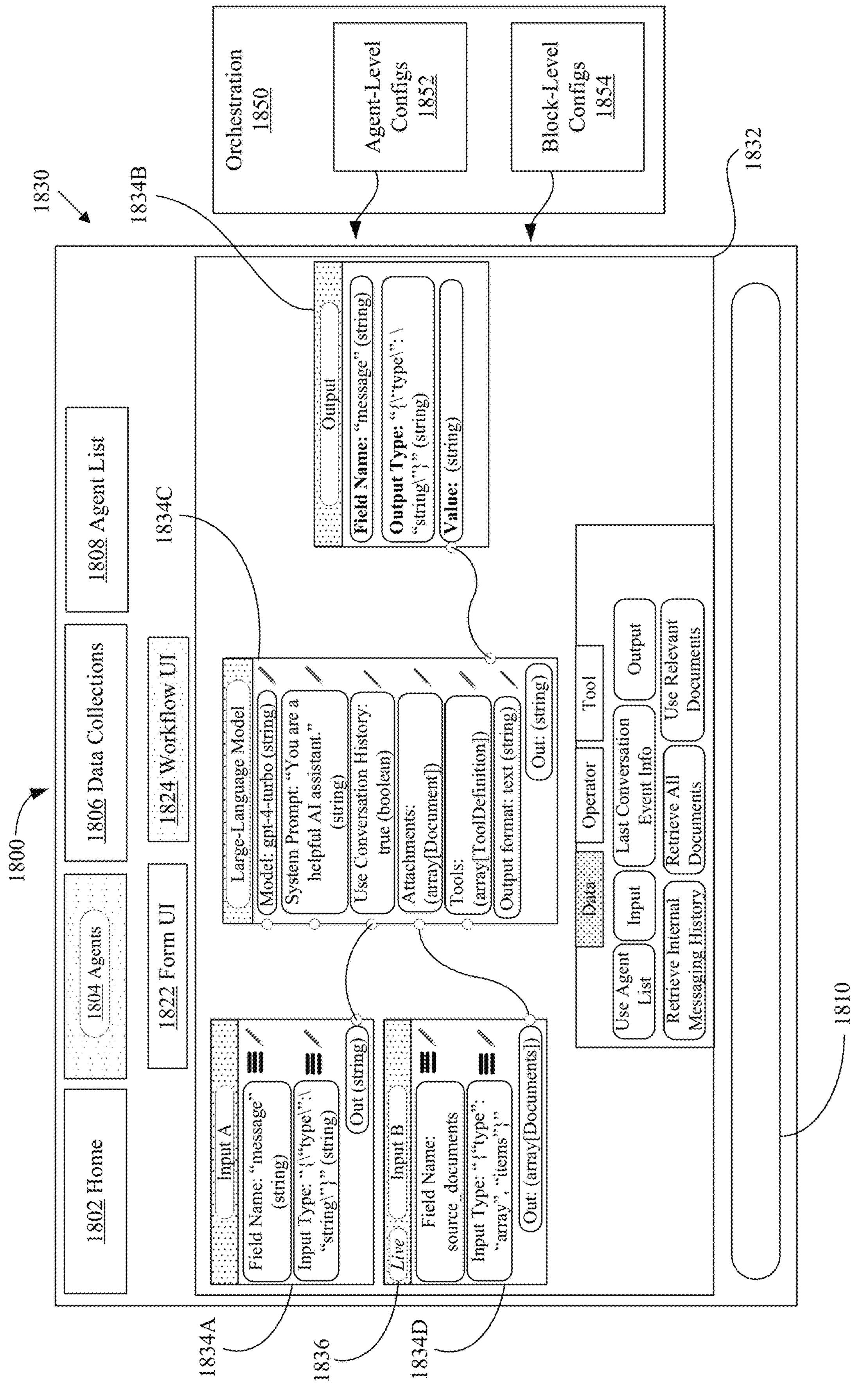

FIG. 18D illustrates an example of a user interface 1830 (e.g., a workflow editor) of the agent-builder application 1800 that includes a workflow representation 1832 of the orchestration 1850. As indicated by the user interface elements 1822 and 1824 (where the user interface element 1824 is now indicated as being selected instead of the user interface element 1822), the workflow representation 1832 can be presented based on a user input toggling between the form view and the workflow view. In some embodiments, FIG. 18D illustrates a transition from FIG. 18C in response to a user selection of the workflow UI element 1824.

As depicted by FIG. 18D, the workflow representation 1832 is constructed to represent a node architecture 6106 of the orchestration 1850, which may be based on the agent-level configurations 1852 and the block-level configurations 1854. In some embodiments, every workflow representation 1832 configurable by the agent-builder application 1800 includes respective blocks 1834A and 1834B representing an input and an output of the orchestration 1850. For example, the input represented by the block 1834A may include textual content of a prompt, and/or an embedding generated based on the textual content of the prompt (as described with respect to the example applications and orchestrations described with respect to FIGS. 18A and 18B). The workflow representation 1832 may also include one or more blocks representing machine-learning models (e.g., a block 1834C representing a large-language model that was configured in FIG. 18C). In some embodiments, the workflow representation 1832 is an interactive representation (e.g., a drag and drop representation) in which a user may select an output and then select an input to couple the input to the output (or vice versa). In accordance with some embodiments, each input and output has a corresponding data type (e.g., indicated by a color and/or label). In some embodiments, the system provides suggested building blocks (e.g., agent modules, models, tools, and/or other types of building blocks) based on user prompts. In some embodiments, the system provides a list of available building blocks and the user may drag and drop the building blocks into the workflow representation to add them to the agent module.

In some embodiments, the agent building blocks described herein include data building blocks, operator building blocks, and/or tool building blocks. Non-limiting examples of data building blocks include an agent listing block (e.g., obtains a listing of available agents), an input block (e.g., accepts a value from a user), a message block (e.g., returns a recent message (and optionally associated metadata) from a conversation), an output block (e.g., returns a response such as a message or document), a history block (e.g., returns a message history), a retrieval bock (e.g., retrieves data, such as documents, from a database or collection), and a semantic block (e.g., identifies semantically similar documents and/or text). Non-limiting examples of operator blocks include a storage block (e.g., configured to store bits of data and/or set common data values with various types), an array block (e.g., configured to transform (e.g., combine) inputs into arrays), a map block (e.g., configured to execute a sub-assembly for inputs in an array and return an array of results), a JSON block (e.g., configured to convert input text to an object via JSON parsing, and optionally validate against a provided schema), an XML block (configured to convert input text to an object via XML parsing, and optionally validate), a status block (e.g., configured provide information about execution status), a template block (e.g., configured to output text in accordance with a given template), and a tool block (e.g., configured to wrap an assembly consumable by another block). Non-limiting examples of tool blocks include an agent tool block (e.g., configured to interface with an agent module), a similarity block (e.g., configured to provide a similarity score for documents), a web block (e.g., configured to operate as an HTTP interface), and a model-tool interface block (e.g., configured to interface between a model and a tool (e.g., ask a model to use a tool)).

The workflow representation 1832 in FIG. 18D illustrates an example super agent module that has been configured to understand agent building blocks and assemblies (e.g., what building blocks are available, what each building block is configured to do, what data collections are available, and how to connect individual building blocks and collections). In the example of FIG. 18D, the large language model block 1834C is provided with a prompt to provide assemblies (orchestrations) with a functionality that satisfies a user request.

Figure 18E:
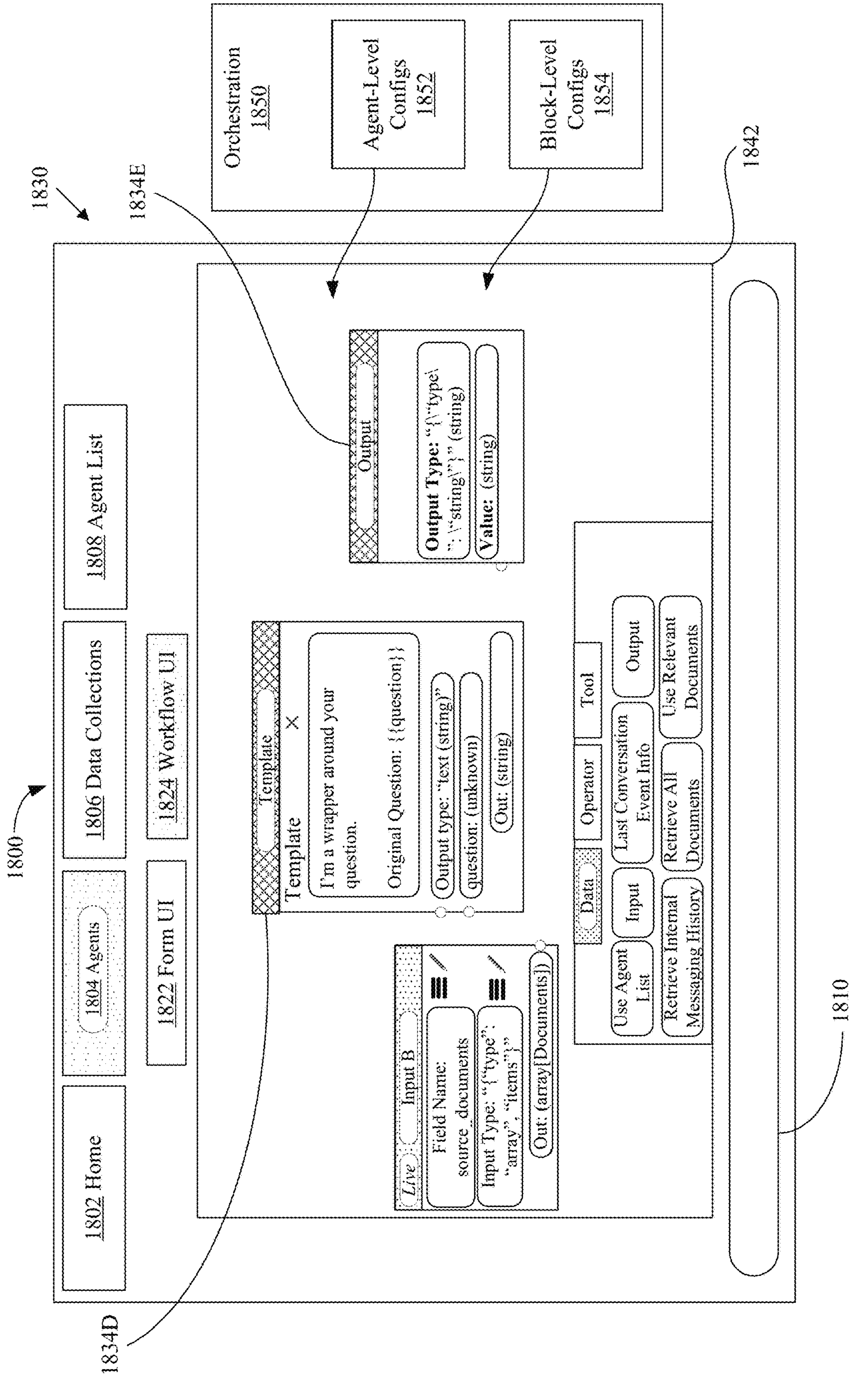

FIG. 18E illustrates another example of the user interface 1830 that includes a workflow representation (e.g., the workflow representation 1832 after instantiation of a plurality of additional blocks (e.g., including one or more nodes)). As shown in FIG. 18E, the user interface 1830 may include a plurality of different user interface elements corresponding to each of the respective nodes of the task-specific orchestration. For example, the representation of the orchestration 1850 shown in the user interface 1830 includes a block user interface element 1850A corresponding to the user input to the task-specific orchestration 1842. The representation of the task specific orchestrations further includes a block user interface element 1850B corresponding to a data input component of the task-specific orchestration 1842 (e.g., a specification of relevant documents to use with one or more other nodes of the task-specific orchestration). The representation of the task-specific orchestration further includes a block user interface element 1850C corresponding to a templating prompt pre-processing component of the task-specific orchestration 1842, where the templating pre-processing component receives a prompt from the user and determines an output prompt (e.g., a transformed and/or reformatted prompt) to provide to a task-specific machine-learning model of the task-specific orchestration (e.g., a large-language model as represented by a block user interface element 1850E).

As shown by the example representation of the task-specific orchestration 1842 in FIG. 18E, different blocks representing different nodes of the task-specific orchestration 1842 may include different respective visual indicators (e.g., visual indicator 1852B of the block user interface element 1850B) from other visual indicators of the other blocks in the representation shown in FIG. 18E. In some embodiments, a first visual indicator (e.g., a red bar, an alert symbol, or other type of indicator) indicates that the block is missing a connection (or other integration requirement) to be properly integrated with the orchestration 1850. In some embodiments, visual indicators are used to indicate a block type (e.g., a tool block, a model block, a routing block, etc.). FIG. 18E includes blocks 1834D (e.g., a template block) and 1834E (e.g., an output block).

Figure 18F:
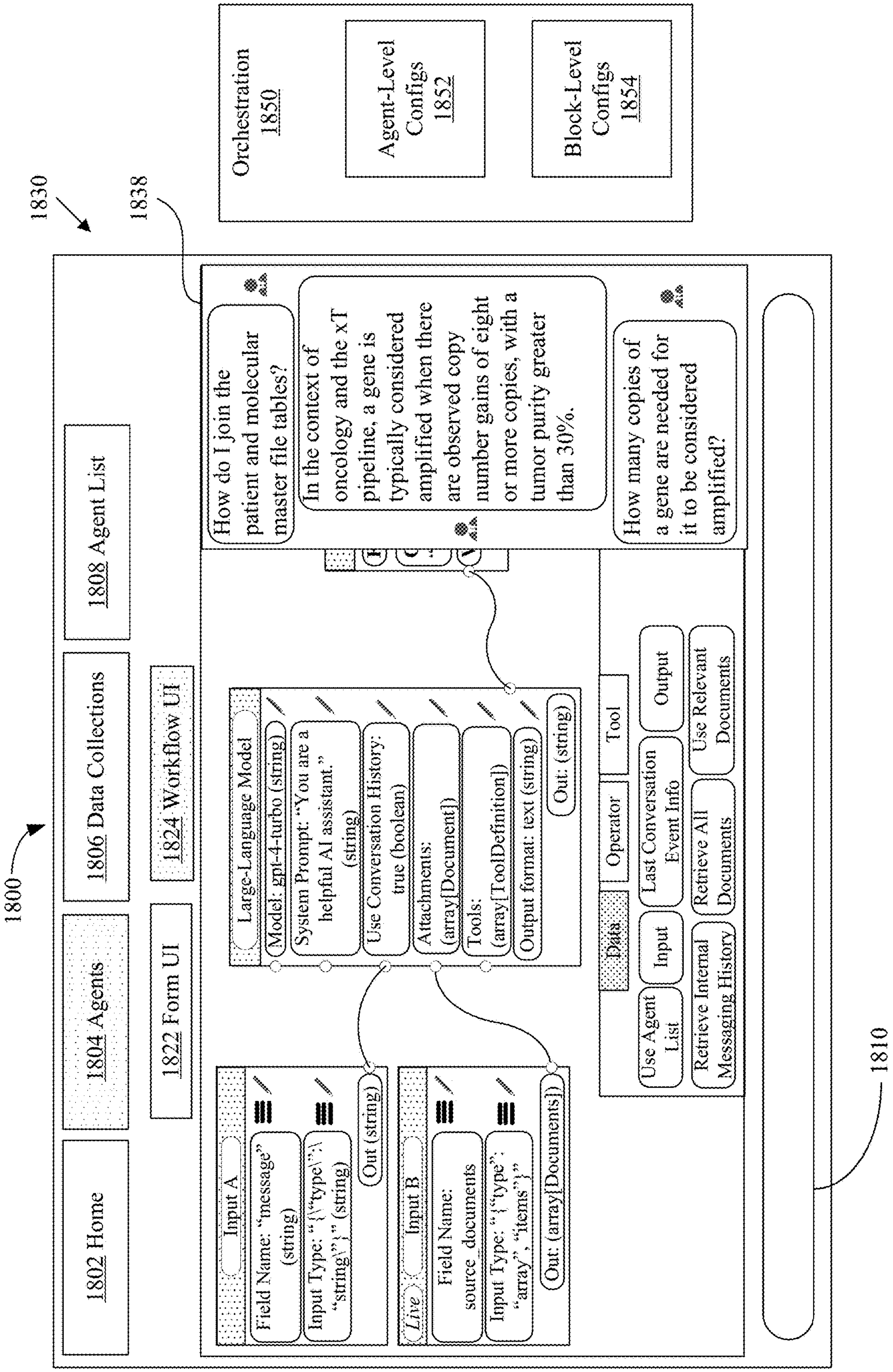

FIG. 18F illustrates another example of the user interface 1830 in which the user is providing a prompt to a textual input within a chat user interface 1838, where the chat user interface is configured to facilitate an interaction between the user and the orchestration 1850 that the user modifying via the user interface 1830. In accordance with some embodiments, when the user edits the orchestration 1850, and/or data of a data source in electronic communication with the orchestration 1850 is updated, the user interface 1838 is responsive to updates to the orchestration 1850 and/or data in electronic communication with the orchestration 1850. For example, the user may provide a first prompt to a first configuration of the orchestration 1850 and receive a first response. Then, after editing the orchestration 1850 (e.g., adding a block corresponding to another machine-learning model), the user may provide a second prompt to a second configuration of the orchestration, where the second prompt is identical to the first prompt, but the orchestration 1850 provides a different response to the prompt based on the modification to the configuration of the orchestration 1850.

Figure 18G:
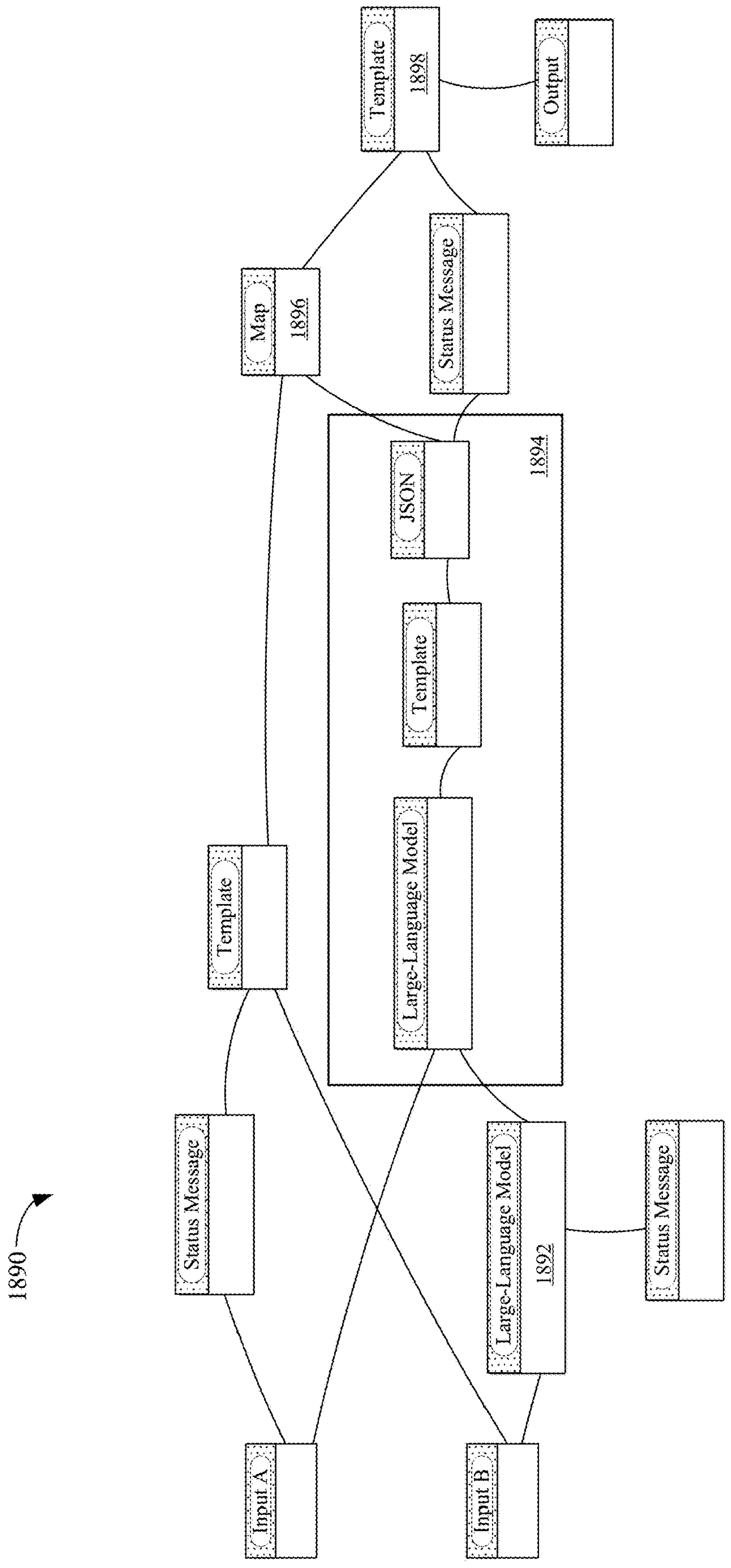
FIG. 18G illustrates an example workflow in accordance with some embodiments.

FIG. 18G illustrates a workflow 1890 for generating and executing orchestrations in accordance with some embodiments. In accordance with some embodiments, a first block (e.g., block 1892) is tasked with rephrasing a user query into a statement requesting a functionality (e.g., a tool) that satisfies the user query. In some embodiments, the statement requesting the functionality is provided to an agent builder module (e.g., module 1894), e.g., a super agent module, configured to generate assemblies (orchestrations). For example, the agent builder module may have access to a block assembly language and a listing of available building blocks. In some embodiments, the agent builder module is configured to generate a JSON assembly. In some embodiments, the generated assembly is passed to a verification module configured to verify, streamline, and/or revise the generated assembly. In some embodiments, if the generated assembly does not pass the verification, the generated assembly is passed back to the agent builder module to revise the assembly. In some embodiments, the verified assembly is passed to an execution block (e.g., block 1896) configured to execute assemblies. For example, the verified assembly and the user query (or a follow-up query) are provided to the execution block to obtain a response to the user query. In some embodiments, the response is provided to a formatting block (e.g., block 1898) (e.g., to generate a natural language response).

In some embodiments, a super agent module comprises a machine-learning model (e.g., a large language model) with a corresponding prompt that describes building blocks, assemblies, agents, and/or data collections. In some embodiments, the super agent module is provided with a prompt that includes a list of building block types and a description of the functionality, input types, and output types of each. In some embodiments, the super agent module is provided with a prompt that indicates guidelines for generating assemblies, orchestrations, and/or agent modules. In some embodiments, the super agent module is provided with a prompt that includes one or more example assemblies, orchestrations, and/or agent modules.

Figure 19A:
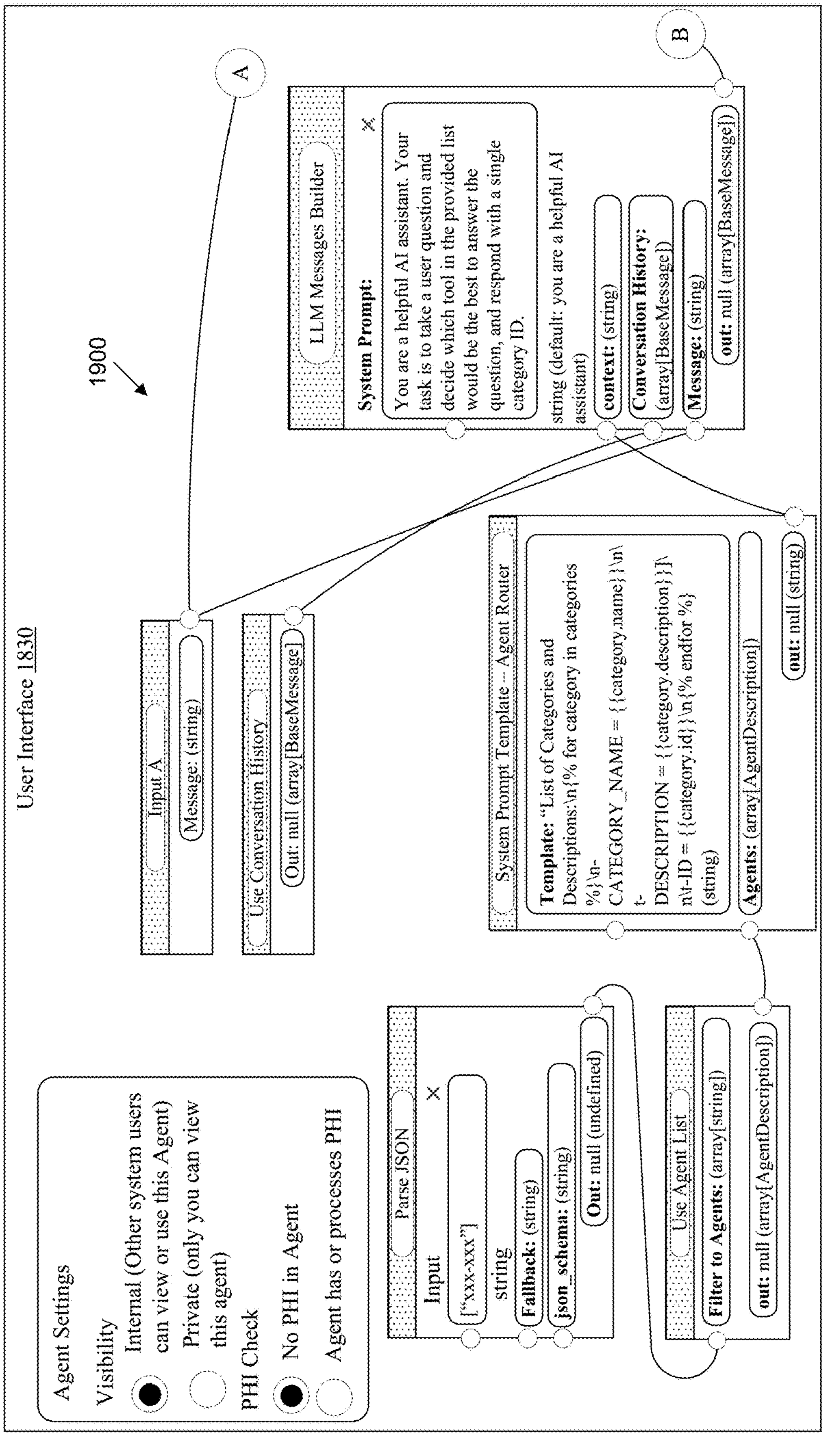
FIGS. 19A and 19B illustrate an example workflow representation of an orchestration composed based on a user prompt in accordance with some embodiments.
Figure 19B:
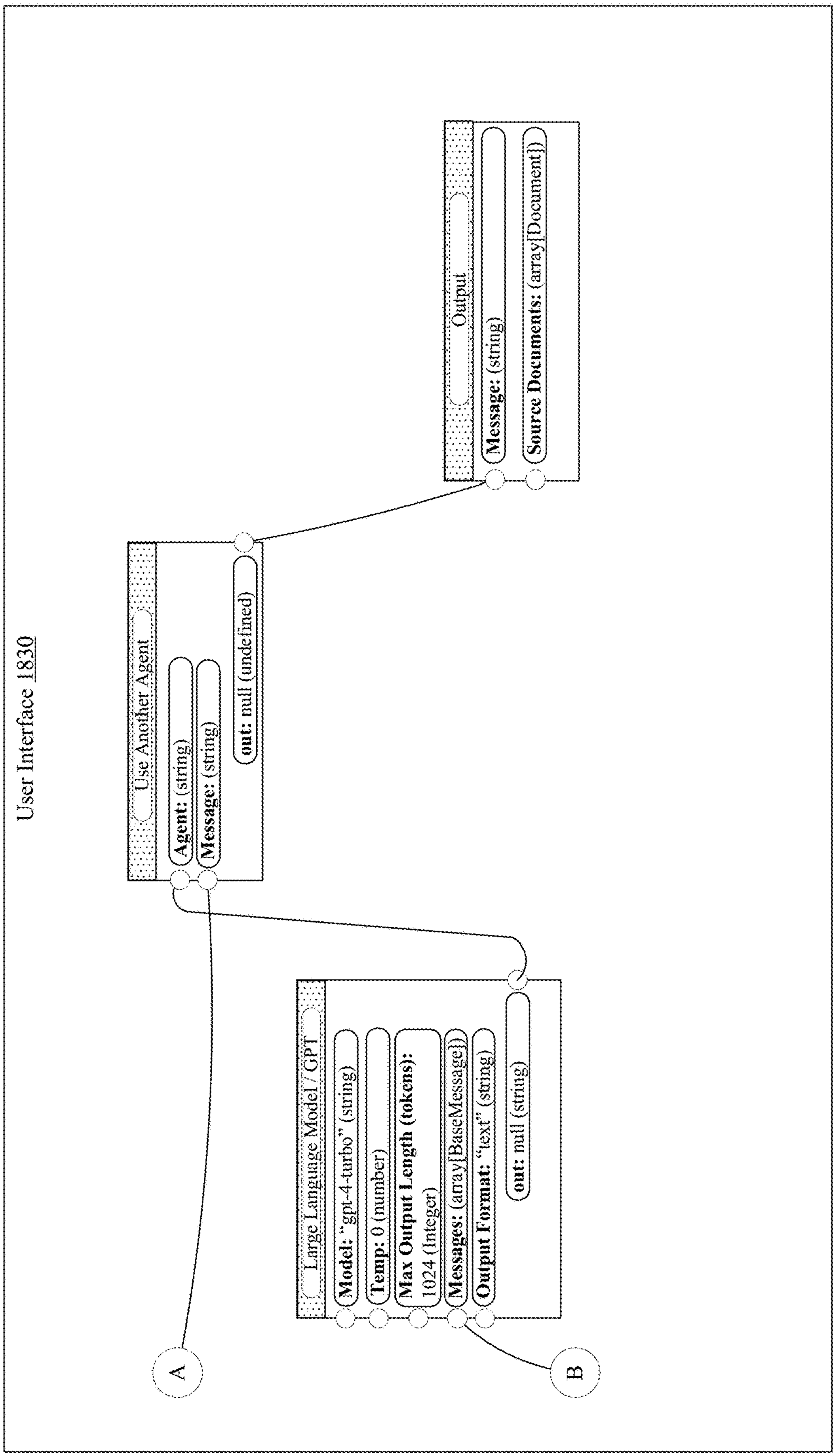

FIGS. 19A and 19B illustrate an example workflow representation 1900 of a composite orchestration (e.g., a super agent or chain agent) configured to compose orchestrations (e.g., different respective agent modules 6102, including other composite orchestrations (e.g., chains of agents)) based on a user prompt, in accordance with some embodiments. In some embodiments, the composite orchestration is configured to determine one or more other orchestrations (e.g., agent modules 6102) to use to provide a response based on an input received by the application (e.g., from the client device 102 or a user). In this way, the composite orchestration may be configured to generate responses to prompts corresponding to a plurality of task-specific and/or domain-specific tasks without being trained (finetuned) for each respective task or domain of the plurality of task-specific and/or domain-specific tasks.

In some embodiments, one or more blocks of the workflow representation 1900 representing the composite orchestration are configured to provide multi-agent routing capabilities for the composite orchestration. For example, the parse JSON block of the composite orchestration contains a list of agent IDs that the composite orchestration is capable of selecting from for creating a task-specific orchestration based on the prompt provided by the user. In this example, the use agent list block is configured to generate an array of agent names and descriptions from the list of agent IDs. The system prompt template of the routing agent is configured to format the array for use by the LLM. The use another agent block is configured to receive an agent ID and invoke the agent corresponding to the identified agent ID.

In some embodiments, by using the list of agent IDs, the agent-builder application is able to create a message to pass to the machine-learning model that, in conjunction with the prompt provided by the user, allows the composite orchestration to determine which agent is the appropriate agent to answer a particular query (e.g., a query determined based on an identified intent of a user prompt).

In accordance with some embodiments, after a set of task-specific orchestrations (e.g., task-specific agents) has been selected for use by the composite orchestration, a routing agent may be invoked by the composite orchestration to determine an order and/or flow of data across a different composite orchestration generated by the composite orchestration (e.g., an output orchestration of the composite orchestration).

Thus, in some embodiments, the composite orchestration is configured to receive an input prompt from a user, and, based on the input prompt, generate an entire node architecture (e.g., the node architecture 6106) for most effectively providing a response to the user based on the prompt. In some embodiments, after the composite orchestration determines the node architecture, it causes a workflow editor to be presented to the user that includes the composite orchestration generated by the composite orchestration and one or more options to edit or revise the generated composite orchestration.

In this way, agents (agent modules) can be generated and deployed without engineering assistance. For example, an end user (e.g., a medical professional) may generate and deploy agents by selecting user interface elements (e.g., clicking on buttons) to update values (e.g., generate configuration files) for the agents. This low-code/no-code editor allows agents to be developed with comparable capabilities as with traditional programming languages, but without the need to manually enter/edit code. In addition, the agent builder includes safeguards such as requiring user authentication and authorization, enforcing data typing between components, and deidentifying data. In some embodiments, the agent builder allows users to select a particular model or model version. In some embodiments, the agent builder recommends a particular model or model version based on the user's expressed intent, system capabilities, and/or associated data sources. In some embodiments, the agent builder utilizes an assembly language that is Turing complete (and agnostic to any type attributed to an agent module). For example, agent modules are generated and deployed without needing to be categorized or assigned a module type.

An example cohort building process includes receiving a user query at a cohort agent module. In this example, the cohort agent module maps the query to a set of cohort criteria (e.g., inclusion/exclusion (IE) criteria). In some embodiments, the cohort agent module uses a model (e.g., an LLM trained to understand mapping of a query to IE criteria) to map the query to the set of cohort criteria. In this example, the cohort agent module maps the IE criteria to a set of filters. In some embodiments, the cohort agent module uses a second model (e.g., an LLM trained to understand mapping of IE criteria to filters) to map the IE criteria to the set of filters. In this example, the cohort agent module identifies respective filter values for the set of filters. In some embodiments, the cohort agent module uses a third model (e.g., an LLM trained to understand filter value mapping) to identify the respective filter values.

In some embodiments, the cohort building process further includes a second cohort agent module configured to receive the user query and identify specific concepts from the user query (e.g., medication, assays, diagnosis, etc.). In this example, the second cohort agent module is configured to identify one or more filters (and corresponding filter values) for each specific concept. In some embodiments, the second cohort agent module uses a model to identify the one or more filters (and corresponding filter values) for a specific concept. For example, the second cohort agent module may use an LLM trained to understand diagnosis and/or medication concepts to identify the corresponding filter(s). In some embodiments, the second cohort agent module includes a block configured to traverse an ontology tree and match an ontology with a specific concept from the user query.

In some embodiments, the cohort building process further includes a third agent module configured to receive and reconcile the filter and filter values from the cohort agent modules. For example, the third agent module may include a model (e.g., an LLM) trained to understand filter overlap and expansion. In some embodiments, the third agent module is configured to provide the reconciled filter and corresponding filter values to a user (e.g., the user who submitted the user query).

Figure 19C:
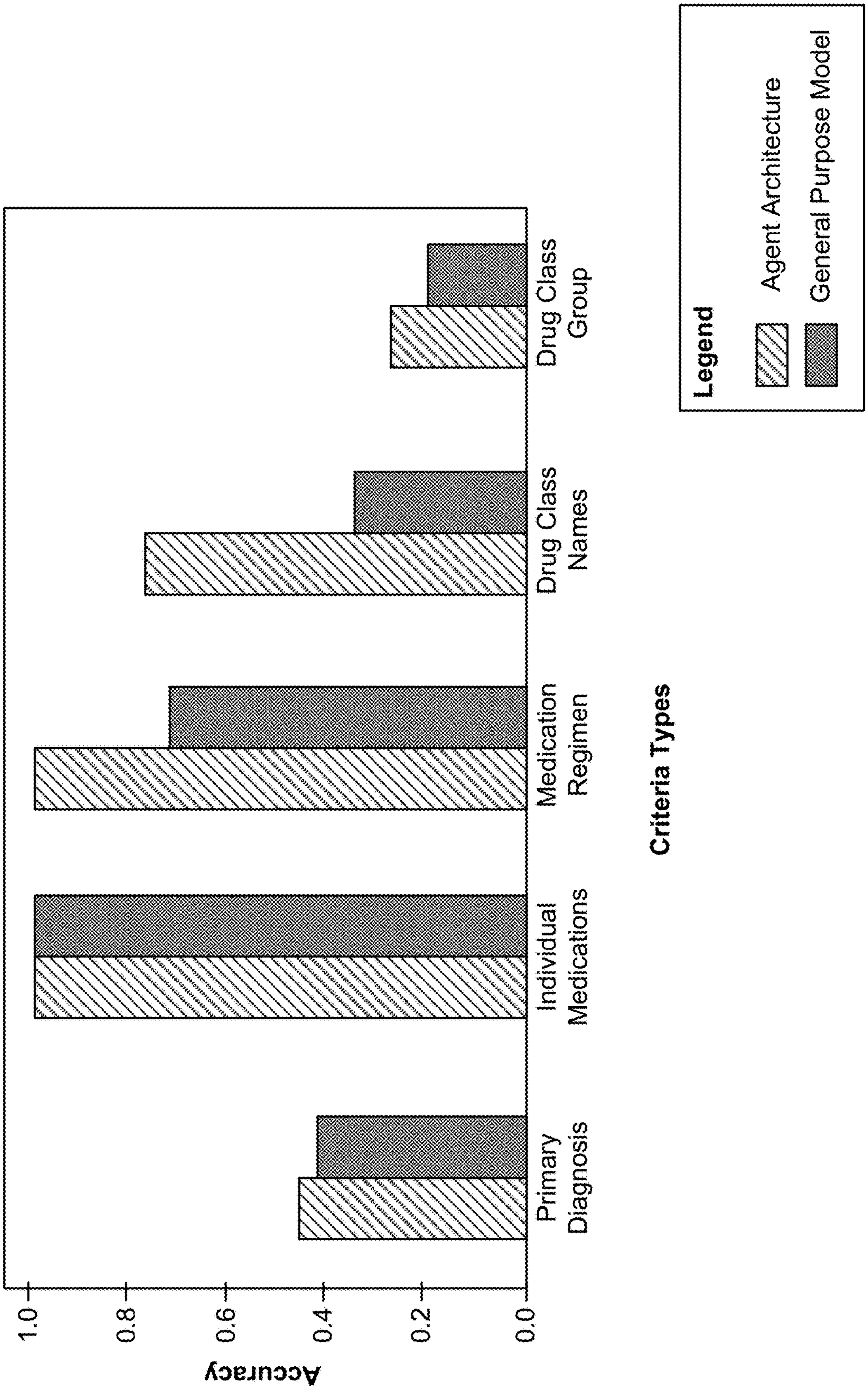
FIG. 19C illustrates an accuracy comparison between an agent architecture solution and a single model solution.

FIG. 19C illustrates an accuracy comparison between an agent architecture (e.g., an agent module configured for cohort building) solution and a single model (e.g., a general-purpose large language model) solution. In the single model solution, the model is provided with a description of the task and examples illustrating the task of identifying the criteria mentioned in the user query. In the agent architecture solution, the agent module is provided a task description and examples (e.g., as in the single model solution) and is also prompted to generate additional information about the criteria. The additional information is used to interpret the output from a model (e.g., a language model) of the agent module. Additionally, the agent module in this example is configured to use relationship information from medical databases (and/or datasets) and map model outputs to information from the medical databases (and/or datasets) to identify cohort requirements/criteria. In this way, the agent module provides improved accuracy over the single model as illustrated in FIG. 19C.

As shown in FIG. 19C, the agent architecture solution has improved accuracy as compared to a single model solution for several different criteria types. The agent modules described herein may improve accuracy while having a reduced size and compute requirement. Moreover, general-purpose models don't have guardrails (e.g., hallucinate) and the user is not allowed to specify particular data collections, require a particular format of output, or request particular processing workflows. In some embodiments, the agent modules described herein are configured to cite source material when providing a response (e.g., to allow a user to double check any conclusions in the response). In some embodiments, a verification block is used to determine whether a conclusion in the response is consistent with the cited source material. As an example, a document similarity block (e.g., using an embeddings model) may be used to determine whether an output response is similar to a cited document and/or an input document. In some embodiments, language models used by the agent modules are restricted from performing low-accuracy tasks (e.g., tasks that have an accuracy below a predetermined threshold), such as fact generation. For example, language models may only be employed for high-accuracy tasks, such as natural language processing, query parameter extraction, and document formatting. In some embodiments, the agent modules described herein are provided only (e.g., are only connected to and/or trained on) appropriate documents (e.g., from domain-specific and/or curated data collections). In some embodiment, agent module accuracy is tracked over time and agent modules are reconfigured for, and/or restricted from, particular tasks based on tracked accuracy.

Now that details of a platform for hosting a variety of agent modules 6102 for facilitating channel-based question-and-answer engagement with clients through such agents modules 6102 has been described along with various example components and workflows, flowcharts of processes and features of the system in accordance with some embodiments are disclosed with reference to FIGS. 21-28.

FIG. 21 is a flow diagram illustrating a method 2100 of interacting with a task-specific orchestration (e.g., an agent or agent module) in accordance with some embodiments. The method 2100 is performed at a computing system (e.g., a client device, server system, and/or service platform) having one or more processors (e.g., the CPUs 202 and/or 302) and memory (e.g., the memory 218 and/or 310). In some embodiments, the memory stores one or more programs configured for execution by the one or more processors. At least some of the operations shown in FIG. 21 correspond to instructions stored in a computer memory or a computer-readable storage medium. In some embodiments, the computing system is the platform 100, the client device(s) 102, and/or the server system 106.

The computing system obtains (2102) medical data from one or more data collections. In some embodiments, the computing system obtains other types of data (e.g., in addition to, or alternatively to, the medical data). In some embodiments, the one or more data collections are obtained from one or more databases (e.g., the external database(s) 108, the database(s) 404, and/or other types of databases).

The computing system presents (2104), at a user interface displayed at a display, a set of user interface elements (e.g., the user interface elements illustrated in FIGS. 18A-18F and 19A-19B) selected from a plurality of user interface elements, where each respective user interface element of the set of user interface elements represents a respective task-specific orchestration (e.g., an agent module) of a plurality of task-specific orchestrations, and each of the respective task-specific orchestrations comprises one or more respective machine-learning models fine-tuned (or otherwise trained) for a specific task or domain based on the medical data from the one or more data collections. In some embodiments, the computing system includes the display. In some embodiments, the computing system is communicatively coupled to the display.

Responsive to a selection by a user of a respective user interface element representing a respective task-specific orchestration, the computing system provides (2106) at least some of the medical data from the one or more data collections to the selected respective task-specific orchestration, and presents a different user interface to the user for communicating with the selected respective task-specific orchestration (e.g., the selected agent module). In some embodiments, the different user interface indicates the specific task of the task-specific orchestration. In some embodiments, the different user interface indicates the at least some of the medical data.

In accordance with receiving a prompt provided by the user at the different user interface, the computing system presents (2108) a response object, where the response object is generated by the selected respective task-specific orchestration based on (i) the prompt provided by the user, and (ii) at least some of the medical data from the one or more data collections. In some embodiments, the response object is presented on the user interface (e.g., in addition to, or alternatively to being presented on the different user interface).

Although FIG. 21 illustrates a number of logical stages in a particular order, stages which are not order dependent may be reordered and other stages may be combined or broken out. Some reordering or other groupings not specifically mentioned will be apparent to those of ordinary skill in the art, so the ordering and groupings presented herein are not exhaustive. Moreover, it should be recognized that various stages could be implemented in hardware, firmware, software, or any combination thereof.

Figure 22:
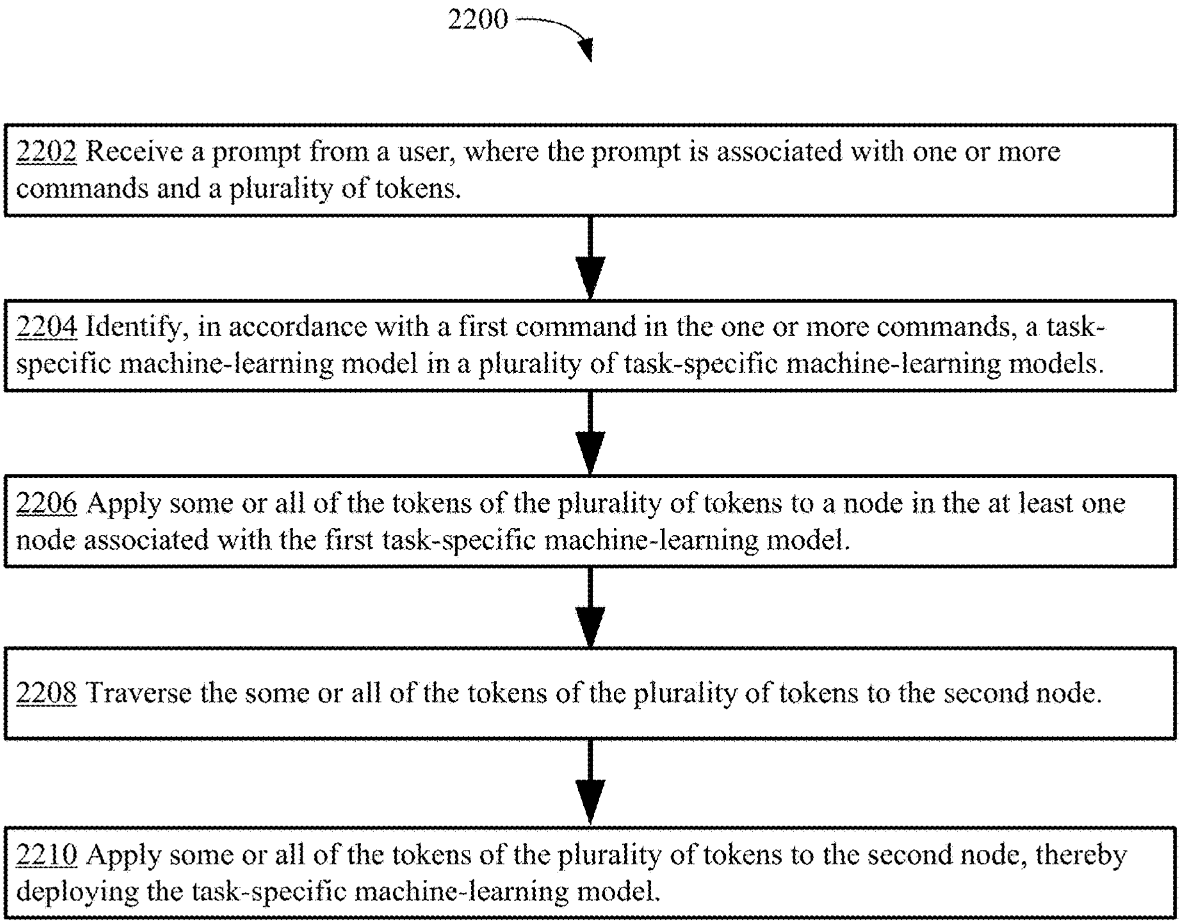
FIG. 22 is a flow diagram illustrating an example method of deploying a task-specific machine-learning model in accordance with some embodiments.

FIG. 22 is a flow diagram illustrating a method 2200 of deploying a task-specific machine-learning model in accordance with some embodiments. The method 2100 is performed at a computing system (e.g., a client device, server system, and/or service platform) having one or more processors (e.g., the CPUs 202 and/or 302) and memory (e.g., the memory 218 and/or 310). In some embodiments, the memory stores one or more programs configured for execution by the one or more processors. At least some of the operations shown in FIG. 22 correspond to instructions stored in a computer memory or a computer-readable storage medium. In some embodiments, the computing system is the platform 100, the client device(s) 102, and/or the server system 106.

The computing system receives (2202) a prompt from a user, where the prompt is associated with one or more commands and a plurality of tokens. In some embodiments, the prompts provides an initial instruction or command for an agent module 6102, setting the tone and providing a framework for how the agent module 6102 should navigate its corresponding node architecture 6106. In some embodiments, the prompt includes one or more commands or questions posed to a model 228 and/or other information such as context, inputs, or examples to aid in providing to better results. For example, referring briefly to FIG. 15, the prompt may be received from one or more client devices in text form (e.g., one or more text strings) and/or audio form (e.g., one or more utterances by the user). In some embodiments, the prompt is received in graphical data form. In some embodiments, audio and/or graphical inputs are transformed by an agent module (e.g., a transform agent module) to a text, vector, embedding, or other type of representation.

In some embodiments, the prompt and/or context information is received from one or more client devices 102, external databases 108, and/or external services 110. In some embodiments, a first prompt is received from a first client device 102 that is a mobile remote device, such as a smartphone device, a second prompt is received from a second client device through a client application executed at the second client device, and a third prompt is received from a third client device that is dedicated to receiving prompts and providing responses to the user.

In some embodiments, the prompt received from the user does not set forth an intent of a query and/or one or more search conditions, but rather provides niche information associated with a particular domain of subject matter. Accordingly, rather than applying the prompt to a general-purpose model (e.g., a model 228), the system deploys a task-specific agent model associated with a task-specific machine-learning model that specializes in understanding context associated with the particular domain, such as by training within the particular domain using knowledge database 404. In some embodiments, the prompt is associated with one or more commands and/or one or more tokens. In some embodiments, the one or more commands are determined from the prompt, such as by parsing the prompt in order to obtain one or more commands inferred from the prompt. In some embodiments, the one or more commands correspond to an intent of the prompt.

In some embodiments, the prompt is associated with a plurality of tokens. In some embodiments, the prompt is parsed, such as by applying the prompt to an input node 6108 of a node architecture 6106, in order to generate the plurality of tokens. One of skill in the art will appreciate that certain language models have limited context windows and function by predicting a subsequent or future token based on one or more inputted tokens, such as the plurality of tokens associated with the prompt. In some embodiments, parsing the prompt into the plurality of tokens allows for structuring the prompt into a form that is optimized for input for a particular agent module 6102, model 228, and/or node 6108. Advantageously, the plurality of tokens provides for delineations of the prompt into one or more commands represented by various subsets of tokens, which can be provided to various nodes 6108 of one or more agent modules 6102.

In some embodiments, the plurality of tokens comprises between 10 tokens and 100,000 tokens. In some embodiments, the plurality of tokens comprises at least 10 tokens, at least 500 tokens, at least 1,000 tokens, at least 5,000 tokens, or at least 50,000 tokens. In some embodiments, the plurality of tokens comprises at most 10 tokens, at most 500 tokens, at most 1,000 tokens, at most 5,000 tokens, or at most 50,000 tokens. In some embodiments, the plurality of tokens collectively represents the entirety of the prompt. In some embodiments, the plurality of tokens collectively represents less than all of the prompt. In some embodiments, the plurality of tokens comprises one or more character tokens, one or more sub-word tokens, one or more word tokens, one or more phrase tokens, or a combination thereof.

Accordingly, by associating the plurality of tokens with the prompt, the system advantageously allows for applying some or all of the plurality of tokens to different agent modules 6102 associated with different domains of subject matter, such as a first set of tokens in the plurality of tokens being used for application with a first agent module 6102 associated with evaluating prescribing information for a first class of pharmaceutical compositions and a second agent module 6102 associated with evaluating population phenotypes.

The computing system identifies (2204), in accordance with a first command in the one or more commands, a task-specific machine-learning model 228-1 in a plurality of task-specific machine-learning models (e.g., models 228). In some embodiments, each task-specific machine-learning model is associated with at least one node 6108 in a plurality of interconnected nodes that collectively form a node architecture 6106. In some embodiments, each task-specific machine learning model (e.g., each model 228) defines a conditional logic 6112 for performing the specific task of the task-specific machine-learning model.

In some embodiments, each respective node 6108 in the plurality of interconnected nodes 6108 is associated with a corresponding classification in a plurality of classifications. In some embodiments, the plurality of classifications include a function performed by the node (e.g., a data source node, an input node, an output node, etc.). In some embodiments, the plurality of classifications include one or more data source classifications, one or more machine-learning model classifications, and/or one or more conditional logic classifications.

In some embodiments, the conditional logic 6112 of a respective task-specific machine-learning model is defined, at least in part, by a different user. In some embodiments, a first user modifies one or more parameters associated with a first node 6108 and stores the corresponding agent module 6102 at the server system 106. In some embodiments, a second user different from the first user further modifies at least one parameter in the one or more parameters associated with the first node, which allows the second user to either modify the corresponding agent module 6102 stored at the server system 106 and/or generate an additional agent module 6102 that is stored at the server system 106, which allows for building a library of agents 226 through user-generated modifications.

Advantageously, by having each task-specific machine learning module, via the agent module 6102, be associated with both the logic 6112 and the node(s) 6108, the computing system allows for deploying task-specific agent modules 6102 that not only augment the language models by accessing external database 108 in accordance with internal data control flows defined by the logic 6112.

The computing system applies (2206) some or all of the tokens of the plurality of tokens to a node 6108-1 in the at least one node 6108 associated with the first task-specific machine-learning model (e.g., a model 228). In some embodiments, the computing system communicates, via a communication network, to a remote device, such as a second client device 102-2 of FIG. 15 and/or server system 106 of FIG. 1, an access token associated with the user, the first task-specific machine-learning model, and/or a corresponding agent module 6102. Advantageously, the access token allows the node 6108-1 to access up-to-date information and data stored remotely from the agent module 6102, such as via a first access token stored at the data module 240. In some embodiments, the node 6108-1 retrieves, via the communication network, a plurality of restricted data, such as a plurality of personal health information or personally identifiable information associated with a patient from one or more electronic health records. In some embodiments, the node 6108-1 retrieves the secure data elements in accordance with an authentication of the access token from a source other than the first task-specific machine-learning model. As a non-limiting example, a given data source, such as a client device 102, external database 108, and/or external service 110 may issue access tokens, such as application program interface ("API") keys and tokens, where the API key identifies a particular client device 102 belonging to a particular entity and the API token indicates the identity of source message or content.

In some embodiments, the applying includes determining a correlation between the first node and a second node. In some embodiments, the correlation is based on an evaluation of one or more restricted data in the plurality of restricted data, such as one or more biomarkers identified in the plurality of restricted data, one or more phenotypes associated with the plurality of restricted data, or the like. In some embodiments, the second node is interconnected with the first node, which allows for directly communicating data between the first node and the second node. In some embodiments, the second node is indirectly interconnected with the first node, such that one or more additional nodes are interposed between the first node and the second node. In some embodiments, when the correlation between the first node and the second node satisfies a threshold condition of the first node, the method 2400 includes generating a plurality of text data different from the prompt, in which the text data is responsive to the prompt.

In some embodiments, when the correlation between the first node and the second node fails to satisfy the threshold condition of the first node, the computing system repeats applying some or all of the tokens of the plurality of tokens to the first node. In some embodiments, the computing system repeats applying some or all of the tokens of the plurality of tokens to the first node for at least 10 instances of the repeating. In some embodiments, the computing system repeats applying to the first node until a second threshold condition is satisfied associated with the first node. For example, the second threshold condition may be associated with a maximum allowed character length of the response, and the first threshold condition may be associated with an accuracy and precision of the response.

In some embodiments, determining the correlation between the first node and the second node comprises determining one or more vector embeddings associated with the prompt, such as one or more vector embeddings of embeddings 6240 of FIG. 14 and/or database 6240 of FIG. 8B. In some embodiments, each vector embedding in the one or more vector embeddings is a predetermined vector embedding, which reduces a computational burden in comparison to having to generating such embeddings. However, the present disclosure is not limited thereto. In some embodiments, determining the correlation between the first node and the second node comprises identifying one or more data sources associated with the first node and the second node.

The computing system traverses (2208) the some or all of the tokens of the plurality of tokens to the second node. In some embodiments, the prompt progresses through the node architecture by progressing some or all of the token from the first node to the second node or applying an output from the first node based on the some or all of the tokens to the second node.

The computing system applies (2210) some or all of the tokens of the plurality of tokens to the second node, thereby deploying the task-specific machine-learning model.

Although FIG. 22 illustrates a number of logical stages in a particular order, stages which are not order dependent may be reordered and other stages may be combined or broken out. Some reordering or other groupings not specifically mentioned will be apparent to those of ordinary skill in the art, so the ordering and groupings presented herein are not exhaustive. Moreover, it should be recognized that various stages could be implemented in hardware, firmware, software, or any combination thereof.

Figure 23:
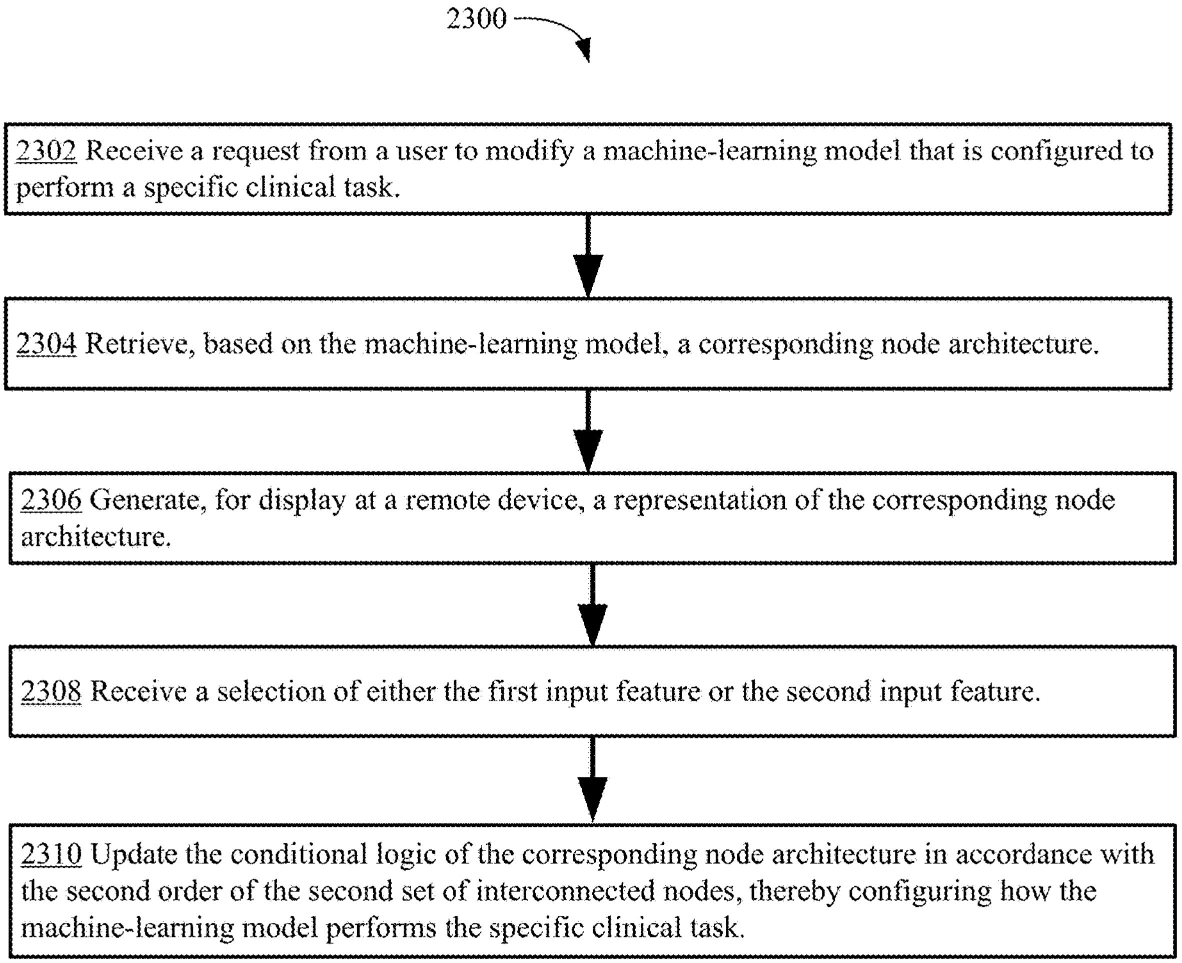
FIG. 23 is a flow diagram illustrating an example method of configuring a task-specific machine-learning model in accordance with some embodiments.

FIG. 23 is a flow diagram illustrating a method 2300 of configuring a task-specific machine-learning model in accordance with some embodiments. The method 2300 is performed at a computing system (e.g., a client device, server system, and/or service platform) having one or more processors (e.g., the CPUs 202 and/or 302) and memory (e.g., the memory 218 and/or 310). In some embodiments, the memory stores one or more programs configured for execution by the one or more processors. At least some of the operations shown in FIG. 23 correspond to instructions stored in a computer memory or a computer-readable storage medium. In some embodiments, the computing system is the platform 100, the client device(s) 102, and/or the server system 106.

The computing system receives (2302) a request from a user to modify a machine-learning model that is configured to perform a specific clinical task. In some embodiments, the request is generated by the user by selecting and/or arranging graphical user interface elements within a user interface associated with the corresponding node architecture. In some embodiments, the user interface comprises an agent builder component in a control plane of the computer system. In some embodiments, the request comprises a plurality of text data comprising one or more text strings inputted by the user. In some embodiments, the specific clinical task includes generating a summary report of a patient's medical records, guiding a patient through a care plan, creating patient care guidelines based on a patient's health profile, identifying patients requiring follow-up at a hospital, identifying changes in a standard of care for a disease setting, and/or evaluating unstructured data associated with a patient to identify a cohort of similar patients.

The computing system retrieves (2304), based on the machine-learning model (e.g., a model 228), a corresponding node architecture (e.g., a node architecture 6106) defining a conditional logic for performing the specific clinical task by the machine-learning model. In some embodiments, the corresponding node architecture 6106 is associated with one or more agent modules 6102, each of which is further associated with one or more machine learning models, through a plurality of interconnected nodes 6108 associated with the agent modules 6102. In some embodiments, the node architecture 6106 defines a conditional logic, such as a coarse-grain or high-level logic, for performing the specific clinical task, such as by using the machine-learning model. In some embodiments, the conditional logic of the node architecture is executed in accordance with a first order of a set of interconnected nodes 6108 from the plurality of nodes. In some embodiments, each node represents a data object (e.g., executable code) that implements a fine-grain or low-level logic function based on the corresponding conditional logic 6112. In some embodiments, the plurality of nodes includes an input node configured for parsing data elements and/or receiving data from another source, at least one output node for communicating data to another source and/or generating new data, and/or one or more intermediate node connected between the input node and the at least output node, and the first set of interconnected nodes comprises one or more data source nodes, one or more machine-learning model nodes, and one or more conditional logic nodes. In some embodiments, the one or more data-source nodes use a retrieval-augmented generative (RAG) process to zero-shot information, such as component 6236 of FIG. 14, using a model 228. For example, the computing system may apply the RAG process to entire patient records, which allows for applying the entire patient records to the model 228 with excess computational burdens, such as opposed to focusing solely on a specific type of clinical note.

In some embodiments, this RAG process is used to analyze clinical mentions throughout a patient's entire record without the need for predefined sections of interest. However, the present disclosure is not limited thereto. In some embodiments, the RAG process utilizes one or more vector embeddings, such as a plurality of predetermined vector embeddings in which each predetermined vector embedding is associated with a corresponding text string, or snippet. Advantageously, this RAG approach can be more efficient and effective than providing the LLM with larger context windows.

In some embodiments, the input node is configured to receive a prompt from a user associated with the specific clinical task. In some embodiments, the input node is an initial terminal node in the node architecture that receives the prompt from the user in a raw format (e.g., as instructed data). In some embodiments, the output node is configured to generate a response to the prompt from the user based on a respective task-specific machine-learning model associated with the output node. In some embodiments, each respective machine-learning model node in the one or more machine learning model nodes is configured to obtained information corresponding to the prompt obtained using a corresponding domain associated with the respective machine-learning model. In some embodiments, each respective machine-learning model node in the one or more machine learning model nodes include one or more parameters and one or more functions for interacting with other nodes in the plurality of interconnected nodes.

The computing system generates (2306), for display at a remote device (e.g., client device 102), a representation of the corresponding node architecture 6106. In some embodiments, the representation of the corresponding node architecture 6106 shows a graphical representation of one or more edges connecting each node in the plurality of interconnected nodes (e.g., as illustrated in FIGS. 19A and 19B). In some embodiments, the representation represents a plurality of input features, which allows a user to manage and/or configure each node, such as an order of the nodes in the plurality of interconnected nodes, a removal of a node from the plurality of interconnected nodes, an additional of a node from the plurality of interconnected nodes, and a modification to one or more parameters of the node. In some embodiments, the presentation includes a first input feature for configuring the conditional logic of the corresponding node architecture, which allows for a coarse-grain or high-level modification to the corresponding node architecture 6106. In some embodiments, the first input feature allows for the end-user to rearrange the order of the nodes by changing a position of a first node within the representation (e.g., drag and dropping the node from a first position to a second position) so the node is adjacent to a second node. In some embodiments, the representation includes a second input feature for configuring a parameter 6110 of a corresponding node 6108 in the first set of interconnected nodes, which allows for fine-grain or low-level modification to the corresponding node architecture 6106. In some embodiments, the second input feature allows for the end-user to modify how the node processing graphical data from a first modality based on an authorization and/or authentication privilege of the end-user and/or a geographic location of a client device 102 associated with the end-user.

The computing system receives (2308) a selection of either the first input feature or the second input feature. In some embodiments, the section is received through an input of the client device 102, such as through a mouse and/or keyboard of the client device 102. In some embodiments, the selection of either the first input feature or the second input feature defines a second order of a second set of interconnected nodes from the plurality of nodes. In some embodiments, the selection modifies a first node so the output of the first node no longer inputs to a second node but rather a third node when a threshold condition is satisfied. In some embodiments, the representation modifies a visualization of a node if the output of the first node when inputted to a second node does not satisfy a logic 6112 of the second node. As an example, if the second node is trained on a domain of the knowledge database 404 associated with two-dimensional graphical data and the first node is configured to output three-dimensional volumetric graphical data, then a visualization of the first node and/or the second node is modified to visualize that the output does not satisfy a threshold condition of requiring input of two-dimensional data at the second node. In some embodiments, the selection of the first feature may allow for disposing and/or generating a third node interposing between the first and second nodes, in which the third node is configured to splice three-dimensional data into two-dimensional data, which then satisfies threshold condition of requiring input of two-dimensional data at the second node.

Advantageously, the representation, through the plurality of input features, provides a visual way to manage and/or configure the nodes 6108 and structure of the node architecture to form various configurations of interconnected nodes without requiring extensive coding or computational knowledge by the end user.

The computing system updates (2310) the conditional logic of the corresponding node architecture in accordance with the second order of the second set of interconnected nodes, thereby configuring how the machine-learning model performs the specific clinical task. Advantageously, by updating the conditional logic, other users can access the agent module and benefit for the gained learning provided by the updated conditional logic.

In some embodiments, the computing system generates a configuration file for the corresponding node architecture. In some embodiments, the configuration file setting a working environment for the corresponding node architecture 6106 and one or more type-specific machine learning models (e.g., models 228) associated with the corresponding node architecture.

Although FIG. 23 illustrates a number of logical stages in a particular order, stages which are not order dependent may be reordered and other stages may be combined or broken out. Some reordering or other groupings not specifically mentioned will be apparent to those of ordinary skill in the art, so the ordering and groupings presented herein are not exhaustive. Moreover, it should be recognized that various stages could be implemented in hardware, firmware, software, or any combination thereof.

FIG. 24 is a flow diagram illustrating a method 2400 of performing a clinical task in accordance with some embodiments. The method 2400 is performed at a computing system (e.g., a client device, server system, and/or service platform) having one or more processors (e.g., the CPUs 202 and/or 302) and memory (e.g., the memory 218 and/or 310). In some embodiments, the memory stores one or more programs configured for execution by the one or more processors. At least some of the operations shown in FIG. 24 correspond to instructions stored in a computer memory or a computer-readable storage medium. In some embodiments, the computing system is the platform 100, the client device(s) 102, and/or the server system 106.

Advantageously, by deploying the task-specific agent (e.g., agent module 6102 trained for a particular domain), the computing system is capable of responding to prompts and/or request for information that are associated with niche domains that are otherwise too computationally complex to utilize with an untrained model within the domain.

The computing system receives (2402) a prompt. In some embodiments, the computing system is in communication with a machine-learning model (e.g., a model 228) that was trained to assist in performing one clinical task, such as by storing the model 228 at the first computing system or via a communication network 104. In some embodiments, the one clinical task is selected from the group consisting of: (i) generating a summary report of a patient's medical records, (ii) guiding a patient through a care plan, (iii) creating patient care guidelines based on a patient's health profile, (iii) identifying patients requiring follow-up at a hospital, (v) identifying changes in a standard of care for a disease setting, and (vi) evaluating unstructured data associated with a patient to identify a cohort of similar patients. In some embodiments, the clinical task includes (i) generating a summary report of a patient's medical records, (ii) guiding a patient through a care plan, (iii) creating patient care guidelines based on a patient's health profile, (iii) identifying patients requiring follow-up at a hospital, (v) identifying changes in a standard of care for a disease setting, (vi) evaluating unstructured data associated with a patient to identify a cohort of similar patients, or a combination thereof.

In some embodiments, the clinical task is generating a summary report of a patient's medical records. In some such embodiments, the machine learning model is trained using other patient's medical records other than the patient's the report is based on. In some embodiments, the agent module 6102 generates a clinical summary report of a patient's entire medical record that is accessible to the agent module 6102, such as a first electronic medical record associated with the patient during a first epoch obtained from a first secure database and a second electronic medical record associated with the patient during a second epoch obtained from a second secure database. In some embodiments, the computing system generates the clinical summary report when a threshold condition is satisfied when evaluating some or all of the patient's entire medical record, such as any time an important event in the patient life cycle was happening including: an upcoming appointment, a significant change in the care of the patient, an update to the records that changes a previous result on a clinical summary report, or a combination thereof. In some embodiments, generating the report further includes communicating the report to a client device 102 associated with the patient and/or a medical practitioner associated with the patient for display at the client device 102. In some embodiments, the clinical task comprises a literature search, a cohort builder, an insurance claim builder, a patient query, or a handbook query.

In some embodiments, a patient query agent module comprises a set of input blocks, a set of template blocks, a set of document-retrieval blocks, a set of model blocks, and a set of output blocks. For example, a first input block is configured to receive user queries and a second input block is configured to receive a patient identifier. As another example, a first template block is configured to generate an object (e.g., a JSON object) for the patient identifier and a second template block is configured to reformat the user queries from the first input block (e.g., to determine a command, intent, and/or domain from the query). A third template block may be configured and used to convert information from a document-retrieval block into an object (e.g., a JSON object). A first model block (e.g., an LLM model) may be configured and used to answer questions based on the information from the document-retrieval block (e.g., answer yes or no questions). The set of output block may be used to output data from the document-retrieval block, the model block, and/or the various template blocks.

In some embodiments, the report provides one or more real-time clinical summaries directly to a patient via a user interface display at the client device, in which the report includes information updated with self-reported outcomes and data from external services and/or databases associated with the subject, such as a connected fitness client application. In some embodiments, the report is configured to provide the patient with a diagnosis, track the health data of the patient during a third epoch, and/or visualize a health summary in real-time, such as through one or more charts or tables of the report.

In some embodiments, the clinical task is guiding a patient (or other subject) through a first care plan. In some such embodiments, the machine-learning model is trained using a second care plan different from the first care plan. In some embodiments, the agent module 6102 is configured to maintain a database of one or more medical/clinical standards, guidelines, regulations, information, or a combination thereof by continuously obtaining up-to-date data from external sources and ensuring accuracy with recent testing results. In some embodiments, the agent module 6102 includes one or more nodes 6108 that obtain updated clinical information from a subject and/or new medical publications from additional testing associated with a subject, and synthesize an overall clinical care guide for the patient and/or a medical practitioner, such as by recommending next steps in a care plan or gaps in the care plan.

In some embodiments, prior to generating a natural language response to the prompt, the computing system selects a repository of data from among a plurality of repositories based on an identification of a domain, in a plurality of domains, associated with the repository of data. In some embodiments, each respective repository of data from among a plurality of repositories is associated with a corresponding domain in the plurality of domains. In some embodiments, the machine-learning model is selected by a conditional logic from among multiple available machine-learning models based on content of the prompt. In some embodiments, a first node includes a corresponding logic 6112 that evaluates an intent inferred from the prompt and identifies a corresponding domain associated with the intent. In some embodiments, generating the report of the patient's medical records includes de-identifying personally identifiably information from the patient's medical records in accordance with one or more rules defined by task-specific machine-learning model.

In some embodiments, generating the report of the patient's medical records includes determining demographic information associated with the patient. In some embodiments, generating the report of the patient's medical records comprises determining a past medical condition of the subject. In some embodiments, generating the report of the patient's medical records includes determining one or more care plans for the patient. In some embodiments, generating the report of the patient's medical records includes determining one or more therapies administered to the patient. In some embodiments, generating the report of the patient's medical records includes determining a summary of specific care instructions for the patient.

In some embodiments, guiding the patient through the care plan includes evaluating one or more clinical publications associated with a different care plan. In some embodiments, guiding the patient through the care plan includes conducting an assessment of the patient. In some embodiments, the assessment includes one or more prompts configured to elicit information from the patient. In some embodiments, the assessment includes a biometric assessment of the patient. In some embodiments, the assessment is configured to elicit responses from the patient that inform the agent module 6102 about a status of the care plan and/or the patient, such as whether the subject has started the care plan, whether the patient has had an adverse reaction to the care plan, whether the patient had strictly adhered to the care plan, whether the patient has notice improvements in one or more conditions exhibited by the subject, or a combination thereof.

In some embodiments, guiding the patient through the care plan includes generating an agent module 6102 configured specifically to the patient, which, advantageously, allows for the patient to conversationally engage with the agent module 6102 to guide the patient through their care plan, explain next steps in the care plan, answer prompts about follow-up care, or a combination thereof. For example, after a treatment plan is determined by the agent module 6102 using a first node 6108, the agent module 6102 could provide personalized guidance and answer specific patient queries using a second node 6108 that evaluates the treatment plan based on other user-specific needs. In some embodiments, the agent module 6102 is usable by physicians associated with the patient to evaluate recommendations and/or understand the underlying guidelines and personalized data points that led to the recommendation. In some embodiments, the agent module 6102 provides the recommendation and human verifiable support for the decisions made using the logic 6112 to arrive at the recommendation.

In some embodiments, creating the patient care guidelines based on the patient's health profile includes evaluating one or more clinical publications. In some embodiments, creating the patient care guidelines based on the patient's health profile includes determining one or more discordances between a first therapy and one or more biometrics or health parameters associated with the patient's medical records. In some embodiments, creating the patient care guidelines based on the patient's health profile includes generating one or more charts specific to the patient.

In response to receiving the prompt, the computing system generates (2404) a natural-language response that is responsive to the prompt and is based on an analysis by the machine-learning model of a repository of data that is determined to be relevant to the prompt. The computing system provides (2406) the natural language response to a second computing system that is distinct from the computing system. For example, the computing system causes the natural language response to be displayed at a remote display.

Although FIG. 24 illustrates a number of logical stages in a particular order, stages which are not order dependent may be reordered and other stages may be combined or broken out. Some reordering or other groupings not specifically mentioned will be apparent to those of ordinary skill in the art, so the ordering and groupings presented herein are not exhaustive. Moreover, it should be recognized that various stages could be implemented in hardware, firmware, software, or any combination thereof.

Figure 25:
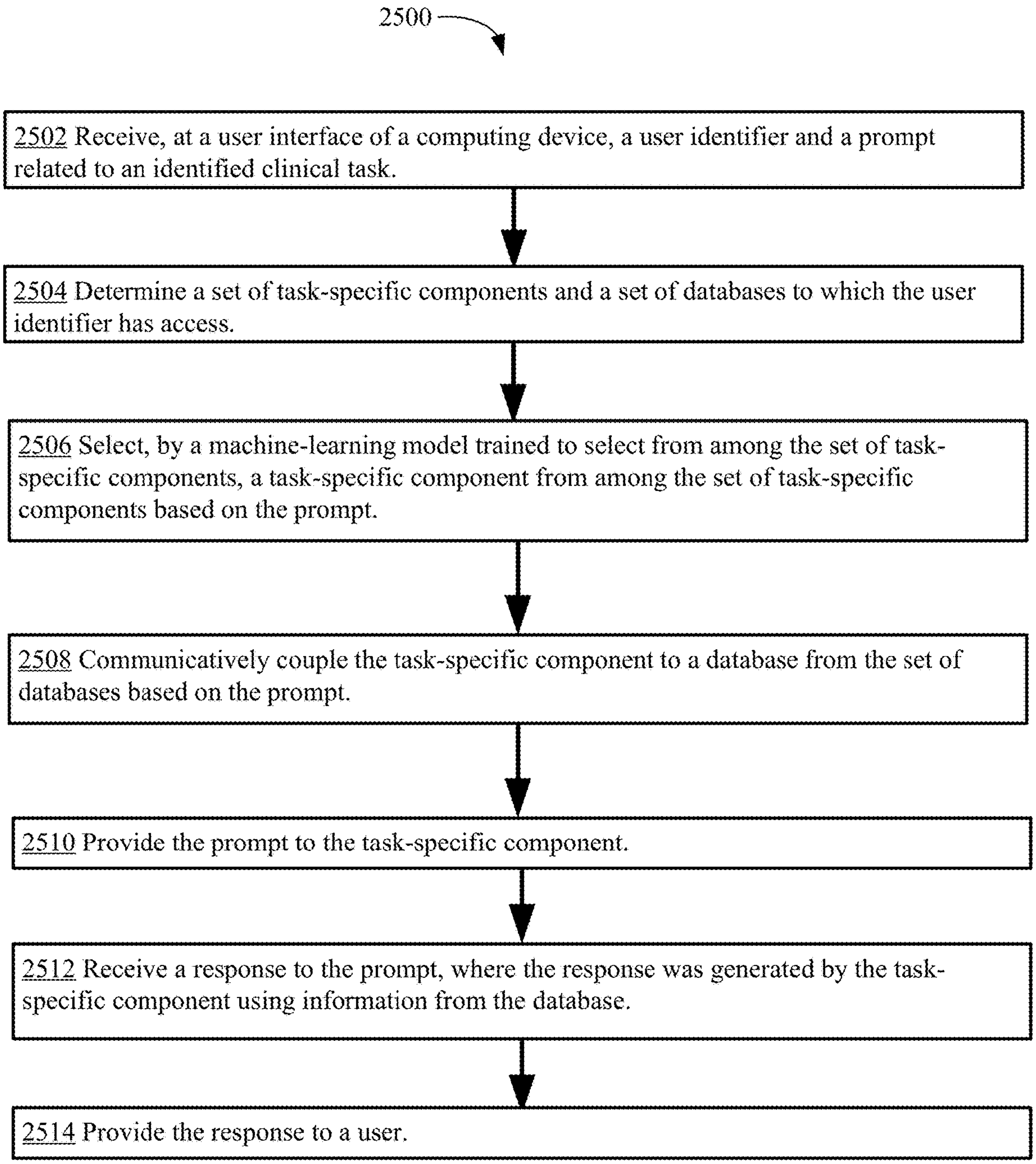
FIG. 25 is a flow diagram illustrating an example method of enabling third-party access and use of an agent module in accordance with some embodiments.

FIG. 25 is a flow diagram illustrating a method 2500 of enabling third-party access and use of an agent module in accordance with some embodiments. The method 2500 is performed at a computing system (e.g., a client device, server system, and/or service platform) having one or more processors (e.g., the CPUs 202 and/or 302) and memory (e.g., the memory 218 and/or 310). In some embodiments, the memory stores one or more programs configured for execution by the one or more processors. At least some of the operations shown in FIG. 25 correspond to instructions stored in a computer memory or a computer-readable storage medium. In some embodiments, the computing system is the platform 100, the client device(s) 102, and/or the server system 106.

The computing system receives (2502), at a user interface, a user identifier and a prompt related to an identified clinical task. In some embodiments, the user identifier is received with the prompt (e.g., in the same communication). In some embodiments, the user identifier is received before the prompt (e.g., the user identifier is received when the user communicatively connects to the computing system or when the user authenticates with the computing system).

The computing system determines (2504) a set of task-specific components (e.g., agent modules) and a set of databases to which the user identifier has access. In some embodiments, the sets of task-specific components and/or databases are determined based on an access level and/or permissions associated with the user identifier. In some embodiments, the databases (and/or data within the databases) are subject to different access control lists. In some of these embodiments, the user identifier is checked against the access control lists to determine what data the user is authorized to access.

The computing system selects (2506), by a machine-learning model trained to select from among the set of task-specific components (e.g., a super agent module), a task-specific component from among the set of task-specific components based on the prompt. For example, the machine-learning model identifies an intent and/or a command from the prompt and selects the task-specific component in accordance with the identified intent and/or command.

The computing system communicatively couples (2508) the task-specific component to a database from the set of databases based on the prompt. In some embodiments, the task-specific component is communicatively coupled to the database via a connection tool or block (e.g., an API tool).

The computing system provides (2510) the prompt to the task-specific component. In some embodiments, the computing system provides one or more commands, intents, and/or tokens corresponding to the prompt, rather than the prompt itself.

The computing system receives (2512) a response to the prompt, where the response is generated by the task-specific component using information from the database. In some embodiments, the response is transformed and/or formatted by the task-specific component and/or a frontend component (e.g., an interfacing agent module).

The computing system provides (2514) the response to a user. For example, the computing system causes the response to be displayed to the user (and/or audibly output to the user). In some embodiments, the computing system provides a transformed (e.g., summarized) and/or reformatted response to the user. For example, the computing system may provide a natural language version of the response.

Although FIG. 25 illustrates a number of logical stages in a particular order, stages which are not order dependent may be reordered and other stages may be combined or broken out. Some reordering or other groupings not specifically mentioned will be apparent to those of ordinary skill in the art, so the ordering and groupings presented herein are not exhaustive. Moreover, it should be recognized that various stages could be implemented in hardware, firmware, software, or any combination thereof.

Figure 26:
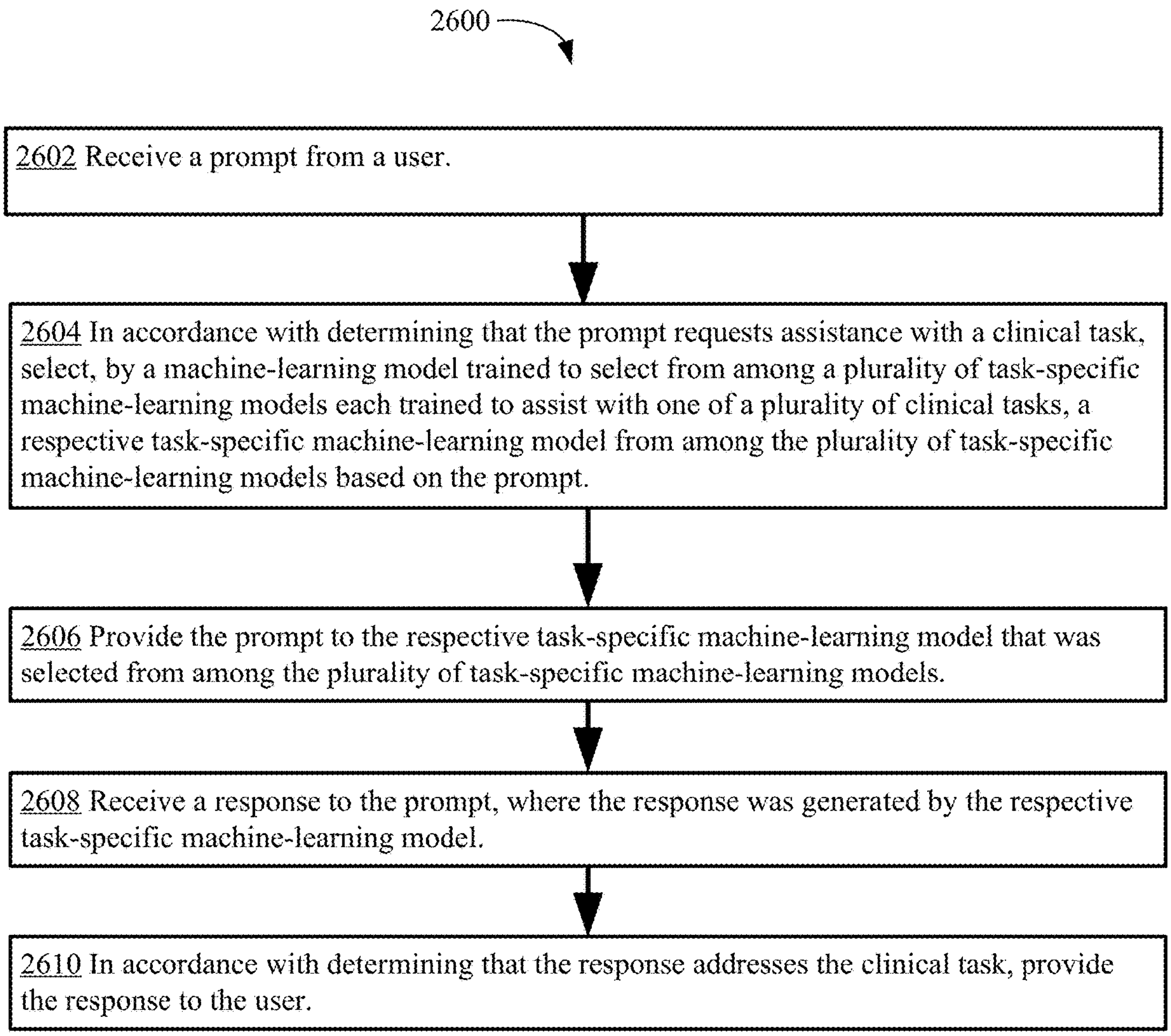
FIG. 26 is a flow diagram illustrating an example method of selecting models for a clinical task in accordance with some embodiments.

FIG. 26 is a flow diagram illustrating a method 2600 of selecting from among task-specific machine-learning models for addressing a clinical task in accordance with some embodiments. The method 2600 is performed at a computing system (e.g., a client device, server system, and/or service platform) having one or more processors (e.g., the CPUs 202 and/or 302) and memory (e.g., the memory 218 and/or 310). In some embodiments, the memory stores one or more programs configured for execution by the one or more processors. At least some of the operations shown in FIG. 26 correspond to instructions stored in a computer memory or a computer-readable storage medium. In some embodiments, the computing system is the platform 100, the client device(s) 102, and/or the server system 106.

In some embodiments, the computing system selects from between 10 task-specific machine-learning models and 1,000,000 task-specific machine-learning models. In some embodiments, the computing system selects from at least 10 task-specific machine-learning models, at least 50 task-specific machine-learning models, at least 1,000 task-specific machine-learning models, or at least 100,000 task-specific machine-learning models. In some embodiments, the computing system selects from at most 10 task-specific machine-learning models, at most 50 task-specific machine-learning models, at most 1,000 task-specific machine-learning models, or at most 100,000 task-specific machine-learning models.

In some embodiments, the clinical task includes generating a summary report of a patient's medical records, guiding a patient through a care plan, creating patient care guidelines based on a patient's health profile, identifying patients requiring follow-up at a hospital, identifying changes in a standard of care for a disease setting, or evaluating unstructured data associated with a patient to identify a cohort of similar patients.

The computing system receives (2602) a prompt from a user. In some embodiments, the prompt comprises a plurality of text data comprising one or more text strings inputted by the user. In some embodiments, the prompt is provided in text form, such as by inputting a text string via a keyboard at a client device 102. In some embodiments, the prompt is received from the user by having the user identify one or more data sources for obtaining information. In some embodiments, the prompt from the user is received in the form a one or more data files, such as one or more portable document files, one or more text files, one or more two-dimensional graphical images, one or more three-dimensional graphical images, one or more longitudinal data sets, or a combination thereof.

In some embodiments, the prompt includes an identifier for a patient, an attribute of the patient, a test result of the patient, a diagnosis for the patient, or a combination thereof. For example, the prompt may include an identifier for the patient that the end-user is about to see in a clinical setting, which allows for the method to retrieve data elements associated with the patient, such as based on a look up structure associated with the identifier. In some embodiments, the attribute of the patient allows for the computing system to utilize one or more agent modules 6102 trained on various domains particular to the patient. In some embodiments, the attribute of the patient includes demographic information, medical conditions of the patient, therapies administered to the patient, biometrics of the patient, allergies of the patient, lifestyle information of the patient, and/or the like.

In some embodiments, the prompt is generated by the user by selecting and arranging graphical user interface elements within a user interface associated with the plurality of task-specific machine-learning models and/or the machine-learning model. In some embodiments, the user arranges the graphical user interface elements, each of which corresponds to a node 6108 further associated with the plurality of task-specific machine-learning models and/or the machine-learning model.

In some embodiments, the respective task-specific machine-learning model is selected from among the plurality of task-specific machine-learning models based on a divergence of a principal component analysis of the prompt for each respective task-specific machine learning model in the plurality of task-specific machine-learning models. In some embodiments, the selecting the respective task-specific machine-learning model from among the plurality of task-specific machine-learning models is based on an identification of the first domain through an associated with the prompt. In some embodiments, the selecting the respective task-specific machine-learning model comprises generating the task-specific machine-learning model having a conditional logic configured to respond to the prompt. In some embodiments, the selecting the respective task-specific machine-learning model includes identifying a first classification of machine-learning models and selecting the respective the respective task-specific machine-learning model based on an association with the first classification of machine-learning models. In some embodiments, the selecting the respective task-specific machine learning model includes forming a first order for a plurality of interconnected nodes.

In some embodiments, the computing system selects at least two task-specific machine learning models from among the plurality of task-specific machine-learning models based on the prompt. In some embodiments, the computing system provides some or all of the prompt to each respective task-specific machine-learning model in the at least two task-specific machine learning models that was selected from among the plurality of task-specific machine-learning models. In some embodiments, the computing system receives respective information from each task-specific machine learning models in the at least two task-specific machine learning models, where the response corresponds to a combination of the respective information from at least two task-specific machine learning models.

In some embodiments, the computing system selects a first task-specific machine learning model in the at least two task-specific machine learning models as an initial terminal task-specific machine learning model. In some embodiments, the computing system selects a second task-specific machine learning model in the at least two task-specific machine learning models as a final terminal task-specific machine learning model.

In some embodiments, the computing system provides the prompt to the first task-specific machine-learning model. In some embodiments, the computing system receives respective information from the first task-specific machine-learning model. In some embodiments, the computing system provides the respective information to the second task-specific machine-learning model. In some embodiments, the computing system receives the response to the prompt from the second task-specific machine-learning model, where the response was generated by the second task-specific machine-learning model.

In accordance with determining that the prompt requests assistance with a clinical task: the computing system selects (2604), by a machine-learning model trained to select from among a plurality of task-specific machine-learning models each trained to assist with one of a plurality of clinical tasks, a respective task-specific machine-learning model from among the plurality of task-specific machine-learning models based on the prompt. In some embodiments, determining that the prompt requests assistance with a clinical task further comprises parsing the prompt into one or more commands, thereby forming an intent of the prompt for requesting assistance with a clinical task. In some embodiments, determining that the prompt requests assistance with a clinical task further comprises identifying a first domain in a plurality of domains associated with the intent of the prompt.

In some embodiments, determining that the prompt requests assistance with a clinical task further comprises applying the prompt to a machine-learning model, thereby generating a first response different from the prompt and responsive to the prompt from the user. In some embodiments, determining that the prompt requests assistance with a clinical task further comprises obtaining a first domain in a plurality of domains of an input space associated with the prompt. In some embodiments, determining that the prompt requests assistance with a clinical task further comprises evaluating the value of the first response. In some embodiments, when the value of the first response satisfies a threshold condition, communicating, via a communication network, the first response to the user. In some embodiments, when the value of the first response fails to satisfy the threshold condition, the method includes identifying a first task-specific machine learning model associated with the first domain.

In some embodiments, when the value of the first response fails to satisfy the threshold condition, the method includes applying the first response and/or the prompt to the first task-specific machine-learning model, thereby generating a second response different from the first response and responsive to the prompt.

In some embodiments, the respective task-specific machine-learning model is trained on a first domain in a plurality of domains. In some embodiments, each respective domain in the plurality of domains comprises at least one task-specific machine-learning model trained on the respective domain.

The computing system provides (2606) the prompt to the respective task-specific machine-learning model that was selected from among the plurality of task-specific machine-learning models. In some embodiments, providing the prompt to the respective task-specific machine-learning model comprises applying the prompt to a first node in a plurality of interconnected nodes, thereby generating the response different from prompt and responsive to the prompt from the use. In some embodiments, the first node is associated with a first domain-specific machine-learning model in the plurality of task-specific machine-learning models, each task-specific machine-learning model in the plurality of task-specific machine-learning model (i) is associated with at least one nodes in the plurality of interconnected nodes and (ii) defines a conditional logic for performing a specific task. In some embodiments, each node in the plurality of interconnected nodes is connected by an edge to at least one node in the plurality of interconnected nodes.

The computing system receives (2608) a response to the prompt, where the response is generated by the respective task-specific machine-learning model.

In accordance with determining that the response addresses the clinical task, the computing system (2610) provides the response to the user. In some embodiments, the computing system provides a transformed and/or formatted version of the response to the user. For example, the computing system provides a natural language version of the response.

Although FIG. 26 illustrates a number of logical stages in a particular order, stages which are not order dependent may be reordered and other stages may be combined or broken out. Some reordering or other groupings not specifically mentioned will be apparent to those of ordinary skill in the art, so the ordering and groupings presented herein are not exhaustive. Moreover, it should be recognized that various stages could be implemented in hardware, firmware, software, or any combination thereof.

Figure 27:
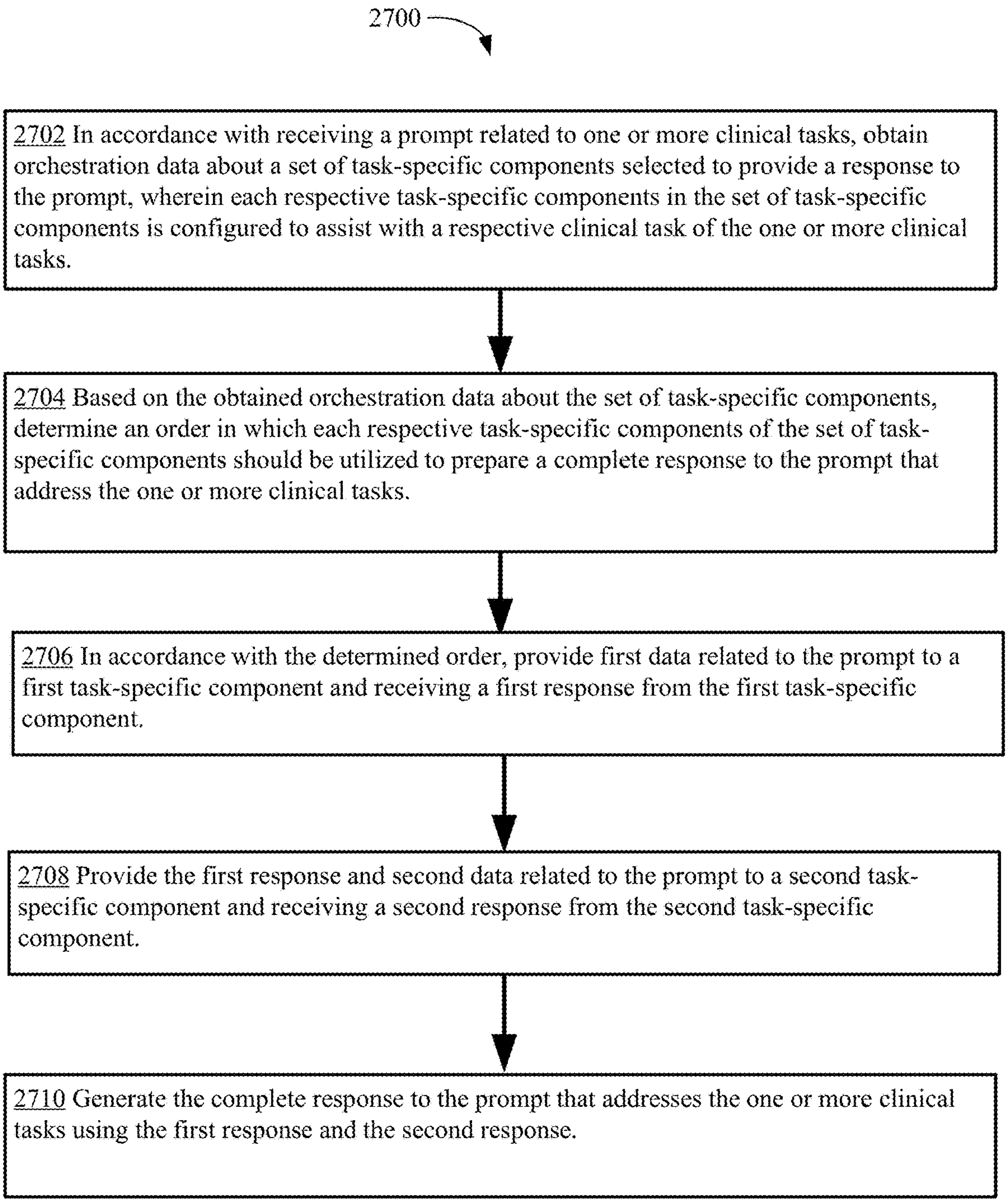
FIG. 27 is a flow diagram illustrating an example method of interacting with a routing agent module in accordance with some embodiments.

FIG. 27 is a flow diagram illustrating a method 2700 of interacting with a routing agent module in accordance with some embodiments. The method 2700 is performed at a computing system (e.g., a client device, server system, and/or service platform) having one or more processors (e.g., the CPUs 202 and/or 302) and memory (e.g., the memory 218 and/or 310). In some embodiments, the memory stores one or more programs configured for execution by the one or more processors. At least some of the operations shown in FIG. 27 correspond to instructions stored in a computer memory or a computer-readable storage medium. In some embodiments, the computing system is the platform 100, the client device(s) 102, and/or the server system 106.

In accordance with receiving a prompt related to one or more clinical tasks, the computing system obtains (2702) orchestration data about a set of task-specific components (e.g., a set of agent modules and/or tools) selected to provide a response to the prompt, where each respective task-specific components in the set of task-specific components is configured to assist with a respective clinical task of the one or more clinical tasks.

Based on the obtained orchestration data about the set of task-specific components, the computing system (e.g., a routing agent module of the computing system) determines (2704) an order in which each respective task-specific components of the set of task-specific components should be utilized to prepare a complete response to the prompt that address the one or more clinical tasks. In some embodiments, the routing agent module is configured to send a query (or tokens from a query) to multiple blocks and/or agent modules to obtain data response to the query. For example, in response to a query about whether a patient has lung cancer, the routing agent module may query a document agent module regarding whether any document in a document collection indicates that the patient has lung cancer, the routing agent module may also query an image analysis agent module regarding whether an image (or set of images) indicates that the patient has lung cancer. In this example, the routing agent module may reformat/transform the query to be appropriate for each downstream module. In some embodiments, the routing agent module includes conditional logic (e.g., if a first component has a first type of reply, then a routing agent module may follow up with a second component, and if the first component has a second type of reply, then the routing agent module may follow up with a third component instead of the second component).

In accordance with the determined order, the computing system provides (2706) first data related to the prompt to a first task-specific component and receives a first response from the first task-specific component. In some embodiments, the computing system provides data to two task-specific components concurrently. For example, a first portion of data is transmitted to a first component and a second portion of the data is transmitted to a second component asynchronously.

The computing system provides (2708) the first response and second data related to the prompt to a second task-specific component and receiving a second response from the second task-specific component. For example, the first response includes data from a medical database, and the second task-specific component is configured to analyze the data from the medical database.

The computing system generates (2710) a complete response to the prompt that addresses the one or more clinical tasks using the first response and the second response. In some embodiments, the computing system generates a summary or other indication of the first and second responses. In some embodiments, the computing system provides the second response to the user of the system.

Although FIG. 27 illustrates a number of logical stages in a particular order, stages which are not order dependent may be reordered and other stages may be combined or broken out. Some reordering or other groupings not specifically mentioned will be apparent to those of ordinary skill in the art, so the ordering and groupings presented herein are not exhaustive. Moreover, it should be recognized that various stages could be implemented in hardware, firmware, software, or any combination thereof.

Figure 28:
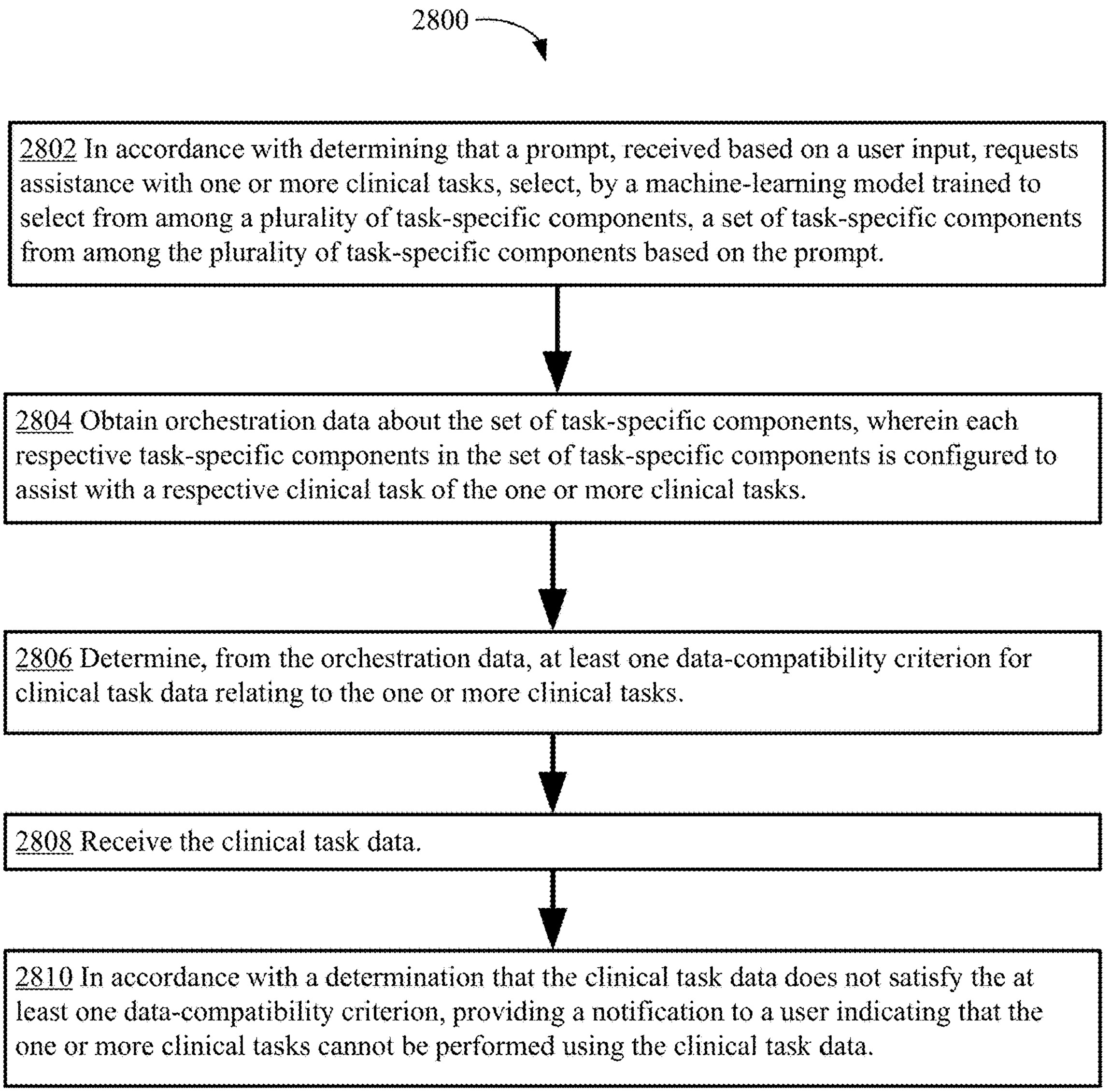
FIG. 28 is a flow diagram illustrating an example method of verifying data compatibility in accordance with some embodiments.

FIG. 28 is a flow diagram illustrating a method 2800 of verifying data compatibility in accordance with some embodiments. The method 2800 is performed at a computing system (e.g., a client device, server system, and/or service platform) having one or more processors (e.g., the CPUs 202 and/or 302) and memory (e.g., the memory 218 and/or 310). In some embodiments, the memory stores one or more programs configured for execution by the one or more processors. At least some of the operations shown in FIG. 28 correspond to instructions stored in a computer memory or a computer-readable storage medium. In some embodiments, the computing system is the platform 100, the client device(s) 102, and/or the server system 106.

In accordance with determining that a prompt, received based on a user input, requests assistance with one or more clinical tasks, the computing system selects (2802), by a machine-learning model (e.g., a super agent module) trained to select from among a plurality of task-specific components (e.g., agent modules and/or tools), a set of task-specific components from among the plurality of task-specific components based on the prompt (e.g., based on an intent and/or command of the prompt).

The computing system obtains (2804) orchestration data (e.g., operating parameters, purposes, domains, tasks, and/or other types of orchestration data) about the set of task-specific components, where each respective task-specific components in the set of task-specific components is configured to assist with a respective clinical task of the one or more clinical task.

The computing system determines (2806), from the orchestration data, at least one data-compatibility criterion (e.g., an input data type, a data quality requirement, or other criterion) for clinical task data relating to the one or more clinical tasks. In some embodiments, the at least one data-compatibility criterion corresponds to a transform to be applied to the clinical task data.

The computing system receives (2810) the clinical task data. For example, the clinical task data comprises image data, text data, audio data, and/or other types of data. In some embodiments, the clinical task data is received from one or more databases (e.g., the database(s) 108 and/or the database(s) 404). In some embodiments, the clinical task data is obtained using one or more interfacing agent modules.

In accordance with a determination that the clinical task data does not satisfy the at least one data-compatibility criterion, the computing system provides (2812) a notification to a user indicating that the one or more clinical tasks cannot be performed using the clinical task data. For example, the notification may indicate that the clinical task data is of a wrong type or has insufficient quality to use to perform the one or more clinical tasks.

Although FIG. 28 illustrates a number of logical stages in a particular order, stages which are not order dependent may be reordered and other stages may be combined or broken out. Some reordering or other groupings not specifically mentioned will be apparent to those of ordinary skill in the art, so the ordering and groupings presented herein are not exhaustive. Moreover, it should be recognized that various stages could be implemented in hardware, firmware, software, or any combination thereof.

In some embodiments, a task-specific agent module includes one or more machine-learning models (e.g., language models, transformer models, etc.). In some embodiments, each machine-learning model is restricted to a particular set of domains, a particular set of databases, and/or particular types of data. In some embodiments, each machine-learning model is fine-tuned on a particular set of domains and/or a particular set of data. In some embodiments, a task-specific agent module is composed of a machine-learning model, short- and/or long-term memory, an action space, decision making tools, and/or action procedures (e.g., internal and/or external actions). In some embodiments, a task-specific agent module is composed of a set of blocks (e.g., each block having a set functionality) that are coupled together to perform more complex actions. For example, the set of blocks may include a block configured for document collection, a block configured for document segmentation, a block configured for segment analysis, a block configured for data transformation, and/or a block configured for response formatting. In some embodiments, a first agent module is composed of one or more other agent modules. In some embodiments, each block is configured to perform a single function (e.g., document retrieval, string formatting, model calls, API calls, data routing, etc.). For example, a string templating block may be configured to convert input strings to one or more output variables.

In some embodiments, a task-specific agent module is configured to retrieve and analyze data and generate corresponding content (e.g., an article, summary, report, description, insight, etc.). In some embodiments, the output of a task-specific agent module is personalized/customized to a particular user or subject (e.g., patient). For example, the task-specific agent module has access to information about the particular user or subject and uses the information to provide directed content for the user or subject (e.g., the task-specific agent module is configured to prepare a letter on behalf of the user or subject using information from one or more databases (e.g., medical databases and/or legal databases) and information about the user or subject. In some embodiments, the information about the user or subject comprises information from one or more documents (e.g., patient records) and/or information about previous interactions with the task-specific agent module (or with other task-specific agent modules in the system).

In some embodiments, a task-specific agent module is configured to interact with a user (e.g., is a frontend agent module configured to interact using natural language). In some embodiments, a task-specific agent module is configured to intake and summarize documents. In some embodiments, a task-specific agent module is configured to intake, revise, and/or generate code in accordance with user requests and/or prompts. In some embodiments, a task-specific agent module is configured to perform a data transform and/or data validation. For example, the task-specific agent module is configured to convert visual data to textual data. In some embodiments, the task-specific agent module is a super agent module configured to determine appropriate agent modules and/or tools to respond to a particular prompt or type of prompt. In some embodiments, the task-specific agent module is a routing agent module configured to route one or more subprocesses corresponding to prompt to appropriate task-specific agent modules and/or tools. In some embodiments, a super agent module is configured to identify multiple domains and route commands and/or requests according to their respective domains.

In some embodiments, a task-specific agent module is an input-to-output agent module, an input-to-model-to-output agent module (e.g., with an LLM or other model component), a document-retrieval agent module (e.g., configured for RAG-based document retrieval), a logical-routing agent module (e.g., incorporating one or more programming languages), a super agent module (e.g., that uses one or more additional agent modules for particular tasks or subtasks), a recursive agent module (e.g., configured to recursively perform an action or function until a condition is met), a filter agent module (e.g., configured to identify and/or adjust search filters based on a user prompt), a language agent module (e.g., configured to convert an input language (e.g., a programming language or natural language) to a different output language).

In some embodiments, a task-specific agent module (e.g., a task-specific orchestration), after being generated, is provided to a user via a digital assistant function. For example, the digital assistant is provided with information about the task-specific agent module and configured to interact with (e.g., call and pass information to) the task-specific agent module when a prompt with an appropriate intent is received. In some embodiments, the task-specific agent module, after being generated is provided to the user via a third-party API service. For example, the task-specific agent module is presented in a user interface and selectable directly by a user of the user interface.

Various example embodiments and aspects of the disclosure are described below for convenience. These are provided as examples, and do not limit the subject technology. Some of the examples described below are illustrated with respect to the figures disclosed herein simply for illustration purposes without limiting the scope of the subject technology.

(A1) In one aspect, some embodiments include a method of configuring a task-specific agent (e.g., the method 1300).

In some embodiments, the method is performed at a computing system (e.g., the platform 100, the client device 102, or the server system 106). The method includes: (i) receiving a request (e.g., via the agent builder of FIG. 6) from a user for an agent that is configured to perform a specific task; (ii) in response to the request, identifying a first agent type from a set of agent types based on one or more requirements for performing the specific task, where each agent type of the set of agent types corresponds to a respective language model; (iii) generating a model component having the first agent type, where generating the model component includes generating (or retrieving) a set of operating instructions for the model component (e.g., the system prompt of the large-language model represented by block 1834C stating "You are a helpful AI assistant."); (iv) generating an implementation component for the agent, the implementation component configured to communicatively couple the model component to a set of components based on the one or more requirements for performing the specific task, where the set of components include one or more of: a set of data sources (e.g., the Conversation History component of the LLM Messages Builder in FIG. 19A), a set of tools (e.g., the array of Agent Descriptions output by the Use Agent List component in FIG. 19A), and a set of output components; and (v) deploying the agent to a working environment (e.g., the control plane of the client device 102 in FIG. 6), where the agent includes the model component and the implementation component. In some embodiments, the first agent type is identified based on one or more characteristics of the user (e.g., types of data and/or work the user has performed). In some embodiments, the system identifies the set of agent types based on the one or more characteristics of the user and presents the set of agent types to the user. In some of these embodiments, the system receives a selection, from the user, of the first agent type from the presented set of agent types.

For example, the specific task may be to assist an end user with query expansion (e.g., by comparing an embedding corresponding to the user's input prompt to one or more vector embeddings of embeddings 6240 in FIG. 14), providing guidance/needs related to a particular condition or treatment, answering questions about treatment methodologies, assisting an end user in identifying an appropriate data source for a query or request, assisting an end user with specifying a particular subject cohort, and/or persona-specific guidance. Example tasks include identifying molecular landscapes, identifying relevant code, and suggesting subsequent analysis.

(A2) In some embodiments of A1, the first agent type is selected from the set of agent types based on a divergence of a principal component analysis for each agent type (e.g., as described previously with respect to FIGS. 7A-7E). For example, label-dependent spectra from the output of a pre-trained model may be compared using Jensen-Shannon (JS) divergence of the principal component analysis (PCA) decomposed output spectra. Models which are better suited for a downstream task may have a larger JS divergence. The final downstream performance of a fine-tuned model may also have a correlation to the JS divergence. For example, PAC JS divergence may be used for determining each model's potential downstream performance on a particular classification task.

(A3) In some embodiments of A1 or A2, at least one of the set of components is a second agent, the second agent configured to perform a second task. For example, a chain of agents (e.g., respective orchestrations of a composite orchestration) can be configured to communicate with one another to complete the specific task (e.g., the block representing the agent router of the representation 1900 in FIG. 19A indicates a connection between the agent router orchestration and the LLM messages builder orchestration). In some embodiments, the agent includes two or more models, each of the two or more models configured to operate on a different type of data. For example, an output from the large-language model represented by the block 1834C in FIG. 18D can be provided as an input to another large-language model for performing a different task.

(A4) In some embodiments of any of A1-A3, the set of components include the set of data sources, and the set of data sources comprise a vector database (e.g., the vector database 6240). In some embodiments, the set of data sources include one or more of: a document index, a static corpus, a dynamic corpus, a set of document chunks, a set of document embeddings, and document metadata (e.g., document classifications). In some embodiments, each data source of the set of data sources has a corresponding application programming interface. As an example, the set of data sources may include the external database(s) 108, the data modules 240, the server data modules 330, and/or the database(s) 400.

(A5) In some embodiments of any of A1-A4, the set of components include the set of output components, and the set of output components include an interactive console. In some embodiments, the set of output components include an interactive user interface (e.g., as illustrated in FIGS. 10A-10C, 11A-11C, and 12A-12D), such as a digital assistant user interface.

(A6) In some embodiments of any of A1-A5, the set of components include the set of tools, and the set of tools include parameters and functions for interacting with other components of the set of components. For example, the set of tools provide a mechanism by which the agent can integrate with the outside world (e.g., other systems and components). As another example, a tool may include some parameters that are specified when configuring the agent and some parameters that can be specified at invocation time by the agent itself. Tools may be general-purpose, or custom built for a particular integration. In some embodiments, different agent types have different access to tools. For example, a first type of agent is configured with a set of available tools, and the language model itself can choose when and how to use them. In this example, the second type of agent may follow a fixed sequence of steps, and a corresponding agent configuration defines when and how tools are invoked. Example tools were discussed previously with respect to FIG. 6.

(A7) In some embodiments of A6, the set of tools include one or more of: an authenticated request tool configured to fetch a URL using a user access token; an external request tool configured to fetch a URL external to the computing system; and an email tool configured to send an email.

(A8) In some embodiments of any of A1-A7, the method further includes generating a configuration file for the agent (e.g., as shown in Examples 4 and 5 above), the configuration file setting a working environment for the agent and one or more type-specific configuration objects.

(A9) In some embodiments of any of A1-A8, the request is received via an agent builder component in a control plane of the computing system.

(A10) In some embodiments of A9, the method further includes, after deploying the agent: (i) receiving, at the agent builder component, a configuration update for the agent; and (ii) transmitting update information from the agent builder component to the agent.

(A11) In some embodiments of any of A1-A12, deploying the agent comprises deploying the agent to an agent host (e.g., the agent host discussed above with reference to FIG. 6) in the working environment. For example, the agent host includes a frontend component (e.g., for authentication and user interaction with deployed agents). The agent host may also include a backend component that includes a database layer, a document loader, a listener component (e.g., update listener and/or subscription listener), a websocket, and/or API access.

(A12) In some embodiments of any of A1-A11, the request from the user for the agent includes an access token (e.g., an okta token) corresponding to the working environment.

(A13) In some embodiments of A12, the method further includes authenticating the agent with one or more of the set of data sources using the access token. For example, the agent forwards an end-user's access token for authentication rather than granting a permission role to the agent's machine user. In some embodiments, the agent is restricted to certain endpoints and/or access methods (e.g., only GET requests) so that the agent can't be used to perform admin tasks on behalf of a user with write permissions. In some embodiments, the agent is configured with a fixed base URL so that the agent can't be used to make authenticated requests to some other service.

(A14) In some embodiments of any of A1-A13, generating the model component includes selecting a number of hidden layers for a model of the model component. For example, the number of hidden layers for the model is selected based on calculated PCA for output at each hidden layer of the model. For example, the model is reduced as discussed previously with respect to FIGS. 7A-7E.

(A15) In some embodiments of any of A1-A14, the method further includes: (i) obtaining, via a retriever component, one or more documents; (ii) extracting text from the one or more documents; (iii) obtaining a set of text snippets from the text; (iv) generating a set of embeddings for the set of text snippets; and (v) storing the set of embeddings in the set of data sources (e.g., as illustrated in FIG. 9A). For example, the one or more documents may include one or more PDF documents. In some embodiments, the one or more documents are obtained from one or more medical databases (e.g., the external database(s) 108, the data modules 240, the server data modules 330, and/or the database(s) 400). In some embodiments, the medical database (i) are owned/operated by different entities, (ii) have different modalities of data, and/or (ii) have different data structures and/or formats. In some embodiments, the set of text snippets are tokenized. In some embodiments, the documents are multimodal (e.g., include text and images) and a first embedder component is used for embedding a first type of data and a second embedder component is used for embedding a second type of data.

(A16) In some embodiments of any of A1-A15, the method further including, after deploying the agent: (i) receiving, at the agent, a user query from a second user; (ii) generating a query embedding from the user query; (iii) identifying one or more embeddings stored in the set of data sources, where the one or more embeddings are identified based on a similarity score with the query embedding; (iv) obtaining information corresponding to the one or more embeddings; (v) generating, at the agent, a natural language response to the user query based on the obtained information; and (vi) presenting the natural language response to the second user (e.g., as discussed previously with respect to FIGS. 9A-9C). In some embodiments, a first subset of the embeddings correspond to data stored in electronic health records and a second subset of the embeddings correspond to metadata for the electronic health records. In some embodiments, the similarity score is based on a cosine similarity.

(A17) In some embodiments of A16, the natural language response includes an answer, a rationale for the answer, and supporting evidence for the answer. For example, the user query may be "does subject X qualify for trial Y" and the response may be "Yes, because the EHR for subject X shows that subject X meets the inclusion and exclusion criteria for trial Y listed below . . . "

(A18) In some embodiments of A16 or A17, the method further includes determining a user intent from the user query and generating the query embedding based on the user intent (e.g., as discussed previously with respect to FIGS. 9A-9C).

(A19) In some embodiments of A18, the method further includes identifying, based on the user intent, one or more tools (e.g., a retrieval tool, an embedding tool, and/or a formatting tool) from the set of tools, where the information corresponding to the one or more embeddings is obtained using the one or more tools.

(A20) In some embodiments of any of A16-A19, the method further includes identifying a set of parameters from the user query and generating the query embedding based on the set of parameters (e.g., as discussed previously with respect to FIGS. 9A-9C).

(A21) In some embodiments of any of A1-A20, the set of data sources include a medical database (e.g., the database(s) 400). For example, the medical database stores a set of electronic health records.

(A22) In some embodiments of any of A1-A21, the method further includes, after deploying the agent: (i) providing a user interface to an end user; (ii) receiving a query from the end user via the user interface; (iii) generating a response, via the deployed agent, to the query; and (iv) providing the generated response to the end user (e.g., as illustrated in FIGS. 12A-12D). In some embodiments, the query includes identification of a type of data to be searched and/or identification of one or more databases to be searched.

(A23) In some embodiments of A22, the user interface is an assistance interface for a medical application (e.g., the user interface illustrated in FIGS. 11A-11C).

Figure 12A:
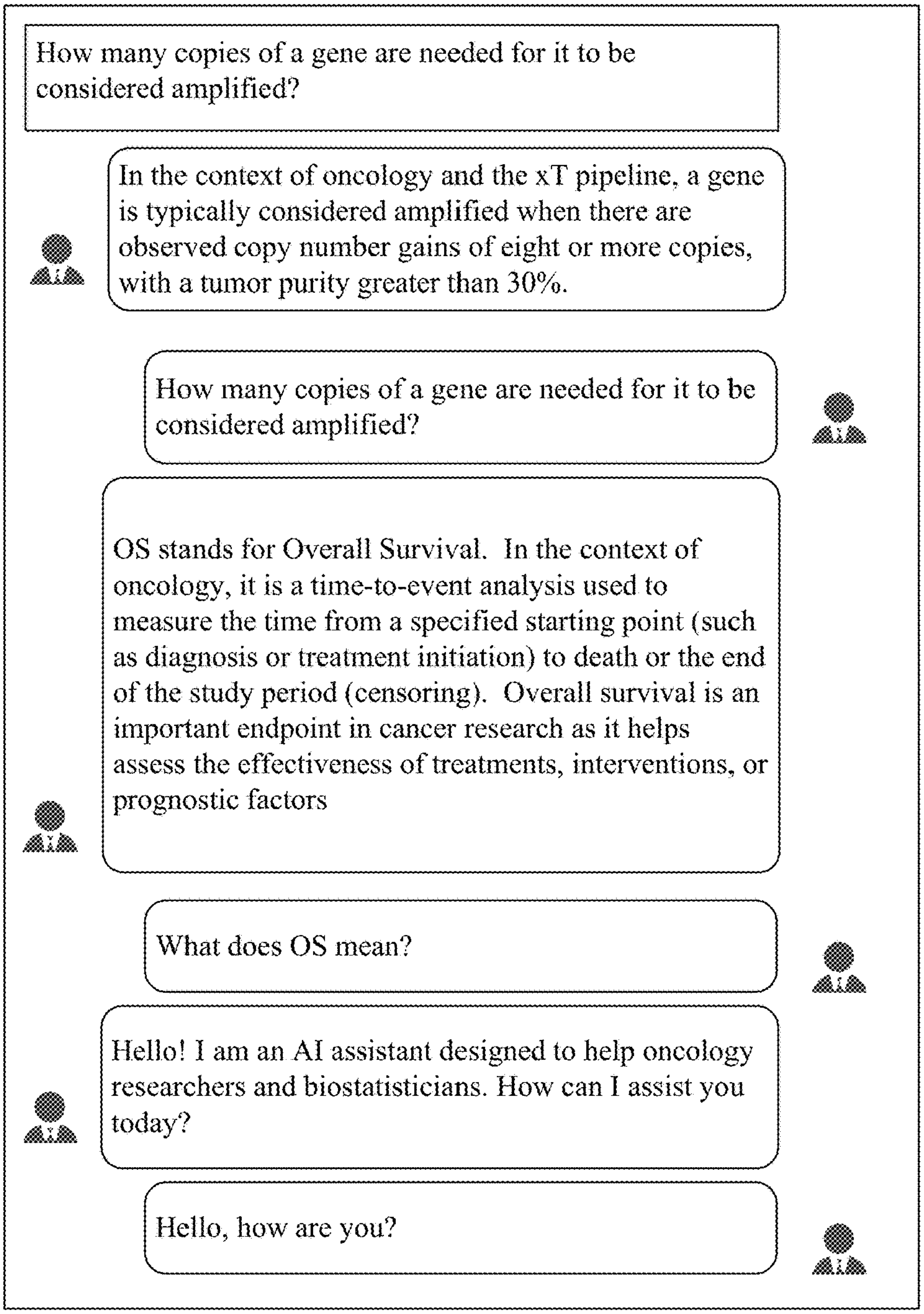
Figure 12B:
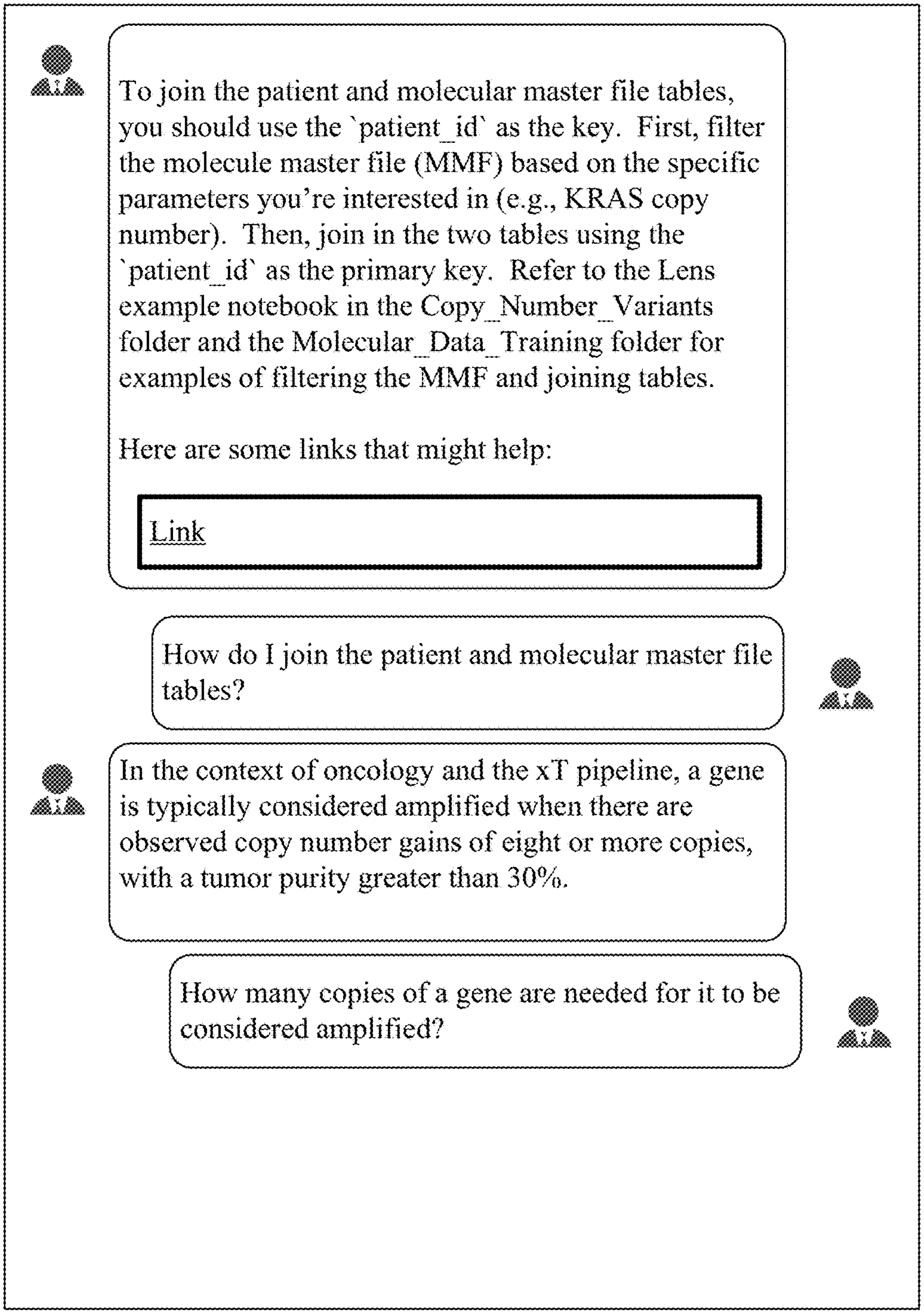
Figure 12D:
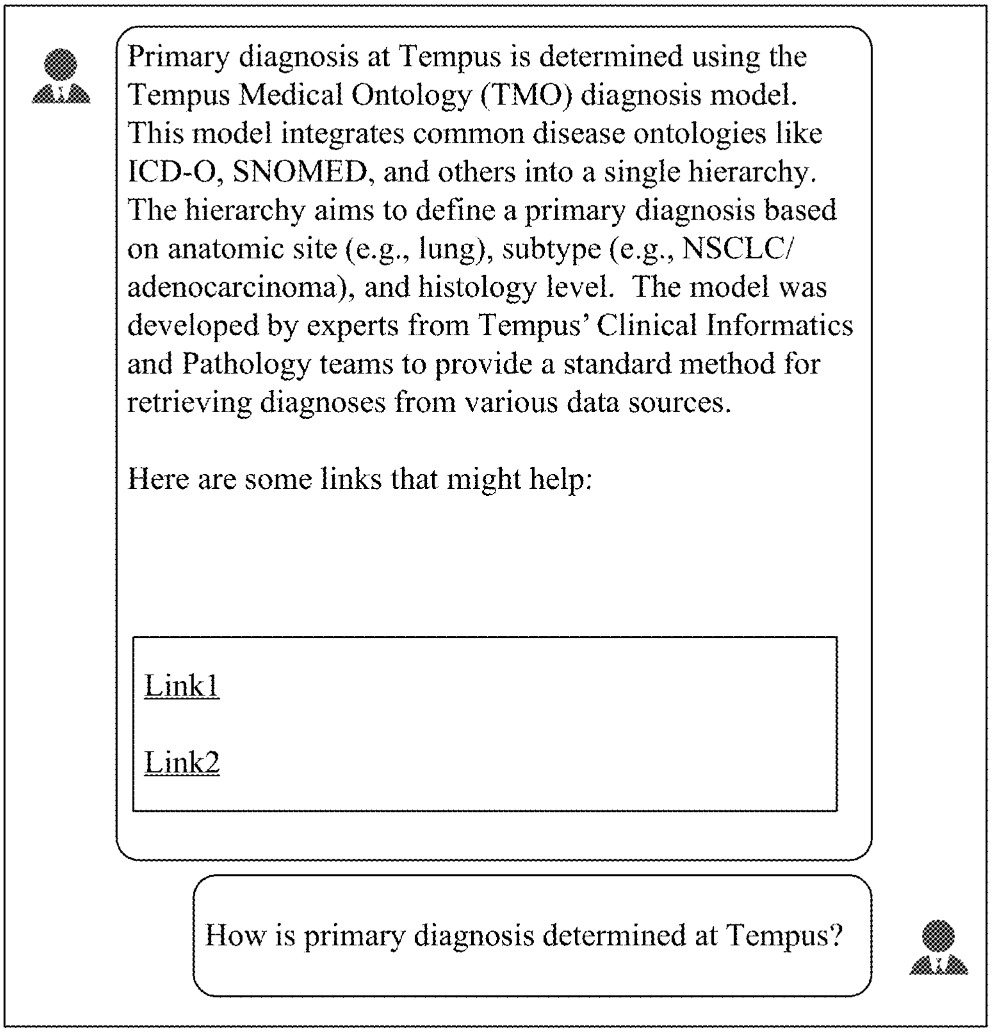

(A24) In some embodiments of A22 or A23, the query relates to joining two tables of data, and the response includes information from a table joined from the two tables. For example, the agent joins the two tables and provides the joined table and/or data from the joined table. In some embodiments, the response includes instructions for joining the two tables of data (e.g., as illustrated in FIGS. 12C and 12D).

(A25) In some embodiments of A22 or A23, the query relates to interpreting a data source, and the response includes interpretation information for the data source. For example, the query relates to understanding a data model, understanding a column of data, and/or understanding how data was derived.

(A26) In some embodiments of any of A22-A25, the response is generated based on the query and context data obtained by the agent. In some embodiments, the context data includes a chat history for the end user (e.g., as illustrated in FIGS. 8A and 8B).

(A27) In some embodiments of any of A22-A26, the query is a natural language query, the agent is configured to generate a structured query from the natural language query, and the response is generated based on the structured query. For example, FIG. 9C shows a natural language query being converted into a vector (e.g., by an embedding component of an agent) and the vector being used to search a set of vector databases.

(A28) In some embodiments of any of A22-A27, the response includes an answer to the query, a rationale for the answer, and supporting evidence for the answer. For example, the query includes a task for the agent, and the agent provides a breakdown of the task and executes on each part using provided tools (e.g., as illustrated in Example 1 above).

(A29) In some embodiments of any of A22-A28, the agent calls a function in response to the query, the function call includes one or more filters identified based on the query, and the response is generated based on information obtained from the function call.

(A30) In some embodiments of any of A1-A29, the agent is fine-tuned based on data from the set of data sources. In some embodiments, the fine tuning includes providing example queries and instructions on how to respond to each. In some embodiments, the fine tuning includes providing question and answer sets (e.g., as illustrated in FIG. 8B).

(B1) In another aspect, some embodiments include a method of identifying subjects (e.g., as members in a target population). In some embodiments, the method is performed at a computing system (e.g., the platform 100, the client device 102, or the server system 106). The method includes: (i) receiving a request from a user to identify subjects meeting a set of criteria; (ii) obtaining, via a language model component, a set of protocols from the request; (iii) generating, via the language model component, one or more structured queries based on the set of protocols; (iv) transmitting, via the language model component, the one or more structured queries to one or more databases; and (v) in response to transmitting the one or more structured queries, receiving, from the one or more databases, a set of subjects meeting the set of criteria.

(B2) In some embodiments of B1, the one or more databases includes one or more of: a clinical database, a therapies database, and a medical database (e.g., the database(s) 400). In some embodiments, the one or more databases include one or more datasets and/or data collections (e.g., document collections). In some embodiments, the one or more documents store multiple types of documents (e.g., text documents, images, audio files, etc.).

(B3) In some embodiments of B1 or B2, the one or more structured queries include one or more SQL queries (e.g., the structured query shown in the user interface illustrated in FIG. 11C). In some embodiments, the one or more structured queries are in a data definition language, a data query language, a data manipulation language, a data control language, and/or a transaction control language.

(B4) In some embodiments of any of B1-B3, the set of protocols are obtained by abstracting one or more criteria specified in the request. In some embodiments, the one or more protocols comprise one or more commands and/or one or more parameters.

(B5) In some embodiments of any of B1-B4, the language model component includes two or more task-specific agents. In some embodiments, the task-specific agents are trained using one or more abstraction sheets and/or a ground truth. For example, the task-specific agents may be any of the task-specific agent modules or orchestrations described herein.

(B6) In some embodiments of any of B1-B5, the set of criteria include a set of inclusion criteria and a set of exclusion criteria. In some embodiments, the set of criteria include one or more criteria for a subject (e.g., age, gender, etc.). In some embodiments, the set of criteria include one or more criteria for a medical condition of the subject.

(C1) In another aspect, some embodiments include a method of interacting with a task-specific orchestration (e.g., the method 2100). In some embodiments, the method is performed at a computing system (e.g., the platform 100, the client device 102, or the server system 106). The method includes: (i) obtaining data (e.g., medical data) from one or more data collections and/or databases (e.g., data from the database(s) 404, the array of documents provided to the orchestration represented by the block 1826B); (ii) presenting a set of user interface elements selected from a plurality of user interface elements (e.g., the set of user interface elements 1818A to 1818C in FIG. 18A, which each may correspond to a user command for instantiating a particular task-specific orchestration (e.g., the orchestration 1850)), where each respective user interface element of the set of user interface elements represents a respective task-specific orchestration (e.g., an agent module) of a plurality of task-specific orchestrations, and each of the respective task-specific orchestrations comprises one or more respective machine-learning models (e.g., the models 228) fine-tuned for a specific task or domain based on the data from the one or more data collections; (iii) responsive to a selection by a user of a respective user interface element representing a respective task-specific orchestration: (a) providing at least some of the data from the one or more data collections to the respective task-specific orchestration (e.g., the user-specific data 1828 shown in FIG. 18A); and (b) presenting a different user interface to the user for communicating with the respective task-specific orchestration (e.g., the user interface shown in FIG. 11); and (iv) in accordance with receiving a prompt provided by the user at the different user interface, presenting a response object, where the response object is generated by the respective task-specific orchestration based on (1) the prompt provided by the user, and (2) at least some of the data from the one or more data collections. For example, a user is presented with a set of task-specific agents and, in response to the user selecting a task-specific agent from the set, the task-specific agent is executed and provided with at least some of the data.

(C2) In some embodiments of C1, the data from the one or more data collections includes at least one live data collection that is updated in real-time while the user is using the data. For example, Input B represented by block 1834D in FIG. 18D may be a live data collection of clinical data, as indicated by a data-type indicator 1836. In some embodiments, an agent builder module is communicatively coupled to two or more document collections and configured to restrict access to each document collection based on user authentication data. For example, the agent-builder application 1800 may only allow users to access particular data sources, such as the live collection of clinical data represented by the block 1834D based on a determination that the user is allowed to access the clinical data (e.g., based on authentication credentials provided by the user).

(C3) In some embodiments of C1 or C2, the user interface includes: (i) a first user interface element for performing a chat with a respective customized agent that does not include document reference capabilities (e.g., by selecting the user interface element 1818A shown in FIG. 18A for a basic AI chat session), (ii) a second user interface element for performing an interaction with a customized agent that has capabilities for referencing a medical document (e.g., by selecting the user interface element 1818B in FIG. 18B for initializing a Chat with Documents), and (iii) a third user interface element for duplicating a customized agent that the user has previously interacted with using the different user interface (e.g., by selecting the user interface element 1818C in FIG. 18C for duplicating an existing agent).

(C4) In some embodiments of any of C1-C3, the response object comprises a set of query instructions for accessing portions of data from one or more data collections (e.g., the user interface shown in FIG. 12C includes instructions for joining patient and molecular master file tables in R, based on a prompt provided by the user stating: "How many copies of a gene are needed for it to be considered amplified?").

(C5) In some embodiments of any of C1-C4, the method further includes presenting respective user interface elements corresponding to respective settings of a configuration file for the respective task-specific orchestration, where the configuration file sets a working environment for the respective task-specific orchestration and one or more type-specific configuration objects for the respective task-specific orchestration. For example, the user interface element 1826A includes a selectable user interface element for specifying an environment for instantiating an orchestration (e.g., showing an environment named "Alpha" selected, which may correspond to a particular workload plane of the node architecture 6106).

(C6) In some embodiments of any of C1-C5, the method further includes presenting, adjacent to the user interface, a second user interface element different than the set of user interface elements, where the second user interface element is configured to allow a user to add or modify respective user interface elements of the set of user interface elements representing the respective task-specific orchestration. For example, the user interface 1830 includes a chat user interface element 1838 for chatting with the orchestration 1850 while presenting a modifiable workflow representation 1832 representing the orchestration 1850 that the user is able to modify while interacting with the chat user interface element 1838.

(C7) In some embodiments of any of C1-C6: (i) the set of user interface elements includes a default user interface element corresponding to a default set of data that is automatically provided to task-specific orchestrations created by the user, and (ii) the default user interface element corresponds to precision medicine data associated with the user (e.g., precision medical data related to the user). For example, the user interfaces shown in FIGS. 10A-10C include a user interface element corresponding to a trial identifier, where the trial identifier was selected to represent data associated with a particular clinical trial.

(C8) In some embodiments of C7, the precision medicine data includes a set of patients associated with the user (e.g., a cohort of patients that the user is responsible for).

(C9) In some embodiments of any of C1-C8, the selected task-specific orchestration is an orchestration for selecting other available agents to perform a specific task, and the response object provided in response to the prompt includes a workflow representation of another task-specific orchestration for performing a task identified based on the input prompt. For example, the representation 1900 shown in FIGS. 19A and 19B represents a composite orchestration that allows the user to generate orchestrations based on a prompt, and can optionally present a workflow representation of a generated orchestration after the prompt has been received.

(C10) In some embodiments of any of C1-C9, the different user interface includes an affordance for opening one of (i) a cohort builder tool or (ii) a table builder tool. In some embodiments, the method further includes, responsive to a user selection of the affordance, presenting another user interface element within the different user interface corresponding to the respective selected builder tool (e.g., the user interface shown in FIG. 11B includes a section with the cohort builder tool).

(C11) In some embodiments of any one of C1-C10, the method further includes, further in accordance with receiving the prompt from the user: (i) generating an embedding corresponding to the prompt, and (ii) comparing the embedding corresponding to the prompt to a plurality of embeddings within a vector database (e.g., the vector database 6240).

(C12) In some embodiments of C11, the embedding is generated based upon one of (i) a context obtained by the task-specific orchestration, and (ii) a conversation history of the user with the task-specific orchestration. For example, FIG. 14 illustrates the system determining one or more embeddings 6240 based on a prompt received from the client device 102.

(C13) In some embodiments of C1-C12, the user interface presented to the user for selecting the respective task-specific orchestration is hosted in a control plane defined by access of the control plane to a first set of data sources and/or users. In some embodiments, the different user interface presented to the user for interacting with the respective task-specific orchestration is hosted in a workload plane defined by access of the workload plane to a second set of data sources and/or users, different than the first set.

(C14) In some embodiments of C13, the different user interface includes a user interface element that includes information about the workload plane. For example, the user interface element 1826A includes an indication about a working environment (e.g., a workload plane) that the orchestration 1850 is configured to be deployed into.

(C15) In some embodiments of C1-C14, the response object includes one or more affordances for accessing respective data sources. In some embodiments, responsive to a user selection of a respective affordance of the one or more affordances, presenting another different user interface to the user, where the other different user interface includes respective user interface elements for searching for data within a respective data source corresponding to the respective affordance (e.g., the user interface 500 shown in FIGS. 5A and 5B).

(C16) In some embodiments of C15, the other different user interface includes a user interface for interacting with one of (i) a general purpose language model, and (ii) a task-specific orchestration.

(C17) In some embodiments of C16, the task-specific orchestration is finetuned using information about the respective data source corresponding to the respective affordance. For example, a respective task-specific agent may be specially-designed to interact with the data associated with the user interface 500, such that the user can provide prompts to a chat user interface while interacting with the user interface 500 to gain insight about the data source(s) associated that can be analyzed using the provided filters.

(C18) In some embodiments of C16 or C17, one or more filters are applied automatically when the other different user interface is presented based on the prompt provided by the user. For example, based on the content of the prompt, the user interface shown in FIG. 5A may automatically be presented with the set of filters pre-selected based on content of the user's prompt.

(C19) In some embodiments of C1-C18, the selected task-specific orchestration is associated with a data source that includes a live collection that is updated in real-time while the user is interacting with the task-specific orchestration, and in accordance with determining that additional data has been added to the live collection, providing an indication to the user about the additional data added to the live collection. For example, while the user is interacting with the chat user interface 1838 in FIG. 18F, a clinical sample may be added to Input B (represented by the block 1834B), and based on the additional data, a message may be presented within the chat user interface indicating that the data has been updated.

(C20) In some embodiments of C1-C19, a desired cohort is determined based on the prompt provided by the user, and the response object provided in response to the prompt includes a number of subjects within a subject dataset corresponding to the desired cohort.

(D1) In another aspect, some embodiments include a method of modifying functionality of the task-specific orchestration. In some embodiments, the method is performed at a computing system (e.g., the platform 100, the client device 102, or the server system 106). The method includes: (i) while a user interface of a task-specific orchestration builder is being presented at a display of an electronic device (e.g., the user interface 1830 shown in FIGS. 18D to 18F, which may be described herein as a workflow editor user interface), presenting a graphical representation of a structure of a task-specific orchestration for providing information (e.g., medical information) based on data (e.g., medical data) about the task-specific orchestration (e.g., the workflow representation 1832 shown in FIG. 18D, the representation 1900 shown in FIGS. 19A and 19B), where: (a) the task-specific orchestration includes a plurality of blocks for performing intermediary computational operations between receiving a prompt from a user and providing an output that includes the medical information based on the medical data about the task-specific orchestration, (b) the graphical representation includes (1) a first user interface element for providing inputs for modifying a composition of the task-specific orchestration, and (2) a plurality of second user interface elements for providing inputs for modifying respective blocks for performing respective intermediary computational operations of the task-specific orchestration; (ii) detecting a user input directed to one of the first user interface element of the plurality of second user interface elements; and (iii) in response to the detecting the user input, modifying respective functionality of the task-specific orchestration.

(D2) In some embodiments of D1, the method further includes, in response to detecting another user input, presenting a different user interface, different than the user interface, the different user interface including a set of form user interface elements (e.g., the user interface element 1826A and/or the user interface element 1826B shown in FIGS. 18B and 18C), where: (i) a first subset of the set of form user interface elements are associated with orchestration-level modifications to the task-specific orchestration (e.g., the first set of user interface elements for modifying orchestration-level settings of the orchestration 1850), and (ii) a second subset of the set of form user interface elements are associated with block-level modifications to the task-specific orchestration (e.g., the second set of user interface elements 1826B for modifying block level configurations 1854 of a block associated with a large-language model of the orchestration).

(D3) In some embodiments of D1 or D2, each respective second user interface element of the plurality of second user interface elements includes respective block-level inputs including one or more of: a model type, a specifier indicating a type of output, a maximum output length configured to be provided by a block, a specifier indicating one or more types of input documents that the block is capable of ingesting, a specifier indicating whether to use conversation history from a previous conversation between a user and task-specific orchestration, and a specifier indicating whether metadata should be provided in the output (e.g., the user-configurable settings of the large-language model represented by the user interface element 1826B in FIG. 18C).

(D4) In some embodiments of any of D1-D3, the user interface of the task-specific orchestration builder includes one or more third user interface elements indicating data flow between two or more respective block-level user interface elements. For example, a connector shown connecting the output of the block 1834D and an input for attachments of the block 1834C representing the large language model.

(D5) In some embodiments of D4, a respective second user interface element of the plurality of second user interface elements includes an indication based on a determination that another respective third user interface element is required to be connected between the respective second user interface element and another respective second user interface element in order to be operably integrated into the task-specific orchestration. For example, the user interface elements 1834D and 1834E include patterns (which may correspond to different colors) that indicate that the user interface elements 1834D and 1834E must be connected to other blocks within the representation of the task-specific orchestration 1842 in order for the intermediary computational operations to be performed as part of the operations of the task-specific orchestration 1842.

(D6) In some embodiments of any of DI-D5, the method further includes, in accordance with detecting a user input directed to one of the second user interface elements, presenting another graphical representation, different than the graphical representation, where the other graphical representation corresponds to a different task-specific orchestration corresponding to the second user interface element. For example, the super agent task-specific orchestration represented by the representation 1900 can be presented alternatively as a block within another representation of a different task-specific orchestration.

(D7) In some embodiments of any of D1-D6, a block-selecting user interface element is presented adjacent to the graphical representation, where the block-selecting user interface element includes respective affordances for instantiating additional second user interface elements within the graphical representation of the task-specific orchestration. For example, the user interface 1830 in FIG. 18D includes a block-selecting user interface element for adding blocks to the task-specific orchestration 1850.

(D8) In some embodiments of D7, the user interface corresponds to a portion of a data plane associated with credentials provided before presenting the user interface, and the method further includes determining the respective affordances to present within the block-selecting user interface based on the portion of the data plane associated with the credentials.

(D9) In some embodiments of D1-D8, a respective second user interface element of the plurality of second user interface element includes a data-indicating affordance, and the data-indicating affordance indicates that a data source associated with the respective second user interface element includes a live collection that is updated in real-time.

(D10) In some embodiments of any of DI-D4, the method further includes, responsive to a user input directed to an agent-level user interface element within the user interface, instantiating a block-level user interface element within the graphical representation. For example, the user may select an agent-level setting for an Agent Type of the orchestration 1850, where each of the agent types may include a set of default second user interface elements that are generated upon instantiation of a respective task-specific orchestration having the respective agent type.

(D11) In some embodiments of any of DI-D10, each respective second user interface element of the plurality of second user interface element includes a data-indicating affordance representing one or more of (i) an input for a respective intermediary computation operation associated with the respective second user interface element is configured to receive, and/or (ii) an output that a respective intermediary computational operation corresponding to the respective second user interface element is configured to provide.

(D12) In some embodiments of D11, each of the data-indicating affordances include respective visual characteristics, and the respective visual characteristics are based on respective datatypes of the respective data-indicating affordances.

(D13) In some embodiments of any of D1-D12, a respective second user interface element of the plurality of second user interface elements is configured to provide a list of agents that are identified as being relevant to a prompt provided to the task-specific orchestration (e.g., the Use Agent List user interface element shown in FIG. 19A).

(D14) In some embodiments of any of DI-D13, the first user interface element includes an affordance for indicating whether the task-specific orchestration is configurable to use or process personal health information (PHI). In some embodiments, the task-specific orchestration is configured to recognize whether information is PHI (e.g., during operation and/or interaction with a user) and take appropriate action (e.g., ensure security measures are active).

(D15) In some embodiments of any of D1-D14, the first user interface element includes an affordance for indicating whether the task-specific orchestration will be usable by other users of the task-specific orchestration builder. For example, the user interface 1830 in FIG. 19A includes agent settings where the user can specify whether the task-specific orchestration that the user is creating is visible to internal members of the organization, or whether the task-specific orchestration is only privately viewable by the user.

(D16) In some embodiments of any of D1-D15, the method further includes, responsive to a user input to interact with the task-specific orchestration represented by the graphical representation, presenting a chat user interface element adjacent to the graphical representation, where the chat user interface element is configured to allow the user to interact with the task-specific orchestration. For example, FIG. 18F shows the user interface 1830 including the chat user interface 1838 where the user can interact with the task-specific orchestration 1850.

(D17) In some embodiments of any of D1-D16, a respective second user interface element of the plurality of second user interface elements is associated with a task-specific machine-learning model, and the respective second user interface element includes an informational affordance indicating a system prompt that is configured to be provided to the task-specific machine-learning model while the task-specific orchestration is being used (e.g., the system prompt of the user interface element 1834C stating: "You are a helpful AI assistant").

(D18) In some embodiments of D17, the respective second user interface element includes another informational affordance indicating a conversation history that will be provided as context to the task-specific machine-learning model while the task-specific orchestration is being used (e.g., the user interface element 1834C includes a data-indicating affordance for providing a conversation history as an input to the large-language model represented by the user interface element 1834C).

(D19) In some embodiments of D17, the respective second user interface element includes yet another informational affordance indicating a type of large-language model comprising the task-specific machine-learning model. For example, the user interface element 1834C includes an informational affordance indicating that the large language model corresponding to the user interface element 1834C uses the gpt-4-turbo model.

(D20) In some embodiments of any of DI-D19, a respective second user interface element of the plurality of second user interface elements includes a respective informational affordance indicating a template that is applied to input text received as an input for the set of intermediary computational operations associated with the second user interface element (e.g., the template indicating affordance shown within the user interface element 1834D).

(E1) In another aspect, some embodiments include a method of deploying a task-specific machine-learning model (e.g., the method 2200, model 228, agent module 1602, etc.). In some embodiments, the method is performed at a computing system (e.g., the platform 100, the client device 102, or the server system 106). In some embodiments, the method includes: (i) receiving a prompt from a user, the prompt being associated with one or more commands and/or one or more tokens; (ii) identifying, in accordance with a first command in the one or more commands, a first task-specific component (e.g., a machine-learning model) in a plurality of task-specific components, where each task-specific component (a) is associated with at least one node in a plurality of interconnected nodes and (b) defines a conditional logic for performing a specific task of the task-specific component; (iii) applying some or all of the tokens of the plurality of tokens to a first node in the at least one node associated with the first task-specific component, where the applying comprises: (1) communicating, via a communication network, to a remote device an access token associated with the first task-specific component, (2) retrieving, via the communication network, in accordance with an authentication of the access token from a source other than the first task-specific component, a plurality of restricted data, and (3) determining a correlation between the first node and a second node based on an evaluation of one or more restricted data in the plurality of restricted data, where: (I) the second node is interconnected with the first node, (II) when the correlation between the first node and the second node satisfies a threshold condition of the first node, generating a plurality of text data different from the prompt, and (III) when the correlation between the first node and the second node fails to satisfy the threshold condition of the first node, repeating the applying some or all of the tokens of the plurality of tokens to the first node; (iv) traversing the some or all of the tokens of the plurality of tokens to the second node; and (v) applying the some or all of the tokens of the plurality of tokens to the second node.

(E2) In some embodiments of E1, the one or more commands are determined from the prompt (e.g., derived from the prompt, translation from the prompt, etc.).

(E3) In some embodiments of E1 or E2, the one or more commands comprise an intent of the prompt (e.g., an inquiry associated with the prompt, last conversation event info of FIG. 18F, etc.).

(E4) In some embodiments of any of E1-E3, the one or more tokens comprise between 10 tokens and 100,000 tokens (e.g., at least 100 tokens, at least 1,000 tokens, at least 10,000 tokens, at least 25,000 tokens, at least 40,000 tokens, at least 50,000 tokens, at least 60,000 tokens, at least 75,000 tokens, at least 90,000 tokens, etc.).

(E5) In some embodiments of any of E1-E4, the one or more tokens collectively represent an entirety of the prompt (e.g., a plurality of text data associated with the prompt is translated into the one or more tokens in which the one or more tokens collectively represent all of the information within the plurality of text data).

(E6) In some embodiments of any of E1-E4, the one or more tokens collectively represent less than all of the prompt (a plurality of text data associated with the prompt is translated into the one or more tokens in which the one or more tokens collectively represent less than all of the information within the plurality of text data).

(E7) In some embodiments of any of E1-E6, the one or more tokens comprises one or more character tokens (e.g., each token represents one, or more than one, character associated with a text string), one or more sub-word tokens (e.g., each token represents one or more, or two or more, characters associated with a text string), one or more word tokens (e.g., each token represents a work in the text string), or a combination thereof.

(E8) In some embodiments of any of E1-E7, the conditional logic (e.g., logic 6112) of a respective task-specific component (e.g., agent module 6102) is defined, at least in part, by a different user (e.g., the client device 102, or the system server 106).

(E9) In some embodiments of any of E1-E8, the method includes determining the correlation between the first node (e.g., the first node 6108-1) and the second node (e.g., the second node 6108-2). In some embodiments, determine the correlation comprises determining one or more vector embeddings (e.g., vector database 904, embeddings 904, etc.) associated with the prompt.

(E10) In some embodiments of E9, each vector embedding in the one or more vector embeddings is a predetermined vector embedding (e.g., generated prior to receiving the prompt, generated from an evaluation of a first prompt received from a second user, etc.).

(E11) In some embodiments of any of E1-E10, determining the correlation between the first node 6208-1 and the second node 6208-2 comprises identifying one or more data sources (e.g., data module 240, databases 400, knowledge database 404, domains, etc.) associated with the first node 6208-1 and the second node 6208-2.

(E12) In some embodiments of any of E1-E11, method further includes repeating the applying some or all of the tokens of the plurality of tokens to the first node 6208-1 for at least 10 instances of the repeating (e.g., in accordance with a determination a threshold condition is satisfied, recursively, etc.).

(E13) In some embodiments of any of E1-E12, each respective node 6108 in the plurality of interconnected nodes 6108 is associated with a corresponding classification in a plurality of classifications (e.g., a respective domain in a plurality of domains, e.g., less than all of an input space, or a portion of knowledge database 404, etc.).

(F1) In another aspect, some embodiments include a method of configuring a task-specific machine-learning model (e.g., the method 2300). In some embodiments, the method is performed at a computing system (e.g., the platform 100, the client device 102, or the server system 106). The method includes: (i) receiving a request (e.g., prompt) from a user to modify a machine-learning model (e.g., model 228, agent module 6108, or node 6108, etc.) that is configured to perform a specific task (e.g., a clinical task); (ii) retrieving, based on the machine-learning model, a corresponding node architecture (e.g., node architecture 6106) defining a conditional logic (e.g., logic 6112) for performing the specific task (e.g., method 2400), where: (a) the conditional logic 6112 is executed in accordance with a first order of a first set of interconnected nodes 6108 from a plurality of nodes 6108, and (b) the first order includes an input node 6108, at least one output node 6108, and an intermediate node 6180 disposed between the input node 6108 and the at least output node 6108; (iii) generating, for display at a remote device (e.g., the platform 100, the client device 102, or the server system 106), a representation of the corresponding node architecture (e.g., user interface 1800 or user interface 1830), where the representation represents a plurality of input features including: (I) a first input feature (e.g., orchestration 1850 or agent level-configs 1852) for configuring the conditional logic 6112 of the corresponding node architecture 6106, and (I) a second input feature (e.g., block level-configs 1854) for configuring a parameter (e.g., parameter 6110-1, parameter 6110-2, . . . , or parameter 6110-K) of a corresponding node (e.g., first node 6108-1) in the first set of interconnected nodes 6108; (iv) receiving a selection of either the first input feature or the second input feature, where the selection of either the first input feature or the second input feature defines a second order of a second set of interconnected nodes 6108 from the plurality of nodes 6108; and (v) updating the conditional logic 6112 of the corresponding node architecture 6106 (e.g., conditional logic formed from the collective logic 6112 of the nodes of the node architecture 6106) in accordance with the second order of the second set of interconnected nodes 6106. In some embodiments, the first set of interconnected nodes 6108 comprises one or more data source nodes 6108 (e.g., associated with a data module 240 or knowledge database 404), one or more machine-learning model nodes 6108 (e.g., associated with a model 228), and one or more conditional logic nodes (e.g., associated with logic 6112 for evaluating an input and/or generating an output based on the input).

(F2) In some embodiments of F1, the request is generated by the user by selecting and arranging graphical user interface elements (e.g., orchestration 1850, agent level-configs 1852, and/or block level configs 1854) within a user interface (e.g., user interface 1800 or user interface 1830) associated with the corresponding node architecture 6106.

(F3) In some embodiments of F2, the user interface comprises an agent builder component in a control plane of the computer system (e.g., a first plane configured for managing transmission of data through communication network 104).

(F4) In some embodiments of any of F1-F3, the request comprises a plurality of text data (e.g., "What is PFS?" of FIG. 8A, text prompt of FIG. 9A, text prompt of FIG. 9B, "What is the reason for Linda Watson's order cancelation?" of FIG. 9C, query of FIG. 10A, query of FIG. 10B, query of FIG. 10C, entered text of FIG. 11A, Yes or No or FIG. 11B, etc.) comprising one or more text strings inputted by the user.

(F5) In some embodiments of any of F1-F4, the specific clinical task (e.g., method 2400) comprises: (i) generating a summary report of a patient's medical records, (ii) guiding a patient through a care plan, (iii) creating patient care guidelines based on a patient's health profile, (iii) identifying patients requiring follow-up at a hospital, (v) identifying changes in a standard of care for a disease setting, or (vi) evaluating unstructured data associated with a patient to identify a cohort of similar patients.

(F6) In some embodiments of any of F1-F5, the input node 6108 is configured to receive a prompt from a user (e.g., 6108-1 "Extract Text" of FIG. 9A, 6108-1 "Extract Text" of FIG. 9B, 6108-1 "Embedding API" of FIG. 9C, or 1834C of FIG. 18D, etc.) associated with the specific clinical task (e.g., method 2400).

(F7) In some embodiments of any of F1-F6, the input node 6108-1 is configured to receive a prompt from a user associated with one or more specific clinical tasks (e.g., method 2400).

(F8) In some embodiments of any of F1-F7, the output node 6108 (e.g., node 6108-5 of FIG. 9A, node 6108-10 of FIG. 9B, or 6108-7 of FIG. 9C, etc.) is configured to generate a response (e.g., output, response of FIG. 8A, response of FIG. 8B, relevant chunks of FIG. 9A, response of FIG. 9B, PC-status reason of FIG. 9C) to the request from the user based on a respective task-specific machine-learning model (e.g., model 228) associated with the output node 6108.

(F9) In some embodiments of any of F1-F8, each respective machine-learning model node 6108 in the one or more machine-learning model nodes 6108 is configured to obtain information corresponding to the request using a corresponding domain associated with the respective machine-learning model (e.g., a domain of knowledge database 404, etc.).

(F10) In some embodiments of any of F1-F9, each respective machine-learning model node in the one or more machine-learning model nodes includes one or more parameters (e.g., parameters 6110 of FIG. 2B), and one or more functions (e.g., logic 6112 of FIG. 2B) for interacting with other nodes 6108 in the plurality of nodes 6108 (e.g., a first logic 6112-1 that, when satisfied, traverses data such as a first token from a first node 6108-1 to a second node 6108-2 in the node architecture 6106 adjacent to the first node 6108-1 and/or a second logic 6112-2 that, when satisfied, traverse the data from the first node 6108-1 to a third node 6108-3 adjacent to the first node 6108-1 and the second node 6108-2, etc.).

(F11) In some embodiments of any of F1-F10, the method further includes generating a configuration file for the corresponding node architecture 6106, the configuration file setting a working environment for the corresponding node architecture and one or more type-specific machine learning models 228 associated with the corresponding node architecture 6106.

(G1) In another aspect, some embodiments include a method of deploying a task-specific machine-learning model (e.g., agent module 6102 and/or model 228). In some embodiments, the method is performed at a computing system (e.g., the platform 100, the client device 102, or the server system 106). The method includes: (i) receiving a request (e.g., prompt, "What is PFS?" of FIG. 8A, text prompt of FIG. 9A, text prompt of FIG. 9B, "What is the reason for Linda Watson's order cancelation?" of FIG. 9C, query of FIG. 10A, query of FIG. 10B, query of FIG. 10C, entered text of FIG. 11A, Yes or No or FIG. 11B, etc.) from a user to engage a machine-learning model 228 that is configured to perform a specific task (e.g., a specific clinical task and/or method 2400), where the request comprises one or more commands associated with the specific task and defined by the user; (ii) retrieving, based on the machine-learning model 228, a corresponding node architecture (e.g., node architecture 6106) defining a conditional logic (e.g., collective logic 6112 of nodes 6108) for performing the specific task of the task-specific machine-learning model 228, where: (a) the conditional logic 6118 is in accordance with an order of a set of interconnected nodes 6108, (b) the order includes an input node (e.g., first node 6108-1), at least one output node e.g., node 6108-5 of FIG. 9A, node 6108-10 of FIG. 9B, or 6108-7 of FIG. 9C, etc.), and an intermediate node 6108 disposed between the input node and the at least output node, and (c) each respective node in a plurality of interconnected nodes is connected by to at least one node in the plurality of interconnected nodes (e.g., by an edge, etc.); (iii) applying the one or more commands to the input node in accordance with the order of the set of interconnected nodes, where the applying includes determining a correlation between the input node and at least one intermediate node in the set of interconnected nodes (e.g., traversing some or all of the one or more commands through the order of the set of interconnected nodes); (iv) generating, based on a progression of the one or more commands through the order of the set of interconnected nodes to an output node in the at least one output node, one or more data elements associated with a result of the one or more commands (e.g., output, response of FIG. 8A, response of FIG. 8B, relevant chunks of FIG. 9A, response of FIG. 9B, PC-status reason of FIG. 9C); and (v) communicating (e.g., for display at a computer system, via communication network 104, etc.) the one or more data elements. In some embodiments, the set of interconnected nodes comprises one or more data source nodes, one or more language model nodes, and one or more conditional logic nodes.

(H1) In another aspect, some embodiments include a method of performing a clinical task (e.g., the method 2400). In some embodiments, the method is performed at a computing system (e.g., the platform 100, the client device 102, or the server system 106). The method includes: (i) receiving, via a machine-learning model (e.g., model 228) that was trained to assist in performing a task (e.g., a clinical task, trained on one or more domains of knowledge database 404, etc.), a prompt (e.g., "What is PFS?" of FIG. 8A, text prompt of FIG. 9A, text prompt of FIG. 9B, "What is the reason for Linda Watson's order cancelation?" of FIG. 9C, query of FIG. 10A, query of FIG. 10B, query of FIG. 10C, entered text of FIG. 11A, Yes or No or FIG. 11B, etc.); (ii) in response to receiving the prompt, generating, at the first computing system, a natural-language response (e.g., output, response of FIG. 8A, response of FIG. 8B, relevant chunks of FIG. 9A, response of FIG. 9B, and/or PC-status reason of FIG. 9C) that is responsive to the prompt and is based on an analysis by the machine-learning model 228 of a repository of data that is determined to be relevant to the prompt (e.g., first domain, some or all of knowledge database 404, vector database 904, or data module 240); and (iii) providing the natural-language response to a second computing system that is distinct from the first computing system (e.g., the other of the platform 100, the client device 102, or the server system 106). In some embodiments, the task is: (i) generating a report of a patient's medical records, (ii) guiding a patient through a care plan, (iii) creating patient care guidelines based on a patient's health profile, (iii) identifying patients requiring follow-up at a hospital, (v) identifying changes in a standard of care for a disease setting, or (vi) evaluating unstructured data associated with a patient to identify a cohort of similar patients.

(H2) In some embodiments of H1, the task is generating a summary report of a patient's medical records, and the machine-learning model (e.g., a model 228) is trained using medical records of patients other than the patient (e.g., trained on data associated a first population of subjects that excludes the patient).

(H3) In some embodiments of H1, the task is guiding a patient through a first care plan and the machine-learning model (e.g., a model 228) is trained using a second care plan different from the first care plan (e.g., trained on lung cancer care plan when guiding the patient through a breast cancer care plan, etc.).

(H4) In some embodiments of any of H1-H3, the method further includes, prior to the generating, selecting the repository of data (e.g., first domain, some or all of knowledge database 404, vector database 904, or data module 240) from among a plurality of repositories (e.g., system database(s) 400 of FIG. 4) based on an identification of a domain, in a plurality of domains, associated with the repository of data.

(H5) In some embodiments of H4, each respective repository of data from among a plurality of repositories is associated with a corresponding domain in the plurality of domains (e.g., a first domain associated with Somantic DNA, a second domain associated with Germline DNA, a third domain associated with RNA, a fourth domain associated with DNA Methylation, a fifth domain associated with treatments, . . . , and N-th domain associated with clinical guidelines of FIG. 4, etc.).

(H6) In some embodiments of any of H1-H5, the machine-learning model 228 is selected by a conditional logic (e.g., logic 6112) from among multiple available machine-learning models 228 based on content of the prompt (e.g., determining a cosine similarity between the content of the prompt and the corresponding domain associated with the machine-learning model 228).

(H7) In some embodiments of any of H1-H6, generating the report of the patient's medical records comprises deidentifying personally identifiably information from the patient's medical records in accordance with one or more rules defined by task-specific machine-learning model.

(H8) In some embodiments of any of H1-H7, generating the report of the patient's medical records comprises determining demographic information associated with the patient.

(H9) In some embodiments of any of H1-H8, generating the report of the patient's medical records comprises determining a past medical condition of the patient.

(H10) In some embodiments of any of H1-H9, generating the report of the patient's medical records comprises determining one or more care plans for the patient.

(H11) In some embodiments of any of H1-H10, generating the report of the patient's medical records comprises determining one or more therapies administered to the patient.

(H12) In some embodiments of any of H1-H11, generating the report of the patient's medical records comprises determining a summary of specific care instructions for the patient.

(H13) In some embodiments of any of H1-H12, guiding the patient through the care plan comprises evaluating one or more clinical publications associated with a different care plan.

(H14) In some embodiments of any of H1-H13, guiding the patient through the care plan comprises conducting an assessment of the patient (e.g., assessment based on provider panels, provider methods, clinical trials database, clinical conditions, term sheet, provider coverage, knowledge, clinical guidelines, and/or clinical trial questions-answers of FIG. 4, etc.).

(H15) In some embodiments of H14, the assessment comprises one or more prompts (e.g., question of block 6108-7 of FIG. 9B, "How can I assist you today?" of FIG. 12A, response of FIG. 15, response 3606 of FIG. 16, output of FIG. 17, etc.) configured to elicit information from the patient (e.g., end-user of client device, end-user of server system 106, and/or end-user of platform 100, etc.).

(H16) In some embodiments of H14 or H15, the assessment comprises a biometric assessment of the patient (e.g., retrieving one or more data elements associated with the patient, such as from the client device 102, server system 106, and/or platform 100 and/or database 108, etc.) (e.g., one or more fingerprints, one or more vocal prints, one or more facial images, one or more eye images, and/or one or more observable constellations associated with the patient, etc.).

(H17) In some embodiments of any of H1-H16, creating the patient care guidelines based on the patient's health profile (e.g., medical database 242 and/or user database 244 of FIG. 2A) comprises evaluating one or more clinical publications (e.g., assessment based on provider panels, provider methods, clinical trials database, clinical conditions, term sheet, provider coverage, knowledge, clinical guidelines, and/or clinical trial questions-answers of FIG. 4, etc.). In some embodiments, the one or more clinical publications is obtained in response to an identification of a first domain associated with both a condition exhibited by the subject and at least one clinical publication in the one or more clinical publications. In some embodiments, the one or more clinical publications is obtained in response to an identification of the first domain associated with the condition exhibited by the subject and a second domain associated with the at least one clinical publication in the one or more clinical publications.

In some embodiments, the creating the patient care guide includes generating a disease map for each indication associated with the subject (e.g., each medical condition exhibited by the subject), mapping established and emerging biomarkers, treatments, and trials obtained from the one or more clinical publications.

In some embodiments, creating the patient care guide provides enhanced ability to anticipate market changes affecting the patient and strategic decision-making related to the care administered to the patient.

(H18) In some embodiments of any of H1-H17, creating the patient care guidelines based on the patient's health profile comprises determining one or more discordances between a first therapy and one or more biometrics or health parameters associated with the patient's medical records (e.g., a first disagreement between the first therapy and a first health parameter associated with the patient, such as a disagreement to administer the first therapy when the patient has an elevated risk for high blood pressure but the patient's medical records reflect a no risk for high-blood pressure, etc.). In some embodiments, the one or more discordances includes one or more treatment discordances, one or more clinical discordances, one or more patient-provider discordance, one or more diagnostic discordances, or a combination thereof.

(H19) In some embodiments of any of H1-H18, creating the patient care guidelines based on the patient's health profile comprises generating one or more charts specific to the patient (e.g., generating a first chart depicting a first health parameter associated with the subject during a first epoch, generating a second chart depicting a second health parameter associated with the subject during a second epoch, generating a third chart depicting two or more health parameters associated with the subject during a third epoch that includes both the first and second epochs, etc.). In some embodiments, each chart in the one or more charts is presented in a report for display through a user interface. In some embodiments, each chart in the one or more charts is presented in an independent user interface, such as a first user interface associated with a first chart in the one or more charts.

(H20) In some embodiments of any of H1-H19, the method further includes, based on a determination the prompt requires information from at least two machine-learning models (e.g., first model 228-1 and second model 228-2 and/or first agent module 6102-1 and second agent module 6102-2, etc.): (i) routing information between a first machine-learning model 228-1 and a second machine-learning model 228-2, each of the first machine-learning model and the second machine-learning model trained to perform one clinical task (e.g., specific task and/or method 2400); and (ii) generating a natural language response (e.g., output, response of FIG. 8A, response of FIG. 8B, relevant chunks of FIG. 9A, response of FIG. 9B, and/or PC-status reason of FIG. 9C) based on information from each of the first machine-learning model and the second machine-learning model (e.g., forming a compilation based on a first set of data obtained and/or generated by the first machine-learning model 228-1 and a second set of data obtained and/or generated by the second machine-learning model 228-2, etc.).

(H21) In some embodiments of any one H1-H20, the identifying patients requiring follow-up at a hospital comprises obtaining a plurality of physiological data elements associated a subject during an epoch when the subject is at a physical location associated with a medical practitioner, and evaluating the plurality of physiological data elements during the epoch to determine if the plurality of physiological data elements satisfies a threshold condition, wherein, when the threshold condition is satisfied, a notification is communication to a remote device associated with the medical practitioner, and when the threshold condition is not satisfied, a process of repeating the obtaining physiological data elements until the threshold condition is satisfied or the epoch express. For instance, in some embodiments, an agent module is configured to obtain one or more physician reports (e.g., obtain on a recurring and/or periodic, or non-period basis, such as after every scan is performed at hospital, etc.) and applies one or more models 228 in detect one or more patients that need further follow up (e.g., due to an anomaly detected after the scan, etc.). In some embodiments, this agent module also has the ability to generate a request (e.g., communication to the patient and/or medical provider) for the follow up order to direct the patient to the relevant physician and a reminder app to ensure the patients comes back for further care.

(H22) In some embodiments of any one H1-H21, the identifying changes in a standard of care for a disease setting comprises obtaining a first corpus of communications, and comparing the first corpus of communications against a second corpus of communications, wherein when the comparison satisfies a threshold condition, some or all of the first corpus of communications replaces a corresponding portion of the second corpus of communications, and when the comparison fails to satisfy the threshold condition, the first corpus of communications is discarded.

(I1) In another aspect, some embodiments include a method of generating a prediction (e.g., output, response of FIG. 8A, response of FIG. 8B, relevant chunks of FIG. 9A, response of FIG. 9B, and/or PC-status reason of FIG. 9C). In some embodiments, the method is performed at a computing system (e.g., the platform 100, the client device 102, or the server system 106). The method includes: (i) obtaining, via a communication network (e.g., network 104), from a first computer system (e.g., client device 102, platform 100, and/or server system 106), a first plurality of data elements, where the first plurality of data elements comprises a corpus of communications associated with one or more conditions exhibited by a population of subjects (e.g., a first domain of knowledge database 404, database 108, provider panels, provider methods, clinical trials database, clinical conditions, term sheet, provider coverage, knowledge, clinical guidelines, and/or clinical trial questions-answers of FIG. 4, etc.); (ii) applying the first plurality of data elements to a first node (e.g., first node 6108-1) in a plurality of interconnected nodes (e.g., nodes of node architecture 6106 of FIG. 2B, etc.), thereby identifying a first domain in a plurality of domains associated with a subset of the corpus of communications in accordance with a corresponding conditional logic (e.g., logic 6112) of the first node, where: (a) each respective domain the plurality of domains is associated with (I) a historical record comprising one or more parameters of a corresponding condition in the one or more conditions exhibited by the population of subjects (e.g., medical database(s) 242 and/or user databases( ) 244 and/or external database 108, and/or knowledge database 404, etc.) and (II) at least one task-specific machine-learning model in a set of task-specific machine-learning models (e.g., models 228), (b) each task-specific machine-learning model 228 in the at least one task-specific machine-learning model 228 is trained, at least in part, on the historical record of a corresponding domain associated with the task-specific machine-learning model, and (c) each task-specific machine-learning model in the set of task-specific machine-learning models is associated with at least one nodes 6108 in the plurality of interconnected nodes; (iii) evaluating, using each task-specific machine-learning model in the one or more task-specific machine-learning models associated with the first domain, a subset of the first plurality of data elements (e.g., obtaining a first parameter from the subset of the first plurality of data elements, evaluating some or all of the plurality of tokens, etc.); (iv) comparing the first parameter against the historical record associated with the first domain, thereby generating a corresponding validation for each parameter in the one or more parameters associated with the first domain; (v) updating the historical record of the first domain, where: (d) when the corresponding validation satisfies a threshold condition, the updating comprising adding the first parameter to the one or more parameters of the historical record associated with the first domain, and (c) when the corresponding validation fails to satisfy the threshold condition, the updating comprises adjusting a weight of a second parameter in the one or more parameters of the historical record of the first domain (e.g., forming an updated historical record associated with the first domain); (vi) determining a correlation between a first task-specific machine-learning model in the set of task-specific machine-learning models and a second task-specific machine-learning model in the set of task-specific machine-learning models based on a corresponding historical record associated with a second domain and the updated historical record associated with the first domain, where: (f) the first task-specific machine-learning model and the second task-specific machine-learning model are each associated with the first domain, (g) the second task-specific machine-learning model is associated with the second domain excluding the first task-specific machine-learning model, (h) the correlation between the first task-specific machine-learning model and the second task-specific machine-learning model satisfies a threshold condition of the first node; (vii) generating, based on the correlation between the first domain and the second domain, a second plurality of data elements comprising an empirical data element or a second a priori data element associated with the one or more conditions exhibited by the population of subjects; and (viii) communicating, via the communication network, to a second computer system different from the first computer system, the second plurality of data elements.

(I2) In some embodiments of I1, the first parameter is associated with one or more biological markers, one or more associated with therapeutic regimens, one or more pharmaceutical compounds, or a combination thereof further associated with the corresponding condition in the one or more conditions exhibited by the population of subjects.

(J1) In another aspect, some embodiments include a method of generating a cohort. In some embodiments, the method is performed at a computing system (e.g., the platform 100, the client device 102, or the server system 106). The method includes: (i) receiving a request from a user, where the request comprises a plurality of unstructured data elements associated one or more conditions exhibited by a first population of subjects, the plurality of unstructured data elements comprising one or more data elements of a first modality and one or more data elements of a second modality different from the first modality; (ii) applying the plurality of unstructured data elements to a first node in a plurality of interconnected nodes (e.g., identifying a first domain in a plurality of domains associated with at least one conditions in the one or more conditions exhibited by the first population of subjects, where each respective domain the plurality of domains is associated with one or more parameters of a corresponding condition); (iii) parsing the plurality of unstructured data elements in accordance with the one or more parameters associated with the corresponding condition, thereby forming a plurality of structured data elements; (iv) retrieving, in accordance with the identification of the first domain, a plurality of historical data elements associated the one or more conditions exhibited by a second population of subjects different from the first population of subjects; (v) comparing the plurality of structured data elements against the plurality of historical data elements, thereby identifying one or more subjects in the second population of subjects, where each respective subject in the one or more subjects of the second population of subjects is associated with a first parameter and a corresponding patient identifier, where: (a) when the corresponding patient identifier of a subject in the one or more subjects of the second of subjects population matches a patent identifier of a subject in the first population of subjects, the method performs a first process of communicating, via a communication network, to a second computer system, the corresponding patient identifier, and (b) when the corresponding patient identifier of the subject in the one or more subjects of the second population of subjects fails to match the patent identifier of the subject in the first population of subjects, the method performs a second process of forming a cohort of subjects comprising each subject in the second population of subjects associated with the first parameter and communicating, via the communication network, to a second computer system, the corresponding patient identifier for each subject in the cohort of subjects.

(K1) In another aspect, some embodiments include a method of enabling third-party access and use of an agent module (e.g., the method 2500). In some embodiments, the method is performed at a computing system (e.g., the platform 100, the client device 102, or the server system 106). The method includes: (i) receiving, at a user interface of a computing device, a user identifier and a prompt related to an identified clinical task (e.g., information corresponding the trial ID and the query shown in FIG. 10A); (ii) determining a set of task-specific components and a set of databases to which the user identifier has access (e.g., by identifying a level of access of the user); (iii) selecting, by a machine-learning model trained to select from among the set of task-specific components, a task-specific component from among the set of task-specific components based on the prompt; (iv) communicatively coupling the task-specific component to a database from the set of databases based on the prompt; (v) providing the prompt to the task-specific component; (vi) receiving a response to the prompt, where the response is generated by the task-specific component using information from the database; and (vii) providing the response to a user.

(K2) In some embodiments of K1, the method further includes: (i) receiving a second user identifier and the prompt related to the identified clinical task (e.g., by providing a user input directed to the dropdown menu in FIG. 10A for selecting a different trial ID); (ii) determining a second set of task-specific components and a second set of databases to which the user identifier has access; (iii) selecting, by the machine-learning model, a second task-specific component from among the second set of task-specific components based on the prompt; (iv) communicatively coupling the second task-specific component to a second database from the second set of databases based on the prompt; (v) providing the prompt to the second task-specific component; and (vi) receiving a second response to the prompt, where the second response is generated by the second task-specific component using information from the second database.

(K3) In some embodiments of K1 or K2, the set of task-specific components comprises one or more task-specific agent modules. For example, the user may be able to expand the output of the use "Use Agent List" block shown in FIG. 19A corresponding to a list of agents that the user has access to based on a respective token that the user provides as an input to the parse JSON block shown in FIG. 19A.

(K4) In some embodiments of any of K1-K3, the user identifier comprises an authentication token for the user. For example, the input token provided to the parse JSON block in FIG. 19A may be auto-populated when a user uses the orchestration represented by the workflow representation shown in the user interface 1830, based on credentials that the user provides to login to the agent-builder application 1800.

(K5) In some embodiments of any of K1-K4, the set of databases comprises one or more databases storing data owned by the user. In some embodiments, different internal users of the set of databases have different levels access to the various data sources therein. In some embodiments, a superuser of the one or more databases has access to a particular data plane, and each of the other users have access to a portion, less than all, of the particular data plane. In some embodiments, each user has access to a portion of the data plane based on a patient cohort associated with the respective user. In some embodiments, the system automatically restricts the level to which the user can attempt to access data of the particular data plane that the user does not have access to.

(K6) In some embodiments of any of K1-K5, the machine-learning model is a component of a super agent module. For example, the orchestration represented by the workflow representation shown in FIGS. 19A and 19B may be a super agent module that can otherwise be selected by a user as a block component for building a different orchestration.

(K7) In some embodiments of any of K1-K6, the task-specific component comprises an interconnected node architecture (e.g., the interconnected node architecture 1606).

(K8) In some embodiments of any of K1-K7, the task-specific component comprises a patient query agent, and the database stores information from medical documents provided by the user. For example, the medical documents may include clinical notes and/or patient records.

(K9) In some embodiments of any of K1-K8, each task-specific component in the set of task-specific components has a corresponding individual or group-level permission data, and determining the set of task-specific components to which the user identifier has access comprises comparing the user identifier with the permission data. In some embodiments, each task-specific component, agent module, and/or database has an associated set of access control lists (e.g., individual and/or group-level lists). In some embodiments, a task-specific component is integrated in an application (e.g., a third-party application) and associated with an application identifier (and/or an ACL for the application).

(K10) In some embodiments of any of K1-K7 and K9, the task-specific component comprises a care gap agent configured to identify gaps in patient care plans, and the database stores patient care plan data of the user. In some embodiments, care gap agent is provided with a set of criteria and identifies patients (e.g., on a given schedule, a regular basis, or in real-time) that may have a care gap based on the set of criteria and care information for the patients. In some embodiments, the care gap agent is configured to generate a notification for each identified patient (e.g., an EHR notification).

(L1) In another aspect, some embodiments include a method for selecting from among task-specific machine-learning models for addressing a clinical task (e.g., the method 2600). In some embodiments, the method is performed at a computing system (e.g., the platform 100, the client device 102, or the server system 106). The method includes: (i) receiving a prompt from a user; and (ii) in accordance with determining that the prompt requests assistance with a clinical task: (a) selecting, by a machine-learning model trained to select from among a plurality of task-specific machine-learning models each trained to assist with one of a plurality of clinical tasks, a respective task-specific machine-learning model from among the plurality of task-specific machine-learning models based on the prompt; (b) providing the prompt to the respective task-specific machine-learning model that was selected from among the plurality of task-specific machine-learning models; (c) receiving a response to the prompt, where the response is generated by the respective task-specific machine-learning model; and (d) in accordance with determining that the response addresses the clinical task, providing the response to the user.

(L2) In some embodiments of L1, the prompt comprises an identifier for a patient, an attribute of the patient, a test result of the patient, a diagnosis for the patient, or a combination thereof.

(L3) In some embodiments of L1 or L2, the prompt is generated by the user by selecting and arranging graphical user interface elements within a user interface associated with the plurality of task-specific machine-learning models and/or the machine-learning model.

(L4) In some embodiments of any of L1-L3, the prompt comprises a plurality of text data comprising one or more text strings inputted by the user.

(L5) In some embodiments of any of L1-L4, the clinical task comprises: (i) generating a summary report of a patient's medical records, (ii) guiding a patient through a care plan, (iii) creating patient care guidelines based on a patient's health profile, (iii) identifying patients requiring follow-up at a hospital, (v) identifying changes in a standard of care for a disease setting, or (vi) evaluating unstructured data associated with a patient to identify a cohort of similar patients. In some embodiments, the clinical task comprises a literature search, a cohort builder, an insurance claim builder, a patient query, or a handbook query.

(L6) In some embodiments of any of L1-L5, the respective task-specific machine-learning model is selected from among the plurality of task-specific machine-learning models based on a divergence of a principal component analysis of the prompt for each respective task-specific machine learning model in the plurality of task-specific machine-learning models.

(L7) In some embodiments of any of L1-L6, the method further includes: (i) selecting at least two task-specific machine learning models from among the plurality of task-specific machine-learning models based on the prompt; (ii) providing some or all of the prompt to each respective task-specific machine-learning model in the at least two task-specific machine learning models that was selected from among the plurality of task-specific machine-learning models; and (iii) receiving respective information from each task-specific machine learning models in the at least two task-specific machine learning models, where the response corresponds to a combination of the respective information from at least two task-specific machine learning models.

(L8) In some embodiments of L7, the method further includes: (i) selecting: (a) a first task-specific machine learning model in the at least two task-specific machine learning models as an initial terminal task-specific machine learning model, and (b) a second task-specific machine learning model in the at least two task-specific machine learning models as a final terminal task-specific machine learning model; (ii) providing the prompt to the first task-specific machine-learning model; (iii) receiving respective information from the first task-specific machine-learning model; (iv) providing the respective information to the second task-specific machine-learning model; and (v) receiving the response to the prompt from the second task-specific machine-learning model, where the response was generated by the second task-specific machine-learning model.

(L9) In some embodiments of any of L1-L8, determining that the prompt requests assistance with a clinical task further comprises identifying a first domain in a plurality of domains associated with the intent of the prompt.

(L10) In some embodiments of any of L1-L9, determining that the prompt requests assistance with a clinical task further comprises: (i) applying the prompt to a machine-learning model (e.g., generating a first response different from the prompt and responsive to the prompt from the user); (ii) obtaining a first domain in a plurality of domains of an input space associated with the prompt; and (iii) evaluating a value of the first response, where: (a) when the value of the first response satisfies a threshold condition, communicating, via a communication network, the first response to the user, and (b) when the value of the first response fails to satisfy the threshold condition: (I) identifying a first task-specific machine learning model associated with the first domain, and (II) applying the first response and/or the prompt to the first task-specific machine-learning model (e.g., generating a second response different from the first response and responsive to the prompt).

(L11) In some embodiments of any of L1-L10, the respective task-specific machine-learning model is trained on a first domain in a plurality of domains.

(L12) In some embodiments of any of L1-L11, each respective domain in a plurality of domains comprises at least one task-specific machine-learning model trained on the respective domain.

(L13) In some embodiments of L12, selecting the respective task-specific machine-learning model from among the plurality of task-specific machine-learning models is based on an identification of the first domain through an associated with the prompt.

(L14) In some embodiments of L12 or L13, providing the prompt to the respective task-specific machine-learning model comprises applying the prompt to a first node in a plurality of interconnected nodes (e.g., generating the response different from prompt and responsive to the prompt from the user), where: (i) the first node is associated with a first domain-specific machine-learning model in the plurality of task-specific machine-learning models, (i) each task-specific machine-learning model in the plurality of task-specific machine-learning model is associated with at least one nodes in the plurality of interconnected nodes and defines a conditional logic for performing a specific task, and (i) each node in the plurality of interconnected nodes is connected by an edge to at least one node in the plurality of interconnected nodes.

(L15) In some embodiments of any of L1-L14, selecting the respective task-specific machine-learning model comprises generating the task-specific machine-learning model having a conditional logic configured to respond to the prompt.

(L16) In some embodiments of any of L1-L15, selecting the respective task-specific machine-learning model comprises identifying a first classification of machine-learning models and selecting the respective the respective task-specific machine-learning model based on an association with the first classification of machine-learning models.

(L17) In some embodiments of any of L1-L16, selecting the respective task-specific machine learning model comprises forming a first order for a plurality of interconnected nodes.

(M1) In another aspect, some embodiments include a method of interacting with a routing agent module (e.g., the method 2700). In some embodiments, the method is performed at a computing system (e.g., the platform 100, the client device 102, or the server system 106). The method includes: (i) in accordance with receiving a prompt related to one or more clinical tasks, obtaining orchestration data about a set of task-specific components selected to provide a response to the prompt, where each respective task-specific components in the set of task-specific components is configured to assist with a respective clinical task of the one or more clinical tasks; (ii) based on the obtained orchestration data about the set of task-specific components, determining an order in which each respective task-specific components of the set of task-specific components should be utilized to prepare a complete response to the prompt that address the one or more clinical tasks; (iii) in accordance with the determined order, providing first data related to the prompt to a first task-specific component and receiving a first response from the first task-specific component; (iv) providing the first response and second data related to the prompt to a second task-specific component and receiving a second response from the second task-specific component; and (v) generating a complete response to the prompt that addresses the one or more clinical tasks using the first response and the second response.

(M2) In some embodiments of M1: (i) the first response includes a patient cohort, and (ii) the second response includes an elevated level of risk of a disease for one or more members of the patient cohort.

(M3) In some embodiments of M1 or M2, medical data is provided with the prompt related to the one or more clinical tasks.

(M4) In some embodiments of any of M1-M3, the method further includes: (i) in accordance with receiving the prompt, presenting a workflow representation to a user, the workflow representation comprising a plurality of interconnected nodes, where each respective node of the plurality of interconnected nodes is associated with a respective task-specific machine-learning model of the set of task-specific machine-learning models; and (ii) determining an output response to the prompt by providing query data associated with prompt to a first node of the workflow representation.

(M5) In some embodiments of any of M1-M4, the orchestration data includes one or more of: (i) a set of input parameters for the set of task-specific components, where the set of input parameters includes respective data types for each respective input parameter of the set of input parameters; (ii) a set of output parameters for the set of task-specific components, where the set of output parameters includes respective data types for each respective output parameter of the set of output parameters; and (iii) a respective domain of a plurality of domains of an input space corresponding to query data associated with prompt.

(M6) In some embodiments of any of M1-M5, the order is determined by a routing agent module.

(M7) In some embodiments of any of M1-M6, the set of task-specific components comprises a set of task-specific machine-learning models and a set of tools.

(N1) In another aspect, some embodiments include a method of verifying data compatibility (e.g., the method 2800). In some embodiments, the method is performed at a computing system (e.g., the platform 100, the client device 102, or the server system 106). The method includes: (i) in accordance with determining that a prompt, received based on a user input, requests assistance with one or more clinical tasks, selecting, by a machine-learning model trained to select from among a plurality of task-specific components, a set of task-specific components from among the plurality of task-specific components based on the prompt; (ii) obtaining orchestration data about the set of task-specific components, where each respective task-specific components in the set of task-specific components is configured to assist with a respective clinical task of the one or more clinical tasks; (iii) determining, from the orchestration data, at least one data-compatibility criterion for clinical task data relating to the one or more clinical tasks; (iv) receiving the clinical task data; and (v) in accordance with a determination that the clinical task data does not satisfy the at least one data-compatibility criterion, providing a notification to a user indicating that the one or more clinical tasks cannot be performed using the clinical task data.

(N2) In some embodiments of N1, the method further includes identifying a set of one or more data interfaces based on the obtained orchestration data, where each respective data interface of the set of data interfaces corresponds to a respective task-specific component of the set of task-specific components, and where the at least one data-compatibility criterion is determined based on one or more attributes of the set of data interface.

(N3) In some embodiments of N1 or N2, the method further includes, in accordance with a determination that the clinical task data satisfies the at least one data-compatibility criterion, providing another notification to the user indicating that the clinical task data is validated for the one or more clinical tasks.

(N4) In some embodiments of any of N1-N3, the method further includes: (i) receiving the prompt as a textual input from the user; (ii) identifying an intent of the textual input; and (iii) determining that the prompt requests assistance with the one or more clinical tasks based on the identified intent.

(N5) In some embodiments of any of N1-N4, the clinical task data comprises image data, and the at least one data-compatibility criterion relates to at least one of: a size of the image data, a resolution of the image data, and a color spectrum of the image data.

(N6) In some embodiments of any of N1-N5, the orchestration data comprises one or more of: one or more attributes for the set of task-specific machine-learning models, one or more input parameters for the set of task-specific machine-learning models, and one or more configuration parameters for the set of task-specific machine-learning models.

(N7) In some embodiments of any of N1-N6, the at least one data-compatibility criterion comprises at least one of: a data formatting requirement, a data type requirement, and a data labeling requirement.

(N8) In some embodiments of any of N1-N7, the plurality of task-specific components comprises a plurality of task-specific machine-learning models.

(N9) In some embodiments of any of N1-N8, the plurality of task-specific components comprises one or more transform components, each transform component of the one or more transform components configured to apply a transform to biological data to generate an output.

(N10) In some embodiments of any of N1-N9, the method further includes, in accordance with a determination that the clinical task data satisfies the at least one data-compatibility criterion: (i) obtaining one or more task results by performing, via the set of task-specific components, the one or more clinical tasks; and (ii) providing an output to the user indicating the one or more task results.

(N11) In some embodiments of N10, the output comprises a natural language output that summarizes the one or more task results.

(N12) In some embodiments of N10 or N11, the output is generated by a machine-learning component using the one or more task results.

(N13) In some embodiments of any of N10-N12, the method further includes obtaining subject data about a subject, where the output indicates how the one or more task results relate to the subject.

(N14) In some embodiments of any of N10-N13, the output is personalized to a particular subject.

(N15) In some embodiments of any of N10-N14, the user input includes a user query, and the output provides an answer to the user query based on the one or more task results.

(N16) In some embodiments of N15, the user query relates to a particular subject (e.g., a particular patient).

(O1) In another aspect, some embodiments include a method of generating agent modules. In some embodiments, the method is performed at a computing system (e.g., the platform 100, the client device 102, or the server system 106). The method includes: (i) receiving a request from a user for performance of a specific task; (ii) in response to the request, generating an agent module to perform the specific task, where the generating includes: (a) selecting a set of agent building blocks (e.g., nodes) from a plurality of available agent building blocks, where each agent building block in the plurality of available agent building blocks has a respective assigned function; and (b) connecting the set of agent building blocks to form the agent module; (iii) causing the agent module to execute and providing, to the agent module, information from the request; (iv) in response to providing the agent module information from the request, receiving a response from the agent module corresponding to performance of the specific task; and (v) providing the response to the user. In some embodiments, the agent module is generated by a super agent module.

(O2) In some embodiments of O1, the method further includes obtaining information about a plurality of previously generated agent modules, where the agent module is generated in accordance with a determination that none of the plurality of previously generated agent modules are configured to perform the specific task. In some embodiments, a super agent module is provided with information about a set of pre-generated agent modules (e.g., respective tasks that the pre-generated agent modules are configured to perform).

(O3) In some embodiments of O2, the method further includes, in accordance with a determination that a first agent module of the plurality of previously generated agent modules is configured to perform the specific task, forgoing generating the agent module. For example, a super agent module only generates a new agent module in accordance with a determination that no existing agent modules are suitable for performing the specific task.

(O4) In some embodiments of O3, the method further includes, in accordance with a determination that a first agent module of the plurality of previously generated agent modules is configured to perform the specific task, providing the information from the request to the first agent module. For example, a super agent module selects and uses a pre-generated agent module when the pre-generated agent module is determined to be suitable for the specific task.

(O5) In some embodiments of any of O1-O4, the plurality of available agent building blocks include one or more of: a set of data building blocks, a set of operator building blocks, and a set of tool building blocks.

(O6) In some embodiments of any of O1-O5, the method further includes obtaining specification information about the plurality of available agent building blocks, the specification information for each agent building block comprising the respective assigned function, one or more input data types, and one or more output data types.

(O7) In some embodiments of any of O1-O6, the agent module is generated and executed automatically without further input from the user. For example, the user does not need to provide any information for how to generate the agent module (and may not be aware that the agent module is being generated).

(O8) In some embodiments of any of O1-O7, the method further includes: (i) validating the agent module, where the agent module is executed in accordance with a determination that the agent module is valid; and (ii) in accordance with a determination that the agent module is invalid, generating a revised agent module using invalidity data of the agent module. In some embodiments, validating the agent module comprises determining whether the agent module is capable of performing the specific task. In some embodiments, validating the agent module comprises determining whether the agent module has sufficient data to perform the specific task. In some embodiments, validating the agent module comprises determining whether the agent module has valid building block connections.

(O9) In some embodiments of any of O1-O8, the agent module comprises one or more machine-learning models (e.g., a model 228). For example, the agent module may include one or more large language models.

(O10) In some embodiments of any of O1-O9, the agent module comprises a template building block coupled to an output of the agent module and configured to convert information obtained by the agent module to a natural language response. For example, the information obtained by the agent module may include information generated by a model of the agent module and/or information retrieved from a database (e.g., the database(s) 404) or dataset.

(O11) In some embodiments of any of O1-O10, the agent module comprises a second template building block coupled to an input of the agent module and configured to convert a received input to a programming language object.

(O12) In some embodiments of any of O1-O11, the method further includes receiving a user identifier for the user, where generating the agent module further comprises: (a) identifying one or more datasets accessible to the user based on the user identifier; and (b) connecting the set of agent building blocks to the one or more datasets.

(O13) In some embodiments of any of O1-O12, the method further includes storing the generated agent module (e.g., for use with subsequent user queries involving the specific task). In some embodiments, information about the generated agent module (e.g., the functionality, input types, and/or output types) is added to a list of pre-generated agent modules.

In another aspect, some embodiments include a computing system (e.g., the platform 100, the client device 102, or the server system 106) including control circuitry (e.g., the CPUs 302) and memory (e.g., the memory 310) coupled to the control circuitry, the memory storing one or more sets of instructions configured to be executed by the control circuitry, the one or more sets of instructions including instructions for performing one or more of the methods described herein (e.g., the methods 1300, 2100, 2200, 2300, 2400, 2500, 2600, 2700, 2800, A1-A30, B1-B6, C1-C20, D1-D20, E1-E13, F1-F11, G1, H1-H20, I1-I2, J1, K1-K10, L1-L17, M1-M7, N1-N16, and O1-O12 above).

In yet another aspect, some embodiments include a non-transitory computer-readable storage medium storing one or more sets of instructions for execution by control circuitry of a computing system, the one or more sets of instructions including instructions for performing one or more of the methods described herein (e.g., the methods 1300, 2100, 2200, 2300, 2400, 2500, 2600, 2700, 2800, A1-A30, B1-B6, C1-C20, D1-D20, E1-E13, F1-F11, G1, H1-H20, I1-I2, J1, K1-K10, L1-L17, M1-M7, N1-N16, and O1-O12 above).

Various types of models and algorithms may be used with the agents and components disclosed herein. In some embodiments, a model is a supervised machine learning algorithm. Nonlimiting examples of supervised learning algorithms include, but are not limited to, logistic regression, neural networks, support vector machines, Naive Bayes algorithms, nearest neighbor algorithms, random forest algorithms, decision tree algorithms, boosted trees algorithms, multinomial logistic regression algorithms, linear models, linear regression, GradientBoosting, mixture models, hidden Markov models, Gaussian NB algorithms, linear discriminant analysis, or any combinations thereof. In some embodiments, a model is a multinomial classifier algorithm. In some embodiments, a model is a 2-stage stochastic gradient descent (SGD) model. In some embodiments, a model is a deep neural network (e.g., a deep-and-wide sample-level classifier).

In some embodiments, a model is, or includes, a neural network (e.g., a convolutional neural network and/or a residual neural network). Neural network algorithms, also known as artificial neural networks (ANNs), include convolutional and/or residual neural network algorithms (deep learning algorithms). Neural networks can be machine learning algorithms that may be trained to map an input data set to an output data set, where the neural network comprises an interconnected group of network nodes organized into multiple layers of network nodes. For example, the neural network architecture may comprise at least an input layer, one or more hidden layers, and an output layer. The neural network may comprise any total number of layers, and any number of hidden layers, where the hidden layers function as trainable feature extractors that allow mapping of a set of input data to an output value or set of output values. As used herein, a deep learning algorithm can be a neural network comprising a plurality of hidden layers, e.g., two or more hidden layers. Each layer of the neural network can comprise a number of network nodes (also sometimes referred to as neurons). A network node can receive input that comes either directly from the input data or the output of network nodes in previous layers, and perform a specific operation, e.g., a summation operation. In some embodiments, a connection from an input to a network node is associated with a parameter (e.g., a weight and/or weighting factor). In some embodiments, a network node sums up the products of all pairs of inputs, $x_i$, and their associated parameters. In some embodiments, the weighted sum is offset with a bias, b. In some embodiments, the output of a network node is gated using a threshold or activation function, f, which may be a linear or non-linear function. The activation function may be, for example, a rectified linear unit (ReLU) activation function, a Leaky ReLU activation function, or other function such as a saturating hyperbolic tangent, identity, binary step, logistic, arcTan, softsign, parametric rectified linear unit, exponential linear unit, softPlus, bent identity, softExponential, Sinusoid, Sine, Gaussian, or sigmoid function, or any combination thereof.

The weighting factors, bias values, and threshold values, or other computational parameters of the neural network, may be "taught" or "learned" in a training phase using one or more sets of training data. For example, the parameters may be trained using the input data from a training data set and a gradient descent or backward propagation method so that the output value(s) that the ANN computes are consistent with the examples included in the training data set. The parameters may be obtained from a back propagation neural network training process.

As an example, a variety of neural networks may be suitable for use in analyzing an image of an eye of a subject. Examples can include, but are not limited to, feedforward neural networks, radial basis function networks, recurrent neural networks, residual neural networks, convolutional neural networks, residual convolutional neural networks, and the like, or any combination thereof. In some embodiments, a machine-learning model uses a pre-trained and/or transfer-learned ANN or deep learning architecture. Convolutional and/or residual neural networks can be used for analyzing an image of a subject in accordance with the present disclosure.

A deep neural network model may include an input layer, a plurality of individually parameterized (e.g., weighted) convolutional layers, and an output scorer. The parameters (e.g., weights) of each of the convolutional layers as well as the input layer contribute to the plurality of parameters (e.g., weights) associated with the deep neural network model. In some embodiments, at least 100 parameters, at least 1000 parameters, at least 2000 parameters or at least 5000 parameters are associated with the deep neural network model. As such, deep neural network models require a computer to be used because they cannot be mentally solved. In other words, given an input to the model, the model output needs to be determined using a computer rather than mentally in such embodiments. See, for example, Krizhevsky et al., 2012, "Imagenet classification with deep convolutional neural networks," in Advances in Neural Information Processing Systems 2, Pereira, Burges, Bottou, Weinberger, eds., pp. 1097-1105, Curran Associates, Inc.; Zeiler, 2012 "ADADELTA: an adaptive learning rate method," CoRR, vol. abs/1212.5701; and Rumelhart et al., 1988, "Neurocomputing: Foundations of research," ch. Learning Representations by Back-propagating Errors, pp. 696-699, Cambridge, MA, USA: MIT Press, each of which is hereby incorporated by reference.

Neural network algorithms, including convolutional neural network algorithms, suitable for use as models are disclosed in, for example, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference. Additional example neural networks suitable for use as models are disclosed in Duda et al., 2001, Pattern Classification, Second Edition, John Wiley & Sons, Inc., New York; and Hastic et al., 2001, The Elements of Statistical Learning, Springer-Verlag, New York, each of which is hereby incorporated by reference in its entirety. Additional example neural networks suitable for use as models are also described in Draghici, 2003, Data Analysis Tools for DNA Microarrays, Chapman & Hall/CRC; and Mount, 2001, Bioinformatics: sequence and genome analysis, Cold Spring Harbor Laboratory Press, Cold Spring Harbor, New York, each of which is hereby incorporated by reference in its entirety.

In some embodiments, a model is, or includes, a support vector machine (SVM). SVM algorithms suitable for use as models are described in, for example, Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genom analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastic, 2001, The Elements of Statistical Learning, Springer, New York; and Furey et al., 2000, Bioinformatics 16, 906-914, each of which is hereby incorporated by reference in its entirety. When used for classification, SVMs separate a given set of binary labeled data with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space can correspond to a non-linear decision boundary in the input space. In some embodiments, the plurality of parameters (e.g., weights) associated with the SVM define the hyper-plane. In some embodiments, the hyper-plane is defined by at least 10, at least 20, at least 50, or at least 100 parameters and the SVM model requires a computer to calculate because it cannot be mentally solved.

In some embodiments, a model is, or includes, a Naive Bayes algorithm. Naïve Bayes models suitable for use as models are disclosed, for example, in Ng et al., 2002, "On discriminative vs. generative classifiers: A comparison of logistic regression and naive Bayes," Advances in Neural Information Processing Systems, 14, which is hereby incorporated by reference. A Naive Bayes model is any model in a family of "probabilistic models" based on applying Bayes' theorem with strong (naïve) independence assumptions between the features. In some embodiments, they are coupled with Kernel density estimation. See, for example, Hastie et al., 2001, The elements of statistical learning: data mining, inference, and prediction, eds. Tibshirani and Friedman, Springer, New York, which is hereby incorporated by reference.

In some embodiments, a model is, or includes, a nearest neighbor algorithm. Nearest neighbor models can be memory-based and include no model to be fit. For nearest neighbors, given a query point $x_0$ (a test subject), the k training points $x_{(r)}$, r, . . . , k (here the training subjects) closest in distance to $x_0$ are identified and then the point $x_0$ is classified using the k nearest neighbors. Here, the distance to these neighbors is a function of the abundance values of the discriminating gene set. In some embodiments, Euclidean distance in feature space is used to determine distance as Typically, when the nearest neighbor algorithm is used, the abundance data used to compute the linear discriminant is standardized to have mean zero and variance 1. The nearest neighbor rule can be refined to address issues of unequal class priors, differential misclassification costs, and feature selection. Many of these refinements involve some form of weighted voting for the neighbors. For more information on nearest neighbor analysis, see Duda, Pattern Classification, Second Edition, 2001, John Wiley & Sons, Inc; and Hastie, 2001, The Elements of Statistical Learning, Springer, New York, each of which is hereby incorporated by reference.

As an example, a k-nearest neighbor model is a non-parametric machine learning method in which the input includes the k closest training examples in feature space. The output is a class membership. An object is classified by a plurality vote of its neighbors, with the object being assigned to the class most common among its k nearest neighbors (k is a positive integer, typically small). If k=1, then the object is simply assigned to the class of that single nearest neighbor. Sec, Duda et al., 2001, Pattern Classification, Second Edition, John Wiley & Sons, which is hereby incorporated by reference. In some embodiments, the number of distance calculations needed to solve the k-nearest neighbor model is such that a computer is used to solve the model for a given input because it cannot be mentally performed.

In some embodiments, a model is, or includes, a decision tree. Decision trees suitable for use as models are described generally by Duda, 2001, Pattern Classification, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4.5, MART, and Random Forests. CART, ID3, and C4.5 are described in Duda, 2001, Pattern Classification, John Wiley & Sons, Inc., New York, pp. 396-408 and pp. 411-412, which is hereby incorporated by reference. CART, MART, and C4.5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety. In some embodiments, the decision tree model includes at least 10, at least 20, at least 50, or at least 100 parameters (e.g., weights and/or decisions) and requires a computer to calculate because it cannot be mentally solved.

In some embodiments, a model uses a regression algorithm. A regression algorithm can be any type of regression. For example, the regression algorithm may be logistic regression. In some embodiments, the regression algorithm is logistic regression with lasso, L2 or clastic net regularization. In some embodiments, those extracted features that have a corresponding regression coefficient that fails to satisfy a threshold value are pruned (removed from) consideration. In some embodiments, a generalization of the logistic regression model that handles multicategory responses is used as the model. Logistic regression algorithms are disclosed in Agresti, An Introduction to Categorical Data Analysis, 1996, Chapter 5, pp. 103-144, John Wiley & Son, New York, which is hereby incorporated by reference. In some embodiments, the model makes use of a regression model disclosed in Hastie et al., 2001, The Elements of Statistical Learning, Springer-Verlag, New York. In some embodiments, the logistic regression model includes at least 10, at least 20, at least 50, at least 100, or at least 1000 parameters (e.g., weights) and requires a computer to calculate because it cannot be mentally solved.

Linear discriminant analysis (LDA), normal discriminant analysis (NDA), or discriminant function analysis can be a generalization of Fisher's linear discriminant, a method used in statistics, pattern recognition, and machine learning to find a linear combination of features that characterizes or separates two or more classes of objects or events. The resulting combination can be used as a model (e.g., a linear model) in some embodiments of the present disclosure.

In some embodiments, a model is a mixture model, such as that described in McLachlan et al., Bioinformatics 18(3): 413-422, 2002. In some embodiments, in particular, those embodiments including a temporal component, a model is a hidden Markov model such as described by Schliep et al., 2003, Bioinformatics 19(1):i255-i263.

In some embodiments, a model is an unsupervised clustering model. In some embodiments, a model is a supervised clustering model. Clustering algorithms suitable for use as models are described, for example, at pages 211-256 of Duda and Hart, Pattern Classification and Scene Analysis, 1973, John Wiley & Sons, Inc., New York, (hereinafter "Duda 1973") which is hereby incorporated by reference in its entirety. The clustering problem can be described as one of finding natural groupings in a dataset. To identify natural groupings, two issues can be addressed. First, a way to measure similarity (or dissimilarity) between two samples can be determined. This metric (e.g., similarity measure) can be used to ensure that the samples in one cluster are more like one another than they are to samples in other clusters. Second, a mechanism for partitioning the data into clusters using the similarity measure can be determined. One way to begin a clustering investigation can be to define a distance function and to compute the matrix of distances between all pairs of samples in the training set. If distance is a good measure of similarity, then the distance between reference entities in the same cluster can be significantly less than the distance between the reference entities in different clusters. However, clustering may not use a distance metric. For example, a nonmetric similarity function s(x, x') can be used to compare two vectors x and x'. s(x, x') can be a symmetric function whose value is large when x and x' are somehow "similar." Once a method for measuring "similarity" or "dissimilarity" between points in a dataset has been selected, clustering can use a criterion function that measures the clustering quality of any partition of the data. Partitions of the data set that extremize the criterion function can be used to cluster the data. Particular exemplary clustering techniques that can be used in the present disclosure can include, but are not limited to, hierarchical clustering (agglomerative clustering using a nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. In some embodiments, the clustering comprises unsupervised clustering (e.g., with no preconceived number of clusters and/or no predetermination of cluster assignments).

In some embodiments, an ensemble (e.g., two or more) of models is used. In some embodiments, a boosting technique such as AdaBoost is used in conjunction with many other types of learning algorithms to improve the performance of the model. In this approach, the output of any of the models disclosed herein, or their equivalents, is combined into a weighted sum that represents the final output of the boosted model. In some embodiments, the plurality of outputs from the models is combined using any measure of central tendency known in the art, including but not limited to a mean, median, mode, a weighted mean, weighted median, weighted mode, etc. In some embodiments, the plurality of outputs is combined using a voting method. In some embodiments, a respective model in the ensemble of models is weighted or unweighted.

In some embodiments, a model is a reinforcement learning model. In some embodiments, the reinforcement learning system comprises four main elements—an agent, a policy, a reward signal, and a value function, where the behavior of the agent is defined in terms of the policy. In some embodiments, the reinforcement learning system comprises a learning algorithm. In some implementations, the learning algorithm is an on-policy learning algorithm or an off-policy learning algorithms. On-Policy learning algorithms evaluate and improve the same policy which is being used to select the agent's actions. Off-Policy learning algorithms evaluate and improve policies that are different from the policy being used for action selection. Reinforcement learning is further described, for example, in Sutton R S, Barto A G, "Reinforcement learning: an introduction," IEEE Transactions on Neural Networks. 1998; 9(5):1054-1054, which is hereby incorporated herein by reference in its entirety.

As used herein, the term "instruction" refers to an order given to a computer processor by a computer program. On a digital computer, in some embodiments, each instruction is a sequence of 0's and 1's that describes a physical operation the computer is to perform. Such instructions can include data transfer instructions and data manipulation instructions. In some embodiments, each instruction is a type of instruction in an instruction set that is recognized by a particular processor type used to carry out the instructions. Examples of instruction sets include, but are not limited to, Reduced Instruction Set Computer (RISC), Complex Instruction Set Computer (CISC), Minimal Instruction Set Computers (MISC), Very Long Instruction Word (VLIW), Explicitly Parallel Instruction Computing (EPIC), and One Instruction Set Computer (OISC).

As used herein, the term "parameter" refers to any coefficient or, similarly, any value of an internal or external element (e.g., a weight and/or a hyperparameter) in an algorithm, model, regressor, and/or classifier that can affect (e.g., modify, tailor, and/or adjust) one or more inputs, outputs, and/or functions in the algorithm, model, regressor and/or classifier. For example, in some embodiments, a parameter refers to any coefficient, weight, and/or hyperparameter that can be used to control, modify, tailor, and/or adjust the behavior, learning, and/or performance of an algorithm, model, regressor, and/or classifier. In some instances, a parameter is used to increase or decrease the influence of an input (e.g., a feature) to an algorithm, model, regressor, and/or classifier. As a nonlimiting example, in some embodiments, a parameter is used to increase or decrease the influence of a node (e.g., of a neural network), where the node includes one or more activation functions. Assignment of parameters to specific inputs, outputs, and/or functions is not limited to any one paradigm for a given algorithm, model, regressor, and/or classifier but can be used in any suitable algorithm, model, regressor, and/or classifier architecture for a desired performance. In some embodiments, a parameter has a fixed value. In some embodiments, a value of a parameter is manually and/or automatically adjustable. In some embodiments, a value of a parameter is modified by a validation and/or training process for an algorithm, model, regressor, and/or classifier (e.g., by error minimization and/or backpropagation methods). In some embodiments, an algorithm, model, regressor, and/or classifier of the present disclosure includes a plurality of parameters. As such, the algorithms, models, regressors, and/or classifiers of the present disclosure cannot be mentally performed. In some embodiments, the algorithms, models, regressors, and/or classifier of the present disclosure operate in a k-dimensional space, where k is a positive integer of 5 or greater (e.g., 5, 6, 7, 8, 9, 10, etc.). As such, the algorithms, models, regressors, and/or classifiers of the present disclosure cannot be mentally performed.

In some embodiments, the methods described herein include inputting information into a model comprising a plurality of parameters, where the model applies the plurality parameters to the information through a plurality of instructions to generate an output from the model.

In some embodiments, an algorithm, model, regressor, and/or classifier of the present disclosure comprises a plurality of parameters. In some embodiments the plurality of parameters is n parameters, where: $n\geq2$; $n\geq5$; $n\geq10$; $n\geq25$; $n\geq40$; $n\geq50$; $n\geq75$; $n\geq100$; $n\geq125$; $n\geq150$; $n\geq200$; $n\geq225$; $n\geq250$; $n\geq350$; $n\geq500$; $n\geq600$; $n\geq750$; $n\geq1{,}000$; $n\geq2{,}000$; $n\geq4{,}000$; $n\geq5{,}000$; $n\geq7{,}500$; $n\geq10{,}000$; $n\geq20{,}000$; $n\geq40{,}000$; $n\geq75{,}000$; $n\geq100{,}000$; $n\geq200{,}000$; $n\geq500{,}000$, $n\geq1\times10^6$, $n\geq5\times10^6$, or $n\geq1\times10^7$. In some embodiments n is between 10,000 and $1\times10^7$, between 100,000 and $5\times10^6$, or between 500,000 and $1\times10^6$. In some embodiments, the plurality of parameters is at least 1000 parameters, at least 5000 parameters, at least 10,000 parameters is at least 50,000 parameters, at least 100,000 parameters, at least 250,000 parameters, at least 500,000 parameters, at least 1 million parameters, at least 5 million parameters, at least 10 million parameters, at least 25 million parameters, at least 50 million parameters, at least 100 million parameters, at least 250 million parameters, at least 500 million parameters, at least 1 billion parameters, or more parameters.

In some embodiments, the plurality of instructions is at least 1000 instructions, at least 5000 instructions, at least 10,000 instructions is at least 50,000 instructions, at least 100,000 instructions, at least 250,000 instructions, at least 500,000 instructions, at least 1 million instructions, at least 5 million instructions, at least 10 million instructions, at least 25 million instructions, at least 50 million instructions, at least 100 million instructions, at least 250 million instructions, at least 500 million instructions, at least 1 billion instructions, or more instructions.

It will be understood that, although the terms "first," "second," etc. may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "set" refers to a group of one or more objects. As used herein, the terms "request," "prompt," and "query" are used interchangeable unless expressly stated otherwise. As used herein, the term "model" refers to a machine learning model or algorithm. In some embodiments, the model is a task-specific model (e.g., a task-specific machine-learning model). As used herein, the term "task-specific" refers to a component that is specifically configured to perform a single task or a subset of tasks (e.g., a single class of tasks). In some embodiments, the model is an unsupervised learning algorithm. One example of an unsupervised learning algorithm is cluster analysis.

As used herein, the term "if" can be construed to mean "when" or "upon" or "in response to determining" or "in accordance with a determination" or "in response to detecting" that a stated condition precedent is true, depending on the context. Similarly, the phrase "if it is determined [that a stated condition precedent is true]" or "if [a stated condition precedent is true]" or "when [a stated condition precedent is true]" can be construed to mean "upon determining" or "in response to determining" or "in accordance with a determination" or "upon detecting" or "in response to detecting" that the stated condition precedent is true, depending on the context.

The foregoing description, for purposes of explanation, has been described with reference to specific embodiments. However, the illustrative discussions above are not intended to be exhaustive or limit the claims to the precise forms disclosed. Many modifications and variations are possible in view of the above teachings. The embodiments were chosen and described in order to best explain principles of operation and practical applications, to thereby enable others skilled in the art.

What is claimed is:

1. A method, comprising:

in accordance with receiving a prompt related to one or more clinical tasks, obtaining orchestration data about a set of task-specific components selected to provide a response to the prompt, wherein each respective task-specific components in the set of task-specific components is configured to assist with a respective clinical task of the one or more clinical tasks;

based on the obtained orchestration data about the set of task-specific components, determining an order in which each respective task-specific components of the set of task-specific components should be utilized to prepare a complete response to the prompt that address the one or more clinical tasks;

in accordance with the determined order, providing first data related to the prompt to a first task-specific component and receiving a first response from the first task-specific component;

providing the first response and second data related to the prompt to a second task-specific component and receiving a second response from the second task-specific component; and generating a complete response to the prompt that addresses the one or more clinical tasks using the first response and the second response.

2. The method of claim 1, wherein:

the first response includes a patient cohort, and the second response includes an elevated level of risk of a disease for one or more members of the patient cohort.

3. The method of claim 1, wherein medical data is provided with the prompt related to the one or more clinical tasks.

4. The method of claim 1, further comprising:

in accordance with receiving the prompt, presenting a workflow representation to a user, the workflow representation comprising a plurality of interconnected nodes, wherein each respective node of the plurality of interconnected nodes is associated with a respective task-specific machine-learning model of the set of task-specific machine-learning models; and determining an output response to the prompt by providing query data associated with prompt to a first node of the workflow representation.

5. The method of claim 1, wherein the orchestration data includes one or more of:

a set of input parameters for the set of task-specific components, wherein the set of input parameters includes respective data types for each respective input parameter of the set of input parameters;

a set of output parameters for the set of task-specific components, wherein the set of output parameters includes respective data types for each respective output parameter of the set of output parameters; and a respective domain of a plurality of domains of an input space corresponding to query data associated with prompt.

6. The method of claim 1, wherein the order is determined by a routing agent module.

7. The method of claim 1, wherein the set of task-specific components comprises a set of task-specific machine-learning models and a set of tools.

8. A computing system, comprising:

control circuitry;

memory; and one or more sets of instructions stored in the memory and configured for execution by the control circuitry, the one or more sets of instructions comprising instructions for:

in accordance with receiving a prompt related to one or more clinical tasks, obtaining orchestration data about a set of task-specific components selected to provide a response to the prompt, wherein each respective task-specific components in the set of task-specific components is configured to assist with a respective clinical task of the one or more clinical tasks;

based on the obtained orchestration data about the set of task-specific components, determining an order in which each respective task-specific components of the set of task-specific components should be utilized to prepare a complete response to the prompt that address the one or more clinical tasks;

in accordance with the determined order, providing first data related to the prompt to a first task-specific component and receiving a first response from the first task-specific component;

providing the first response and second data related to the prompt to a second task-specific component and receiving a second response from the second task-specific component; and generating a complete response to the prompt that addresses the one or more clinical tasks using the first response and the second response.

9. The computing system of claim 8, wherein:

the first response includes a patient cohort, and the second response includes an elevated level of risk of a disease for one or more members of the patient cohort.

10. The computing system of claim 8, wherein medical data is provided with the prompt related to the one or more clinical tasks.

11. The computing system of claim 8, wherein the orchestration data includes one or more of:

a set of input parameters for the set of task-specific components, wherein the set of input parameters includes respective data types for each respective input parameter of the set of input parameters;

a set of output parameters for the set of task-specific components, wherein the set of output parameters includes respective data types for each respective output parameter of the set of output parameters; and a respective domain of a plurality of domains of an input space corresponding to query data associated with prompt.

12. The computing system of claim 8, wherein the order is determined by a routing agent module.

13. The computing system of claim 8, wherein the set of task-specific components comprises a set of task-specific machine-learning models and a set of tools.

14. The computing system of claim 8, wherein the one or more sets of instructions further comprise instructions for:

in accordance with receiving the prompt, presenting a workflow representation to a user, the workflow representation comprising a plurality of interconnected nodes, wherein each respective node of the plurality of interconnected nodes is associated with a respective task-specific machine-learning model of the set of task-specific machine-learning models; and determining an output response to the prompt by providing query data associated with prompt to a first node of the workflow representation.

15. A non-transitory computer-readable storage medium storing one or more sets of instructions configured for execution by a computing device having control circuitry and memory, the one or more sets of instructions comprising instructions for:

in accordance with receiving a prompt related to one or more clinical tasks, obtaining orchestration data about a set of task-specific components selected to provide a response to the prompt, wherein each respective task-specific components in the set of task-specific components is configured to assist with a respective clinical task of the one or more clinical tasks;

based on the obtained orchestration data about the set of task-specific components, determining an order in which each respective task-specific components of the set of task-specific components should be utilized to prepare a complete response to the prompt that address the one or more clinical tasks;

in accordance with the determined order, providing first data related to the prompt to a first task-specific component and receiving a first response from the first task-specific component;

providing the first response and second data related to the prompt to a second task-specific component and receiving a second response from the second task-specific component; and generating a complete response to the prompt that addresses the one or more clinical tasks using the first response and the second response.

16. The non-transitory computer-readable storage medium of claim 15, wherein:

the first response includes a patient cohort, and the second response includes an elevated level of risk of a disease for one or more members of the patient cohort.

17. The non-transitory computer-readable storage medium of claim 15, wherein medical data is provided with the prompt related to the one or more clinical tasks.

18. The non-transitory computer-readable storage medium of claim 15, wherein the orchestration data includes one or more of:

a set of input parameters for the set of task-specific components, wherein the set of input parameters includes respective data types for each respective input parameter of the set of input parameters;

a set of output parameters for the set of task-specific components, wherein the set of output parameters includes respective data types for each respective output parameter of the set of output parameters; and a respective domain of a plurality of domains of an input space corresponding to query data associated with prompt.

19. The non-transitory computer-readable storage medium of claim 15, wherein the order is determined by a routing agent module.

20. The non-transitory computer-readable storage medium of claim 15, wherein the set of task-specific components comprises a set of task-specific machine-learning models and a set of tools.

* * * * *